United States Patent
Saint-Pierre et al.

(10) Patent No.: US 12,048,308 B2
(45) Date of Patent: Jul. 30, 2024

(54) GRASS ENDOPHYTES

(71) Applicant: RAGT 2N, Rodez (FR)

(72) Inventors: Laure Saint-Pierre, Rodez (FR); Marie-Christine Gras, Rodez (FR)

(73) Assignee: RAGT 2N, Rodez (FR)

( * ) Notice: Subject to any disclaimer, the term of this patent is extended or adjusted under 35 U.S.C. 154(b) by 0 days.

(21) Appl. No.: 17/294,044

(22) PCT Filed: Nov. 15, 2019

(86) PCT No.: PCT/EP2019/081536
§ 371 (c)(1),
(2) Date: May 14, 2021

(87) PCT Pub. No.: WO2020/099660
PCT Pub. Date: May 22, 2020

(65) Prior Publication Data
US 2021/0400987 A1    Dec. 30, 2021

(30) Foreign Application Priority Data
Nov. 15, 2018   (NZ) ........................................ 748421

(51) Int. Cl.
*A01H 15/00*   (2006.01)
*A01N 63/30*   (2020.01)
*C12N 1/14*    (2006.01)

(52) U.S. Cl.
CPC ............. *A01N 63/30* (2020.01); *A01H 15/00* (2013.01); *C12N 1/145* (2021.05)

(58) Field of Classification Search
CPC .................................................... A01H 17/00
See application file for complete search history.

(56) References Cited

U.S. PATENT DOCUMENTS 7,976,857 B2 *   7/2011   Tapper ................... A01H 15/00
                                                      424/405

OTHER PUBLICATIONS

Bluett et al., Effects perennial ryegrass infected with either AR1 or wild endophyte on dairy production in the Waikato, New Zealand Journal of Agricultural Research, vol. 48, pp. 197-212, 2005.
Christensen et al., Infection of tall fescue and perennial ryegrass plants by combinations of different Neotyphodium endophytes, Mycol Research, vol. 104, No. 8, pp. 974-978, 2000.
Fletcher et al., The occurrence of rygrass staggers and heat stress in sheep grazing ryegrass-endophyte associations with diverse alkaloid profiles, New Zealand Veterinary Journal, vol. 65, No. 5, pp. 232-241, 2017.
Hettiarachchige et al., Phylogenomics of asexual Epichloe fungal endophytes forming associations with perennial ryegrass, BMC Evolutionary Biology, 15:72, pp. 1-14, 2015.
Johnson et al., The exploitation of epichloae endophytes for agricultural benefit, Fungal Diversity, vol. 60, pp. 171-188, 2013.
Tian et al., Characterization of novel perennial ryrgrass host—neotyphodium endophyte associations, Crop & Pasture Science, vol. 64, pp. 716-725, 2013.
Young et al., Indole-Diterpene Biosynthetic Capability of Pichloe Endophytes as predicted by Itm gene analysis. Applied and Environmental Microbiology, vol. 75, No. 7, pp. 2200-2211, 2009.
Patent Examination Report 1 dated Nov. 29, 2021 in New Zealand Application No. 759735.
Patent Examination Report 2 dated May 9, 2022 in New Zealand Application No. 759735.
Patent Examination Report 3 dated Jun. 9, 2022 in New Zealand Application No. 759735.
International Preliminary Report On Patentability issued on May 18, 2021 in PCT/EP2019/081536.
Christensen et al., Infection of tall fescue and perennial ryegrass plants by combinations of different Neotyphodium endophytes, Mycological Research, vol. 104, No. 8, pp. 974-978, 2000.
Fletcher et al., The occurrence of ryegrass staggers and heat stress in sheep grazing ryegrass-endophyte associations with diverse alkaloid profiles, New Zealand Veterinary Journal, vol. 65, No. 5, pp. 232-241, 2017.
Young et al., Indole-Diterpene Biosynthetic Capability of Epichloe Endophytes as Predicted by Itm Gene Analysis, Applied and Environmental Microbiology, vol. 75, No. 7, pp. 2200-2211, 2009.
International Search Report and Written Opinion mailed Jun. 30, 2020 in International Application No. PCT/EP2019/081536.

* cited by examiner

*Primary Examiner* — David H Kruse
(74) *Attorney, Agent, or Firm* — Knobbe, Martens, Olson & Bear, LLP

(57) ABSTRACT

A method of improving the viability, persistence, and/or vigor of a host plant in the form of *Lolium multiflorum Lolium×hybridum* and *Lolium perenne*, (host grass) includes artificially inoculating the host grass with an LpTG-3 endophyte RGT18 strain. The LpTG-3 endophyte RGT18 strain can produce at least one alkaloid or combination of alkaloids that provide the host grass with a favorable alkaloid profile and/or protect the plant from biotic stresses.

17 Claims, 55 Drawing Sheets
Specification includes a Sequence Listing.

Figure 6

Information used to produce the sequence listings for strains of *Epichloë festucae*

First letter into the brackets is the nucleotide observed on AR37 and the second letter after the "/" is the nucleotide observed on RGT18 locus_12991
    CTTTACCTAAAGCATTAACTTAGGGTTTAAAGGAATACCTCCTCTAAGAA[T/A]AATTTCTAAAT
CCTTCGCTCCTATAAGGTATTACTAAAGGTACTTCTAAAG C364892_m_1351
    GACCGACTGCGCAGATCCCGTCAAGTTGTCATGCCGATCTGAAACTCTAG[A/G]CCCCTCCC
ACTCTTCACTGCACAACTCGACAGCCGGTTTGTGTCAGTGAA C369440_m_2614
    ATTCCTTAAACTAGTTATCTTAAGATATTATAGAATTACTTACTATTAAG[G/A]AGAATAAAGTT
ATAAAGATAAGAAAGAGAGAAAAAGAGTTAAGGGAGTAA C369562_m_3539
    CTCCTGGGTCTCCTGGTCTAGTCGCGAGATAAGTCGCGAGATAAGATAAG[A/G]CTGGACAG
CAACAAGCTGCTGTTGTTGCATGTTCCAACAGCCATTGAGC C369930_m_1465
    TAGCTCATCACAATAATTCATGAGAACAATTTTTTATTATTATTATTATT[C/A]TTCTTCTTCTTC
TTCTTCTTGTCCTTCTCCTATTTAGCCGCCATTTCC C370040_m_4739
    CGGCCGGCCAGGAACATGGGAATGGCAGTGGACGCGGTTTGCAGGATGAC[C/A]CCCAGGT
TGAAGACCCAGCATGAGATGATGAGAGCCAGACGCCGGCCAATG C370074_m_1987
    ATACAGAATGGTGTAATTGTAAGTCCTATACAAAGAGAGAGAGAGAGAAA[A/G]GGGGGGCA
AAGGAGAGAAAACATCATACGCACCAGTCCCAAGATCAGAAAC C370138_m_5622
    ACGCCATCATCGGGGCCTCGGCCGCCCTCGCCGGCGTAACACGCATGACG[G/A]TATCCAT
CGTCGTCATCATGTTCGAGCTCACGGGCGCGCTGACGTATGTGC C370190_m_3124
    ATTTTTTTTTCGATGGATGCGGGCGGTTTTCGATGGTATTGGCGGTCGGA[A/T]CGGGTCAGA
GGAGGACGACTCACCACTGCGACTCTACCGGCAACAGAGACG C370288_m_385
    TTTCCCTGAATCCATTCGTTCCCTGGTCCCTGGTCTAGGTGTGGGAGTGA[A/G]TTGGTGGA
GCAATTTACGGATCCGTACCCGAGCTCTGATCGACGAGCGGAC C370290_m_421
    TGGTGTTCCAGGTGACGAGGTTCGGGCTGACGCCATGCTCTCGCATGATT[T/C]GAAGGATC
TGCTCGGCCAGCAGGCGGTCGCGGCCGTTCATCAAACCCCGCA C370362_m_885
    ATGGGTGCGTCTAGCAGGACAAGCCAGACGTATATCCTCAAGGGTGACTA[A/G]CCGGGAAA
ACCCCTCCAATGTCAGTAAAAGACGACTGCTTTTCTCGAACTG C370774_m_7352
    TGTTGTTGTGTGTTGTGTGCGGGCGAGGAGGGGCAGTTTTCCATACCTAT[T/C]GTGTGACC
CCGCTGCTCCATGTAGTCAAAGAAGGCCTTGCGCACCCGCGCA C370830_m_6184
    CCGTCTACGGAGACTCCCGTGAGAAGAAAAGTTACCAGGCTGTTGCACAC[G/C]CCCCGACA
CTAGAGGCGTCATCTTCTTCTTGTCCCCACCGCCTGGCACCAC C371228_m_6920
    ACGAGCTCTAGAAGTACTTCTTGCGCATTGCTGTTGCCGCTGAGTCGACT[T/G]CTATTGATG
AAGGGGAATTCGGATACCTGATCTATCGAGGGTAGGCGCACA C371274_m_9715
    AGAGCTCAATGACTGCCACGCCAGAGTACATGGCCCCCAGGCCCAATATC[G/A]CCAGGCC
CGGGCAAGCGCAACAAGACTCTGAGGAATACATACTGCAATAAG C371494_m_5533
    TCCCCCACTACATCACGTGTAAGGAAAGGGGCTGGGCGCTGGCATGTATT[C/A]GGGCACAC
TCCAGGCCACCCTGCTCAGGTCCATCTGCTTACTGTTGGTTGG

Figure 6 Continued

C371548_m_10171
CACTGCACTGCACTGCACGTAGCACCCATCTCGTTCAAATCTAGGTCCAA[C/G]GGAAGCGT
CCCTTTTTTTCAAAGAGAAGAAGGAATGCTGAGACATCGGGAC

C371558_m_7272
GCAAGACTGCAAGACTGCAAGATTGCACTGCGACAACACCCAGGTTGGTA[C/T]CACCAAAC
ACCCCCAAACACCCCCAAACACCCCAGGCAGCCACCCGGACGT

C371668_m_4548
CGCCGCAGGAGCCGCAGGAGCCACAGGAGCCACAGGGACTACGGGAGCCA[T/C]TGATGG
AATCCACGGCCAACTCCAGCGTCACGGCGGCCAATCACATCTGCA

C371926_m_13193
GATACTTGTTACTTATCACAAAGAAGAGATTAAAAATCTAGTTAATTCTA[G/A]CGCATTTCTTA
ACTATAGCCCTAGAGGACAATAACTTAACCGCGGTCTCTA

C372064_m_4214
GCATATTAACTCATGGCTGCTCATAGGTCGATTTGATTGAATGTATGGTT[T/C]TCTCTCACCG
TGAGAACAATCCACCCCTCTCGTGGAAGAGTCAATGTTTTT

C372142_m_2442
CCTTCCTTATGCCTCCTAATAAACTCATCTTTGATAGGAAAAGTGTGGAG[T/C]GGAACCACC
AGCTATATGTATAGACATGTATCAGCTGCCTGCAAAAGACCT

C372160_m_5782
GGAAGATGCCATGAAGAACGAACTCGGAACTATTTTAACTGGCCTCCAGG[A/G]CAGGCTCC
TTGCTCAGGTACCGGCGTACATGATCCCGTCCGCTTACATTCC

C372206_m_23391
AGCAGCCTCCTCTGCTTGGTCTACGGCCACGGCCACGGCCACCCGACGC[T/C]CACAGAT
TTTGCAGGCTCCGCCTCGTCCATGGCGTCAGTTGCTGGGAAGTC scaffold10_m_1124
AACTTTATTTTCTAATATCTTTAGTATATTAACTTATAAATTATAACTAC[T/C]TTATATTAACTTT
ATTACTTAGCTATTACTTATAGTTATTAATAATTTCTC scaffold1004_m_2494
TATAAGGGGTTAATGGGAAGAAAATCACCTAGGGAAAGGGCCTATGTGAT[G/A]ATCTAGGC
TTTGCCTAGAGCTAGCAATATAGGTGTTAATTGCATAAGTTAC scaffold1015_m_9809
ATTCTAGAAATAACGATAAATCTTCGCCTTTCCTCTATTTATCTTTATTA[C/T]ACCTAACCTTA
GTCGTGGCAATTTGCCACTAGCTATAATAACAATAGCGCT scaffold1042_m_1357
CGTGCCTAAATAATAATAAGCAATTATTAAAGCTATCTATAAGGAACTTA[G/A]CTATAAAGGA
GTTAAAGTGGTTTTTTAAGTAATAAAGTAATAATACTAGTG scaffold1044_m_525
CCTAGCCGATCTAAATCCTATTATACTAGGACTAGGTATATAATAAAGGT[G/A]TCCTTTAGCT
TATTAAAGGCATTATTCTGTTTAAGTCCTTATTAGAAAGGG scaffold1048_m_914
CTTTTATAGTTACTCTTACTATACTAATATCCTATTTTATTAGTAAGTAC[C/T]TTATAAAAGGAA
ACTCTAATAATAAATAGTATACTATACTTAAATTAGTCT scaffold1092_m_3126
CCTGAGCACTGGCGCTCTACTATGGACTACGCCGGACACGAGTCCAGGGA[G/A]ACCGAGA
CCCAGCAGCGGCTCAAACGGGACTTTGAGGATCCCAATGGATGGC scaffold1093_m_539
ATTAAACTTCTCTTATTATTTTAGAAGAAAACATAGCTAATTTTATTAAG[G/A]ACTTTAAGGTA
AAGATAAAAGCAATAGGTATTCCTAAGGCAAATTAGCGTA scaffold110_m_1461
ATTATAATACTTATTTAAATAGTAAGTAAGGTAAATTCAGTACTTAACTA[C/A]TAAGTCAGATA
TAGTACTTATACTAATTTAGCCTAAATAAAAGTCTCTTTT scaffold1104_m_1604
TTATAGTTTCTAGAGTTTTTCTAGCTAAGTAATTTACTTTATTATTACTA[C/T]AGCTTTAATAGT
AAGGGTTAAGGGTTTGAATCTAAGTATAGTCTTTATAAA scaffold1106_m_994
GAAGATATAATAGATAATATTACCTAGTAAGGAAAGAAGTAATAAGTGCC[T/C]TATAAAAGGC
TTATAATAAGTCTAGGTATTTTAAAGCAAACCTAACCTAGT scaffold1111_m_204
CTAGAATAGTATTATATACCTAGTTACTTACTACTTTACTAGCCTTATAT[T/C]CTTATAAAAAAA
CTATATAATTTATAATAAAAAACTATTAGCTATTATCTT

Figure 6 Continued scaffold1113_m_662
TCTTATTAATAAGTTCTTTAAGATCCTTTAATAGTATTATTAATATACTC[C/T]TAAAAAGTTACT
AATATATTAAATAGTTTAAATAGTATTATAAGATATTTA
scaffold1120_m_946
TTAGCTTAATTACTATATTATTAGTAATTAGGTTAAGATAGCTTCCTTTC[T/C]CTTATTATTATG
CCCTTATATAATAAGGTATAATTTCTTATATAGTGATTT
scaffold1121_m_1159
AGGCACTTAAGCTTACTCTTTTTAGGGTTTTAAGTAATAATATTCTTAAG[A/G]GTAATATTACT
TTACTTATAGTAATAATTATAAGAGAGGTTCTTACTAGTA
scaffold1122_m_691
GTAGTTCCTAGGCATTAAAATCATTAGGAATCGTAATACTAAAGAGATAT[A/G]GTTATTATAG
GAATTATATATTTAAAAGATAGCTTAGAAGTTTATGCCTAA
scaffold1124_m_789
AAGAATATATAGCTAAATTAGCTATAATATAAGTAATTTACTAAAGAGTA[A/G]TTAAGCCCTCC
TAGGAGTAAAAATTCTCTTTAACCTAAGTATATATATTAG
scaffold1130_m_2651
TAGTTATAGAATTTATATTTTATTAGTTATTAGTATTATAAGGATTAAAA[A/G]AATGCTAGTTAT
ATAAAAGCTTTTATTATTACCTATTTTATTTAATTAGTT
scaffold114_m_222
AGATTTATATTATAAGTAGTATCCCTCCTAATAGCATTTAGCTAACTTTA[C/T]TTCTAATACCT
ATTTAGCTTATTATATATTTATAGTAAGCTTTAGACTCTT
scaffold1141_m_9497
TCGCTCGGCGGCTGGCTGGCTGATCATGGCCCTCTTCTTTTTTTTTTTTT[C/T]TTTTTTTTTTT
TTTTTGGTTGTAACAGTTCCATTTTGCCGCGTCGCGGACC
scaffold1143_m_625
TTATTATAATTTAGTTATTTAGTTATAAATTCTTAAAGTTTAAGATTATT[T/A]AGATTATTAAGCT
AAGTATAGGTATATAGAAGCTAAATATAGTATATTTTA
scaffold1147_m_207
TTTATTTAGTTTATTATAGCTAACTTATATCTATTATAGCTAACTTATAG[C/A]TAGTTTACTATA
TCTAAGTCTTATATTAGAACTTTACCTTTATTACTACCT
scaffold1149_m_1266
AGGTATAAAATCCTATATAATAGCACTGTTAGTAGTATATAGAATCTCTT[C/T]TAGATATAAAA
TCCTATATAATAGCACTCCTATATTAACTTTCTTTAAGTT
scaffold1156_m_5691
CCTTCTAGGTCTCTTACAAAGTGCAAAATGCATATAACCGGACGCGCTAG[T/C]TATTTTCATT
AGCTAAGATCCATACAAATTCATGGAATTTTATCTAAATTA
scaffold1161_m_1033
ACGGTTAGGGACTAGTAGAACTACCACATTGAATATTTATTTAACGTGAC[G/A]TAACGGAAG
GTTTTAGCAGTTATTAACTAATAGAATTTAATCTAGATGACT
scaffold1170_m_3687
ACATTCGCCGTGACGGCAACGTTTTCTACTCTTTACCATTACTAGATGAT[G/A]GGTCCAGCA
AAAAAAACTAAGCATGCTCATGCTATACTAGATTTGGCTAAT
scaffold1172_m_1853
TTATTTTCTTAGTTTATGTGGCTATTCCCCTATAGGTTAACTAGTGCTA[T/C]AAAGGTAGTAA
ACTATCTATAGGCTTAGATAAATAGGTTATTGCTTACTCT
scaffold1173_m_8668
CTAAATGATGAGAAAGCAGACACAGATGGCGTCAACTTCGACACGATGGA[C/T]GATGACGA
TGATGAAGATGATGACAATGACGACGAAGCATTGACAAATCTT
scaffold1180_m_4421
ATAAGGGTTCTATTAACTAATTTTCTATTAATCCTAATAATAACCTTAGT[G/T]AATAAAAAGTTA
TACTTTTTTTTACCTAACAATACATTTGTATTGTTTATA
scaffold1189_m_1202
CTTAAGGTATAGGATAATACCTACTAAATTACTAAGGGTTAGTAAGACTA[T/C]ATATTCCTAAT
AGACCTAAGTATAACATTATAGGCTAAAGCTAGGTAATTA
scaffold1190_m_2601
ATACTTATTTTCCTATAGTATTAAGTACTTAAAATAGTCTAATAAATCTA[A/G]GGGTTAGCTTT
TATTTTATATTCTTAAGCCTAATATTCTTTACTAATAGTA
scaffold1191_m_952
AATCTAAGGTATATAGCTAGAAAACCACACTAAGGGCTTAACCTAGAAAT[A/G]AATAAAAGG
GAGCTTATAAAGTTACTTACTCCTATATTCACTCTAGGCTAT

Figure 6 Continued scaffold1198_m_941
AGGCATTAAAGCTTAGAGAAGTATAGTAAACTACTTATATATTAGAGAAG[C/T]GTAGTAAATT
ACTTATATATCTCTTTATATATTATAGTTAGTTTACTAATA
scaffold1199_m_1163
TAACTAAAACGTATAGCTTTTTCTATAGTAATTTACTTATACTTACTTAT[G/A]TTTATATTTAAG
CTATTTATTTATTATTTAATTTTAATTAAACTTTAACAC
scaffold1204_m_5834
GTATAATAAGGTAATAATACAAAATATACTAATTTGTTAAGGTATAGAAG[T/C]ATTTAGTAAGA
GCTTTATAATATATAAGATTTTATTAATAGTTAACTTATT
scaffold123_m_401
AGTATAATTAGGGATTTAAGCTATAGCTACTATAGTAAGATAGTAATTTA[T/C]ATAGTCTTAGG
CTAGTTTATCTCTAGGATGTCTAGAGAAAGTTATTTTACT
scaffold1232_m_548
TTCTATAAAAAGGATTTTCAGTACGAATAGAAGACTTCCCTTCTATAAAA[T/C]TGGAAGCGCA
CGAGTAATATAGAAGCATTCCCTTTTATAAAAAGGAAGTTT
scaffold1235_m_1011
AGCTACCCCTATAGGAAGCTATAAAGCTAATTACCTTAAGGTAGTAAAAG[T/C]AAAGGTAATT
AAGGCCTAGGCTTATAATCCTAATATCCTTATACTTATTAA
scaffold1236_m_246
CCTTTAAGCTTAGCAGTCTTAGGGAAGCTAGTCTTAGGGAAGCTATAAAC[T/C]CTCTTATTAA
ATTCCTTAATAATCGAATTATTAAAGGCAGCTTATATAGAG
scaffold1242_m_365
AGCCGGCCCCTATCTTCTATTAGATAGACTTTATAAAGTTCCTTTTTAA[T/G]TCTTTAGATAT
AACGTAAATCCGGTCTAATTAGAAGACAATCATCCACATA
scaffold1246_m_909
AATTACTAGGAGAAGATAAATAGGGGCGCGCTACCTCTATTTAGAGTTAT[A/G]CTACTACTA
CTATAGCTATAGTATTATTATTACTAGGTAATAGTTATAGTA
scaffold1248_m_2117
TTTTAGTTAGATTAATACCCGTTAGATAATTCTAGCCTTAAGGTTATTATT[A/G]ATTATTGTAGTT
ATAATGTATTCCTTAGTAGTAAAATATACGCTTATATCT
scaffold1249_m_1860
TGGCTAGAGTTAGTGTTTAATTAACTACGCACTAAATTACTAAGGGTTAG[T/C]AAGACTATAT
ATTCCTAATAGACCTAGGTATAATATTATAGGCTAAAGCTA
scaffold125_m_2468
AATAGTATAAGGGGTTTTCTAATATACTAAGACTAGGTAGTTATTCCCTA[A/G]AAGCTTATCT
TATAATAAGAGCTTTTATAGCTATACTATAATAATTTACTA
scaffold1260_m_36299
TGGATGGATGCATGGGTGCGCGGCCTTTTTTTTTTTTTTTTTTTTTTC[A/C]CCGGGCTAGG
CACGATATTGGCGTTGGCTGTTTGTATTCATGCTTTTTGGA
scaffold128_m_67766
GGATCCTGGTCATTTCCATGTCTGGGGTTCTTCAACTACCTACCTCTATG[A/G]ACCTGGCTA
TTAGCCCATGGACCTGGACATTAACCCATGACCGTTTTGGTG
scaffold1282_m_507
TGGTAGTTATTAACTAATAGAATTTAATTTAGATAACTTTTACAATATCT[T/C]ATATACTAATAG
AATTGATTTTAGTGACGTTATACGGGCAATGCAGCTGTT
scaffold1285_m_1278
TAGGTAAGGGTAAAGTAAAGGTAACTAAAGGTATAATAATAATTTATAAA[A/T]AACTTATTTAG
TGTTATAAAAGAGAAAGTATATAATATAATAGGGAGTTA
scaffold1294_m_12186
ATTTCTTAACTAGTCGCTGAAGAGTATTTCGCGTCTGACTAATCAGAAGA[G/A]ACATCTCTAT
AGGATGGCCTTATTTTAATAAAGGGAAAGCGGGAAGCTTCG
scaffold1327_m_1224
ATATTATAATTTAGTATTAGTTATTTTCCTTAATATAAATATAACTAGGT[G/A]CTAGTAACCTAG
GACTAATATTATAAGTATAGCCTTAATTATATATCTAGA
scaffold1344_m_3680
GTAAAATAAAAACCTATCCCTATAAGTAACCTATATAATAGTAATAAGGC[C/T]TTATTTACTAT
ATAAAAGTTTTTAATAGAATATAAACTATAGGTAAATAAG
scaffold1346_m_4930
TCTATAATAACTATAAGGTATTATAGCCTCTTTAGAGATATTACTAGTAA[G/C]TTTATTATAAA
GTCTATAGAAATCTAAGACTAGAACTAGTTAGGGATAAGT

Figure 6 Continued scaffold1349_m_1292
    ATATTAAATAGGCTCTTACTACTAGTGTCTTAAACTATTATTTACCTTAA[C/A]GTAAGGAGTTA
TATTCTCCTTATTAGTAGTATTATATTACCTATATATAGT scaffold1350_m_1080
    TACTTTTAGAAGAAACTATATAACTAGGAAAGGAAACTAAAGATAGTAAA[C/T]ATTATTAAACT
TACTTTTAAAGCTTATTTTTAAATACCTTTAATATTAATA scaffold1356_m_1213
    TAATATAACTAAAGAAAAAAGGGTATTATAATACTAGACCTTAAATTAAA[T/C]CTATAATTACC
CCTTAATCTAGACTTATAATTACCTCTTAAATATTAGCTA scaffold1357_m_107
    AATCTTACTTTACTTATATTATTTACTCCTTTCCTTATCCTTCTATAATT[T/C]TAATAATTTCTAT
ATTAACTCTTTCTCTATACTAATATAAAGTAAGTTTGC scaffold1362_m_1213
    GTTTATTACTATTATTAGATAAATAGAAAAGCCCTTAGCTAGTTTAAGTT[C/T]TTCTTTAAAGA
TAACTATAACTTTAACTATAAGATTATTATTAATATTATA scaffold1371_m_2716
    ATTAACCTAAAGTTTAGCTAGTTAAAGTAATGATTTTTATAAGAATTTAG[C/T]GTAGCTACTAG
AGAAGTCCCTAGAAGAAGATATAGTAATGTATTTTATAGG scaffold1384_m_722
    CTAGTATTCTCTAATTATATCCTAAATATTATAAGCTTTCTATTTCTTAG[A/G]GTTAAGGAATTA
AGCTACTTAAAATAAGGTTACTATTGAAATGTAGGGAGC scaffold1387_m_193
    ACCTATTAGGGACTAAATTCCTTGCTATAATCTATAGGGGAGACCCTAAA[A/G]GTATAGCTA
GCAAAAGCTTAATAGGTTATTGTGACAGTGATTTTATAGGGG scaffold139_m_1233
    AGTAATATTATTACTTTATAAGCACTTTAATTATTATCTTTTTTTTCCTT[T/C]AATAATATTACTA
ATAGTATTCTTAAAGCTTAGACTACTATTATATAGGCT scaffold1392_m_1294
    TTATATATGCTATTATAGGAGTTATAGAAAATAAGTTTATTACCCTTAAA[A/G]ATAATAAGGTA
AAAGTATATAAAACTATTAAAGATATCCCTAAGAAACTAT scaffold1393_m_147
    TATAAGTAGGTGTTTTTATTACTTAATAAGGAAGGCCTAACTGTTTATAG[G/A]GCTATTAAGG
GCTTCTTTAAAGGGCTTAAAAATTAACTAGGTTAATATCCT scaffold1395_m_4127
    TTTTCCGCAAAATTTATTTATATATAAAATCTAAAAAATTAACTTACTAC[T/C]ATACAAACTAGC
AACCTATATGCACTAAATTTTAGTCTAAAAAATATTCCT scaffold1406_m_50956
    ATAATAAGGTATAATAAATACTACTTAATCCTAATTTAAGTAAAGGTATA[T/A]ATAATATAACTA
AAGAAAAAAGGGTATTATAATAATACTATAAGGTTATAT scaffold1416_m_526
    TTTTACTAGTAAAAGACTTAAATTAGACTTATAATATAATTCTAGTTATT[A/C]TTAACTATTTTA
TAATATATAGTATTTATATTCCTATTTTAATATAACTAA scaffold1428_m_500
    AAGTTATCTATAGTATCTAAAGCCCTAAATTATGAGGCTAAAGTCATCTA[C/T]AGTATCCAAA
GCCCTGAATTATAGGGCTAAAGACCTAGAAAAGGGTACTAA scaffold143_m_185
    ATATAAAAAGCCTAAGTATATATTCTTTACGCTAGGTAGCTAATTATGTA[T/G]CTATTCCTAGT
ACTCCGACTGCTTAGTTAAGAGGGAAAACCCTTAACTAGG scaffold1433_m_421
    TATTATTATAAGTTACCTATAAGAATAGGTTTATATTTTACCTTAGGT[A/C]TAGTTAAGACT
AGGTTAAAGGTAAGAGATAAAGTAAGGTTAATTACTAATA scaffold1438_m_1202
    TCTATTAGTTAATAACTACTATATCCTTCCGTTACGTTACGTTAGTTATT[C/T]TAACGTGGTGG
TTCTACTAGTCCCTAACTGTAGAGCTGCACCTGTACAGCT scaffold1448_m_1162
    GCACTAAAGAGTATTATATCTAATAAGGGATTAGTCTTTATAAGCTAATT[T/C]TAGTTAAACTT
ATATTACTTATTATATATAAAGTAAAGGCTTTTTATAGTG scaffold1454_m_1432
    CCTTAAAGAATAAAAATCACTATATAAATATTATAATTAGAGGTTTAGTG[A/G]AAGAAACTAG
GGATAGGAATTGGTATTTACGTAGTTAGTAATATAAGTAAA

Figure 6 Continued scaffold1455_m_269
　　　　AATAAGAAACTAATATAATCCTAGTAATTAATATAGCTAAACTAGTAAAG[C/G]TATTTTATAAA
GAGATTAAGCTATAATTTAAAGCCCTAAAAGGCATTATAT
scaffold1456_m_14569
　　　　GAACATGATGAGGGTTAAGAAGCTTATGTAAATGGGGGATTGGGATTGGG[C/A]TTGGGATC
ATCATGTCTTAAAGCGAAGACATACCATGTAAAAATATACTGA
scaffold1460_m_1028
　　　　AGTAATAGAAAATAAGAAGGTAATAAATAGAAAATTAATTTTAGAAAGGT[T/A]AAATATATTAT
TTAATATAATAATTCTAGAGGACTTATTAAGGGATATATA
scaffold147_m_691
　　　　TTATTTAGCTTTATAAATAGCAAGACTAACTATAGCTTTAGCTAATAAAT[A/C]AAGACTATATA
TAAATACCTTATTAGATTAATAAGCTTATAAAAAATTCAA
scaffold1490_m_431
　　　　CTTATATTACTCTTTTTAAGAATTATTAATAGATTTTATTACTAGACTTT[C/T]ACTAGTAAAAGA
CTTAAATTAAACCTATAATATAATTCTAGTTATTATTAA
scaffold1500_m_2057
　　　　GCCTAGGGCGTTCTAAGCCACTAGGATTTGCTTAACCTAATATTCCTTAA[T/C]AAGTTTATTA
TTACCTTCTATAGGGACCTATTCTAGTCCTAGATAGGAGTC
scaffold1501_m_1207
　　　　AGTGTGTACTATATAGGTAATTAAGGAGGTATTCTCCTATACTCTCTTTC[T/C]CTTTCTTTTTA
TTTTTACTATAGTGTACTATATAGGTAATTAAGGAGGTGT
scaffold1503_m_18812
　　　　TAGTGTAAGATATATATCTTTAGATTATTAATATTAATCTTTTAACCTTA[T/G]CCTTTATCTAGA
GGTTTAATCTTATATAATACTAATAATAACTTTCTCTTA
scaffold1507_m_43317
　　　　GGTTCCGACCGAACATCTCTCGGGTGTGTACTACGTGCATGGCCTGGGGG[A/T]CCAAAGAC
CACACGAGATTGCCATGTGGCCTGGCATATATGAAGTGGTGCT
scaffold1508_m_1723
　　　　CCCGGCGTACAGGGTAGCCTGCTTACCTAATTACTAGTGCCGCGGTTATGG[T/C]TACGCTTG
CAGCTACAATGCAATTGACTAATCCACAATTAATTGGAATTAG
scaffold1510_m_1479
　　　　AACCCTTTGCACTAGTGTAATATTCCTTAGTGTAACTAATACTAATTAGT[A/G]GTTAAATATAA
CTATAAATAAGCTAGGTATTATAAGAAAAGACATTTCTAT
scaffold152_m_1051
　　　　ATTCTCTAGCGTTTTCTATTTAATCCTAGCTAGTTATATTAAACTATAAG[A/G]GTATCTCTTCC
TTAGACTTCTTTTAAGATTATAATATAGTTAGTATCTTAA
scaffold1520_m_9944
　　　　TTTAGCTGCTTTTAGGTGCTCTATATAGGGCCTAGCTAGTGCTATAGGGC[T/C]TAGCTAGTG
CTATAAATAGCCACTAAAGTGTAAAGGCTATGTCTAGCCTTA
scaffold153_m_802
　　　　TTAGAGCAAAAGATCTAGTATATACTTATTATAGTTAATTATTTTTCTTA[G/A]TTTATATAGCTA
TTTCCCTATAGGTTAACTAGTACTATAAAGGTAGTAAAC
scaffold1547_m_5107
　　　　GTTTATAAATACTAAATATAATTATAGTATAGTAAATTAAAAGCTACTTA[T/C]TATAGTAAAGTT
ATTTAAATACTAGTAATACTATATTAAAGATATAGTAAC
scaffold1550_m_29509
　　　　ATAATGGCCGCCAATCGGCACACTGGAGAGCTCAGGCCAGCGGGCTAAAT[A/G]GAATATGT
GGGCTAGGCAGGGGGGGTGGTGGCAGGGGGGTGGTGGCAGCA
scaffold1553_m_371
　　　　CTAAGTATCTCCTCTAAAGGTAATATAACTTAGCTTATATAACCTTATAG[T/C]GTTATTATAAT
GCCCTTTTTCTTTAGTTATATTATCTATATCTTTACCTA
scaffold1557_m_822
　　　　CTAGAGCTAGCTAGCCTTTAGCTAGAAATAATATTCCTTATCTTACTAGG[A/G]TTACTATTTTT
ACTTACTATTCTCTTACTAGTACTTTTATTATACCCTTAC
scaffold1577_m_445
　　　　TTTATAAAATACACTTATAATAACCTAAGGTATTAGTTAAAGAGAAAGAG[C/T]ACTAAAACTAA
GGCTAGTAACTAAATTAAGGAATTAGTATATTAATAGAAC
scaffold159_m_6030
　　　　ATACTAGTTTAATTAGTATAGACTTAGGAATATAATCTTACTATAAAGTA[A/C]CTTATAGATAA
TAAAATAAGAATATAAGTATCTTTATAATAAGATAACTAG

Figure 6 Continued scaffold1592_m_1136
TAAAGATATTATAAAGAAAATAAGATATTATAGAGAAAATAGAAAATAAG[G/A]ATAAGAATAGT
AATAAATCTAATAAGGAAAAGAATAAGCTTAACCTAAAGA
scaffold1598_m_1686
TAAGGTTTAATATTAGGATGAACTTTAAACTTATAATTAAAGTTAAGGAG[C/T]GTAAAGATAAA
GTTATATTTATTAAGGGACTTTTAGTAGCTTTATCTAATT
scaffold1606_m_321
AATAGTAAAGTTAGGGATAAAAGATAATATTATAACTATAATAGCCTAGA[C/T]TACCTTATAAA
TAAGTGTAGTAAGCGTATAAAGATATTAAAATAGTAGTAA
scaffold1613_m_487
TATATTACATCCTTCTAATGTTCCCTCTTTCTAATATATATATTATATCT[A/G]AGTTTTGCTTAT
CTTATATTTAGAGCTTATTTCTTCTTTATCTAGTAATAT
scaffold1622_m_13087
TATAGCTTAAAGAAAAACCTTCTTATTATATTATTTACTATTTTTATTAA[T/C]TATTTTGTATTTC
TATAAATTATTATTATTACTTATTTAAAAAAAACACTA
scaffold1623_m_206
TATAGTGTAAAAAGGCAGTGAATTACTATTGCCTAGGCTATATAGCCTA[A/G]GTTAGCTAG
CTAAAGCTAAAGAACTATATATACCTCCTAGATAGCTATAGC
scaffold1625_m_3085
TAACATAGCCTTATAATTATTATCTATTATTTTGCAGTCCTTATATAGTC[T/C]TTAAGTGTAATA
TTAGACTAATTAAACTAAGAAACTATAGTTTTAGACGCT
scaffold1628_m_761
TAAAGCTTCTCTTACTAGCTACCTAAGAGTAATATAGGGGGGAGAATTAC[C/T]TAATTTACTA
GAGTAATATTAGTAAGGGTAACACTATAGGTATAAATATGC
scaffold1638_m_2464
TTACTTTAGAGAAGACTTTATAAAAGACTTTATAGGTATAAGCTAAATAA[A/G]GGTAAAAAACT
AAGATAAATAAGGATAAATAATAATAATAATTAGGGACTA
scaffold164_m_34046
AAAGTGTTGGTTGTAGCAGCGTCACATCTTAGGCATCACTATCGCGATGT[C/A]TTCCCTCTT
CGAGGCCTTGTTGCGAGACCTCGGCACTTAGGGCAAAGACTC
scaffold1640_m_3271
TTAAGCATTTAAACCTATGCCTTAAATAAGTCTTATCTAGAAGTAATTAC[A/G]TCCTAATTAAT
TAGTGTCTAGGTTAGGAATTTTACTTCTAGTAGTAAAATT
scaffold1642_m_2592
ATCCTTCTATCCTAATAGTTACTAAATTACTTATAATAAACCTCTTAAAT[G/C]CCTTATTTAGTA
ATACCTTTGTAAATATATTTGCAAGGTTATTATCCCTAT
scaffold1650_m_52505
CACGATCCCGCCGCCGCCCACAAGTATGCCACCCTGCTAAGCCAATTGTC[A/G]GAGAAGCT
GTCCAAAGATTTGTGCATCATCATGCGCGCCTACCTCGAAAAG
scaffold1669_m_5977
GATAAGGAGGGCTAATATATAGAGGCCTATCTCCTTACTAAATATTATTA[A/G]GAAAATTATA
AAAGCAGTGATTATAAATAACTTATAGCCTTTACTAAGGT
scaffold167_m_1972
AAGCTTAAGCTAAGGTAAAAGCTAAGTTACTTAAAGAAATCCTTATATAT[T/C]TAAGAATTACT
ATCTTTTTAATAGCTTAAATAATACTATAAGAAAGTAAAT
scaffold1674_m_483
GGAAAGGGGATTAGCATACTAAACCCCTTAACTAGCTAATAGGGTTATAT[C/T]TAGAGGACT
TATAATTAGGACTCTTAGGGAACTTACTAAATCTAGAGGAAT
scaffold168_m_14508
TCGTCCTGGCGCTGCTGCTTACTGTCTTCTTATTCGCACTTGATATGGTA[C/A]CGGATTCCA
TCCACGAAAGCGTCAGGAAGATAAACCATGCTGATGCTTATT
scaffold1684_m_1117
ATTAATAACTTAATCTTTATAAGTATTAAATTTAATATCTTTAAATAAGC[G/A]CTATAGACTTAT
AGTCTCCTTTACTACCTATTATAAAGTAAGTAATTTAGC
scaffold1686_m_1489
TACCAATAGAATTGATTTTAGTGACGTTGTACAGGCAATGCGGTACCGAC[T/C]GTATTGGTG
GATCCAGACCGCTAAAGAGGTCTTATAGGCTACTTTTTATTT
scaffold1689_m_306
CCTAGGGCTAGGTTTACGTGACACTAGTAAGCCGCTAGCTATAAGATAGT[G/A]ACTTATATG
TATAATATATTTAGACTTAGTAAGCTTTAGTTAATATACTAA

Figure 6 Continued scaffold1690_m_639
    TCTAGGGATAGTGCTAGCTGCTAACTTCTAGGCTTTAGGTTATTTTTCTA[A/G]GGGGATTAGA
ATCTTATAGTGAGATCCTATGGCTCTAATACTGCTAATATT
scaffold1695_m_1048
    GACCCCTAATAAGGGGGTAGGCTATTAGCTCTAGCCTTATTAAAAAGGTC[T/C]GTGAAGTTA
GCTAACTCCTTAGGTAATATTAACGTGTCTAGGCTATTAGGC
scaffold1696_m_214
    TTTAACTATTATACTATTATAGAAAGCTACTACTACTATTTTTACCTAGC[T/C]CTTTACTCTTCT
TATTGCTCTATATTCTATTAGATTAATAGTAATCTAATA
scaffold1705_m_262
    ATTATTACTTTATATGTAACTACCTATATATACTACCTTAGTTATATTAT[C/T]CTTAAAGGTATA
GTAGTTTAATTTAAATAATATATTTAAGTTTACTAAGAA
scaffold1709_m_13556
    TCTCGTCGTGTGAAATTCAAGATGCTCCCGACTTCCGTGTTCTGGGGACT[T/A]GCCATCTTT
TATAAGTCCATCGATGAATAATTTATTAATCAATCAATCGGC
scaffold1711_m_3305
    TAACTTTATATCTAGATATTCGATCTTAGCTAAACCCTCTAAAACCTATT[G/A]CCTAGCTATAT
AAGGCAGGGTTATAAGTAGTGGTTATAGCGCCTTAATTAT
scaffold1718_m_1223
    TAAGTAATCTAAGGTATATAGCTAGAAAACCACACTATAAGCTTAACCTA[G/A]AAATAAATAA
AAGGGAGCTTATAAAGTTACTTACTCTTATATTTACTTTAG
scaffold1719_m_1178
    ATCTCTAATACTTTATAGCTAATAACTAATAAATATAGCTTAAGTTACTT[C/T]TAATAGCTTAAT
TTACTTATAATAATATAGTAAATAAGACTATAAGCTACT
scaffold1721_m_2286
    GAGTTAGCTAACTTCGCGGACCTTTTTAATAAGGCTAGAGCTAATAGCCT[A/T]CCCCCTTATT
AGGGATCCCTTAATTACCACATACACTTGCGTAAGAATTAG
scaffold173_m_1905
    AACGGGCGCAGTGACTTTGGTGAGGGGCGGGCTCCCAACGTTGGCCGCAG[T/C]GATCCAA
TCAAAACCAGCTGCGGTTGGGCAACGCCTTCCCTTTGGCGCAAG
scaffold1752_m_978
    AATACTCTTATAGAAAAGCCTAGCCTTATTAGCTACTATTATACTTTAA[T/C]TAATAGTCTAG
GAATTACTACTAAAAAATAAAAGAAAAAAGCCCTAAAGGT
scaffold1757_m_2409
    TATAAAGGGATTATTAATTTAATAATAAACCTCTCTAAGGTTTATAAGAA[G/A]GTTACTTAATA
GGTAAATATTTTATAAGAGTTAAATATAGAATATATATAC
scaffold1763_m_179
    AATAAAGGCATTCTTTAGCTTATTAAAGATATTATTCTCTTTAGGTTCTT[A/G]TTAAAAAGAGG
TATTTCTCTTAGTTAATTATATTAGTAATGCTACTAGCTC
scaffold1767_m_2368
    TCGCTAACTTCTAGTAAAACTTTAACTTAGCTACTAAGGCTATGTAACTA[A/G]AGAGCTTAAT
ATTAACTAAAACTTTATTAATATTAATTAAATAACTAGAGA
scaffold1768_m_9765
    TTAAATTATTATGCTAACTTAAATATAATTATAAGCTACCCTAACTATAC[T/C]TAATATTATTTA
GTACTAGGGAAGTAATACTAATAAGGTCTATACTTTATT
scaffold1776_m_728
    TAATTACTTTAAAAGCTAAGAATAAAGATATATATATATTAATTACTATA[A/G]ACTATATAATAA
GGTTTATATTAAGATAATCCTATATAAAGGTAACTAGAG
scaffold1781_m_579
    CCTAATCCTTAGGAGTAGCCTTTAGCTTATAAAGCTTTAAATAAATTATA[A/G]GATTCCTATTA
CTTTAAGGTATCTTTAATATTATAACTAGAGTATCTAGGG
scaffold179_m_1283
    TATTAAGTTCTATAGTTATTAGATTAATCATTTAATTATTTAGTTATTTA[A/G]TTATTTAGTTATT
TAGTTATTTAGTTATTTAGTTATTTAGTTATTTAGTTA
scaffold180_m_1258
    TAATATTATATATATATATTCTTTACACTAGATAGCTAATTATGTAGCTA[A/G]TCCTAGTACTC
CATCCGCTTAGTCAAGAGGGAAAACCCTATATAATAATAT
scaffold1805_m_602
    GCTAGAATATTATAATATAATGGATACTATAGCTAGAATATTATAATATA[G/A]TTATTTATATAG
TAAAACAGTAATTAGTTATTAAAGTAGTAAAGGGCTTAT

Figure 6 Continued scaffold1807_m_2089
TACTTTAAGATAAAAAACCTTATTTTAACTTTACTACTTTATTATGTAAT[T/C]TAATTACTAAGT
AAGTTAAATTTAGCTTACTATATAAATAACTTAGCTATA
scaffold1818_m_11723
ACTAATTCTTATAGTTCTAATACTATAATAGTCTTTAGGTTTATTTATAG[A/G]ACTTATATTCTA
GTTTATTAATATACTAGATATAAGTAATAATAAGATTTT
scaffold182_m_1170
ATATATATAAAAGGGTCTAGTAGCTTTAATCTATCCTATTAAATCTAGCT[A/G]TTTACTATTAA
CTTTTTTCCTTTATTATTACTATTCTATAGGCAGATTAAG
scaffold1827_m_22598
CTATAATATAAATTATCTACTTATTATTATACTAGATAATTAATAGAGAA[G/A]GGACCTATATG
CTAATATTATAAAGTAATTTACCTAGAGATATACGCTCTT
scaffold1830_m_942
AAGTAGCCTAATTCCTTAACCTTAAGAAGTAAAAAGCTTATAATATTTAG[C/A]ATATAATTAAA
GAGTGCTAGATTAATATATATCTAGGCCCTCTAGACTAGA
scaffold1832_m_1076
GCTATAGCTATATAGGGGTAAAGCTACCCTAGGAATATATCTTTAGAAAA[G/T]GAACTTATTA
AGGCTAATCTTTCCTATATATAGTTATATTATTATAAAAGA
scaffold1833_m_1450
TAGGAAGGGGCCTAGAGGTTTCCTATTAAGACACTTATAAGAGAATAGGT[A/G]GTAAATTAC
TCTATAAGGCACTTATAAGAGAGTAAGTAGTAAATTGTTCTA
scaffold1834_m_8109
GGAAACTTAAGGGTAAATATAAGAGGGAAAGCATAGAAGTAAACTCTAGG[T/A]GTAGCTTTA
GTATAAGGGGTAGGCTAGTTTATCTTACTAACCCCTTCCACT
scaffold1835_m_555
GAGTTTTAGGTCTTTACCCCCTATATAAAATAATAAATATATTAAGGGAA[T/C]TATTAGCTAGC
TAGGCTTATAGGCTAATACCCTAGGGAGTAATTAGTCTAT
scaffold1839_m_3941
TCGTTATTAATAATATTAGGGATAAACTTCTAAGCTATCTTTTAAATATA[T/C]GATTCCTATAAT
AACTATATCTCTTTAGTATTATGATTCCTAATGATTTTA
scaffold184_m_769
ATACAAAACACCATAGATATAAGGGTAATTTTGCCTACTAGATAGTAGCC[C/T]TTAATTAATC
TAGAATAGTATAAATAGAACGTTTTGCTAATCTATTTTGCT
scaffold1856_m_979
AGTATCATTAGCTATAAAGAATAGTTAGTACTTAATACCTAATAGTATAT[A/T]GTTAGTAACTT
ACCTAGTGGAATTTTAGTTATATTGTAATTTATTACTAGT
scaffold1869_m_396
GGGTACTTACTTTAAGTGTAAAGTTACTAGATATTATACTATAAACTATA[G/C]TATAACTAGAA
ATAATTTATTATAATAATAGGAATCCTTATAGTTAAAATT
scaffold1881_m_438
TAACTATAGTATTTACCTCTTTACCGTTTAACTTCTATAAGTAATAAATTA[T/C]ATATAGTTAGCT
TCTTAATTATTACTATCTCCTTAAGTTTATATAGTCTTA
scaffold1884_m_7608
ACGTGTATGCAAACACTTCCAAAAACGATGCGCAGAATGGAGCTCCTGAT[G/A]TTTGAGGAA
CATCTCGTGGTCTACTAGGGCACTGGGACAATTATTGGCTGT
scaffold1889_m_213
TTGTAAAGGAAACTAGCTATTTTAATAAAAGTTTTAAGACTTAATAAATT[G/A]CTTAGAAAAAT
CATTTTTTAAAAGGCTTTAAGTCTATTATTAGTGTTAATA
scaffold1898_m_586
ATAGCTATAGGGTAACCTGCGTACAGGGTAGCCTGCTTACCTAATTACTA[G/T]TGGCGTGGT
TATGGCTGCGCTTGCAGCCATAACGCAATTGACTAATCCACA
scaffold1899_m_681
CCTAAGGTAATATTTTCCCTTTTTTTAATTTAATAGTATAAGTATAACCT[C/T]TTAGTTTAAAAA
GCTTACTTACTAACTCTTTAGAAAAAATATTTATAAACT
scaffold1903_m_5961
GGGGGATCGAAGTCATGCCGTCGGTTCCCGGTCAGTAACTTGGGGGCCAC[A/T]CGCGCAA
ATGCAATGTAGTGTCCACTTTGAAGCGAGTCGCCTCTATGACAA
scaffold1909_m_1922
TTAAATTCAATACCTATAAAGATTAGGTTATTAATTATAATAATTAATAA[A/G]TAATTTAGCTTA
TACTTAATAAGAGTAAATAATTAAATACTTAACTATATT

Figure 6 Continued scaffold1913_m_906
AACTAGATTAAACTAGGAAAAAACCCCTATTATACACTTATTCTAAGTTA[A/G]AATAAATATCT
TCTGAAGATTCATTAGAAGAATCTTTAGAGATATTCTAGT
scaffold1916_m_1068
ACCTTAATACTAAGGCTCCTATACTAATTTTATATAGGAGTTTTTTATTA[A/G]GTATTCCTAAG
GCCTTAATACTAGATTACATATAAAATATTAAGTTAATAG
scaffold192_m_1317
CTGCTATTAGTGCGGCTGCCCCGTATTTTAAATCCACTCCCTCTGCTGTG[A/G]CTTACCACT
ACATATAACTTTATGGAGTTAAATGTGAATATTAGAAGCATT
scaffold1925_m_787
AGTTTTTTTCTTTTAAATAATTATTTCCTTTACTAAAATGCCTTAATACT[G/A]AACTAATGCCCT
TACTTCTATAGCTTTAGTAGCTACTCCTATAGTTACTCT
scaffold1932_m_2159
ATATTTACTTATAAAGTGTTTAATTATATATATTAACCTTATTATTAAAA[T/C]AAATAAAATCTA
GTATAGCTTTTAGGTTATAGTATAGATTTATATAAGGTT
scaffold1948_m_4673
AATTAGGTTATAATACTTAAGAATTAGGCTTTTTAATATGCCTTACTTAA[G/A]TAAAAGCTATA
CCTTAAAGAGCCTTTTAATAAGGATATTTTAATTTATTAT
scaffold1968_m_10551
CTACTCTGGTGCCAATCTGCTGAACCAGGTCCTTGAGAGCCTGTTGAGCA[A/G]TCTCCTGA
GGACCAGTGGCATCAAACCGAAGGCGGCCATTGGATGCCGTAG
scaffold1971_m_15539
CTATATTCTCTAAATATTATATAAATACTAGTATACACTTATAGATTATT[A/G]TTATAGACTTTG
CATTTGCTATAATTCCTTAACCTTTCTTATCCTTAATAC
scaffold1985_m_298
AATATCTTAGTTTACTTAGGGGAATTAAGGAAAAACTATATAGCTAAGGT[C/T]TAGCTAATATT
AGGCTATCTAAGAGCTATAGGTTTATACTTAGATCTTAAT
scaffold1988_m_411
ATAAAAAGTAACTAATTAATCCTAACTAAGGAGTATAATATTATCTAAAA[G/C]TTTCCTAATTA
ATCTAAACTATAATCTATAATAATTAATTAAGGAAACCCC
scaffold1991_m_662
TATGGCCAAAGTGTAAGTCTACTAAAGGGATACACGTAATGTAATTAGCT[A/G]CATTATAGGT
AACCCTATACTATTTATAGTGGCTTTACACTACTACCTTAC
scaffold1994_m_430
AGCTATATTTAATAATAGCTAGGATTAAAAAGGAGGTCTTTTATCTTTTC[C/T]TGTTTTTCCCT
TTTATCTATTTTTATCTAAAAGTTATTGTTTACCCTATAG
scaffold2005_m_1059
TATAATTAGTTTAAATAAATAAGGTACCTAATACTATAGTTTTAAATAGT[A/C]TAACTAAAGGG
CTTATATTATAGTTACTATAAGTTTATAGCTATTAGGCAT
scaffold2009_m_1941
TATAGATTTATATAATATCTATAAAGCTTATATTTAACTTCTAGTGTAAT[G/A]TTTTTATGTTTT
ACTTAATATGTCTAAGAGTCCGGAGGAAGCCACAGTTTG
scaffold2016_m_647
CTTATTTATTTAAAATCTTTAAAATTACTAATCTAAGACTAGTAATCTTT[G/A]CTAGATTTACTA
CTAATAGTAGTAGGGTTAGCTTTTTCCTTTCCTTTTCCC
scaffold2020_m_1183
ATCTTATAAAAGAGTAATTACTTAACTAAATATTATAATACTAGTAAGAT[A/T]TTCTTAGAGAAA
GACTTTTAATAAGGTAATATTTATAGTAATAAGTAACCT
scaffold2027_m_5360
ACATTGCACATGCCTAGCATATGCTTAGCATATGGCTAGCATTAGCCTAG[T/C]ATATGCTAA
CTATATGTAAAATTTTCTTAAAGATCTTAAATATACATAAAG
scaffold2056_m_2217
ATTTAACTAGTAGCCTCTCCCTAATATTGCGTTTATTTCGAAATAGCGCT[T/C]CTTATCTAGAT
TAAATAAACCTATATAATTTGTCTAATAAGTTTATTATTA
scaffold2059_m_1734
TATAGCTAGCTTCTTACTAGGTTATCTTAGGTTAATATTCTTTATTAATA[C/A]TAAAATATAGTT
ACTAACTTTAAACCTTATTAGAGTTCTCTTCTAGTTATA
scaffold206_m_3874
TAAAGCTTTGGTTAAAGCATTAGTTATAATCTCTCTAATTATAACATTAG[C/T]TATAATCCCTT
TAATTAACGCCTTAGTTGTAATCTCTTTAATTAATGCTTT

Figure 6 Continued scaffold2067_m_464
TATATAAAGAAATATATAAATAGTTTACTACCCTTATTTAAGTGCTTACC[T/C]CTTATTACTATA
GTAAGAACTAGTATTATTATTAAATTACTAAGTTAAGTA
scaffold2089_m_483
AAGTACTTATACTTATTTACTTAACTCTATTTATACGTAAATTTATTCTA[G/A]GAAGGTTAGAC
TTAGTAATTACTATTAAAAGGGCTTTCTTTTATAAGATCC
scaffold2090_m_503
GCGTATATATTAGAATAAAGAGTAATTAAGCTCTCTTAGAAGTAAAGATT[C/T]TCTTTAGCCTA
AGCGTATATATTAGAATTTATATTAATTAAAATATAAGCT
scaffold2095_m_2168
AGACGGTCAGATTAATTGGTCTAACAACGGAAGCTTTCGTTAACGGCAGA[G/A]GCCTTATTA
GAAGACCTTCTGTACGTCAGATTCCCCTTTAAAAGTCGGAAG
scaffold2107_m_237
AAGGTATTAGTAATATTAAACTCCCTATTAGCAAAGGCTATTTAGAACTA[T/C]CTAATACTTAA
TAGGCACTAAAGGCTAAAGTTAATATAATTTTACTAGGCC
scaffold211_m_3532
GATATTAAACGCAATGCAGGAAGCTGCATTATTAATTAAAGAGAGGATAA[C/T]AAGAGTGAT
GCCTAATATCTAAGGCTATAATATAAGGCTGTGAATATCCTT
scaffold2113_m_368
TCCGTAACTATAAGCTAACCTAATAGTTAATTCTATTATATTAAAGCTAG[A/G]ATCTAAATATA
AAGGTATCCTACTTATATTTACTTATAAAGTGTTTAATTA
scaffold2133_m_1012
ACTAGATTTAGACTTTAGATAAAAAGAATTAACTTTCTTTAGATATCTTA[C/T]CTTATACCTAAT
AGTAGCTCTTATAGTAAACTTAGTATAACCTTATAATAG
scaffold2145_m_643
ATAATTTAATATGCTTTAGAGCCTTTATTATTATTAGAAACGCCTTATAT[T/C]TATAAGCTTATA
GATATATAATTAAGGGCTTTTAAACTTCTAATATCTATA
scaffold2158_m_384
TTTATTATTCTAGTTTTTAGCTATTTTAGAAAATTTACCTAGGTAATTAA[A/T]AAATAATTTATAT
ACTTATTTATAGCTATATAATATATTTATTATTACTTT
scaffold216_m_1198
AGTTAGTAATATCTAAATAGCAGCCTATACATAGCTTTAATATAGTAAAA[T/C]AAATGTTATTA
CCTATTATATAGCTAGAAGAAAAAAAAATAGATAACCTAT
scaffold2168_m_1053
AGATACTTATCCTATCCTAGAGATACTACTATCTCCTATCCTATCTTAGA[G/A]ATATTACTATC
TTATTAGTTACTAAAATACTCTCCTTAACTAAGTGTAGTT
scaffold2169_m_1445
AGAAAATAGGGCTTTTATTTAATGCAGGAATATTTTTTAGACTAAAAGTT[A/G]GTGTATATAG
GTTACTAGTTTGTATAGTGGAAGTTAATTTTTTAGATTTT
scaffold2172_m_1520
AGAGATATATAAGCCCTTTACTACTCTAATAACTAATTACTATTTTACTA[T/C]ATAAATAACCA
TATTATAATATTCTAGCTATAGTATCCCTAGTATTATATC
scaffold2182_m_5088
GATTTAATATATTATAAATAGCTTTAGTTATTACTATAGTAATAAAGTAA[A/G]AGAGCCTTAAG
GAAGTATATAAACTAATTTTAAAATTCTTAGTATATAGAG
scaffold2198_m_1969
ATTATAAGATATATTCTCTAGTTTATACTTACTAAGTTATTTTAAGAAAA[T/C]TACTAGAATATA
TATTACTAAGGCTATTTTAGAGAATCTATTAGGATCTTT
scaffold2216_m_4847
TAAAAAGAAAAAAATAGATAACTTATATTAATTTTTATAATTAGTTTAAA[T/A]AAATAAAGTACC
TAATACTATAGTTTTAAATAGTCTAACTAAAGGGCTTAT
scaffold2217_m_2102
TAATTTTATAGTAATTATATACAGTTATAGTTATAGTAGTTAACTATAAT[T/A]TAATACTAGTTT
TCTTTTACCTAGCTATAGCTATAGAAAGGTAATGCTACC
scaffold2221_m_3777
TAAACTAAGGTTTTATATTTACTAGTGGTTTTTAAATAACTTTTTATTAT[C/T]TTCTTATAACTA
AGTAGCTACTTAGCTTTATTATTTTCTTATAACTAAGTA
scaffold2225_m_3214
TATCTATATTATAGGTAATAGCCTAGATTATACCTATTATATTAGCGTGC[G/A]TATGTTTAATA
TAATGCTACCTTATAACACTCTTACTAATTATACTAAGCT

Figure 6 Continued scaffold2229_m_2659
  ATTTTTAGCCCTTTTCTAGTTAAAGGACCTTTTTTATTACTAGCTTGCATC[G/T]CAAGCCTAACA
GCTGCACTGCAGCTGTTAACGGTCACGCAGGTAACTGTCA
scaffold2232_m_1832
  TAGAAAGAGAGAATTACTAAACTTAATATAGGTAAAATACTAATTAAATT[C/T]AATAAATAAAT
TAATACTTTAAAATAAAGCATAGTTTAAAAGGATAAGTAT
scaffold2252_m_1659
  TCCCTTTATAATTCTTATTAGTCTTTTCTAAAGGTATATTAATAACTAGC[A/G]CTAGTCCCTTT
ATAATTTCTATTAGTCTTTTCTAAAGATAACTATTCTCTA
scaffold2259_m_7435
  CAAGCCTCTTTAACCTCTTATTTTTCTATGAAAAGGCCTTAAAATAATAC[T/A]ATTATAGAGGA
ATTTTCATCTAAAAAGGCTATTACTCTAGTTATTAAGTTT
scaffold2260_m_2176
  CTTTAAACGCTATAGATAGCTCTAAAGGGAATTAGAATATAGTTATCTAT[A/G]ATTCTAGAGC
TAATGTTTATATTTTAATAATATTTATTAGTTTAAATAGT
scaffold2287_m_1451
  ATTTATCTAATAAAAGGTTCTTTACCTTTATAACTATTTTATTATAATTA[T/A]AAGTAATTACTTT
AATTTTTTAGTCTTTTTTACTTAAAAGAAAAGTAAAAA
scaffold2298_m_3021
  ATAAGACCAGATTCAGTATCTTACCTTATACCTAATAGTAGCTCTTATAG[T/C]AAACTTAGTAT
AACCTTATAATAGTAAATCCATTAGCCTCTCTAATAGATT
scaffold23_m_3484
  TTAGATAAATCCTATATCTATATGCCTTTCCTAGATAATATTATAGTAAA[G/A]GGACTAATAAT
AATATATAATAAGAAGGAAATTATGCTAGGAGTATATAAA
scaffold231_m_151
  ATATAAAGGAAACTATAATATATAGTATTACCTATACCTCTTAGTTTACT[C/T]TCTTTATATTAC
TATTAGTCTATAGGTAATATAATATAGAAAGTAACTAAT
scaffold2321_m_2404
  TATAAGTACTTAAAATAGTCTAGTAAATCTAGGGGTTAGCTTTTATTTTA[T/C]ATCCTTAAGCC
TAATGTTCTTTGCTAATAATAGTACTAGGTTACCTCTTTT
scaffold2324_m_258
  GTGTATATAGGAGGATTTATTATTTATAGAAGAGAGTTTACTTAGGTATA[A/T]AAGGCTTAGT
TCTTAAACCATAAAAATAACACTTAAATTTAGTTTCTAATA
scaffold2327_m_1414
  CTTAGATAAAGCCTAGATTTAGTAGGAATTTTATTAGGTATAAAAACTAT[T/G]ATTAAGGAGC
TTCCTATAGCCTATATAATACTCTTATTATTTTCTAGAGAT
scaffold2332_m_3584
  TATATTTAATTTTTATATTCTAGGGATAGCTTATAAAACTAAAATTACTA[T/G]ATATTTTATAGT
AATAGTAAATATAATACTAAATCTAAGACTAAAATTATT
scaffold2334_m_714
  AATAAACAGGCTAGCTAGCTATAAGATAGCTATATGCTTATAAAGCAGGG[T/C]ATTTATTAAA
GACTATGTATATTATTAGTGTAAGGTTAGAGATTAAAACCT
scaffold2342_m_1207
  GGAGATAAAGAACTATATAAGAATCCCTAATATTATAGAAATAACTTACC[T/C]TAGAGTTATAA
GCCTTATAGGAACTAAAGGAATAAGAACTAGAAAAGAGC
scaffold2344_m_914
  ATAGCTATTCCTAAATAATTAGCTTCTATTACTATAGGGAGATCTAGGTC[T/C]TATTATACTAG
TACTAGGTATGTAATAAAGGTATCTTTTAGCCTATTAAAG
scaffold2351_m_3742
  GAATAGCTTTAATTATTAAAGCTATAATTACTAAGGACTATAGGACTTAA[A/G]TAATAGGTTTA
AGAACTATAAGGCTTAGATATACTAGCTAAAAGACTAATA
scaffold2367_m_1637
  TATTAAAGTTTTTTTCTTTCTTAAAGAAGTTATTATTACTAAGGCCTAGT[G/A]TATTATTTATTT
ATATTCCTATAATTCTAAAGAGATTCTTATTATTTAAGG
scaffold2376_m_962
  GTTAATCCTTATGCTATATTATTACCTAAAGGTAGTGTCTCTAAATCTAG[T/C]ATATATTCCTA
GTAACCTAGTTAATCCTTATGCTATATTATTATAGTAATA
scaffold2401_m_1796
  GCTAGAAAACCACACTAAGGGCTTAACCTAGAAATAAACAAAAGGGAGCT[T/C]ATAAAGTTA
CTTACTCTTATATTTACTCTAGGCTATTAGATTTAGTTTTTT

Figure 6 Continued scaffold2404_m_469
AGGAAACCTATTACTAGTTATAAAAGCATTATACTCTAATATCTAATGTA[A/G]ACCTAATAGGATAGAAAACTATAATAATCTAGTCTAACTATATCTATAAGG scaffold2405_m_491
TATATATATATATATAACTATCTTATTAATAAGAGAATATTAAAATTTAA[A/C]TAATAAAGAAGTTCCTAGTAATATAGCTATTTTATTAGAATTATAAATAAT scaffold2423_m_856
AGTAACTTTAAAGATATTAGAATTAGCCTATAATAATAGCCTAATTTAAA[A/G]GGGTTTATTACTTTAAGTATAAAGTTATTAATAAAATTAGTTACTTAGACT scaffold2424_m_259
ATTTTTAGAGACTATAGAGCCCTAGAAGGTATTATAATAGACTAAGGTTT[T/C]ATATTTACTAGTGGTTTCTAGATAACTTTTTGTTATTTTCTTGCAATAAAG scaffold2450_m_931
ATTTTATAAGGAATATTAAGTCTTATTATATAGTAGTTAAGGCTAATAGG[A/G]AGTTAAAGGCTATTACTTATAAAAACGCTATAAATAATAAAGAGTTAAAC scaffold2457_m_19692
AGATCCTCGGCGCATCTCTAGAGTCTAGCCTTTTTTTTTTTTTTTTTG[G/T]TCTTGTCTCTCTGTCTTTGGTTCTCAAATCCTTAGATTCTGTCATCTCCTG scaffold2459_m_597
CTAGCTTCCTTACTAAACTATTGAATAATTACACATAGAATTAATTCTAT[A/G]TATAATTCCTCTAAGCATTAGATTATTTAGTAAATCTAATATTAGTTATAA scaffold2483_m_620
AATAAAAAGGAGGGAGTTCTTATTTTCTAAGAGAGTTTTAGGTCTTTACC[C/T]CTTATATAAAATAATAAATATATTAAAGGAACTATTAGCTAGCTAGGCTTA scaffold249_m_680
ACCTTTTATATTATTTACTAAAACCTATTAGTTATATTTACTTAGCTAAC[T/C]CTTTTATTTTACTAGGTATTTATTACCTCCTTAACCTCCTTAACTTTATAT scaffold2492_m_1197
AAGCCCTATCTTCTAGCTTTAATTTACTATATATAAGACTTTTATATAAC[T/C]TCTAGTTAAAGAGAAAATCGCTATTAAAGATAGCTATAGGGTAACCTGCTT scaffold2501_m_421
AAAAATTAGTTTTAATTAATTATATTATAGCTTATTTACTTAGTTATAGG[T/G]TTTTTTTATTAAAAATAAGCTTAAGAGATAAGTTCTATTAGTTCTATTAGT scaffold2502_m_1086
ATAAAGAGATTAATAAGCTAAAGGAATAAGGAATATAGTGGTAAATAAAG[T/C]ATTCTATAGTATAATTAAAGCTATTACTATTAAAATAAGTGTTTTCTTATA scaffold2511_m_491
AAAATAAAGTACTTAGTAAATTAGTCTATAATTACTAGAATTATATTAGT[C/T]TTTTATTTACTTACTTAAGTAATTACTATAATATTAGTAAGAATTTAAGGC scaffold2516_m_2186
TATATATTTATTAAGATATTCTTAAAGCTTATAAGCTCCTTCTAGTCCTA[A/G]ATTATATTAACTCTATATATATTTATTAAGATACTATTAACTAATAAAATA scaffold2525_m_3028
ACCACTTTAACTCCTTTATAGCTAAGTTCCTTATAGATAGCTTTAATAAT[C/T]GCTTATTATTATCTAGGCACGTTAATAACTAGCGCTAGTCCCTTTATGATT scaffold2527_m_370
TTTACCTAAAAGTAAGAAATTATATTTTTCTTATTAGTAATACTATATTA[C/T]TTATATATAGTATACTAAGCTTCTATTTACTAACTTATAACTTTACTATAC scaffold253_m_658
AGAAAACTATAATAAGGCAAAGAAGTTTTACCTAGAGATAGAAAACTA[C/T]ATAATAAGGCAAAGAAGTTTTACCTAGAGAATAGTTATCTTTAGAAAAGAC scaffold2533_m_191
TAATATAGGTAGAACTAGACTATTTTAATTCTAGGTTTGCCCTAGCTTTA[C/T]AATATAGGTATAAAGTTTAATATTAGGAACTCTAAACTTATAATTAGAGTT scaffold2545_m_1932
CTAGGTTATATATAGCAAACTTTAATATCCTATTATATATTTTAAAGTATTA[C/T]ACTTTATTATAATATGTAATTCTTTATTATAGTAATAATAATAATTTAACT scaffold2550_m_3185
GAGTAAGAATATATCTAATATATACTTATAATATATAATATACTTAACTA[G/A]AACTACCCTTAGGTATAGTATAACTATATAAGTAGCTATTTATTTTCTTAA

Figure 6 Continued scaffold2558_m_248
  TATTTTAATAAGATTACCTTATAGACTATAGGTAAAATTATAGCTAATAT[C/T]TAAGGGGTAAT
TATAAGTCTAAATTAAGGGGTAATTATAGGTCTAATTTAA
scaffold257_m_630
  TTAAAAAGGGATTTTATTACTAAAGAAATTATTAATAATTATAAGTAATA[C/G]CTAAGTAATAA
AGTTAATATAAGGTAATTATAATTTATAAGTTAATATACT
scaffold2574_m_199
  CATAAATCCCTTAGTAATAAGTTAGGCCTTGTATTTTAAAGGATTATTTT[T/C]TTTATCCTTAG
GCCTTGTATTTTAAAGGATTATTTTCTTTATCCTTTTTAA
scaffold258_m_4900
  GGTGGCCGTCAATGGCTACGTCGCAGCTGTCAACAGCTACGACCGTTATT[T/C]AACTGCGT
TGTGGCTGCAAGCGTAGCCACAACTATAACGCCACTAGTAATT
scaffold2582_m_1429
  ATAAGGATAATAAAGGCATTACTAATTATATTTCTAAGGGCCTAAAGGAG[A/G]TATATAAATT
AGATAAAAAAGGTAAAATAAGATTTTTCCTAGGGATCTAGA
scaffold2583_m_609
  AGTTTATATCTTTAAAAAGGTTAAGAGAGATTAATTTATTATAGCTTATA[C/T]TAAAAGGTTAA
GAATAAAGTAATAGCTAAGACTATTATAGTTACTACTAGA
scaffold2587_m_672
  CTATAACCCTTAACTAGGTTTAAGGTTTATTAAGATAGTAATAACTTTAA[C/T]TAGGTAATACT
AATTAAACTAGGGTAGGATTAGTTAAGCTAGTAAAACTAT
scaffold2592_m_782
  CACTTTTATTTATCTTACTAGGTCTACTATTTAGTTAGTAGCTTATTTCT[C/T]TCTTTACTATTA
TTCTTTTATTTATTTTTATAGTAATTCTATTCTAGCTAT
scaffold2596_m_235
  TATCTAACTATATTATAAGCTTAAGTAAGTAAATAAAAGACTAATATAAT[T/C]CTAGTAATTATA
GACTAATTTACTAAGTACTTTATTTTCTTACTTATAACT
scaffold2599_m_353
  CCATCTATCTTATCTCTTGACCCCGCCATCGTCAAGGATCGTCAAGCCCC[G/T]CTTGTCTCC
ATCAGCTTTCTCAAAGTGCGGCTACCTTCTACCTTGATCGTC
scaffold26_m_1691
  GCTAAGATTAATGCCTTATAAGCTTATAATATGTTTAGATTTATAATATT[T/C]AATCTAGCAAA
GCATAGAGGCCACTGGATCTTTAATTCTTATATGGTCTAA
scaffold2607_m_4707
  AATTATAAGGCTATAATAGCACTTATAGTAGCTTACTATAAGCTTATAAG[A/G]GTATTAATAAG
GGCATTAAATTACATAGCTAGGCTAGCTAGGGTATTATAT
scaffold2610_m_730
  TAGCTATAAGGTATATTATATTTAAGCTATATTTTATAAAGATTTATTTA[G/A]GGCTCTTAATTA
TAGTATTTACGTCTTTTAGCTTTAACTTCTATAAGTAATA
scaffold2620_m_6828
  TCTTCGGGCATCTGTGCGAGGAAAGTTTCCACATGATCCGAATTGGGAGA[A/G]ACACAACTT
GCAACTGCCAGCAAAATGATGGTGCATGTACGGAGTTACTTT
scaffold2622_m_456
  AAGAGGATTTAGAAGCGTTTAAAAATAGCGAATTTTTGCATTATTTTACG[A/G]AAGATATCTC
TTCTATTAAAGAGAGACAAGATTATAAGGAATTTAAGTCCT
scaffold2637_m_2156
  TTATTAGTTATTAGTATTTATAAGGTTAAAAGAAAGCCTTATATAAAAGC[C/T]TTTATTATTACC
TATTTTATTAAATTAGTTATAGAATTTATAATATTATAT
scaffold2649_m_177
  TCTAGCTATTAAGATTTTATTATTAGATAGTTATATTATCTTTTTAGAGG[C/T]AAATAAGTAATA
GTTATATAAGATAAGTTTTAGGTTAGATATTATTAAGTC
scaffold266_m_1203
  GAGGCCTAGCTATCTAGCTAGATTAAAAAGATCTTCTTTCTCTCATATAC[T/C]CACTAACCAT
ATTAGTGAATCCAGGCCGCTAGAGAGGTCTTAAGAGCCACT
scaffold2678_m_735
  AGTTACCTAGAAAGCTAGTAATTAAATAAATATAGGGAGATAGATAATAA[A/G]ATCCTAATTT
CTTTTAGTATTTCTTATATAAAGAATAGGGATATATAGGAT
scaffold268_m_1749
  GCTAATATCTTTAGATTATCCCTCTAATACTATCCCTTTAATGCCTTACT[G/A]CCTTCTAATCT
AGTGGATTTATTAAGAAAACCTTTAGATTTAGCTTTATAA

Figure 6 Continued scaffold2691_m_1629
CTTTAACTTAGTCTATACCTAGGATTATTCCTTTACTTATATTAGTAATA[A/T]AGTAGCTAACTT
AGTAAACCTTTATAAATCCTATACTATCTTTTATTTTTA
scaffold2696_m_772
TTAAGTTTAATAATTACCTATTACCCTTATAGTTCCCCTTAATTTCTAGG[C/T]TACCTCCTAAT
ATTTAATTTAACTCTAGATAATCTTCTATATATTAGCTAT
scaffold2698_m_2599
AGAAAGCCACTACTACTGTTTTTACGTAGCCCTTTGCTTTTCTTATTGCT[T/A]TATATTCTATT
AGATTAATAGTAATCTAATATGTAGGCTTTCCTACCTATC
scaffold27_m_1964
AATTACTACACTATAAACTACACTACACTATAAACTACACTAACTATAAG[C/T]GAAAAAAACT
ATAATATAATATAATATAAATTTTTTTCCTTAAACTACAC
scaffold2704_m_1609
AGAGATTAATATAGCCTTATAGGAACAAATTTAGGAGAGACTAGGAGCTT[G/A]CTTAGAATA
GGATAAACCCTAGTAGAATTTAATTAATCCTATTTAAATCTT
scaffold2709_m_40857
CGCAGGGGTTCTAGCAAACTCCGGACAGGTCGGATCTGTACACCTTGGGA[A/G]TGGTGGA
AATGGGAATTGGGTCATCGAGGCCTTGTCGTAAAAGGCACTGTC
scaffold2717_m_1531
TACCACTACATTTAGCACTCCTAGTATATATGTCACTTTTAAGTTAAATT[A/G]TAATAGATAAT
TTGTAACCTTAGCTAATTTTAGATTAGCCTTATCTAAATC
scaffold273_m_688
ATAACTACCCTACCCTTACCTATTTATAACTTACCTAGTATAAGTGTAAT[A/G]TCTAGTATAAA
TATCTTACTTATACTTACACTATCTTACTTTCCCGTTTAT
scaffold2730_m_1373
ACCTTAGGGTTAGTGCGGAAAAGTATGCAAAGGTTAGATTAAATTATAAT[C/A]GGGTCACAA
ACTATAGTATATATAGCTACATAAGTAAACTATTTTAACCCT
scaffold2731_m_126
TTATATTAACTTTATTACTTAGCTATTACTTATAGTTATTAATAATTTCT[A/C]TAGTAATAAAATC
CCTTTTTAATACCTAAGAATTCTTTAAAGTATTATAGC
scaffold274_m_1201
TATAATAAAATATTACTAAATACTATAAGTATTTTATTATTAGTGCTATT[A/C]TAGTTTTAATTTA
CCTAGGAAATTATAACCTTAGAGAGGTATTACTATAAG
scaffold2746_m_304
ATTTAATAACTTTAATAACTTTAATAACCTTAATAACCTTAATTACTATT[A/G]TTACTATTATTAC
TATTATTACTATTATTACTATAATTACTATTTACTTTT
scaffold276_m_4281
GCCTTTAAAGCATCCTTATAGAAGTCTAAGCTATACCCTTAAGCTATGCC[T/C]TCCCCTTACT
CTTAATCTATCTAAGTTAATAAGTTAATAGGAAGCATGCCT
scaffold2767_m_943
TTTTAAAGATTAAACTAAAGATATATTTAGAAAAGCTACTAATAAGCTTA[T/A]AAGAGAGCTAT
AAAACTCTCTATAAGATAATAATATTTATATTAGCTAAGG
scaffold2796_m_252
GCTAAATTAGCTAGAAGTTTTAGCTATAAACCTTCTAAAGATTAAGTAAT[C/T]TTATTATAAAA
GTCTTTATATAGCCTAAAATAAAGATTAAGGTATCTAACC
scaffold281_m_1185
TTAGCGCTAGTTATTAACATGCCTAAATAATAATAAGTAATTATTAAAGC[T/A]ATCTATAAGGA
ACTTAGCTATAAAGGAGTTAAAGTGGTTTTTTAAGTAATA
scaffold2812_m_1297
GAATTTAACCTTTAATAAATTAGGTCTTTTATGATTAGACCTTTGACCTA[T/A]CCTTCGTTAGC
TAGGTCCGTCGTTATAGATTAATTAATCTAACTATCTAAT
scaffold2822_m_5391
CCATACTAGGTTGCTAGTTATCTAGTACTAGATAACTAGTTAGTTGCCTA[A/G]TTAGGTGAAA
AACCTACTACGATTTGTTTGTTTTAGCTACATACATGGTTT
scaffold2832_m_1867
ATTAAGGTATATTTCTATAAGAATTAGTATTTTCTAAGTATTTAGCTTAT[A/G]TTAATCTTAAAG
AAGCTTAAGTATTTTATAAGTATAATATTAAACTAACTC
scaffold2834_m_339
TCCCTGTGCCAGGAACGCCGGTGCCTGGATTGAACTTATGGCACTCGTGA[G/T]ATGCAATT
CATTGTGCTAATCGTGAATCCTTCATAGACCACACAATCTCCA

Figure 6 Continued scaffold2838_m_629
　　　　CTTTATCCTTTTATAATTATATTTTATTATAATATAAAATATATATCCTT[A/T]AAGTTAACTTCTA
ATCTATTAAATACTATTATAGTACCTTTAAGGGTAAAT
scaffold2840_m_765
　　　　TAAGCTAAAAGTAAAGTTTTAGCACTAAAAGAGAAGTATACTATAATTAA[T/A]TAGCTTTTAAG
TAACTTATAGACTTAGTATAAAAAATATTATAACTAGAAG
scaffold2867_m_1121
　　　　GAGGCATTATTCCTATGCCTAAGGATAAGAAAATAAGGATTAATCTTGTT[A/C]ATAGGTAGTA
ATATTAAATAAGGCTAATTAGACCTTATAGATTAGGTAGCT
scaffold2872_m_120
　　　　TACTTTAGAATAGTAATTATAATATAAAAACTTCATAAAAAGTGCTTTTA[G/C]CTAGATAAAAG
TAAAGATATAAAATCTTATTATTACTTATATCTAGTATAT
scaffold288_m_631
　　　　AACACTAAGAACCCTTTACTAATAATATCTTATAACTTAATAAACGCCTT[T/A]AGTAGTAAATT
AAGCATTAATAATAGGGATTATAGTATATCCCGTTAACTC
scaffold2882_m_1713
　　　　AAGAACATAGTTACTAGCCTATTACTAGTTAGTTACGTTAAAATAGGGAT[G/A]TAAATACTAT
ATTTTGTAAAATAGTTAATAATAACTAAAATCACGTTATAG
scaffold2898_m_1208
　　　　ACTAGCTAAGTAGTAGCTCTCTTACTGGCTAGTATAACTTCCCTATCTAG[A/T]CTATTATAGC
TAACTTATAGCTAGTTTACTATATCTAAGTCTTATGCCTAA
scaffold2902_m_804
　　　　ATCTAGTTCTAATAATAATAGATATAAGATTAGCCTATGTTACTATAGTA[G/A]ATAATAAAAGG
TAAGATCTATATAATTACTTATAAAGTAAAGATTAGTCTA
scaffold2906_m_981
　　　　AAGACTTCTATTCTTAAGGATCTTAATATCTTTCTCTTACTAGTATTACT[A/T]ATAACTATAAAA
GCCTCTTTTTATAATAATAGTTTACTATACTACTAGACT
scaffold2907_m_709
　　　　GTATTTATAAATTTAAATAAAAAGGTAAGAAGTTATATAGTTATTACTTT[C/T]TCTTTCCTTACT
TTACTTACTAAATCTAGTTTTGTTAAAAGTAAGTTAGTA
scaffold2909_m_198
　　　　ATCTTAATGCTATTAAGATATAGGTTAATAAAATCCTTAATATCCCCTTT[G/A]ATATCTTAATCT
AATTAATTTAAAGCCTTAAGGCCTTTCCTAGATAAGGCA
scaffold2916_m_578
　　　　TTACATATTTCTTTACATATAGCGTTTAGGCTACTAATACTATAGTAATA[A/G]GGGGTAAGTA
CCTAGATAAGGGTAGTAAACTATTTATATATTTCTTTACAT
scaffold2927_m_678
　　　　ATTTAACGTATGTAAGATAAACTAATATAATACTAGTCACTAAAATAATA[T/C]AATTAATTAAAA
GTAATTACGGGTTTAAGGCTAATTTAGCTATTATTAAAC
scaffold2945_m_718
　　　　CCTTAATTAATTATTATAGATTATAGTTTAGATTAGTTAGGAAAATTTTA[A/G]ATAATATTATAC
TCTTTAGTTAGGATTAATTAGTTACTTTTTATATTATAT
scaffold2949_m_10115
　　　　GACTAGATTAAAGAATATTTACCTATAATTATATATTAGGAGTATAAATA[G/T]TAGAGATATAT
AGTAATAATAAAATATCTCTCCTTTACTTATAATAAGTAG
scaffold2955_m_15876
　　　　AAGAAGAAGAAGAAGAAGAAGAAGAAGAAGAAGAACAACAACAACAACAA[C/G]AACAACAA
CAACAACGAGACGGACTGACAACGGGCAACCGAGCCAGGGGGG
scaffold2959_m_778
　　　　TTACTTAATTTTATCACAGATATACTAGAAGTATTAGCTATAAATATAAT[A/G]TGGTAAATAGA
AGGATACATAACATATAATTTATTATGCCTAGTAAATTAC
scaffold297_m_3649
　　　　GCGCCACTTTTGTATGCCAATCCCAAGGTCTGCCCGTCAAAGCGGCGAC[A/T]GCTTCTTC
GGATTTGCCAGGGCGACTGCACTTCGATAAAAACCGGAATTAC
scaffold3007_m_501
　　　　ACAGGTCGCGCGAGCGCGGGATACACATTGCCGCGGGATACCTTGTCGGC[A/G]CGGCCG
GGCTGTTGTGGCTCGCCCTCGCGCCCAGCGGCGTGGGCAAATGGA
scaffold3011_m_529
　　　　TATTTATATATTTATTACTACTAGATTCTTTAATTAGCCTTTACCTTTTC[C/T]TTTTTTAATTTTTA
TTTTCTAGAATACTTAGCTTAATCTTTATTACTTTTAA

Figure 6 Continued scaffold3016_m_261
　　　　TTAACTAGTAAATATTAAGATAAATAAAAGATACCTTTTAATAAGTACCT[C/T]TCCTTTATTATT
ATAACCTAAGTTAGCTAGTATATATTAAGATAAATACTT
scaffold3018_m_373
　　　　TATACTAGGAAATTATAACCTTTCTAATGGAGCCCTTAATCTATATAAGA[A/G]ACCTAGCTCT
CATAGGACTAGTTATAAGAGCTCTAGCAATAGTAAGTTTAA
scaffold3024_m_118
　　　　ATAGTATTACTAAGTAATACTATAAATCTAAAGATATAGATTAATATATTTT[T/A]AACTATCTTTAC
TTTATAGCTTAAAATATCCTAATAGTAAGCTTTCTTAAT
scaffold3034_m_1430
　　　　AAAAGGAAAGAAAAAGATAAATAAGCTAGTATTTACTAAAGGACTAGCTA[T/A]GAGAATTATT
AAATTAAAAACTAGACTTAAGAATATATTAAGTAAACTATT
scaffold3035_m_1005
　　　　ATATAAACTTAGCTTAATTACTACTAAAATCTATAAAATTAAATTAATAA[T/A]ATCTAGGAAATC
CTAGATATTATATAAGTATTATAAATAATTAAGGTAATA
scaffold3038_m_299
　　　　CTTCTAACCTTTAGGGGCCTTTTCCTTGTCTTTAGCACCCTTTTCTAGGT[A/C]TTAAGCCCTA
TAATTCAGGGCTTTAGATACTATAGATAACTTATCCCTCTG
scaffold3046_m_1305
　　　　TTAGGTTATAGCTATATAGTAACTTATTTAGGGTAGTAACTAAACTAGCT[C/T]TAGGTTATAG
CTATATAGTAGCTTATTTAGGGTAACTCCTATTATAAAAAA
scaffold305_m_5252
　　　　TAAGGGTATATATAATATAAGTATTATATATATTACTAGGGGATATTATA[G/A]AGAGGAGTTTA
TTAGTAATAAGTAAGTAAGGGTATATATAAGGGCTTAGGC
scaffold3052_m_265
　　　　TCTTAGGCTTTAATAACTATATTACTAGCTTTATAGTCTCCTAAGAAGAC[T/C]TTTACTTACTT
CTCTCTTATAATAGATTTATTTATAATAAGAGTTAATAAA
scaffold3058_m_1521
　　　　TACTTAGTAACTAATAAGGTTAAGCCTTTTTTATAGTATATTTATATTTC[T/C]TTATTAGTACTT
TAATCTAATATTACTACCTTTCTTACTAGACTTACTTTA
scaffold306_m_784
　　　　TTATTAGCTAGAAATCAAAGAAAGCTAGTATAATAGCTCTATTAATATTA[G/A]AAGCTAAAGCT
AACGCTATTTACAAGACCTTCTAGGAGCTATAGTGGCTTT
scaffold3066_m_13958
　　　　CTTGTCATGAAGCAAATGTCTAAATGTTTGAACCATTCGATCTCGGTCAG[A/G]GTATATATCT
TTTGAATGTCAAGTGTTGATGGTCGTAGTCGGAATAGAATG
scaffold309_m_963
　　　　TAAACTTAGTTTAATAACTATTTAGGTAAAGACCCTAATAATAAAGGCAA[G/A]ATACCTAGAT
CTCTTAGAGAGCTTAATATAAAAACCTTTATAAAGCTTCTT
scaffold3096_m_1499
　　　　ATATAAGAATTCCCTTACTTTTACCTAATAATTTATAGATAAATTATTCT[G/A]AAAATACAAACA
TTTTATATAAGTATATATTAATAATATTATTGTATTTTTT
scaffold31_m_284
　　　　AAATAATAGGCTAATAACTAGGATAACCTTAAGGATAACTAGAATAAATT[C/T]TAAACTTAAAT
ACTTATATTACTTAAGGACTTTATAAACTATAATACTTAA
scaffold310_m_2447
　　　　GGGATGCCTAGTGGTCTCTCTTAACTAGTAGCTAGTGAAAAAATCCTATT[C/T]TATTAAATAA
AGAATAAACCTCCTTACTATAGGTGTTATTTATAATGTTAC
scaffold3105_m_1636
　　　　ATAGATTTTATTATAGAATTACCTATTACCTAAGTAAGTAAATAAGAGAC[T/A]AATATAATCCT
AGTAATTATAAACTAATTTACTAAGTACTTTATATTCTTA
scaffold3119_m_1595
　　　　AACTATATTAGTGAATCTAGACTACTAGAGAGGTCTTAAGAGCCACTTTT[G/A]ATTTTCCGTA
AAATTTATTTATATGTAAAATCCAAAAAATTAACTTACCAC
scaffold312_m_295
　　　　AGATTAATAATTCCCTAGTAAGAGGCAAGGGAAAAGCTAGTCTATAGTTA[T/C]ATAGTATAAG
AGGCCTCCTAATATACTAAGACTAGGTAGTTATTCTAGTTA
scaffold3124_m_467
　　　　TAAGATATAAAGGAATATATAATTTATATAGTAAGAGTTAGAGATTTAAT[T/A]AAAAAAAAAGG
GGGAGAGAGAGAAAAAGGAATAAAAGGAAAGAGAGAGAA

Figure 6 Continued scaffold3125_m_336
TTATTAAGATAGTAATAACTTTAACTAAGTAATACTAATTAGACTAAGGT[A/G]AGATTAGTTAAGCTAGCGAAATTATTTAATAGATATCTATAAATTCCTAAG scaffold3132_m_1062
AAATTATAATACCTAGGATAAAGCTAACTATTTCTAACATATTAATATTA[G/C]TAAAGGAGTTAGTAAACTTTATAGACCTCTTTAATAAGGCTAAAGCTAATA scaffold3133_m_797
TTAAGGATATAAAATAAAAGCTAATCTCTAGATTTATTAAACTATTTTAA[G/C]CACTTAATACTATAAGGAAATAAGTATATTAACTTATATTACTTAAAAAGT scaffold3139_m_9202
TCTTAGTTTATATATAGTTATTATATTTATTTAATATCTTAATTTACTAA[C/T]TACTTTTTATAGCTTTAATAAAGAAAAAATCCTTTAATTTTAGTATAAAGT scaffold3143_m_30303
CTCGCTCCGATTCGTATGGGTGACCGAGTTCCCCATGTTCAAGCCCGTTG[A/G]AGAAGGCGAGCCTGGCCAAGGCGGCGCAGCTGGCATCTCAGCAGCACACCA scaffold315_m_324
ATTAATCTTAGCAAGGCTTTAGCTTATACTAGACTAGTAGTTAATTAGCC[A/T]AAGGCTCCTATATCTAGTATAATTCCTCTAAAGATCTCTTTAGAATAGCAT scaffold3155_m_195
TATTACCTAGGACTTAATTATAAAATATATTTAATATTACTAGTCTTAAA[T/C]CTTTTAAAGGGGATCTAATAAATATAGAAAATATATCCTTACTATAAGATA scaffold317_m_584
CCCCCCCTCCTTCTTAATTACTCTTTATTATTATAAAAACTTATTACTAA[A/G]GTGTGTATATACTAGATAGAACCTAGGCATATTAATTTTTTATAGCTAAAT scaffold3171_m_930
TACTACTAACAGAGCGGGGTAGCTTGCGATGCATCTAATCGCATCGCGTG[T/C]ATCCCTTTGGTGGCTCCACTCTTTGGCCACGGTCGGACTATCTATTGTCCG scaffold3175_m_1168
CCTCCGTTTAGAGTTAGTGCTTTACTAATATAGCTATAGCACGTTCGCTA[A/G]GCAATAGTCATAGCACAAAGAGTTATCTGCCTAGGACGTAACCTAGGTTCT scaffold3179_m_1184
CTAGCATAGGCTATGTAAATAATAAAGAGGCTAGCTAGCTATAAGATAGC[T/C]ATATGCTTATAGAGCAAGGTATTTATTAAAGACTATGCATATTATTAGTGC scaffold3190_m_22763
GTGGACCTTTTCTCCTTCTATATTTACATGCGAGATCAGCAAAGATCGGT[G/A]GATTATCTGGACTTTTGGTAAGCAGGATGATTTGAAGGTCTTTATTTTGAC scaffold3194_m_23960
TCACCGTCACATGTTTCGTTGAACATGTAGACGTAGCATGTTGCAGGGGG[C/A]ATGGCGGGAAGCTTGTCAGAGTGTGAGGCGGCAGACGAGCCTGTCGTGTTG scaffold320_m_289
ATAATAAATCCTAATCTCTAGGAAGACCTTTAGGGAATAATATTAGTATA[G/T]ACCCTTAAGATAAACTATAAAGAGACTTAGACTTTTTCTAGTATTTCTTAT scaffold3211_m_9407
CGTGGGTATCGCCTGATGAACAACTTTCTTCACTTTTTCTTTTTTTTTTT[G/T]GGGTTCTTGTCATGACATAACCATTTGAAGTTTACCAGCTTGTTGTGGTGG scaffold322_m_309
ATAGGGCTCTAGCCGTATTTATCTTATCTTGCCTTATAGTTAGTGTGTAT[A/G]TAGTTAAGTGTAAAGAGAATCTTTTAGTAATTATATTAGTATTTTTTCTTT scaffold3228_m_342
CTCCTAATATATAATTATAGGTAAATATTCTTTAATTTAGTCTATACCTA[A/G]AATTATCCCTTTACTTATATTAGTAATAAAGTAACTAACTTAGTAAACCTT scaffold3237_m_377
TTATTATCTCTTCCTTTAGGTGCTTTAAAGTTATAAGGTATTATAGTTTT[C/T]TATAATATAATTAGTATATACTATATATTATAAAAAGCTAGATATTACTT scaffold3238_m_1387
ATAGCTATATTTTAATTCCTAGGGTTAGTAAAGGTACTTATAGTAATTAC[A/C]TTTAGAATAGGTCTTATATAGTAAGCTATAAGTAGGGTTTTACTTCTAGGT scaffold3243_m_641
TATAAGGGCTTAGGCTTTACCTAAGCATATTATAGATAGAAGGAAGGGTA[A/G]GAGTAAGTAAGAATAGGTAAGGAGGAGCTTATATAAGAAGCTAAGGGGGTA

Figure 6 Continued scaffold3258_m_1093
   TTACGCACTAAGATTAGGGGCTAGCTACCTCTAACCTTATTAATTAGTAT[T/C]TATCTTCCTTT
TTATAAAAGGGAAGCCTTTTATTTATACTAATTTCCTTTT
scaffold326_m_1440
   ACTATTATAAAGACTAAAGTATTTATCGTTAAATACTAGCTATTCCCTTT[T/C]CTTAAATATAAA
CTTCCTAGTCTAAATACTATTTTAACTACCTTTTATTAG
scaffold3266_m_3790
   TAGCCTTATATATATTAAGTATATTAATATTACTTACGCTTAGGACTTAT[A/G]TCTATTAGTATT
AGATTAGGTCCTTAGAATTATATTAGTAATATATATTAG
scaffold3270_m_823
   AAATAAACTATTAGTATAATTACTATAGAAAGTATAGGATTAAGATCTAG[A/T]TTTATAAGTAA
GATTAATAATTCCCTAGTAAGAGATAAGGGAAAAGCTAGT
scaffold3279_m_1097
   AAAGTTAGTATAGCCTAGTATAAAAAAGTCAGTAATTTATAGCTATAAGA[A/T]AATAAAATACT
TAGTAACTCACTATCTTATATATATTGCTATATTTATTAT
scaffold329_m_343
   AAAAAAATAGATAACCTATATTAATTTTTATAATTAGTTTAAATAAATAA[A/G]GTACTTAATACT
ATAGTTCTAAATAGTATAACTAAAGGGCTTATATTTATAG
scaffold3294_m_2248
   TCCAATGCAGTCATTCAATCGACGTCACCAGCAGCAAATTGCTGGGCAGG[G/T]GGGAAAGA
ATGACGATGATGATTTCCTTGTCGCATAATCCGTTCACTAAAA
scaffold3305_m_3237
   TAAAGTTATATATATATATCTAAGCTATTTTAAGTATAGTAACTATAGGA[T/C]TTACTAATAATA
TAAATATAGTAATATTTAAAAAGAATATAGCCTAGACTT
scaffold3319_m_6117
   TCTTTTTTTTTTTTTTTTGCTGGACTTGCGACAGGTCATGCGGTAGCATG[A/G]GACGGTCTG
GGGAGTCGCAAGTCGTGGTGGTTCAAAACTAAAAACTCATTC
scaffold3320_m_203
   ACAGTGATGGAGATGTTAAGAAAGATATAGGATTAGGCAGTAACTATTAA[T/A]AAGCTAATAG
AGGAGTAAAAAAGACGTAAAGAACATGCTAGGAAGGTAAGA
scaffold3322_m_337
   ATAGATTTAACCCTTATCTATTAAGTCTATAATCTAGTGCCTAACCTCTA[A/G]AAGCTAGTCC
CTTAGTATATTATATAGTAGTATATTATATAGTAATCCCTA
scaffold3327_m_6368
   TGCACTATTAGGACGCGAATCCATTGAACAACCTCTTTTTTTTTTTTTTT[C/T]TTTTTTTTTTTT
TCCCCTTGCTCGCAGGTTCCCTTGCAGGGTGTCACTGGC
scaffold3341_m_2102
   TTCGAGAACGGGCACTTCTGCGATGGCCCGATGGGTAACTCGTATACAAA[G/T]TAGCGAGC
GTGGTCCCCAACGTGGGATCCCCCCTTCGTCGCCAGGACGTGC
scaffold3344_m_739
   AAGGGAATAGCTAGCGTTTAACTAGCTAAAGAATACCTTTTAATAAGTAC[T/C]TTTTCTTTATT
ATTATAACCTAAGTTAGCTAGTGTGTATTAAGATAAATAC
scaffold3354_m_2549
   TAAATAAGTAGGTATAGTTTTCCATGCCTAATTTTACTAAAGTTTATAGG[G/A]TATAACCTAAT
TCTTATAATACTTCAAAGGCATTTTATTTAGTAAATAAAC
scaffold3368_m_2002
   AATATAATCTTACTATAGAATACCTTATAAATAATAGAATAAGAATATAG[G/A]TATCTCTATAAT
AAGATAACTAGTAGTTAGCTATATAAGCGCTATTTAATA
scaffold3379_m_7219
   CCTCAAGGCGTCGAATTGGATCCAGCCTGTGGTTCATGTCCCGCGGTAGT[C/T]GAGAATCG
AGAAGCCATGGCGCAAGCCAAGTCTGCCGCAAAGTCCCCGTTC
scaffold3387_m_1426
   ACCGGCACAATGACGTGGTTCCAGAAACAATTTACTCTGCCCGCCAAGTC[C/T]CGCGGCTC
CTACCTCATCACTGATCAGATCGTTGGGGCTCTTCCTGAGATT
scaffold339_m_2899
   GGAGTTATATTATAATAGTTTATTAACTAGAAGTATTCTATAACCTTTTA[G/A]TTACTATATAAT
ACTAAGAACCCTTTACTAATAATATCTTATAACTTAATA
scaffold34_m_1098
   AATAATAGTTAATTTATATAGAGATTTTAGAATTATAAGGGGTAGCCCTT[A/G]ATTTCCTGTTT
TCCTATATAAATTAGCTCTTTAGCTTGTCTCTCTATATCT

Figure 6 Continued scaffold3400_m_154
CTTAGTAAGAGGTATATAGTTTTATATAAGAACTAGGTAAAACACTAAAT[G/A]CTTATATCTAA
TAAGCTAAGTATTTAGCTTCTAAGATAAAATCTAATATAT scaffold341_m_429
AACCTTTAGTAAAGTTAATAAATCTCTCCTTCTAATAGGTAAAAAGCAGT[A/G]GTTTCTCTTAC
CTCTAGAAGCTACTAAGGGTAGCCCTATTTACGTACCACT scaffold3421_m_8066
ATCTTGTGTCGCTGGTTGGGGAGATTGGCAATGCCAATCGGCGAGGCACT[A/T]TCCGCAGC
TGGGGCCATCTTGGACAAAAGGGATTTGTGAGTTGGAAAGGTG scaffold3432_m_356
GTTTCTTAAAATACTATTAAGAAAGTAAAAGAAAACTATACTTACCTAGC[T/C]TTCCTTATTTC
CTTTCTTTAATATTTCCTAGTAATAATATTATTTAGATTA scaffold3441_m_995
ATAGTATACTTTTTCTCTTACTTATAAGCTTTAATAATCTCTAGCTATAT[T/C]TTATAGGAAACT
AAGCTAGGTAGTATTACTAAAGTATATATAAATAATATT scaffold3444_m_2356
AGCACTCTCTATATCTTTTACTAGAACCTATTAGTTATATTTACTTAGCT[G/A]ACCCTTTTATTT
TACTAGGTATTTATTACTTTCTTAGTTTTTTCTATAGTC scaffold345_m_316
ACTATATCTAGGATATAGCTATATTACTACTTTTAAGTAACTTTAATTAA[C/G]CTATAGTAAAG
TTATTACCTTACTATACTTTATATAATAAGACTTAAATTA scaffold3469_m_1122
ATAATAGCATTTTAGAGTCTTTATTTTATTAATCCTATTTACCTTAGTAG[C/T]GCTTTACTTACT
AAGGAGGGGGCCTTTATGTATTTCTAGGGTAATTAATTT scaffold347_m_145
TTTACCCCTAGATAAATAGCTAGATAAAACGTTTAAACTAGGTCTTAAAA[C/T]ATTATTTAAGG
GCTTTTACTTATACTAAATAAACTAATTAGGTAATTTAAG scaffold3474_m_2213
GAGAAACTGAGCTAGCCTTCGAGCTAGTTGTTGGCTTTAAGCTGGTTGCT[A/G]GCTTCGAG
CTAGTTGCTAGCTTCGAGCTAGTTGCTAGCTTTGAACTGGTCG scaffold348_m_329
ACACTACACGTTTTAGTGCAATACTCTAGTTATATATAATATTATACTTT[C/T]TTAATAATACTA
TTTAACTTAATACTTTATTTCCCTAATATAACTTAAAGA scaffold3496_m_3312
TTTTATTATAATTTAGTTATTTAGTTATAAATTTATAAAGTTTTACCTTA[C/T]TTAGAAAATTAGC
TATAAGTAAAGGTATAGGGTATATATAAAAGATATTTT scaffold3504_m_1032
TTATTACACATTACATTACATTACATTCATTACAAATGTAATATCAGGGG[G/A]AAAAAAAGTG
GGGTATATTAAGGTCTTATAATATTGTATAGAATTTTCTCT scaffold3515_m_257
AGTAAGCTTTAGACCTTTCTTTTTCTTAGCTAGCTTATTTTATTTCCTTA[A/G]TTAAGTCCTAG
CTATATATTACTACATATACCCTAGTTATTAGTATATTAC scaffold3521_m_451
GATAGGCCTAATAGAATACTAAAAAATTATTAATCTTAGTATATCTTAGA[A/G]GCTTTAAAATA
ATTTAATATACTAGATAGTAAGTATATCTTAGAGGCTTTA scaffold3533_m_675
GTTTTAAGTTATATTAGTAAAATAAAGTATTAAGTTAAATAGTATTATTA[T/A]AAAGGTATAATC
TTATATATAACCTTACTTAGTTATAGTAAAATTATTAAA scaffold3540_m_874
TTTAACGGTCAGAGGCCTTGTCAGACAGTCGGATTAATTAGTCTAACGAC[C/G]GAAGCTTTT
GTTAGCGGTTAGAGACCTCGTTAGAAGACCTTCTATTAGTCA scaffold3565_m_739
TATAATAGAATTTAAGAAATTTGCTAAAAGCTAGATAAATTCGCTAGTTT[A/G]CTAGACTAAGA
GAATGAATTTAGACTAAATTAAAACGGAAATAGTTAGTAT scaffold3568_m_12116
AGGCATTTGATTCAGCCAGCATTGACGACACACATCACATGCTTGCTTTG[C/T]ACATGTGAA
CAACAGGAACAGAAAAGGACTTCGACAGTGGCGACCGAGTGT scaffold3593_m_1869
AGGGAGCGTTAGTTTAGACCTATCCTAATTCTTATATAAGCGTATGTAGT[A/G]ATTAAGGGAC
CCCTAATAAGGGGGAAGGCTATTAGCTTTAGCCTTATTAAA

Figure 6 Continued scaffold3598_m_7160
AATTTATAATATTTACCTTTTTTTAAGGATTTTACTATAACTAGGGTTAT[A/T]TATAATATTATACCTTTTTAATAATACTATTATACTTATTACTTTATTTTA
scaffold3600_m_5156
GACTAGTACTATATTATAGTTAACTACTATAACTATAACTATATATAACT[G/C]CTATAAAACTAGCCTAGAGATATATAGGAAGTGAGGCTAGCCTTAGATAAC
scaffold3601_m_2320
ATTAGTAATATTATATTACCTATATATAATACACTAGGCTTCTATTTACT[T/A]ACCTATAACTCTAATATACCCTTAAGGATCTTAAGGCTAAAATTACTATAA
scaffold3615_m_14094
TTTTCTGCTTTGCGAATTCGCCATAATCGAGTCGCGCCGCTCGCACGGGA[T/C]TTGTGAACAGAAGGACGTGCGCACTTCTACTCCATCGGGCGGGTAGAAGCT
scaffold3626_m_429
AAGGTTAAGGTCTTTTAACTATAGCTACCTTATAATAAGTAATTTAAGAA[G/A]AGAGAAAATCACTATAGCCTAAGACTAAAGACCCTAAAGACTCTAAGGACT
scaffold363_m_10537
TCTAGGCATGTTTTCCTTTATTATTTAGTAGCATAACCTAGGCCTTTAGG[C/T]AATAGTTTTTATAGTAACTAATAAGGTTAGGCCTTTTTTATAGCATATTTA
scaffold3630_m_291
ATAGACCTTTTTAATAAGGCTAGAGCTAATAGCTTACCTCCTTATTAAGA[T/G]TCTCTTAATTACTATATATACTTATACTAAAACTAGGATAAGTCTAAACTA
scaffold3642_m_267
AAGTTCCTAGGTATTATAAGTTAGCTAGATATAAAGAGATACTATAGTCT[T/C]TAGCTATAAAACTTAAGGCACTCTAGTAAGGTAAGTAAGGATAAGTATATA
scaffold3644_m_236
AGGAGACACTCTATTCCTTATTTTAGGCATACTAGTTTATAAAGGTAAAT[A/G]TTTATATAGCGTTTTATAAGCTATAGATTACTAAGGGCTAGGAGCACTTTA
scaffold3670_m_2561
TAGAGGTAACTTACTACTAACTTACTAAGTATTATATTAGCCTTATTATA[A/G]GCTTTAACTATACTAATACTACCTATTATATTATATTTAGTTTAACTAGTA
scaffold3722_m_2534
GTCCGCATAACTTCTTCTACTATAGACTTTAGGATAAGGGGGCCTAAGGT[T/C]ACTCTATAACCCTTAAACTATAATAACACTGTTTTAATTAGGGTTTCCTAG
scaffold3733_m_313
CTTAGCCCTAATACTTAGATTAATAACCTTACTATATATAGAATCTAGCT[T/C]TATAATAAGTTTTAATTAAAGTTATAGTGCCTTATAGTATTACTTTACTAT
scaffold3751_m_544
CCTAAGATACCTAAGATTAAGTGTCTTTTCCCTTAGGCTTTATTATCTAA[C/T]CTAGCTAAGGCCTATGCCTCTAAGCGCTATATTTAGTATAAGAAGAGAGGT
scaffold3755_m_672
TTATATAATTCCTTAGGAATATCTTTAATAGTTTTATATACTTTTACCTC[T/C]TTATTATCTTTAAGGGTAATAAACTTATTTTCTATAACTCCTATAATAGTA
scaffold376_m_737
TATAACTTCTTATATAGTGATTTAGTGCCTTTACCTTTAATCTCTTAGAT[T/A]ATATAAGAATTAAAGATCTAGTAGCCTTTATACTTTACTAGATTAAATATT
scaffold3768_m_1429
GGATTTACTATTATAAGGTTATACTAAGTTTACTTTAAGAGCTACTATTA[G/A]GTGTAAGGTAAGATTTCTAAAGAAGGTTAATTCTTTTATCTAGAGTCCGA
scaffold377_m_496
TACAATTATTAGTAGCTTCTTACCTCTTTTCCCTTTAATCTAGGTTAGCT[G/A]GATTAAATCCCTTCGTTCTGATTAATTAATCTAGGTTATCTAACTAATCTA
scaffold3785_m_18071
GCACGATTCATTGCAGGGGCCGGCCACCTGCCCCCACGTGCGCTGCGCCC[A/G]CCTGCGCCCACCTGCGCCCACCTGCCTGCGCCCACCTGCCCCACCTCGAA
scaffold3796_m_28285
TCCAGGTTCAAGTGCGCGCGCACCGGAAAAACAATATGCATCGCCCACGC[A/T]GGCCACCATGCGTGCTGCGATCAAACAGAAGAGCAACGATTCATCGGTGGG
scaffold3801_m_4312
TATTAATATTATAAAGCTTAGTAATAGGGCACTTTCCTTAGAATAAAAAG[C/T]ACTTCTTCTAATTCTAATAGATTCTTACTTTTATAAGAATTATTACTAATA

Figure 6 Continued scaffold3802_m_1127
TGTAGTTAGTGTAGTTTAGGGGAAAAAATTTATATTATATTATATTGTAG[T/A]TTTTTCCTGCT
TGTAGTTAGTGTAGTTTGTAGTGCAATACTCTGCTCTTAG scaffold3845_m_6529
AGGTTATGGCAGTTATTAACTATTATTAACTAATAGAATTTAATCTAGAT[A/G]ACTTTTACAAT
ATCTTATATACTAATAGAATTGATTTTAGTGACATTATAC scaffold3848_m_757
AAAAAAGGAAAATATTACCTTAAAGGCCTATATATAATTTAGCTAAGAGA[A/G]AGCTAAAGGT
CCTTAGAGAGTACCTTATAAGTATATAGCTTAAAGGGTAAA scaffold3850_m_1541
ATAATTAGACTATCTTAATAGTATATTTATAATTAGACTATCTTAATAGT[G/A]TATTTACTAGGT
TACTTTTCCCTAGTCTATACCTAATTATAAAGTAAAAGG scaffold3858_m_3362
GAAAGCAACGGCTAAAAACGACAAGAATTTTCTCGTAGTGGGAGCCCACG[T/C]ACCAGTTTA
TGCTCGCCATTGTTATTGTGCCCCTTCTTCGTAGAATCTAC scaffold3864_m_576
AATTACTTTCTCTATAGTATAGTAAAAGTAATAAACTACTATAACCTAGG[C/G]TATATACCTAG
GGTTAGAGAGCTAGAGCTAAAGGACTTATCTTACCTCCTA scaffold3882_m_650
ATTATAGATTTAAGTAAGAAAGCTATAGATAAGTTACTAATAGTTATAAG[A/G]ACCCACTTATG
GACCCACTTTTATTAAAACCGATTAAAAACCCTCTCTTTA scaffold3886_m_833
AGTTTAGCAATTCCAGTGGTAGCAAGAATAGCATTAACAGGACCTTTAGG[T/A]CCTAAGGAC
CTAATATCTATAGCAGTAGTAGCAATTAGAGTAGCAATTATA scaffold3887_m_17925
CCACCCACCATCATCAGAAGTGGGCAACAATGTATCTCCATCACAGATCC[G/C]AAACCACCA
CGTCTCATTCGTCTCGTCTCAACGAGTCAATCGCCCCCTTCA scaffold389_m_535
AAGTATTAAGAAATAATATAGTTTAACTAAAGTAAAAGTAGCTATAATTA[T/C]ATAGAGTGTTA
GGAAGCTCTAAAAAATAGTTTAATCTAATAACACGGTGGT scaffold3898_m_14459
TAAATCTTAAACTATAAATTAAAATATTATAAACTATTTATACTTTATAG[C/A]TAAAAATATTCTA
ATAGTAAGGCTTCTAAATATTTATAGCTGATACTTTAC scaffold390_m_236
AAAACCTTCCGTTGCGTTGCGTTAAATATTTAACGTAGTGGTTCTATTAG[A/T]CCCTAACCGT
AGAGCTGCACCTGTACAGCTGTTGCCAGCCAGCAACTAGCT scaffold3907_m_1604
AGCAAAATAGCCTAGGATAGGCATATTATTAGACTAGATTTACACTAGGA[G/A]GGGGTATAG
TTACCCTTATTTTAGTAAATCTTTCCTTTATCTTTCTTTTCT scaffold3908_m_1411
GATTAGTTAAGATCTTATTAGAATAAAGCTTAAAAAGAATAATCCTACCT[C/T]TTTACTATTAG
CTATAGGCTAGGAAAATAAGCAGTTTAAAGTAAAAACACC scaffold3925_m_730
TAGACTATTTTAAGTACTTAATACTATAGGAAAATAAGCTTACTAACTTA[C/T]ACTACCTAAGA
AGTATAGCTAACTATATAATATATTTTATATTAGCTTACT scaffold3947_m_571
TTCCTATAATAATTATATTATCTATATATAGAAGAAGTATAATATTATTA[T/C]ATTAAAAAATAC
AGAGTTTGCTTAATAGCCTCTTAAAGCCTTACTATTTAA scaffold395_m_2914
TTAATAGATTACCTTAGAGGGAATTAACTAGTAATATTTAAACTAAAACC[T/C]TATAAGTTAGT
AGTATTTAAAGAACTTTAATAAAGATTTTAAAAAGCGCTA scaffold3951_m_137
TACACTATATAAATAGTGTTTACTAGCTTATATAGTGCTTTATAAATATA[C/G]CTTTAAAAAGT
AACTAAGGTATTAGTTAGCCTAAAGGGTATTATAAGATAT scaffold3958_m_494
CTTTAAGTGTAAAGTTACTAGATATTATACTATAAACTATATTATAACTA[G/A]AAATAATTTATT
ATAATAATAGGAATTCTTATAGTTAAAATTAATAATACT scaffold3961_m_942
TATATATAGTACACTAGGCTTTTATTTACTAACCCTTATCTCTATTATAT[G/A]TTAAAGGATATT
AAGGCAAAGATTACCTTAGGTATATATATTATTAAACCT

Figure 6 Continued scaffold397_m_975
AACTATTTTACTAGCTAATATAAAGTAAATATAGTATTTTATTACCTTTA[C/T]TATATATAGGCT
ATTATAGCTTATACTAAATAAGTACTTTTTTAAAGGTAC scaffold3994_m_287
ATTAAGATATAGATAAAAATACCTATATATAAAGAGAAAATATATAAAAG[G/C]TTATAAAATTT
CTTAGTAAACTTAAATAAATTATTTAAATTAAATTACTAT scaffold3996_m_976
GCTTAGTATTAAACCACTTCTTATAATTTAAATATACTTTATATAAGTAT[T/C]TAATATACTCTT
TATATTTCTCTTAAGATAATATATTTAAAAGAGATATAA scaffold3997_m_12754
ACGCTGCGGTTGTACTCGTTAGAACAGCAGCGCGACCGTCACGGCGGAGG[A/G]CATAACT
TGCACATACAGGCAACGATCATCTACGACCTTTATGACACTGCG scaffold4003_m_1027
ATATTAACACTCTTTACCTAATTATATCTTACTAGCTTAGATATTTTACC[G/C]TTTTAGGTTTTA
TTATCTTTATTTATTTTAACTACTTAATATACTTAGAGT scaffold4018_m_366
TTATTAACTTTATAATAAACTTACTAGCATTTAGATTAATTAGGAAAATT[C/T]TAGATAATATTA
TGCTCCTTAGTTAGGATTAATTAGTTACTTTTTATATTA scaffold4028_m_902
TATATAGTTCTTTTATAAGGATATAAGGCTAGTAAAGTAGTAGGTAACTA[A/G]GTATATAACG
CTATCCTAGCCTTACTAGGAAAGGTTAGCTTTTACTACTAT scaffold4040_m_148
TAAGTTTATAAAGGTAATATATAATAAGACTATTATATATACTATTATAA[A/G]AGTTATAGAAG
ATAAATTTATTACCCTTAAAGATAAGAAAAAAGTAAAAGT scaffold4050_m_167
TTATATATTTTTAATAAAGCTTATTAAGCCTTTAGAGTTTATTTTAGTTT[C/A]TTTCTTAAGACT
TTTTCTTTTTAAATTAATAGCTTTTCTAATTATATTATC scaffold4067_m_4476
CTTCTCCCGACCCTTGTATCCCCTACCAAAAAAAAAAAAAAAAAAAAAAA[A/T]GTCCCATCGA
CATGCCCCTTCAGTCCGTAGCGATATTCCACAGCCCATCGC scaffold4068_m_227
AGCTAGCTATAGTTTACATTAGGACTAATACTTAGTTAGTCTAAGGTATA[A/G]GTTTAGCTAG
CTATAGTTTATATTAGAACTAGTACTTATTCTCTATAGTAA scaffold4075_m_279
CTAGATAAATACTAGCTAGGGGCAGGTATATAAAGGTTTTAATCTCTAAC[T/C]TAGCACTAAT
AATATATATAGTCTTTAATAAATACCTTACTCTACAAGCAC scaffold4086_m_715
ACTAGATAGTAGCGCTTAATTAATCTAGAATAGTACAAATTAAACGCTTT[C/A]CTAATCTATTT
TGCTTATAGATATAGGGACTAGAAGTTATAAATTTAATCG scaffold4095_m_2264
ATATATAAGTAGTTTACTACGCTTCTCTAAGCTTTAATACCTTATTACTA[A/G]GATAAAATCTA
GTAATATATTTAAATTACTAGGTTAAGTAATAAATCTCTT scaffold4098_m_1478
TCCTTAATATTCTTATATTATCTAATAGTAATATTTTCTAACCTTAGCTA[G/A]ATAATCTCCTTA
AGTATAGTAATAACTATAGCTATATTTTATTATTTTTCT scaffold41_m_327
ATTAAACCTAACTAAGCCACAAAGCTAAGGGATTAGCCTATACCTATAAG[C/A]TTACTTAACC
TCTTAATTAACTTACTAGGGATGTAAGCTAGTAATAGGGAG scaffold4120_m_1511
TAAGGTCTTATAAAGCCATTCCCTATGTCTATTTATTAGTTATATATAAA[T/C]AATTTACCACT
CTCTCCTATAGTTATAAATCTAAATCTTTATTTACTATAT scaffold4125_m_147
ATTAAATCTTACTAACTTACTTTTAAGAAGACTAGATTTTATAAGTAAGG[C/A]AAGAAAAGAGA
AAGTAATAACTATATAACTTCTTACCTTTTTATTTAAATT scaffold4134_m_28756
GATTGTTGAGATGGCGTACCTGCGTACGTTCGACCCTTATCAAAACAAAA[C/G]AAAAGAAAA
AGCATCGGTCCGCTATGCGCGGACCGGGCAAACCCAAAGAAA scaffold4136_m_1307
AAACTTTTATTTATTATCTTTAATAGTATCTTATAGTAAGAACGCATTTT[A/C]TATATTTATTAA
GTCCCCTTTAAAAGGTTTAAGACTAGTAATATTAAATAT

Figure 6 Continued scaffold4158_m_645
AGTATTATTAATATACTCCTAAAAAGTTACTAATATATTAACTAGTTTAA[G/A]TAGTATTACTAG
ATATTTAAAGTAACTATATTAATAATAAAACACTATTTT
scaffold4159_m_1259
CTACTCTTTATATTATCTTTATTTAATTATCTCTTATTTATTTAGCACTA[C/G]TCTTAACTCCTTT
ATGTTCTTAGAGATAATTAATTATATAGGATAATTTTA
scaffold4160_m_808
CCTTTAGATATTATATACTAGGATAAGTTCCCTAGTTTTAATTAATCTTT[C/T]CTAAGAGAAAT
AGCTTAGTTCTTATTAGTTTAGTTTATAAGGCATTGCCTA
scaffold4172_m_3003
ATTTAAATAAGAAAATCTTGTTTTTATATATATTTTACTTATTTAATTAT[G/A]AATTTCTAAAACT
TTAGCTTATTTAGAATAATAAGCTAAGAATAGGCTAAG
scaffold4195_m_375
AAGTTATTTTATATAACTATTAATCTTTTACTTCTAAAAAGATCTCCTAG[T/C]TTAGCAAAGAG
TCTAGAATACTAGATTATTCTAATCTAGTTTATGTGTAAA
scaffold4218_m_107
TAAATTAAAACTAGAATAATACTAATAATAGAATACTTATAGTATTTAGT[A/G]ATATTTTATTAT
AAATTTCTATATAAAATATTAGTAATTAAACTAGTATTA
scaffold4220_m_2396
TTATATTACTTAAATATATTACTTTAAGTATTAAGAAACTATATAACTTA[T/G]AAGTCTCTTTAT
TCTTATTATAGATATTATCCTTATAATATTTAATTATTA
scaffold4241_m_15908
ATAATAAGACGCTTGAAAAGCTTGTGAAAGACTTGCTAGGACCTAAATGG[A/T]AACCATGCC
CGGCGTGGCTCAAATGTTTGTCGATCTGTCACACATGCCATT
scaffold4249_m_369
ATAATAGCGAAGTTAGGGATAAAAGATAATATTATAACTATAATAGCTTA[G/A]ATTACCTTATA
AATAAGTATAGTAAGCTAAGGAAAGAGCCCTAAGATAGCT
scaffold4256_m_21513
CTGTTACTCTTCCCAGACCGTTGACTAGCGCTGCGACCTTTTTTTTTTTT[G/T]TTTTTTTTTTT
TTTTGTTTCGAGAAAGGACATGAGTTGATGAGGGGCCAAC
scaffold427_m_1631
TGCTACTATAAATATTTATAATTAAACTAATAGAAGATTTTAACTTAAAT[A/G]CTCTATAGTAAT
TAATTAGTTTAAAAGCTAGAAAACTTTATTCTAATTACT
scaffold4270_m_741
ATCTCTTTATATATTATAGTTAGTTTACTAATAACTTATTAGTTTTATTA[A/G]AATAAAACACTT
ATAGCTTACTATATAGAGTAAGCTATACTATAGCTAGCT
scaffold428_m_285
GAAAATAAGCCTTATTACTAAAGGATAAGGACTTTAAATGTATAGCTTAT[G/A]ATTAATCTAAG
GTAGTACAAAGACCTAGGAAGTTAGCTATCCCTAACCCCC
scaffold4286_m_15963
TATCTCAAAGCGTTATGCAGGGGACTAATATAATGAGCCGAGTATTATAT[T/A]GAGAAAGAA
GGCAACCCGCAACTGGTCTAGTCAACAATGGTGGTTCCATCT
scaffold432_m_198
AGGAGAGAGCTCTTAGAATACCTATAATAAGATAGCTAATAGTAGCTTAG[G/A]ATAGAATAAA
TAATAAGGACTTATTATTAAGAAGTAGTATTATAATAGAGA
scaffold4322_m_1461
AAATCGGAAGGGCCAAGCTTTGAACTGACTCTGGTCCTGGGCCATGTCTC[C/T]ATGCTCACT
TCCCTCGTTGTCGCGGAGAGCCAAGGAAAGAAGTACATCTTG
scaffold4339_m_23249
GCATGGACCGGTAACGTTTTTCCTGAAAGAATGAGCCAAGTCAGTTAGAG[C/T]CAGATTGGA
GGCACGAGGCAAAGTGCCGTTTGAAGAACGTTTGGCGCAATC
scaffold4342_m_12826
ACCATGCCCATCCGTTGCATGAATAATTGCACCCCTCTCCAGAAGCAGAC[C/T]GACGATGCT
CGCATGTCCTTCACAAGCAGCCCATGAGAGAGGAGTACGGCC
scaffold435_m_1749
CTATAGGGTAACCTGCTTACGTCACCCTAGCTTACCTAATTACTAGTGGC[A/G]CTGCGGTTG
TGGCTACGCTTGCAGCCATAACGCAATTAAATAATCCATAAT
scaffold4377_m_2049
TCTCTCCGAATTCTTCTCACCGACCTCAACTTGCAGACAGAACCTCCCCC[C/G]CCCCCCCC
CCCCCCCGCCCCCACCCCCACCATGTCGTCAGCCCTCATCTCC

Figure 6 Continued scaffold4382_m_4477
GTAGCTTTATATAAGTAAGTAAATTACTAATTATATCTCTTAAATATATA[A/G]AAGGTTTAGTA
AATTTATTATAATAAAGCCTCTTATTATAAATAAAGCTAT
scaffold4397_m_551
AATAAAATTAAGGCTTTAGCTAAGCTAACTAATCTTCTAATTTAGCCTTT[T/A]AGCTATATACT
TAACTAATCTTTTAATTTACCCTTTAAGCTATATACTTAT
scaffold4408_m_1639
GAGACTATAGTATAAGTTAAAATATACCCTAGTCTAATTACCTAACTATA[C/A]TAGCTTACTAT
TAAAGTATTATACTAGATATTAAGTCTTACTAATTAGAGA
scaffold442_m_502
ATATTTACTATACTTAAATATTTACTAATATTACTTATAAGGTAAAATAT[T/A]ATAAATATACTAT
AATAGTATTACTAAGTAATACTATAAATTTAAAGACCT
scaffold4428_m_17646
AGGGGTGCATGCTCGAGAAACTGCCCAACTTGTTCTATTCCATGGGCTAC[G/A]TCGACGCG
AGCTGGACGCTCGGCGCCGACGCCACCGCCCAGCTCGTCTGCC
scaffold443_m_893
TAATAGCTCTATTAATATTAGAAGCTAAAGCTAACGCTATCTGCGAGACC[A/T]TCCGGGAGC
TACAGTGGCTTCAGGGCTTGATTAATATTAGAAGCTAAAGCT
scaffold4438_m_155
TTATAGTAAGCTTTAAGGAGTAATTTAAGTAAGAAAAGAGTTTAATTATT[T/A]GTCTAGTAAAT
TTAGGAGGATTTAGATGCCTATAACTAGGTGCTTTAGGAT
scaffold4464_m_6452
TATTTTAAAAGCAAGGACGCGGGGTTTGGAAAGAGAACGGAAGTCTGGGG[G/T]TTTTTTTTTT
TTTTTTTTTTTTGCTAGCCATGCTTTAGTAAATTTTTTTTT
scaffold4468_m_261
TAATAAAAAAGGGAGTTATTACCTAACTTACTATAGTAATAAGGGATAAG[C/T]ACTTAGATAA
GGGTAATAAACTATTTATATATTTCTTTATATATAGTGTTT
scaffold447_m_2965
AATTATGTTATAAAAAATCAGATGCATTGGCTATAGCCAATGAGGTAAAA[A/T]TTTTTTTTTTT
AAAATCAATAAATCAATAATTGTTAGTATCTATTAGGATA
scaffold4470_m_648
TAAGGAGAGTATTTGTTGTGCTGAAGTCTGACGGTGGTGGTGGTGGTGAC[A/T]GCAGAATA
GGCAAGGAGAAGCCAGGAGAAGCATAAGCTCCGGAACCGGGTT
scaffold4482_m_478
AAAGGTCCTAATATCTTAAGATAAGGGTAACTTATATAGCTCTATTATAG[T/G]CTAATAAGTAA
GTATTTTAAATATAGGTTTTCTAAATGCTAGTAAAGGTAG
scaffold4495_m_220
AAAAATAGTTTACTAAGGTAACTATAGCTATATTTATTTATACTTATAAA[A/T]GACTAGGAAGA
GCTTATTTAACTAGACCTAGAGATTACTATATAGCCTAAG
scaffold450_m_524
TTAAAGGACTCTTATAGTTCTTATAAGTAGAGCTTAAAGTAATAACTAAT[G/A]CTTAAATCCTT
ACTAAACATATATAACTATTTAAATTTAATATTATATTAG
scaffold4500_m_2927
TCAACATGGCGCAGGCAAAGAAGAACCTCCTGCTCCTTACGATTAGGGAA[A/G]TTGACGCA
GAATGGAAAAGGAGAAAGTCAGGTAGGATATTTGCGTATCGGC
scaffold452_m_15327
AAGAACTATATTCGTATTTCTTAAGATCTATATATACTTACTTTAGTGTA[T/A]AATTTACACTAT
AAAGTTAATTAACTATAAATATAATATTAGGTTATATAA
scaffold4525_m_115
TTAATTTTATTCTATTAGTTTAGGGTATTTTTTATTTAAAATAATAATAA[A/T]AAAATATAAAAAT
ATAAAATAATTAATAATAATAGTAAATAAAATAATAAG
scaffold4528_m_7220
GATGCGTTGACCCCACGCGGACATACACCAACGACCTGTGGCAGATTGT[C/T]GAGGTGTT
TGGCATTGAAGCTGCCCGTTCTGCTCGGTGAAGGAGCTGACC
scaffold4534_m_2007
CCAGAGTATTGCACTACAATTGATTTGTAGTGTATTTTTTATTTAACAAA[T/C]AATATATATCT
AATCTTAGAAAAATATGTAAAGATATAAAACTTCTTTTTTT
scaffold4544_m_1169
ATTAGTAATTTAGTATTACTAGAATTTTATATTAAGATTATAATAGAATC[C/A]TACTATTAATTT
AACTAGGTTTAACCTGATTTTTACTATAATAGTAACATT

Figure 6 Continued scaffold4547_m_694
>TAGTGTTTAGCTTTGCTAAAGCCTAATCTTATATAAAGTAATTAAGATAG[G/A]AAACAGGAGT
TTAATAGTTTCCTAGGATAGATTAGTGTTAATAAAGGATAA scaffold4553_m_2124
>AGATCTTTAAAATAAGTCTAGGTAAGGATATATTAGTAAAGTTTAAGTTT[T/C]CTCTTTTATCC
TAGTAATTATAATCTTTTCCTATCTATAATATTTAATAGC scaffold4577_m_430
>TTCCTTCTAAAATCCTATATAAGCTTAGATAGTAATCCTAAATAGCTTAG[T/C]ACCTAATTAAT
ACTCTTAAAGTAACTTAGTGTTATAATTATTAGCTATAGG scaffold4588_m_6001
>CCCAAGCGACCCAGGCGGCCATAATCTTAAACAGCATTTCCCTTTTGCAA[C/T]ACGCTCGAA
TGTTTTCCTAAAAAGTGAACAAGTAATCATTGTCTAGATAGG scaffold4590_m_1568
>TAATAAGATAATAGCATAGAATTATTACTCTCTCCTATTAATTAAGAAAA[A/C]ACTTTACTTCTT
ATTTTAGGTATATTAGTTTATAAAGGTAAATATTTATAT scaffold460_m_1269
>TACTATATAAATAACTAGATTAGAGAATTAACTAATAAAACTAAGGATAG[T/C]AAGGACTATA
GTATAGACTTAGTAATATACTTAAATAGTGTGGGTTATACG scaffold4623_m_1047
>CCTTAATAAAATTAGCTATATTTTCTCCTAAAAACTACTAAATATTATAC[T/C]TATTTTATATAG
TAATAAGAGAAGTTTAATATACTATTATTTCTCTAAGAA scaffold463_m_805
>ATAAAGAGATTAAATAGTAAAGCTATTTTATAAAGAGATTAAGCTATAAT[T/A]TAAAGCCTTAG
AGGGCATTATATTTAATAGAGAATTAGTCTTTATAAGTTA scaffold4639_m_2585
>ATTATTAGGTACTGCATTTTCAGTATTAATAAGATTAGAATTAAGTGGAC[T/C]AGGAGTTCAA
TTCATATCAAATAACCAATTATATAATAGTATCGTTACAGC scaffold464_m_1495
>AATAATCTAGTATTCTAAAATCTTTACTAAGCTAGGAGATCTTTTTAAAA[G/A]TAGAAAATTAA
TAGTTATATAAAATAACTTTAAGATCTAATATTATAAGGT scaffold4650_m_17534
>CTAACCATCTGCTATCTAGTCCAATTCGCTCTTCTTCGTGTCTACGCAGT[T/C]AAACTTGCTC
CTCTCCCTCTCCCAAGCGGCGTGACTTAACTTCTTAGTCAC scaffold4661_m_923
>AGTTATCTTCTATAATAATCTATTCTCCTAGCTAAATGGCAATTTTGCCT[G/A]GTTTTCTATGG
GTAATTAGGTATTACCTTCTAGCACTATTTTAACGTGCTT scaffold4668_m_26419
>TCAACAACAACCTCCAATATAGACAGTTGTGACACCCCAGTAAAATCTCT[T/C]CCAATTAATG
CAATAGGGTATCAAAACAAGAGGCTCAAAAGACAAAGGAGA scaffold467_m_6110
>AACTTTAAGAAAAACCTTCTAATTATTTTATTTACTATTATTATTAATTA[C/T]TTTATATTTTTAT
TATTAATTTAATTAAAAAATACCCTAAACTAATATAAT scaffold471_m_7897
>TCTATAGGAATCCTTATTTTCTTATTATAAAGAAAGATAAAGGGATTTAC[T/C]TAATTCTATTTA
CTATAAAGTATAATAAGGTAATAATATAAGATATGCTAA scaffold4715_m_347
>ATATTATAATATTGCAATTTTTAGCAATATAGCCTTTATTTTTTGCCTTA[C/T]GTAAAGATTTTA
ACCAAGTCTTGTATAATCCTTGGTTATTCTTGATAATAA scaffold4724_m_6984
>GTTTGACATGGAATGCAAGCAGCAGGACATTTTCGACTTCTCCATTCGTC[G/C]CACTGTTGA
CGACATCTTGAACGGCTACAATGGCACTGTCTTCGCCTACGG scaffold4754_m_14148
>GGATGATGTGGAGAAGTAGACTCACTTCTAAGACTGCGATACGGAATAGT[T/C]AGGGAAAG
CGGAGCTTTGCCGCAAATGGACAAATGGACAAATAGACGAATA scaffold4778_m_753
>TAGTTAGTTTTCTCATATAGATAATAAGATTAATAATTAACTAAATATCC[C/T]GGATAGATATA
ATAAGGTTATATCCTATAAGCCTAAGGGTTAATAGATTAA scaffold4781_m_507
>TAGCTAGTAGCTTGCTAGTGTTACATAAACCTAGCCCTAGAGCCTTACTA[A/G]CCTATAAGG
TGCATAGGTATACCTATTATTGTAAGTAAGGCCTTATAATTA

Figure 6 Continued scaffold4782_m_1926
    ATCCTTCTTATTTACATTTGTAAGGGCTTAGACTTTGCCTAAGCATTGTC[T/C]GTATAGTAGTT
AGAGAGGGGATTAGTAAAAGCAATTAGGGTAAGGAAAAGG
scaffold48_m_374
    TTTATTACTAAGTTAAATACTTTAATTATAAGTAATTTATTACTAAGTTA[G/A]ATACTAAGCACT
TAATTTACTCTCTAAAGACTAGAATATACTAAACTAATA
scaffold4800_m_8121
    AAACTCAGTTGAACATGTCGGCCGAGATCTGAGTGATCCTCGCCCACGCA[A/C]TCACGCCA
GGCCGGGCAGGCGTCTTCTGCAGCCTCGTCTTGATGGTGTCGA
scaffold4803_m_3263
    ATGTAATCAGGCCGGCTGTCCACGAACTCTCCCAAGGAAAGCGCCCTACA[A/G]AAGTGTTC
CAAATGAGACTTGGCGTTGTCAAAGTCAAGTCTTGCCCCAGTA
scaffold481_m_9752
    GAGTAGAGAGCAGACAAACAAGGAAAAAAAAAAAAAAAAAAAAAAAAAAA[G/A]AAAAAAAAA
AAAAAAAAAAAAAAAAAAACCCGTGTAGCAGTTCAAGTACAAT
scaffold4810_m_287
    ATATATATCTTAACTATTAGTTTTAGTATTTCTAAGTTTAATAGTTAATA[G/A]AAGCCCTATATA
TAATTAGTATAGGATAATTAAATATAATATATATATCTA
scaffold4817_m_11318
    CCCCAAAAAGAAAAGAAAAGAAAAAAAAGAACGCCTCGCTTACTCTGCCT[G/C]CCCCACGC
TCCACCACAATCACGCAGCAGATATTACTCTGCCTCCCCCACG
scaffold482_m_1913
    TATAGGGATACCTATATTATTTATAGGGTAATCCTTTAAACCTTAATTTA[A/G]ATCTTATTATTA
TACTAAATTATTTTCCCCCTCTAAAGGGTTATCCCCTAT
scaffold4834_m_1388
    TTATTACACATTACATTACATTACATTCATTACAAATGTAATATCAGGGG[G/A]AAAAAAAGTG
GGGTATATTAAGGTCTTATAATATTGTATAGAATTTTCTCT
scaffold4853_m_6855
    GGTCCGGGCGGGCAACTCGAGCCGGGAAAAAGGGGGGGGGGGGGTTTTTT[C/T]TTTTTTTT
TTTTGTAATAAAGATTGCCCGAGATGAGGTTTGCCTGGGGGGGG
scaffold4856_m_4697
    TTCAAGCTGGTACGGGGGCTTGGATTAAAATTGCCACATCTACCCTACCT[T/C]CCCTAAATT
GAAGCGACATCGAAGCGACATTGAAGCGCGACATGAACAAAA
scaffold4865_m_25940
    AGTAATCATGGCTGCAATGCACTGATCTTGGGTGTACGAATTGGCCGCCG[G/C]TCATGAGA
GGAGATTGAAATCTTGTCTATTTTTTGGGAATTATCAATGCTC
scaffold4886_m_296
    TATATTAATAAGATTAGGGAAAAATTTAGGTAAGTAAGAAAAGGCACTTT[T/C]CTTACTATACT
AATCCTAGTAGTAAAGTATTATAAGTTTAAGGGTTACTAT
scaffold49_m_4162
    TAAACTTATTAAGGGCCTATATTTATACTATATTCTCTAATAGTTCCTAT[A/G]TAGGCTATATA
TAGCCCGCTTACTTAATAAGTATATTATATCTCTTGCCCT
scaffold492_m_242
    CCTTAGATATTAGCTATAATTTTACCTATAGTCTATAGTAATTATATAGT[A/G]AGGTAGTCTTA
TTAAAATATAAATAAAAATGCTTATATATAAAGGGGAAAC
scaffold4940_m_21612
    TATTGAGATGCATCAAAAATGTGACAACCTAAAAAAAAAAAAAAAAAAAA[A/G]AACGAAAAGA
ACTCGCAGGATATCGTGTCCAAAGACGTGCGGAATTAAAGT
scaffold4980_m_520
    TCTTTTGCGACAACCTCAACTTACAACCGCCACGACGCCAATGATCCTCA[A/T]TGTCCCACG
AGCAATATCGTCACCCACGAAAACAACCAGCGAACAATCTTC
scaffold4989_m_4820
    TGAACTGGATACAGCATAGGTGTAGTAGACGTTTCTTTTTTTTTTTTTTT[C/T]TTTTTTTTTTAA
AAAAGCCCATTCGACTGTTGAAGCTTGTTTCTGTTTCCA
scaffold5010_m_13835
    TTCCGGCGGATCGGGACGACGCTCCCAGGGCGTGGAGCTTGAGCGACGGG[C/T]GTTGGG
CGAGGAGGAGGATGAAGCGCTGGCCGACGGAGCCTGTGGCTCCAA
scaffold5025_m_2345
    TATTTGACATTGAGACTTGGCATGATGGAACTTGAGGACGACTGCTCTCT[C/A]TAGCAATTC
ATCATGGCAGGTGTTTGCGAGATTCCATGTCATGGTTTTCAA

Figure 6 Continued scaffold5043_m_16469
TGTACACAGCGAAATCGGGGACCGAAAAAAAAAAAAAAAAAAAAAAAA[A/C]CTACCCTCC
GCTCAGTGAATACGGAACTAGGATCCATCTCTTGTTTTTGGA scaffold5057_m_32065
ATCTAGGTTAGTGAACTGGAACTGCTTCTTCTCGCCTGCTCCAGCACTAG[A/G]CCGTGGAG
GAGCTGTCCCTTCTGGCTGGCCACCCGCGAGGCTCGCCCTTCT scaffold5065_m_641
TAGGGTTAGAGGGCTAGAGCTAAAGGACTATTCTTACTTTCTAAGGGTTA[A/G]AGGGCTAGA
GCTAAAGGACTATTCTTACCTCCTAGATAAATATAGTATTCT scaffold5084_m_3518
TTCGACAAGGGTCAGATACAGCTGCCTCAGCCAACACGCTCTGTCCAGCT[A/G]ATTTATCAT
ACATGATGCTGTTTCATCATGTCCACGCAGAAACGCCTCTTG scaffold5089_m_17633
GGAGCGGGTAGGCAGTCTTGGTAAGATAATGGTGGAGTTGCGCCGCACGA[A/G]CCGACAA
ACCGCCAAAAGAGGAGGCAATGGTGTTGAACTCTACCTGCTTGA scaffold5094_m_3323
CAAGGATGGGGGACTGGTTGCGTAAGCAAAACAGAGCGAAACGGAGGGGG[G/A]AGACCAC
AACAAGATGCACCAGACTCATGGCATGGCTCATCGGGAAGTTCC scaffold5098_m_13754
ACAGACAGTTCGATTTGCTTCTGACAAGGATGTGTGACGTTTACTCATTT[G/T]TCAGTCTGC
GCTACTTTATGAGCTTTTGTGTTTGTAGCAGAGATTGACGAT scaffold51_m_404
ATAATATATAAAGAAAGAATATAATAAACTAATATTTATAATCTATTAAT[T/A]AATAATTAATAG
TATTATTTTAATTACCTTATATAGCTTAATTAAGCTATA scaffold510_m_2194
TACTAATAATATTATAGTACTAGTGCCTTAGATTCTTAATTAATTATATC[T/C]TATAAGACACA
CACTATAGCGCTTAAGGCTTACCTAGCTACCCTAGATTAG scaffold5103_m_4781
GCTACAGCTCTAGTTTGCACTCTCAACATGAGGTGAATAGACTGTCACCC[G/A]ACAGCTCCG
TCAACGAGCTACACATTCACCCACTCTTTCGGTCTGACTCTC scaffold5104_m_21258
TACAAAGCTATGGCGCATCCCGGCGTTCAGGACGGTGAAAGCTTTACGGG[A/C]AACTATTC
AAACTGAAGAGATTTTGTCGTTCATCTACTTGCTTAGGGTAGA scaffold5113_m_29387
GACAACAAGGCGGCAATTGGGAGCAGAAGCAGACGACAACGGTGAGGGGG[G/T]GGTGGA
GAGGGGGAGGGGGAAGAAGAAGCAATCATCAAAGGACCCTGACGA scaffold5120_m_15718
AATGGTCGAGCCAGGCCAGATCGTAAGACCGGCCAGCGCATGCAGCACAT[G/C]CAGCACA
AGGAAGCACCTTCGCGGCCTGGCCGGAATCACTGTCCAGAGTGA scaffold5122_m_903
ATACTAGCCCACAGTCATAGGTAGCAGTAACGTCTGCTTACATTAGAAAA[G/C]TTAATTAACT
TAACAGTAGTAATTATAATAATAGCTAAATCTATCTTTATA scaffold513_m_591
TAGAGTTATTAAAGAGATTATAAGTAAATTATTAATTAGAGTTTAATATA[T/C]TTTAATTAAACT
AAGTACTATTAAAAACTTACTTAATCTTATAAAGAATCC scaffold5130_m_34645
GGCCATGCGGCTGGGTTGGGCGTCGTCGAGGTCTTTGACACGGGGAGTGT[A/T]GGGAAGG
GCGTACGGGCAACGGGGGCATGACCAGCTTTCAAAAGACTTGTT scaffold5132_m_12068
AACTATCAATATTATCTGTACTATTAATATTATCTGTACTGTTAATATTA[C/T]CTGTACTATCAA
TATTAGCAATACAATCAATATTATTAATACCATTAATAT scaffold5137_m_8301
TCAACAACCCCAGACCAAACGAAAATGAACAAAAAAAAAAAAAAAAAAA[G/A]AACAAAAAAA
AAAAAAAAAAGGCCTCCTCTTCCTTCCAAGTGGATGCCCG scaffold5140_m_1256
CCACTACATTCTCCAGGCGGCGTCCTCTTTCCTCCCCTGCATGGCCCTCG[A/G]CCCGCAAG
AGAACGAGCGCGTGCTCGACATGGCCGCCGCCCCGGTGGCAA scaffold5142_m_1318
GAGACCCGAGCTTGGTCGCTCGTACTCGTACTCGGATGCTGCCATTGTCA[T/C]GCCCAGGC
ACCACGGCACGTCGCCGTCGCTGAGTCAAAGCCAAGAATTACC

Figure 6 Continued scaffold5146_m_572
AAGGCTAGAATAAAACTAGTATAGGATAGCTAAGACTTACCACTACCCCC[T/C]TAATTAATAT
AGTAATATTATAAGTCCTCTTCTAGAATATAAATAAGAAGG
scaffold5155_m_369
GAGCGCACTAACAAAGAAAGGGGAGGGGGGGGCGGAAAGCAAGAAAAGA[T/A]ACGTGGA
GGATCGAGATCTGCCCCCCCAGCACTGGAATGTCAACACGTACC
scaffold5156_m_42710
GCGCTTGTTGCGTCAGCATGGTATGTCTCATCTTGTCTTTTTTTTTTTTT[C/T]TTTTTTTTTTTT
TCCCCTTTCAAGTCAAAAGGGCATTCATTCATCATCGAG
scaffold5168_m_5682
ATTTGCTCTCATCTGCCACGCCTGCAGACTGGTCAACGGCCAAGCTCCCC[A/C]CGGGACGA
AGACTCTCGCAGAAATCGGCATGTGGAGGTGCAGCGGGTGCGG
scaffold5169_m_13798
GCCTTTTGCGGGAAGTCGTTGATTTCAAGCGTCGCGTGGAACGCCCCGGC[A/G]TCGGGAC
CCTTGTTGTCGATGGGCTGGCCGGACCGGAGCTGGCCAGCCTTT
scaffold5172_m_2425
CTAGGTCCGTCGCTTGAGGCAAGTCCCACCAAACCGTCCCCAGCCTGCTG[A/C]TCTCCTTG
CACTGTGCAGGCAGGACATGCACGATGGCGGGTTGAGCCTGCA
scaffold5174_m_30982
ACGTATAAGATGATTGCCGTTTTTTTTTTTCAGAACGCACTCGGGCGCCA[G/A]GAGCATGAG
AAAGAAAAGGAGAAGAGAAAGAAGAAGAGAAAGGAAGATGCG
scaffold5179_m_972
CAAGCTTTAGCAGGGGCATGCATCAGGGACCGGGGGGGGGGGGGGGG[G/A]GGACA
AACAATCATGTGGTTTCGTGAAAGCTGGAGAACGGAAGACGCGGGG
scaffold5184_m_1328
GGGAATCTAAACACAGAGATATCAGTCCTGCAAATGTTCATCTCCCCCCC[C/T]CCCCCCTTT
TTTTTTTCTTTTTTTAGAACGGCAAGCTCCCAGTTTCTTCGT
scaffold5187_m_21446
CAAAAGTGGCGTTGAAGGCCGACCAGATCGTGACCGGCCTCCGAGGGAAG[T/A]CAGTCAG
GGTCGTGAAGCCGCGGATCGAAGTCGTAGTCCACGCAAACGACG
scaffold5197_m_198
AGTAAATTAGGTGGTTCTCCCCCCTATATTACTCTTAGGTAGCTAGTAGG[A/T]GAAGCTTTAG
AATTATAAGAATAATAGTAGCTAGGTAAGAGGTATAAGGGC
scaffold5198_m_12563
GGGGAAGCACAAAGTCCATGGGAAAAAAAAAAAAAAAAAAAAAAAAAAA[A/C]CGTTCGAAG
AGCAACCGTCGCTCCGTGAGCAGCTGGTTTGGGTATTGCGAT
scaffold52_m_295
ATTAGTAGTGCTACTAGCTCTAAAAAGTTACTAATAAAGTTATAGTAAAA[G/A]TTAGTAAACC
CTAGGAAGCTATAAACCTATAGTAAAAATTAGTAAACCTTA
scaffold520_m_4408
CAGGGCGTTCCTGGCGCTCATCTTGAAAACCTTGCCAATCTGTGATTTCG[G/A]CCCGCAATT
GATCAATGTCTTCGAGCTCCTCCTGAATAGCGTTAGCACCTT
scaffold5203_m_26971
AAATGATCCGTACCCATATGTAATTGTAATGCAGCATCCCACGCCTTTGC[A/G]CTAAATTTAT
ATGGGGCGCCATGGCAAAAAAAGATATCACCTAATATTAT
scaffold5205_m_32688
ACACGCACCAAATGAGAAGGAGATCCCCGATCGATACCCAGCACCAGCAC[T/G]GTGGACC
GGAAATGTATGTAGAGAGGACTCACTGCTCACTGTCAGAGGAGA
scaffold5210_m_1222
ACGCCTACAACATTTTCTTGGTGGGCGGCCTTGGAGGATATCGACGGACC[A/G]CCTATGCC
TCTCGATCGGTACTTGGTGAAGATCAATAGGCGGACAAGGACA
scaffold5212_m_2949
TGCTCTCGGGGATTTCGGGGGCCCGCTGCCTGCCTGGATGCAACATTGAG[A/G]CTGACCG
ATGCCTTCTTCGGCCTCGGTCCTTTTCCTTTTCCCAACCACCG
scaffold5213_m_2882
GCGAAGGTCGCAAAAGGATGAATCGTGTTTGACACGGGCAGCATCTCAAC[G/A]TCAAGGAT
GGACACGAGCCCGGGGTCCTTGACTGTGCGTGTGCCCGAGGAG
scaffold5215_m_14457
CCTTCGGTTAGTGTGCGTCGGTCGAGGGAGTCCCGGTGGCGCAACGTCTC[C/T]ATTTGGC
CACAGATTGGCAGATTGGGGCGAGAACGGGGGCCTGGAAAAGCT

Figure 6 Continued scaffold5217_m_922
CACGTGCGTCTGCGTTGACGATTTATACCTCTCAACAACATAAACGTTAC[T/C]CGCAGCAAT
CTGCCTAGGTATGTTTCACGACACCGATGCCCTTCATCCTAC
scaffold5218_m_3297
CAGAAGACATCATCTTATTTTCCGCCTTCAACGACTTGTGGAAAAAGAAC[A/G]ACATGTCAA
CGTTCGATGCTGACCAGTTTTGGGGCATTAACGGTGCGGTTT
scaffold5226_m_953
GCATCTGACATGTTATCAAATCGTGTCCACGGATGGCAGCCGGGTATCTC[C/T]TTTTTTTTTT
TTTTTTTTTTTCAAAAGTCCCAAAAGCTCTTTTGAGCAGC
scaffold5227_m_4398
AAAAGGCCGCCTGCCTGTTTCCTGCTGCACTCCTCTCTCAGGCTCTCTGG[A/T]AGAACATGT
GGACCCGCCATCACCGGCCAGTTTTGGCGGCCACGACCACAT
scaffold5228_m_4315
ATCTTCATCATCGAGGGGATCCCGAGCGTGGTGCTGGGCGTGGTGACGTA[C/T]TTTGCGCT
GCCCAACGATGCCGGGACGGCGTACTTTCTGGACGACGCGGAG
scaffold524_m_1781
TAAATAGGTAAAGGCTATGCTAGTTAGGAATGTAATAATACTAGTAATTA[G/A]GAAGTTCCTT
TTCTCCTTAATTAGTAGATTTAGGCTTTTCTGCTTTATAGT
scaffold5240_m_9279
TCACGGAAATGAGACATGAACCCGCGGCCCAATAGTTGGGGCGTTGCACA[A/T]GCCCTTGT
GCGAGCGAGGGCTTAATTCCCCGAAGCTGGACCACGTGCCTTG
scaffold5250_m_606
TTTAATAAAATTATTTAACCTTTATTAAATAATAAAATTATATTATACTC[T/C]ATCTTAATACTTT
TAATTAAATAGTTAATTAAATTAACTTTATATAAAACT
scaffold5254_m_979
GGCAATCTTTGCATTGCCTTGTGTTTTTTTTTTTTTTTTTTTTTTTT[T/C]GGTCAGCAAAGG
TTGAGAACATGGGCAGTCACTGGAAAGGGCGCGGGGCAG
scaffold5268_m_10712
TCTTCTCCCATCGCGCCTCGCCTTCAGCAACCTTGTTGAGATATGACGTC[A/G]CAATGCCCC
GGCTCTGCCGCACCTCACAGCAAGACAGTCGAGCCGCGCATC
scaffold5269_m_9018
TGCTGGCATGCCGTCGATACATCGTTAACGAGGGCAAAAAAAAAAAAAAA[A/T]TTTTTCCAT
CTCACACTCGGTGAAATGTAAATATGTCCCCTCACTTGTAAT
scaffold5275_m_19184
ACCGAGCCCGCTCTTCCCGAAGAAGCCCTCAAGCTGATCGACTGCGGTGA[G/C]GCGGACA
AATTCGGCCTGGCCAAGCAGTTCCAGAATGTCGTTTCTACACAG
scaffold5280_m_4258
CATCAGTATTTTCATGACTGTCAGAGGGCCACCGGGGGGGGGGGGGGGG[T/G]GTCTTTA
CTTACATCCAGTTGGAAATGCAAAAGGCAATAAAAATGCCAAGG
scaffold5286_m_43100
TTTACGAATATCGGGGTCGGCATCGGCAAATTGTCCCACAGAAAGACAAA[C/T]GGTCGTGA
GTGGGCCGGCCGTGGCAAAGGTCAACTGAAAGTTGAGCTTCAG
scaffold5289_m_363
TGTCTCATCAGCAAAAAAGAAAAAGAAAAAAAAAAAAAAAAAAAAA[G/A]AAAAAAAAAA
AAAAAAAAAAAAGGAAAAGGGCCTCGTTTCGTAATTCTAG
scaffold5293_m_785
AGCGTCCCTGAAATATCAAGGGGACTGACAGTGAAATCAAGACGACAAGA[A/G]AAAAAAAA
AAAAAAAAAAAGAAAAGACCAAGGGAAAATGAACCAAATCAA
scaffold5294_m_488
TGTACTCCGTACACACGGATTAAAGAGCACCAGATCTGTGGCTGGTGGTC[C/T]GCCACATC
CGGCATTGGGACTTGTAGGCTTATTAGCGCTCGCATCCCATCT
scaffold5303_m_5061
CGAAGAATTGGGGCATGTAGATTTATAAAATAATTCGGGGGGGGGGGGGG[G/T]GGGTTGTA
CAAAGTGTCTCTCCATCGTGATATCAATATCCCAACGCCCAAA
scaffold5314_m_2954
TTTGAGAAGAAGATGACGCTGAACACACCCTGGCTGGACGGATCGGCGTA[T/C]CTGAAGAG
GCCGGGACGGGGCGGTCGGCTGGCGGCCAAGGCGGTGCCGGTG
scaffold5315_m_6434
GAGGGTGCTGTTGTACAACGTCGGCCAAGTAGAGAGAGATGTGGGATGTA[A/T]AAATTACT
TTCGTCTGGCAGAGGCTGGACGACGGATGCGTCGGTACAACAT

Figure 6 Continued scaffold5323_m_37272
CCTCGCTGTTCAAAGGGCACTTGTTCGCACAGTTGAACGTTCAATGCCCC[C/A]CCAGGAGC
TACGACCCAAACATCACAGCTCAGAAGGACGAAGTGTTGTTTG scaffold5332_m_15423
CTGCGATGAGTTTTGCGCTAGGGGCATAATGAAAGACTGAGGGAGCGTAC[T/C]GTGTGGCC
GAGCGACAGGAGGAGCCATCCCACCGCGGTGACTCTGAGGGAT scaffold5335_m_1748
GCCAGGTATAATATATTAGCCAGCATCTCTTGTGTAGAAAGAACCAACCC[G/C]AAAAAAAA
AAAAAAAAAAAAAAAAACACTCCGAAAATCAATCATGATGATT scaffold5336_m_8414
GCCAGCACCGTTGGGTCCAATCACAGCAATACGAGATCCCAAAGAGCACT[G/C]GAAAGTGA
TGTCGGAAACCTGGGGCTTGGAGGTACCGGGATACTGGAAGGA scaffold5342_m_2360
TCGCCGCAGTTGAAGAAGGCGAACAACAGGCCGTCATCGTCATCCTCCCC[C/A]TCGGCGTT
GCCACGCGCCCGCGCCCGCGTCCGCGCCCGCTCGTACGCCTCG scaffold5345_m_2579
GGCAACCATGACACCATAAACGCGGTATTTTTTTTTTTTTTTTTTTTT[G/T]TTTTTTTTTTTT
TTTTTTTTTTTGCTTTTTTGAATCCCCCAACATGCCG scaffold5349_m_4213
ATTCTTCTTGAGCAAGCGTTTGATGGGCTGGGTGCTCGGTCTCCTTTCAA[G/A]GCGCGAAT
GCCTCACAGTCGTGCATTTTAGATTCAGGATTTCTTGGGTCGA scaffold5366_m_7865
TTTCGGCTGAGACATTGGGAAAAAAGGAAAAAAGGAAAAAAAAAAAAAAAG[G/T]TATGGCTTT
GGTTCTGGTTCCTGACGAAAGCTGCCACCCCCGGCACGGTTC scaffold5367_m_1849
AAAGAGACGTTGATGTGGATAACCCACGGATACGGATTCGCACTTCCCGT[A/C]ATGGTTCG
TGAAGTTTTCGTCGCGGATGAAGGGTGCTTTGCAGTTGAATGG scaffold5383_m_26476
TCTCGCAGTGGAGATCGCCCGCGCAAGTATGTGCGCGTCTGAAATATGTA[C/T]AGGATGCT
GAGGCTTGTTTCCTGGGCGAAGAAGACGAAGAGCTGGACACGA scaffold5385_m_10820
TTCAGGTGGACACGCAGCGCAATATTGTCTTTGCAAGGCTGGGGGCTAAG[A/G]ACTGTGAG
TCGTCGCGCCCGACGTACGCAATGCCCAACACATGGACGCACA scaffold5386_m_1643
AGCAGCGGCAGGCTCAGCTGCGAGAGGGTGAAGGCGCGGTGCAGGTTCAG[C/T]GTGAGG
AGCTTCGTCCACGCCGCGTCGGGGTGCTCGTCGAAGGGGGCGCCC scaffold5387_m_19083
CTGCCAAACGACACGGTTGTCTGTGTAGGTTCTGCTTTTTTTTTTTGGGG[T/G]TTTTTTTTCC
CTACGAATGAGCAAGGATTCGGGAAGCATGCCTGGTGCTAA scaffold5396_m_19311
TCGTGGGTGCCGAATGAAAAAAAAAAAAATAGAAATTTGAAAGCGTTAAAT[A/G]GTGCCAGCT
CAATTGAGAGGTACCGCCGACCAGCTCCCATGTGCCATGAGG scaffold5409_m_2313
CGACGGATTGGATGCATATTTGTGTGCTTGGGGAGGGGCGGGGGGGGGG[T/G]TGAATGC
GCCCCCGGGAAGCATTAATATCAGGTTTCTAGACAATTTTTGTT scaffold5413_m_358
CCTGCATCTGTCCCGGGCAGTCCGTGAGGGCTACGAAAAAAAAAAAAAAAA[G/A]AAAAAAA
AAGTCGCCACCACCACCACCACTCAACATATCGTTTTATT scaffold5421_m_4088
CTCTCGCCCGTTAGCCCCGGCCGCCAGTGCCATTTTTGCCGTTTGCTGCAA[C/T]AGCTGCGA
GAAGAACATCCCCGATGCTCATTATCACTGCTCTACCTGCGAC scaffold5423_m_2295
TCCTATATTCGTCGCTGGTTCGACGACCGTGACTTCGTCTCAGTGCAAAC[T/A]CCTATGCTT
AATCCAATTGCTGGTGGTGCCACTGCCAAGCCCTTCGTTACT scaffold5425_m_8273
GCGTTGGCAGTCGGTCCCCTCATGCATCTGAACGGGGAACAGCACGATCC[A/G]GGACCAG
CGAGCCCAACTGCGCCAACGGCCGGACGCCAATGAAGTCATCCT scaffold5426_m_3992
CCGAACTATGTTATGAAAAAGAAGAGGCCGAGAACTCGAGAACTTCTTCA[T/C]AGCTACCAA
GAGATTGTTTGGGCTACATGTGTTTTTTTCCCTTCCGACCTT

Figure 6 Continued scaffold5435_m_19088
CGTTTCCAGTTTCCCTACTCTGTATTATTTATCTGCTGCGTCGACTCTTT[C/T]CCCCCCCCT
ATCCATGTTCTTTCATGGAACCAAGGAGCTCTTTTCCTTTT
scaffold5439_m_1960
CGTCCAATTAGGATAGCCTTGGGCTCATCCAGGCTACTGGAAGGAGCACC[A/G]CCGTCTTT
GCTCTGATTTTCCATGATGGATGCAATCGTAGCACTCAAGTCG
scaffold544_m_3502
ATTCTAAATAATTAGCTAAAAGAGCAGGTTATTAAGTAACAAGATGCTAT[T/C]AATCTATTATT
ACTTATAAAGCTAGAGGCTCTAACTACAGCTATTAATAA
scaffold5441_m_8333
CTGTTGGGAGACGGTCATGCTGCCTGGGGAAGAGGTGGCGCGACGCGGGA[G/C]TTGGGC
GGCGTTGAGGTCGACTTGGTTCTTTGGTGCGACTTGTTGGACCGG
scaffold5442_m_33999
AGGGAGAAATCGTGTCCCTCCGCTGTTTGTCGGAGAGGAATTGAAATGCA[G/A]CCTCCATT
AGTTCTGCGACGAAAGCCTCGTCATCTCGGAGAAGTTGTCGAA
scaffold5448_m_1433
GGACGACTCGACTTCCTCTAGTGTGTATTCGCACTACGTGTCCTCCGTCT[T/C]ACAATCGGC
GGGGCTCGACACGAATCGCGTGCACGTACTCCGCATGCAGCG
scaffold5451_m_123
TATAGTTATAATAATTCCCTTACTTCCTTATTATATATATATTATATATA[C/T]TATATTATAAGTG
TATTTATACTAATATATTATAGGGACTAGTATATATAG
scaffold5455_m_16094
GACTGACCGACTTGTCTTGAGAATGCGGCACCATCCCATCAATGCCCCCC[C/T]CCCCCCCC
CCCTCTTGAGAATGCGGCACCATCCCATCAATGCCCCCCTCCC
scaffold5459_m_10717
GCCCTCCCTCACGGGACCGGCCTGGCACAATTTGGGGGGGGGGGGGGGG[G/C]GCTTGT
TCGTTGACTCTTCAGATGTTTTCGATGTCTTTTTAACTCTCGCGC
scaffold546_m_455
AAGACTATCGCAGTCGCTACTAGATAGATACTAGCTAGGGGCAGGTGCGT[A/G]AAGGTTTT
AATCTCTAACCTTACACTAATAATATGCGTAGTCTTTAATAAA
scaffold5467_m_8586
CTGGGGGGATGATGAGAGGGACATACTCGTCTTGGTGTCACCAGATTGCA[T/A]GATACAAC
TTGTGCACAGGCTCGCGACGCGAGCCACGTCGAAGCTCCGATT
scaffold5471_m_8442
GCTCCAGCAGCAGGCGCCTATGCAATTTGACAAAAAAAAAAAAAAAAAAA[A/G]AGTCCAGCG
TTAGTATAATCATTGATCATTCAGTTTGTTCCGTATCCTTGG
scaffold5472_m_468
ACTTGCAACAGCACTTCCTTTCGCTGTTTGCATACCAGTCCTTTCCCTTC[T/C]CGCTTCTTTG
AAAGACCGCGTGAACAACTCTCGTTGACGGCCGTGCCGATT
scaffold5477_m_2371
ACTCGTTATCCAAGTCGATGGGTTTGCGTCCTTTTTTTTTTTTTTTTTT[C/T]TTTTTTTCCCCT
CTTCTAATATATTTCTTTTTTTTTTTTTTTTTCTTT
scaffold548_m_542
CTATCAGAGACCCATAAAAGACCCACTTTTTTATATTTACTCTATAAAAT[T/G]AAAATAGTATA
CCTATAGCTTTAAAATTATATAAATCTAGCTAATTTATAG
scaffold5482_m_27596
CCGCATCGCTGGCCTGGACGCTGTAAGAGGTCGTGTGAAAAGGGGGTCTC[A/C]TGTATTGT
TGTTGTTCCATGCCGCAGAAGTTGGAGATGCACACAATTTGCC
scaffold5485_m_456
AAAGAAGAAGAAGAAGAAGAAGCAAAAAAAAAAAACCAAAAAAAAAAAAA[A/C]AAGTTCTGT
ACAGGTGCAGTAAGAAGAGGGTAAGCTGCATATGTGTCTA
scaffold5488_m_2780
GGACTGCCTGCGAGCCGAAGAGTTGTTGCGCGCTGCGAACAGGGCCCAGT[G/A]TAGGTCG
AATCGAGGCGGGATCGGTGGTCTTGGAGGGAGACGCTGATGCCG
scaffold5509_m_12438
GAAATGTGTCTGACGACGCAACATGTGCGTCATCGTCAAAAACCAGATTT[C/T]AGGATAGCT
AGTAGAGTCGAATTCTAAGCAACATTGCAAAGAAGTTCTAGT
scaffold5511_m_1659
ATTGCTGCTGAACTCCGTCCATTGATCGTGGTGGAATTAGAGTGCTCCCA[A/G]CGTTGCGA
GAAACGGCCAGTCGAGCCTCTCGAGGGCGATGATGCCGGTGTG

Figure 6 Continued scaffold5515_m_23278
 CTACTAATCCGTACGGAGCATAGTAATGACTCCTGCAGGAGCTGAGGCAG[A/G]TGCGGCTA
TAGGCATATTACTGGATGGATTGGACTTGCCATAATATGTCAA
scaffold5517_m_8834
 CTTGCTTATCTGCTGCCTTCTTGGCTGCCTTTGCGGCTTTGCTCCCACCT[T/C]CATCGTCGT
CGTCTTCTTCGCCGTCTACCTCCACGACATCATCGTCAATGT
scaffold5522_m_12810
 AATATATAAAAATACACATGTCCCCCGGCTCAACTCGTCGACTTGCTCTCA[T/A]TCAATCGACC
AAACCAACCAACCAACCAACCAACCGTAACACACAGC
scaffold5527_m_10172
 GACGAGCTTTTTGACGCCGTGTCCACCACGAGCCCATCTACGTTCTGTAA[A/G]GCATTCTTC
CTGCTTGCGGCCCTGGGTGTTCTGTCGCTGAATGTCCTCCCT
scaffold5530_m_14884
 GCTCTGCTTCGTCCTTCTCCCACTCGTCGTTGACTGGAAGCTGAGGTCTT[T/A]CGCGCTCTT
TCCCCTTGCCGCTGCGCTGCTGACCCCCGACTCCTCTCTCTT
scaffold5537_m_2730
 AGATGATCTCAGAAGTGGTGTCCCTATAGGAACGGAAGGGTTTGTGATCG[T/A]CAGCGTAG
TAGAGGGTGTCGCTCCTTTTGGGTGTGTACCTTGGAGGAGGAG
scaffold5538_m_15678
 TTGTTGAGGGTGGCTTTGTCGCCGGCGGCAAAGGCCTCGAGCATCTCGCG[G/A]TACATGG
CTTTTGCGGTGGGCGCAATCTTGGCCCTGCGGGCCTTCCATTTC
scaffold5545_m_1070
 TGTGTACTCGCCATTTGGAGAACCAACAAAAAAAAAAAAAAAAAAAAAA[A/C]TATGTATAGA
CACAACAGCGCCTCGACGGAGAATACATCTACTGAACCGTC
scaffold5546_m_5568
 GATGCCAAGGCCACACGAGAGCGTCCACCGCCCAAAAAAAAAAAAAAAAA[A/C]GTCATGAG
GCGAAGCATCCCGCCGAGTAAGATAATCGGGCATGGAATGGGA
scaffold5550_m_6587
 TTCGTGAACGTGGTGTTGGTACTCCAAAAAAAAAAAAAAAAAAAAAAAAA[A/C]ACTATGATGC
TAATTGAAACATGAAGAAGTTGTAGCGACCAAATGTCGCCC
scaffold5551_m_2691
 CGCTCCGTAAACGGAGAAGCGACGGCTACCCCTTCACACTCCGTCGGTAT[C/A]GTGAGCTC
CATAATATTAATCATCAAGTTTTTGACCGACTTCTAATAAGTC
scaffold5553_m_47236
 GAGTAAACGCAAGCACGAGGATGACGATTTTGAGGGCACTCCCGTTTGGG[T/A]GCTCTATG
TAGCCTCAATGGCACTCGTTCTACTTGGTGGTGCTTTTGCTGG
scaffold5554_m_5124
 GGGTTGCAGACCCCCGTTGTTGGATCATTTGTTCTTTTTTGTTTTTTTTT[C/T]TTTTTTTTTTTT
TTTTGCCGTTTTTTTTTTCTTTTTTTTTTTTTTTGCCG
scaffold5556_m_14918
 GTCGAGGTGGCGGTCGATGGCGTCGAGTGCACAGAGATTGTCCTGTCCAA[A/G]CCTCACA
AGTACTACTCTCTGATTTTGGTAAGTTTCTCAACGGTCCCCAAC
scaffold5557_m_1032
 TGTCTGTCCCGACCGTCCTGTACGGAGTAAACTACGGTCCGTATCAAGTC[A/G]CCTCCTCTA
GTCCGTAGGCTCTGGGGCTCTCATCTACAGCGCTCTCGGAGA
scaffold5560_m_7821
 TAGACCGTCCTTTGCATCCAGCAGCAGCAGGACGAAGGGTGGCGGCAAAG[T/C]TCATGGTA
AGATGACCATCAACAAGGGCAAGGGCAAGGGCAAGGGCAAGGG
scaffold5564_m_16339
 TCTTGAGAAAAGGACGGTCTGGTCTCCTTTTTGGGGCGTATCAGGTCTCG[T/A]TCGATCCTG
TCGCGGTCGTCGCGAGGTTCGCGCCAATGTCTGCTTCTGGT
scaffold5570_m_1285
 CGTTGCGAAGCTCTTGGAGACGAGTTTAGACAGGACTGTGCGGCATGAGT[G/A]CTTGCAAG
AACTTGCATTCAGCTATCGACGCCACAGGCTGAAGCTGAACCA
scaffold5575_m_15350
 GAACTGGTTGCCTGGTTTCATGATGTGCCAGCCAATGAGTGGGTATGGAG[A/G]AACATTGG
CTAATATACGCTTGCAGGTTAAATACAAAATTAGTATCAAGGG
scaffold5585_m_1339
 TCAAGGTTGGGTCATGTCGATGCGACGAGCGAAACATGAAAAATTGATAC[C/A]CCCCCCCC
AAAACCGACTGGTGCCCGCCAAGTCGATGTGGAATACGCTTGT

Figure 6 Continued scaffold5588_m_8819
GTTGCTACATCAGCTATACGTCCACGTAGAGCGGACACGGATCAAGATTT[A/G]TCGCGCTG
GAAGAGATGCATTCCTATCTTTATGAATCCATCGCCAGTATCC scaffold5594_m_1722
GGAGGGGGGGGGCAAGCCCAGACCCCCTCAAGCGCGCCCGACTTCTAGAA[C/T]AAGTCTG
CAGCTGATTGTGTGTGGGCTTCATCATATTAGTTTCAGTTACTA scaffold5598_m_3811
GTCTAGCGGCCTTTTGCGCCCTCGTGGGCGAAATGGGGCGAATGGGCGA[A/G]TGGGGC
GAGTGGGGCGAGTGGGGCGAGTGGGGCGAGTGGATCCCCCTGATC scaffold56_m_2491
GTGATTTTAATAGATAATTTTTCTTTAATTTACTTAGCTAGGTAAAGAAT[G/A]AATCTAGTTATA
GTCTAACTATTTCTATCTAGGATAGTTATCTTTTAAGGC scaffold5601_m_15660
TCTGCATCTTTTTTGCGTCCTCGTGCAGGGAACCTTGTGGGTATTTTTTT[T/A]TTTTTGGTTT
CTGCCAGATGCGGTTGGAAATTTGAAGGCTCAGGTTGGGGT scaffold5606_m_9252
TCCAAGAGGGGCTGAGAGCAGACTTGGTCCTGGTGGAGGGTGACCCGTTG[A/T]ATGACATT
CGGGACACTCTAAACCTGAGAGGCGTGTGGAAGAAGGGCATTC scaffold5611_m_30371
GACCATTGAGCATTAGTAACAGGAGTAGATGTGGTTGTCTTTTGTCACAA[G/A]CTGCTCTGA
GTGAGACGTGGCACCGACTGCTATCAGCCGATGGTGAAGTCG scaffold5616_m_15863
GCCCGAAACGTCGAGAAGGCTGGCCTTATCGTAAGACCATTGAAAAAACA[C/G]CAGTCTAT
ACAAGTTTTTTGGTACTGGTCGACAAATGTTTGCTGACAAGAG scaffold5617_m_3516
CGCAGGTCTCGAGCTGCCTCTCGACGAAGACTCGTTGTTGTGTCGGTGTG[C/T]CGCGCGT
GGCTGTGGGGAGATTTCTGTGGGCGTGTCGGAATCGGGGTCGAC scaffold5618_m_13823
GAACAACTGTGGAAACAAAACATGCATCTTCTAGCTTTGAAAGCAAAGGC[G/C]AATCTGTAC
ACGTCGTGGGGGGAAATCGCTATTCGATTTCAAACATCTCGT scaffold5623_m_10615
TTTGTCTTTATCACGATCCCCTCCTCCCCTTACGGAGTACACCCCCCCCC[C/T]GCGATTCCC
CAACCGCAATACTGCCCCCTCGCTCACTCGTGCGGAAAGGAA scaffold5625_m_41344
TTTGTGGAATGGAAAAAAAGAATAAAAAAGAACGCTTTATATTCAATCGC[C/A]AAGGACTCAC
AATTTGGAGTGAAGACGCTATTAACAGAACTGACTTCCAAA scaffold5632_m_1413
CGACCTGCGCAGGGACGAGCGGCCCGAGCTGGGCTATCAGGTCGGCGTGA[T/C]GCTCGA
GGGGACCGAGAGGCCCAGGTGCGCCGTCGACGAGCCCTGCCTGGA scaffold564_m_868
GAGAGAAAGCATAGAAGTAAACTCTAGGAGTAGCTTTAGTATAAGGGATA[G/A]GCTAGTTTA
TCTTACTAATCCCTTTTACTAATCTAGGATAGCTTACTATCT scaffold5644_m_9157
GGTCCTGGTGCGCATGGCCCCTTGTATCTTCAGCACAAACGGGTCCCGTA[C/A]TACTACGC
ACCACAACACCGACCGCTTCGTGAAGAATAGCAACGCAATGGG scaffold5649_m_1400
CGAGGCCCCAGCCGGATGAGGAAGCAACAACTCTCTCTGGACTTTTTTTC[T/C]TTCGATGGT
GGTCGTGAGATGTACCGAGTACCGAGTAATGTATAGTGTGTT scaffold5660_m_6013
AAAGGCGCCGAGAGTCATTGCGCCGAACGTGACAGTTTCATGTTCTCAAC[A/G]TCCGAGAC
GAGTCTGCCAGAAATCAGAATAGACGAGAGTAGCTGTCCTGGC scaffold5661_m_3138
ATCAAATTGGCTCGCGAGTCTCAGGTTCCTGTTCCCCGGATAGAGACGCT[G/A]TATGCCATT
CTCCATAATCTCAACATTGTCAACCGTTCCAGGCCTAAGCCT scaffold567_m_229
AGGTTGAATCTTTTGGTTTAATAGCTTACCCTTATACCTTTAGGTTCTAA[T/C]ATTAATGCTAG
CTCTTATAGGTCTTCTAGTGTACTAGTCCTAGGTTTAATT scaffold5674_m_11897
TGCTCACATGGACAACCCAACCTTCTCTAGTCCAACGACGATGTCTTCAA[C/A]ACCAACCAC
CCCCTCTTCCACTGGATGTTCCGCGCTTCCCGCAACTGGGGC

Figure 6 Continued scaffold5675_m_5789
CTCTGTTCTTTTCTGATGCCTCCTGGTCGTCCGACGTCTCACTGGAAGCT[T/G]ACTCGTTAG
TGACAGCCATCACATGCTCTTCGGGCCGCCACCCATCACCAC scaffold5676_m_35415
CCGCCGCGGGGCAGAGCTCTACGGAGTATTACAGCCTGTCACTCAGTGGT[G/A]CTTGACG
CTCCGTATACTGACATTGAACGAGGCGCAGGGGCGGGCGCCTTC scaffold5683_m_45343
TTAGGGTCATGAAAGCATGGAGATGTATGGAGCAAAGGCTTGTGCAGCAC[A/G]AACAAATG
TGTCGTGTAATTCTCTGCCAACCCAGGAGCTGATGTTTTGGCG scaffold5690_m_9637
CTCGCAGTTTGCATGCGTACCGGCAAGATTCAACCCCATAGTTGTCCGCA[T/C]CATGGCCG
AGTGTGAAATTGCTGAAATCACCTTGCAAGTCATAGCAGCGGA scaffold5697_m_5057
AACATCCAGCTGTCGACTGCCATGGCGAGCGACATATCTGATGAGTCTTC[A/G]CGAGGCTC
TACCATGGCCATAATCGGAGCATGCTTCTCCATTGCCTTTACC scaffold570_m_1203
TAGTAAAATAGCAAAAAACTAAATAGTTTTATAATAGGGAGCGCTAGTAA[T/C]ACTAGTTTTA
CCTAGCCTAAATAAAACACTACCTATATTATTAGATAAATT scaffold5705_m_12649
ACCCAGCTGAAGAGCGCGCGAGCCGAGGCGCGAGCCTCATTTGGCCAAGG[C/T]GGCGAG
GTTATGCTGGTGGAAAAGTATATTGTACGGCCACGTCACGTCGAA scaffold5708_m_5008
TCTACACGACCACAATGTACTCTGAAATGCCATGTCCAACACACCTTTTT[T/C]CGACATCAT
CCGAATCAATCGTCTCAGAACCCAAGCGACGGCTGGCGTGT scaffold571_m_1364
TATTACTATAGTAAATAATAAAAGGTAGGATTTATATAATTACTTATATA[G/A]TAAAGGATAGT
CTATAGTTAAAAAAGGTAAAAGGAAGCTAAAAGTTTACTT scaffold5711_m_918
TACAATAGCAAAGCTTGATTTTCAACTCGGGGGGCGGTTTTTTTCTTCTT[C/T]TTTTTTTTTTT
GGGGGGGGGGGCATCGCATAGCTTGTGTAGAGGGCATGG scaffold5714_m_6005
AGCAGGAGGAGCAGGAGGAGCAGGCTGGTTGTCAGGAGGAGGAGCAGGCT[G/T]GTTGTC
AGGAGGAGGAGCAGGCTGGTTGTCAGGAGTAGGAGCAGGCTTGTT scaffold5716_m_11760
GAAGGCGCTAGACGGGGCGTTGAATCAAGCACGACAGCCGCGGGACATGG[A/G]ACTTGGG
ACTGGAGGCGCACGCCCCCCCCCGGCCTTGGATATGTGGTCCA scaffold5730_m_1001
TGTTTCAAGGTTTTGTCATGAGAGCCGTCAAAGAGAAGGGCCAATATGAC[G/A]AAAAAAAAA
AAAAAAAAAGGGATGAATCTGCATATATTGGTCAAGGAGTCG scaffold5737_m_5950
CACTAGTCTGTTTTTGGCTGTGGCTTCCGAGAGAGCGGTTGGGGGGGGGG[G/T]TCCATTCT
CTTCGCTTGCACACCGGTGACACACGTGACAAGCAGCCCTAAA scaffold5739_m_2327
AGGGCCGTCCTTGGGCTTCCTGGATGCAGGCTCGCTGGCTAGACCGAGGG[G/C]CTCTCTC
ATTTTCTTGCGAGCAAGCTCCTTTTTGGACAATTTTGGTGCACC scaffold574_m_221
TCTAATTAAATAGTTAATAATTAGTAAATAAGTAAGTAAGAAAAATCTAA[C/T]TAAAAAGTAAT
AATCCTTAAGGAAGAAGAAATTAAACTCTTACCTTAGAGA scaffold5740_m_1406
TCCGAGGCCTTTTGTGATTTGGCCGAATACGAGAAGTCCCGAAGAGCTGG[C/T]TCCATGCC
CAAAGCCATGCCCAACAAGCCATGCCAAACGCCAATTTTGGCA scaffold5751_m_1303
GCGTCTCTTGACATGTCGACAAGACGAAGCTGGTTGCGATGAGAACATGT[G/A]TACAATGT
CCAATCATCTGAGCAAAATGATCAAAAACGCCATCCCAGTGTG scaffold5752_m_23900
TGCTATGATACCGTCTTTTGCAGCCAATACTGTCACGACATTGCCCAGGA[G/C]CGCTACCAC
CCATCCGTGTGCGAGAAGGACGTGGATGCTATTGCCAAGGAC scaffold5758_m_1128
TTTTTTTTCCCCCTTTCCTCAACGACAGCCACTTTTTTTTTTTTTTTTT[T/C]CCCCTTTCCTCA
ACGACAGCCACAAAGCGCCAACAGCCGAGGGCTCGCTAA

Figure 6 Continued scaffold5760_m_10152
TACATGTTTGCATGCCAAGCTAGTTAGTCTCATTTGCATGTGTCTCAGCC[T/C]TTTTTTTTTTT
TTTTTTTTTTTAACTTGTGTTGATTCTGCGAAGCCGAATT
scaffold5763_m_18026
TAATTTACGAGCGCGAGTCACCGGAGATAATGGTGCCCAAAGTCCAAAGT[T/C]GGCAACTG
ATTGCGCCGGTTGATCAATCTCCACGTGAACATTCTGCCATTG
scaffold5764_m_3149
TTCTTCCGACATTGTCTGATGAATAACGGCCGTCTCCAACATGTCCCATG[C/T]CTCAGACTG
CGAATCCAAGATCGCCAGAGACTGTGAATATAAGGTTTCCTG
scaffold5766_m_5508
TTTGGACAGTGCCATGACGATGGACTCACCCTCTCTGAAGGCAATCAAGG[C/G]GAAGAAGC
GAAAACGCGAGAGTCTTAACATTCGGCCCGAGAGGGAGCAGAT
scaffold577_m_1747
CCCTAGATTTATTAAATTATTTTAAGTACTTAATACTATAGGTAAATAAG[A/T]ATATAAACTTAT
ATTACCTAAAAAATATAGTTAACTATATAATATATTTTA
scaffold5773_m_13570
AAGGCCTGGAGCTGGAGCCATGATTGGGCAGTGCACGCGTGGCCTGAATT[T/C]TTTACCCT
TGTGCCCCAACTGCCCCTCCTTCAGAGCAGGAATGAAGGGGCC
scaffold5775_m_1184
CTTGACCTTCAAAGACGTCATTAGCCGACTTGGCCGCGGGGGGGGGGGGG[G/C]GGCGCA
GGCACAAGACAAGAAAACAAGCGAGGACTTACAGGCTCCAAAGGC
scaffold5784_m_47676
AAGTCAATAGAGGAGTTTGACAGCGAGGGCGTCGGTTTGATCGGAAAGCG[C/G]CCCCTTTC
ACAGCAGCCAGTCATGGTCAAGGCAAAGATGTGGCAGAGATAA
scaffold5787_m_18906
TCTCCCCCCGGAGTACACGATGCGTCCCATCCGGATGGAGGTTCACGATA[G/T]AATGGACC
TCCGAGGCGAGATCCCTGAGAGAATATGTCTGTTGGCAAGTGA
scaffold5788_m_1672
AGAGAAAGCAGGACGAGGAAGAGGAAGAGCTCGTTTCTCTTCCCGAGGAA[G/C]ATGATGG
CGAGGAGGAAGAAGAGTGAGTGACCAGCGCCAACGAACCCAAGC
scaffold5791_m_29642
AATTGACTACTGGAAAGACCATGCACAAATAATTCACTCATATGGCCCGT[T/C]TGAATGCAC
TCCCATATCTATCAGTCATATCCTGGATCCCGATCGATCTCG
scaffold5797_m_9489
GATGGCCTAACCAGAAGGGGCATCAGCAAAAAAAAAAAAAAAAAAAAAAA[A/T]AGTTCAATA
ATGTAGGAGACTTTTTTTGCGGCTCCCAATTCATACGACGTA
scaffold580_m_1503
ACACTTAGAAGTGGGCAGGGGTTATTATATTGGATAATAAGGCAGTGAGG[C/T]AGGTGCCT
ATTAAACGCTTTATAAATAGCTATTAGTAAGGATAGTTTTTAT
scaffold5800_m_1138
ACGAACTCACGAGAGATAGCCTTACAATCCTTTCAGAGATGGTGTACCAA[T/C]TATGACCAG
CACTATTTCAGAGTCAAGCGCAGTAATATGCCCTGCGCGATC
scaffold5802_m_11191
ATGACGCGTGGAGATGTGTCGAGATTTTCAACCCAAGACCAAAAGTCCTT[T/A]TGTGCACGT
TTTGCATTGGTAAAATCCGTGCTGTTTGCCAAAGGGCATACA
scaffold5808_m_16562
TCCAAGGCCTTGATAGTCTAGAAACAACAGACAGCTCGTGCGAAGCGGTA[T/C]GATTCCAT
CGTTGACCACGTTGGAGTATGTTGTGCGGTTTCTGAATTTCTT
scaffold5815_m_30513
CATCGCGGGCATCACCGGCCCACACTTGATTGTCGTTCCCAAGTCAACAT[C/T]GGACAATT
GGAAGCGAGAGTTCGCCAGGTGGACGCCAGAGGTCAACGTTTT
scaffold5817_m_3645
AAATCTCGGATGAGGACCCGAGAAATCTTGAGCAAGAGCTGGTCTCTTCT[A/G]CTGGGCAA
GCTGTAAATGAACAAAAGTTGGTCGTGTTGACTTCCAAGAAAT
scaffold5818_m_4786
GGCCCGTTTGCCTGAATCAGGGGCATGGACTTTCTGTAAACCTGCCAATA[A/G]GACGGCTG
TGGTTGGTTGTAATTGTATTACATAATAATAAACGAAAGCAAG
scaffold5823_m_12748
GCGGTTACAGCTGCGAGAGGATGGGGCGAACCAGGGACGGCAACGGCGTT[G/A]TGAAAG
CTGGTTGGCTGGCAGGGGACCAAGTTAAGCGCCCGGGCGAGCAGG

Figure 6 Continued scaffold5827_m_10221
ATTTTTGAGTTGCAAATATTCGTCACTTGGTCCAGCCTCTTGTCTTTTTA[T/G]CACGTAGGAG
AGCAGTAGCGATAGCTAGGTGGGACGAGGACTGGAGAAGAG
scaffold5828_m_31167
GGCATGTGCCGATCAATAACACTCCACAAAGGCCATGAGCGTTGCGGAAG[A/G]ACGCAGA
GCTATTTATCTATGTGCCAAACTGGCTCTTCACCCGGCTCGCTT
scaffold5833_m_13138
CGCCAATTGTTTCCCTGTTGGTCTGCGGAGATTCAGTCCTCCGAGCGGTG[T/G]TTTTTCCTC
TTCATGGCATTCCGCAGCGAGGGGATGTTACGAGAGCAGCGA
scaffold584_m_1487
TTAATAGTTTTATTACTATAAGTAAAGTAATATAACCCTTAAAAATATTA[T/A]TACTTAAAACCC
TAAAAAAAGTAAGCTTAAATACCTTAAGATTTTATTAAC
scaffold5848_m_6229
TGTACGTCTTGTACGGACCAACGATAATCGTATGATAATTATTATATAAT[A/T]AACTTTCAAAG
AACACAAAACACTTCCTATGTAGCAAGCTTCCGGAGATTC
scaffold5849_m_4218
GCCCCCTATCAAAGCTGATGCCGCCCCGCACATGCTCCGTGCCGCCGGGG[A/G]AATAGGA
AAATAAGCCGGCTCTTCGTGCCTTTTACTCCGTACCTTGTCCC
scaffold5867_m_48896
TTCGACTCGTCCGTGAGGGCGACGGGAGAGAAGACGGCGAGGTTGCCAGA[T/A]GTGAGTT
TGACTGAAAGAGGGGGGGGGGGGGGGGGGTTGCAGTTGGTCAGT
scaffold5872_m_18962
CTAGGTTCCCCGTCGTCGGCGTCCGCGACGGCCTCGTCTCCAGCGTCGAC[G/A]CAACACT
CTCGGGCAGGGCGGCGTAAAACGCATTCAGGCAATTGATTGTCC
scaffold5873_m_2239
GTACCGTGGGCACAGTGGTTCCTGAGGTTTGAAGTGAAGAGGTCGAGGGG[C/T]TGACCAA
GGTTGAGCCTACAGTAGAGATGCTGCTTGTACTGTCACTGCTGC
scaffold5874_m_8708
TAACCTCACCATCCGAGTCGGCCTCGTTTGAATTCCGAGACGTGGTCAACT[C/T]GTGATCTCT
TGACACGATCCAGGTCGGCATAGAACCTCTTCGCACCGGCAC
scaffold5876_m_25181
GTCGGCAACTGCCAGCTCCTCGATGGACAGAATGAAGCCACAGTGTTGAC[T/C]GATACAGG
AAGAGCTGCCAGAGACTTTGTGGACTTCTTTGCTGCTAGCTTA
scaffold588_m_5575
CCTATCTTTAATCTTTATACTCCTAATATAATACCTCCCTTATATATAAT[A/T]AACCTTAATTAT
AAAATAAGCTACTTACTTAGGGTATAGTTACTATATTAA
scaffold5882_m_26924
AGTCGTACCAAGATGGCGAGGTGTTAGAGGCTTTTTTGTATTATGTGTCT[A/T]CTAGAACGG
CGACGTCGGCATGAAGCGCGAATAGGAGCACACGGCACGACT
scaffold5887_m_6614
GGAAAGAAAAGAAAAAAAAAAAAAAAATAAGTTGTGTGGGGAAAGAAAAA[G/A]AAAAAAAAA
AAAAAAGCACAGCCTAAGCACAAAATGTCCACATGCTTCCTT
scaffold5889_m_17337
GCACCATTGGGCAGGATAACTCTGCTGGCGTACAACGTGTCGACACTGTA[T/C]GCTTACAG
TTTGAGTCAGAAGGTAGATGATGATGACGATGACGAAGGCGGA
scaffold5896_m_12596
CACCCCTCTCCTCTTCCAATCGCCATTCGCCAAATCGCCAAGAATTGAAA[T/G]TAAAAAAAA
AAAAAAAAAAAGGTTGAAGCTTTACTAACCGCTGTGTGCCT
scaffold590_m_11839
CTTTACGAGCTCCTCGGTCCCCCGACTCTCCGTGGCCACTTTTGCGCATC[A/T]ACACCACG
ACGAGATCATGGCGACTCCAGACGCCAAGGCGTCTCGCGCCCC
scaffold5901_m_3336
TGGCCCTCCTCGTCCGGGATCATTGGTGGCCCGAATGAGGTTTGAGGCGA[C/T]AAGACGG
TGTTATAATGACGCCTTGTGCATTCGACGGCATCTTGTTCAGAA
scaffold5910_m_2969
CTGTACAACGCGGCGAGGACAAGAATTTTTGTGGCATGTCTTGCGATAAA[A/C]AGACATTCA
AGAGATTTATATCCCGACATGGGTATATTTGCCATGTGATGT
scaffold5912_m_61954
AGCTTGGCCTCACTTATCCAATTGTTTCTTCGCATTTGGCAACATACTGT[T/A]CGCGAGTTTG
AGTGGGTAACTTCTGGTATTGTCCTTGCTACTTATGGATTT

Figure 6 Continued scaffold5925_m_4906
      CTCAAATGTACGGATCCGTAGAACGTCTGCTTGTTGGCCGTTGTACGCCT[G/A]CCGTTCCTC
TTTTTTCTTTTCTTCTTTTCCCTCAACTTTTCCGTGTGTGGG
scaffold5935_m_18351
      AGACCTGGTACACTTGCATTAGTGCTGTACGCAGACTGCACGGTCCATAT[T/A]GAAAAAAAA
AAAAAAAAAAAAAAAAAAAAAGGCCGTACTCACGTTTCTGAAG
scaffold5937_m_3353
      GCAAAATGGACAAGAATCCGGATTCTCTTTTTTTTTTTTTTTTTTTT[T/A]AGAGGGTCCGG
GTCCCCCTTTGGAATCGCCTCGAAACACCAAAACACCAAC
scaffold5939_m_653
      CTTTCCCCTTCTTTTTCTTCTTGCCTCGCGGCGCGTTCCGGGTCCACACA[T/C]TCCCGGGGA
AGCTGGGAAGCTGGGAAGCTGGGATCTAGGAAGCTAGGAAGG
scaffold5940_m_18895
      AGACACCAACATGCGATTCTTCAGCAACTCAGTGGCTTCTGCTACTCTTT[G/T]GGCCGCTAC
TCTATCTCAAGCGCAAATCCTCATCAATGAGCAAAGCTTTGG
scaffold5945_m_3469
      ATCAGCCAGCGTGTTGCCCGCGTGTTAACGGTCGCTCAATCGGCCCCCCC[C/T]CCCCCCC
AAATTGGTTGAAGACATGCACTGATGACGAGGCGCTGCGGGAG
scaffold5952_m_1756
      GTCACATGGCTCTGCTGCGAAGGACGTGTTCCATGCTGATGATCGATTAG[A/G]TGAAACTT
GTTGCGGTCTTGACAGCTGCAAGGGTCCCGTGGAGATGCCACG
scaffold5954_m_13088
      TCATTGACTGCCTGTGAGACGAAGACCGATGTCGGAAAAGCCATCGAGTC[C/A]TGCACGGA
CGACATGCTGTCGATTCCCGAGAATCCCGCGTTTCGCAAAAGT
scaffold5957_m_4752
      CGTGCAGCTGGCATGCCTAATCTGGTATTTGATCAGCTATTTTCCCATGG[G/C]GTCCACGG
GTCTTCGCCTGGCAGCTTCATTTGGCGCCAGGCAAGCAGCTTC
scaffold5962_m_10238
      GGAACGCAACCGTATACTTGGCATGTTGGCGTTCTGGAAAAAAAAAGAA[A/G]AAAAGAAGA
AAAGAAAAAAAAACCCCATCCGTGGCAAACGGTTGGATGGT
scaffold5967_m_6548
      CTTTGAAGGCAATGCCCTCATTCGCCGTCTCGTCCGCGTTGGTGTCCTCG[A/T]CGAGTCCC
GCATGAAGCTCGATTACGTGCTTGCCCTGAAGATCGAGGATTT
scaffold5968_m_2637
      TGTGGACTATCCTTGGCTGATGGGTATTTCGAAGTTGGAGGCTACGCATA[T/C]TGTGAGCG
GGATGCATGGAGAAGGGTCCAGGCCAGTCATATGCAGAGCAA
scaffold5969_m_4552
      AGCATCAGGTTTCCGAGAGACGGGTCGGGCCCCCGGGGGGGGGGGGGGG[G/T]GGGTC
CCTAATGGATAGATAGACCAAGACTTACGGAGGGAGTGGTTCACGC
scaffold5973_m_8063
      GGACCGCACCGTCCGCCTCTGGAATCGTGACAGGGGCCACTCCCGCGACA[T/A]ATACCAC
ACCAAGCGCATGCAGCGCGTCATGGCAGCCAAATGGACCCCGA
scaffold5980_m_4826
      CTTCGCTGCTTCGCAGAGGTTGGGAATCTCGTTTATGAAACTATTCAGCC[A/C]CTATCGCGG
ACCAAGTATGATCAATGAGTTCCTCGATCCTCACGGCGAAGG
scaffold5982_m_13101
      AAGTCCACCGATGAGTACTCGGAGATCGTCTACGAGAGAAAAGCATTCTG[G/C]AACCACCC
CCACACCCGTACGCAACAAAGGTAGCCGAACTCCTACGCCAAT
scaffold5983_m_7587
      ATATTGCCATTCCAGAGCGAGAATTCGTTCTTAGACCTTTATCGCAGTAA[G/A]CCCAATCTTG
CCCAAACTAAAGGACTTGTTGCTATTGACCACAGTCTCATT
scaffold5984_m_8045
      ATAGCGACGTTGGCGCCTCTGCAGTTGCGCCTGGTCGTCATGGACGCGAC[T/A]CGACTTG
GACACGGGGCCGGTTTTGGTGGGTACTGGGTTGTCCGGCGCTA
scaffold5987_m_5902
      AAATTTGGCATCTGGAGAGTCTTGACACCCGTTTTTTTTTTTTTTTTT[C/T]TTTCTTTTTCTT
TTTTTTTTTTTTTTTTCTTTCTTTTTCTTTGGCCA
scaffold5990_m_15266
      ATCGCCGTAATATCGGTAAATCAAATCCATCGTTGCGTGTTTCCCCGATG[C/T]GGATATGAA
GGCAGAGCGCAAAGCTAAAGCACATCGTCCTTTTAACCAATG

Figure 6 Continued scaffold5996_m_13473
GGATAATCTTGTTGCCTAGCTGAGAGTAAGAACGGCTTTGGGGACATCAT[G/A]CTTCATATT
GGTCATGGAGCATGCCCCTCTTTATACCTGGTTGTGCGGATG scaffold6001_m_11001
CGGTGGAGCAACATTCATCGACGGCGGGGAAAGAGAAACAAAGTCTGTCT[C/G]ACTCTCTC
TAGCAAGCTCCGAGTCCGAGCTGACCAGATGCTGCCGACTTGA scaffold601_m_1895
TTATTATCTTATAGAGAGTTTTATAGCTCTCTTATAAGATTATTAGTAGC[C/T]CTCCTAAATAT
ATCTTTAGTTTAACCTTTAAAATCTTCTCTAAAGTTCTTC scaffold621_m_540
ATTAAAAAAGAGGTAAATAAAGACACTATAAGGATAGATTTAATAAAGCT[G/A]AACTAACTAG
TTCTAGGATAAGTAATTAAGGCTATTATAAGACTATAAGAA scaffold623_m_1649
TTATTTAATAGATATCTATAAATTCCTAAGAAAAGCCTATAAGACACTAA[G/C]TAAAGACTAGC
TTAACTAGTTTAAACTAATTACTATAAGTAAGATTATTAT scaffold631_m_2058
GTTATAAGGGTATTTATGCTAGATAAGTTACTAAGCTAAGGCTATTAAAT[A/G]TTAAGATTTAT
TTTATCTAAGGGAAATAGAATACTACTGCTAATAGGTTAT scaffold634_m_7757
GTGTCATCATCTTGCAGTTGTTGTCCCTCGCACCTGGCACTGCACTGCAC[T/A]GCACAGCA
CAGCACAGCACAGCACAGCACAGCACTGCACTGCACTGACTTG scaffold645_m_8175
CACTAGTCCCTTTATAATTTCTATTAGTCTTTTTTAAAGATAACTATTCT[C/T]TAAGTAAAACTT
CTTTACCTTATTATAGTTTTCTATAGTCCTTTATACT scaffold648_m_873
TAATACTATTATTATAAGGACTATAATTCTCTATAGCCTTACTACCTTTA[T/G]TAGTAATTTTAC
TAGTCTTTATAGTAGTCTTTATATATTTAGTTATTACTT scaffold652_m_469
AAATATGCCGTAAAAAAGGCCTAACCTTATTAGTTACTATAAAAACTATT[A/G]CCTAAAGGCC
TAGGTTATATTACTAAATAATAAAGGAAAACATGCTTAGAG scaffold657_m_4174
TTACTTTAAAGCTAAAATAAAAGGTTTTTAAAGTAATTTATAACTTTAGG[A/G]ATATAAATAGT
AAGACTATTAAATTAGGTTATTTATATTATAATATAGAAG scaffold665_m_337
CTTATTTTCCTTATAAAGCTTTAATATAGTAACTACACCCTAAGTAAGTA[A/G]CTTATTTTATAA
TTAAGGTTAATTATATATAAGGGAGGTATTATATTAGGA scaffold67_m_1628
TATTAAAGATAATAAATAAGAGTTTAAAGTTAACTATAATAGAAGGTATT[G/A]TAAATATCTAG
TTAAATAAAAAGGCTATAATACTTTAGAGAATTCTTAGGT scaffold671_m_2437
TAGAAGAAAAAAATAGATAACCTATATTAATTTTTATAATTAGTTAAAA[T/A]AAATAAGGTACT
TAATACTATAGTTCTAAATAGTCTAACTAAAGGGCTTGT scaffold676_m_1099
TATTAGTAATAAGTAAGAAAAGTCTTTTTATTAATAAGGTATTCTAGAAT[C/A]TTATAAGTACT
ATTTTTTAGGAGAATATTTTATATTATTACTTACTAATAA scaffold681_m_378
TCTATCTCTTATTCTCTTTTTCCTTTACTTAGTAACTATAAGGCTTACCT[T/C]TATCTCTTATTC
TCTTTTTCCTTTACTTAGTAAAGCTATATATTTACCTCT scaffold682_m_897
TAAATAGGATTAATAAAATAAAGACTTTAAAACACTATTATATAAAAACA[G/C]GTGTATAAATA
CTATACTAGATAAAGAAAATAAACTTATATAAGGAAGTAA scaffold693_m_3846
TTGTAGAATCTTGATGTGTTCTTTGCTGCTGCGCGCGGGGGGGGGGGGG[T/G]GAGATTG
CCTCTCGCTGGTTGGAAAACCGTGATATTGCCAAGATGATTGAT scaffold7_m_336
TTACTTAAAGGAAATAATTATTCTCTAAGTCTTTATTTAAATTAATAAAA[T/A]AGCTTATATAAG
TATATATTACCTTTATTTAAAGTTAGTGCTTTACTAATA scaffold70_m_414
AGATTATACAAAAGTCTTATATTTAACAGCGATTTTCTCTTTAACTAGAG[G/A]TTATACAAAAG
TCTTATATATAGCAAATTAAAGCTAGAAGATAGGGCTTTC

Figure 6 Continued scaffold702_m_809
    AGGCTAGTAAACACTATTTATATAGTGTATCTAGATAATATCCTTATTTT[A/C]TTAAAAATATAA
AAGAAGCATACTATATATATTAAGGAAGTTTTAGAATAT
scaffold731_m_7682
    GGGCTGTATGGATCATGGTAAGCAACATCTGCTACTCTTCCCTGTCTTCT[G/A]TGCTTCATC
TCCTTGAATTATTGCGTGTGCATTTGCGTTTCTTGAGTTTTT
scaffold739_m_14951
    ACGTGTTGTTGCCTCTGTGCTAAGCGTCCGCAGTTGAAGCGCATTGCTGA[C/T]CGCAGCCT
CAGCTTCTTGGATTAGTGCTCGCCGTTACACTGTCTTCGTATT
scaffold74_m_535
    TACTATTTTAACTACCTTTTATTAGTATATATAAGGGTACTATAATCCTA[T/A]AGTATTAGTAAA
TAAACCTTTAGTAAAAGTTATAAAATCCTAGGAAAGACT
scaffold740_m_1214
    TCCTAGTATTATTTTTAAAAATAAGTTAAACTTATTTTTTATAGCTTAAT[T/C]AAGCTATATAAG
GTAATTAAAATAATACTATTAATTATTTATTAAAAGATT
scaffold743_m_5917
    TATAAGCTATAGGCAGACAGGGACTTTATTAGAACTAATAAGGATAAGTA[A/G]ATATTTATTT
ACTAGAACCTATCCTCTAAAGTCTAGTCCTAGGTGGCTACT
scaffold748_m_415
    ATAAGCTAATTCTAGTTAGACTTATACTACCTATTATGCGTTAGACTTAT[A/G]CTACCTATTAT
ATATAAAGCAAAGGCTTTTTATAGTATTTCACCCTTAAAC
scaffold749_m_3023
    TTTATGCCTAGTGCTACTTTAGTAATGTTATTATTATCTTAAGAGTTATA[G/A]GAAGTATCTAA
TAGTAATATACTAATAAGTAGCTAGCCTAGTAACCTTCTA
scaffold766_m_226
    GGGACTATTTAATCTATAAAGAGATTACCTATAGCTAGATTCTTTTAAGG[T/G]TCTTTATGCAT
GCCTAACTTTAGATTTTTAACTTAAATGCCTAGCGCTACT
scaffold772_m_1590
    ACCCTTAGGATTATTATCCCCTAGGTCTTTCTTTTTACTAGCTTTACCTC[T/A]AGTCTTTTTAC
CCTTAGTAATTTTTTCTTTAAATATATTACCCTTAGTATT
scaffold778_m_343
    CTATAGTTTGCGTTAGGACTAGTACCTATAGTAAGGGCCTTAATATTAAC[T/C]ATAATCTTAT
AATACTACATAATAGCTATATACCACACGCTTTAGCTAATA
scaffold785_m_186
    TTACTACCTAGGACTTAATTATATAATATATTTAATATTACTAGTCTTAA[A/G]CCTTTTAAAGG
GGACCTAACTAATATAAAGATATATCCTTACTATAAGAT
scaffold789_m_1201
    AAGAGGAATCCATAGTGAAGTGAGTCTAGGTCTTTTTTTCCGATTTTTTC[T/C]GATTTTTTCT
GATTTTTTCCGATTTCTTTCTGATTTTTCTAATTTTCTGAT
scaffold79_m_669
    AAGAAAAAAGATATTAAGATAAAAAGACTTTTAAAAAGTATAAAAAAAAT[T/C]ATTCTATAAAC
TAAACTAAGAATTACTTTATTAAGGTATATAATATAAACT
scaffold795_m_259
    AGGATAGATTTAATAAAGCTAAACTAACTAGTCCTAGGATAAGTAATTAA[A/G]GCTATTATAA
GACTATAAGAAGTTAAATATAATAGGAAGTAAGTAAATATA
scaffold8_m_1327
    CATAACTAAGTGCTAGTAACCTAGTACTAATATTATAAGTATAGCCCTAA[T/C]TATATATCTAG
ATATATCTATCTTCACTCTAAGATATATAAGTAAGTTAAA
scaffold814_m_2725
    ATGCTATATAATAAATAGTTAATTTACTTATTTCTAGTTAACTAAAAGAC[T/C]AGATATAAGTAA
GTTATCTTATTACTAAATAAGGAAGGCCTAACTATTTAT
scaffold815_m_632
    CTAATAACTCTATAGATTTATTATAACCTTAGCTAATTCTTAATATCTAT[T/C]TAGAATAACTTA
TTAGTTACTACTTACTATTATTAAAGAGTTTAGTTTATA
scaffold83_m_3324
    CTAGTGTAAATTAAAGGGGATATAGTAAAGGAAGTAAGATATAACCTATA[C/T]ATTAGCTCCT
TATATAATATCCTTAGGGAGGGAAATGGATTTATAGTTAAA
scaffold835_m_2169
    TATCTATAGTATTACCCTTATTTAATTAGGTATAACTCTTATTTATTAGG[A/G]TTAGGTTATTAT
CTAATATTACTCTTATTTATTAGGGTTAGGTTATTATCT

Figure 6 Continued scaffold854_m_82704
GCCCAACAAGCTGATTCTCCCATCGCCCATTTTTTCCGACTCGCCCCCCC[C/T]CCCCCCAC
CGAAATTTAGCCAACCGCTAAAAAGTGCGGGCTCTTGTCTCAA scaffold855_m_2053
ACTTTTTTTCTTAGCCTTATAGTTAGCTTTAAGTTATTAAAATCTCTTAA[T/C]TAATTATTTACT
TTCTTATAGTATTATTTAAGCTATTTAAAAAGATTATAA scaffold859_m_4037
GCGAATACAGGTAGAATACCTTTACATTTAGATCCTAGCTTTAATATAAT[A/G]GAATTAACTAT
TAGGTTAGCTTATAGTTACTAATTTAGCATAGTAATAATC scaffold869_m_1466
ACTAGTCCCTTATTATTAGGGGTGGCTATAGGTTTATAATAGAGTTAGTC[C/T]CTAAGACTAC
TAGTCCCTTATTATTAGGGGTGGCTATAGGAACTATAGAGG scaffold88_m_822
TTCTCTAATTTTTACTTTAAGCTTACTCTTAGCTTACTTTTTCTTACCTC[T/A]TAATTAATTACT
AACCTATACCTTTTATCTTTTCCTTTCTCTTTCTCTTAC scaffold887_m_1346
GCCTTAAATACTTTCCTATCTTCTTAAAAACTTTATTATAATAAAGTTTA[T/C]AAGCTCTTTTAA
CAAAAACCCTAACTTCACTATCTAATCTTAGTTAAGAGA scaffold895_m_473
CTATAATTCTTTAGTAACTCTATAAGTGTTAGGAGCGCAGAGGTCAGAGA[T/C]AGGATGTTTA
TTAAAGCAAGTCTTCAGAGAACCTTTAGGCTATACGAATAA scaffold896_m_1808
AGAGATCCTAAACTAGTGCTAAGAAGCTTATTACTTCTTAAAGATTAATA[T/C]TAAGAATACTT
ACTATTAAATCTATATTAAAGAGAGTAATAAGTAAAAGAC scaffold901_m_940
ATTAGTAATTATAAGTTAATTTCCTTAATATTCTAACTTTAGCCTTTTTA[G/A]GTTAGAGTTAGT
AAGTTATTAGTATTTTAGGTTAGGATATAGCTATTAAAG scaffold915_m_275
ACTAAAAAAGCCATGTTTAATTTTTATATTCTAGGGATAGCTTATAGAAC[T/C]AAAATCACTAG
ATATTTCATAGTAATAGCAGACGTAATGCTAAATCTAGGA scaffold930_m_1179
ATTTCTATGAATTATTTTATATTTCTATAAATTATTATTATTACTTATTT[A/T]AAAAAAACTATAA
AAGAACTACTAGTAAACTTAATATAAGTAGCTTATTA scaffold936_m_1153
AATTATAGGTCTAGTTTAAGGTCTAGCTAATCCTAGATTTACCTTAAGCT[T/C]TCTAATTTATA
CCTTTATTTATAAGACCTTTTATTTTCTTTAAAGGTAATA scaffold937_m_1767
TATTCTAGATTAACTAAAAGACTATAACTAGGTCCTTAAGGAAGCCCTTT[A/T]GGTATAACCT
ATAATCTCTAGTGCTTAGCTTTACTTATAGTATAAATCTTA scaffold949_m_4278
TCGAATTCATATTACATAAATCACTACGCTTGTTTATGGGAAGTAACAGC[T/G]TCCGAGATCG
TTGGTCACTGGGCTTGGGACTATCTTGAAAAGTCGCACAAC scaffold952_m_2318
TTATAACTAATTATTAAGGTAATTCTCTATAAGAATAAGTATTTTCTTAG[T/C]ATTTAGCTTATA
TTAATTATAAAGAAGCTTAAGTATCCTTTAGGTATAATA scaffold959_m_1009
TGTTATTACTAATCTAGTACTAAAGTAAATAACTTCTAGGTTATAGGGTT[T/A]AATTATTAATA
ATGGCATTAATCTTAGTAAGGCTCTAGCCTATGCTAGACT scaffold984_m_1221
AGCTATATTCCATAGGAAACTAAGCTAGGTAGCACTCTATAGCTATATTC[T/C]ATAGGAAACT
AAGCTAGGTAGCACTACTAAAGTATATATAAATAATATTAG scaffold988_m_144
GAACCTATCTTCTATAAGCTACTAGAGGGTATAAATATATAAGGTTATCT[C/T]TAGAAAATAA
CTAGAGTATTATATAGGCTATAGGAAGCTCCTTAATAATAG scaffold992_m_1017
TTTATAAGATTAATTAAAAGCAGTTTTTACTAAGCCTATATCTAACCTTA[T/C]ACTATCTTACTC
CTAATAGCTAAGTAAAGCAAGACCTAGCAAGCACCTAAG scaffold996_m_831
GGGTTTATAGCTTCTTAGAGCTTTAGGCATGCCTAATTTTCTAGATAATC[T/C]GGATATTTCT
AGGGCGCTAGGGGACGCTAACTAAGCTATTATCCTAATGTT

SEQUENCE LISTING

```
<160> NUMBER OF SEQ ID NOS: 817

<210> SEQ ID NO 1
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 1
ctttacctaa agcattaact tagggtttaa aggaatacct cctctaagaa saatttctaa      60
atccttcgct cctataaggt attactaaag gtacttctaa ag                        102

<210> SEQ ID NO 2
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 2
gaccgactgc gcagatcccg tcaagttgtc atgccgatct gaaactctag sccctccca      60 ctcttcactg cacaactcga cagcccggtt tgtgtcagtg aa                        102

<210> SEQ ID NO 3
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 3
attccttaaa ctagttatct taagatatta tagaattact tactattaag sagaataaag     60
ttataaagat aagaaagaga gaaaaaagag ttaagggagt aa                        102

<210> SEQ ID NO 4
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

```
<222> LOCATION: (51)..(51)
<223> OTHER INFORMATION: S is A strain AR37 or G strain RGT18

<400> SEQUENCE: 4
ctcctgggtc tcctggtcta gtcgcgagat aagtcgcgag ataagataag sctggacagc    60
aacaagctgc tgtgttgttg catgttccaa cagccattga gc                       102

<210> SEQ ID NO 5
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 5
tagctcatca caataattca tgagaacaat tttttattat tattattatt sttcttcttc    60
ttcttcttct tcttgtcctt ctcctattta gccgccattt cc                       102

<210> SEQ ID NO 6
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 6
cggccggcca ggaacatggg aatggcagtg gacgcggttt gcaggatgac scccaggttg    60
aagacccagc atgagatgat gagagccaga cgccggccaa tg                       102

<210> SEQ ID NO 7
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 7
atacagaatg gtgtaattgt aagtcctata caaagagaga gagagagaaa sgggggggcaa   60 aggagagaaa acatcatacg caccagtccc aagatcagaa ac                       102

<210> SEQ ID NO 8
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 8
acgccatcat cggggcctcg gccgccctcg ccggcgtaac acgcatgacg statccatcg    60
```
tcgtcatcat gttcgagctc acgggcgcgc tgacgtatgt gc         102

<210> SEQ ID NO 9
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 9
attttttttt cgatggatgc gggcggtttt cgatggtatt ggcggtcgga scgggtcaga    60
ggaggacgac tcaccactgc gactctaccg gcaacagaga cg                      102

<210> SEQ ID NO 10
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 10
tttccctgaa tccattcgtt ccctggtccc tggtctaggt gtgggagtga sttggtggag    60
caatttacgg atccgtaccc gagctctgat cgacgagcgg ac                      102

<210> SEQ ID NO 11
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 11
tggtgttcca ggtgacgagg ttcgggctga cgccatgctc tcgcatgatt sgaaggatct    60
gctcggccag caggcggtcg cggccgttca tcaaaccccg ca                      102

<210> SEQ ID NO 12
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 12
atgggtgcgt ctagcaggac aagccagacg tatatcctca aggtgactca sccgggaaaa    60
cccctccaat gtcagtaaaa gacgactgct tttctcgaac tg                      102

<210> SEQ ID NO 13
<211> LENGTH: 102
<212> TYPE: DNA
<213> ORGANISM: Artificial Sequence

```
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 13
tgttgttgtg tgttgtgtgc gggcgaggag gggcagtttt ccatacctat sgtgtgaccc    60
cgctgctcca tgtagtcaaa gaaggccttg cgcacccgcg ca                      102

<210> SEQ ID NO 14
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 14
ccgtctacgg agactcccgt gagaagaaaa gttaccaggc tgttgcacac sccccgacac    60
tagaggcgtc atcttcttct tgtccccacc gcctggcacc ac                      102

<210> SEQ ID NO 15
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 15
acgagctcta gaagtacttc ttgcgcattg ctgttgccgc tgagtcgact sctattgatg    60
aaggggaatt cggatacctg atctatcgag ggtaggcgca ca                      102

<210> SEQ ID NO 16
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 16
agagctcaat gactgccacg ccagagtaca tggcccccag gcccaatatc sccaggcccg    60
ggcaagcgca acaagactct gaggaataca tactgcaata ag                      102

<210> SEQ ID NO 17
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18
```

<400> SEQUENCE: 17
tcccccacta catcacgtgt aaggaaaggg gctgggcgct ggcatgtatt sgggcacact    60
ccaggccacc ctgctcaggt ccatctgctt actgttggtt gg    102

<210> SEQ ID NO 18
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 18
cactgcactg cactgcacgt agcacccatc tcgttcaaat ctaggtccaa sggaagcgtc    60
cctttttttc aaagagaaga aggaatgctg agacatcggg ac    102

<210> SEQ ID NO 19
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 19
gcaagactgc aagactgcaa gattgcactg cgacaacacc caggttggta scaccaaaca    60
cccccaaaca cccccaaaca ccccaggcag ccacccggac gt    102

<210> SEQ ID NO 20
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 20
cgccgcagga gccgcaggag ccacaggagc cacagggact acgggagcca stgatggaat    60
ccacggccaa ctccagcgtc acggcggcca atcacatctg ca    102

<210> SEQ ID NO 21
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 21
gatacttgtt acttatcaca aagaagagat taaaaatcta gttaattcta scgcatttct    60
taactatagc cctagaggac aataacttaa ccgcggtctc ta    102

```
<210> SEQ ID NO 22
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 22
gcatattaac tcatggctgc tcataggtcg atttgattga atgtatggtt stctctcacc     60
gtgagaacaa tccacccctc tcgtggaaga gtcaatgttt tt                       102

<210> SEQ ID NO 23
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 23
ccttccttat gcctcctaat aaactcatct ttgataggaa aagtgtggag sggaaccacc     60
agctatatgt atagacatgt atcagctgcc tgcaaaagac ct                       102

<210> SEQ ID NO 24
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 24
ggaagatgcc atgaagaacg aactcggaac tattttaact ggcctccagg scaggctcct     60
tgctcaggta ccggcgtaca tgatcccgtc cgcttacatt cc                       102

<210> SEQ ID NO 25
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 25
agcagcctcc tctgcttggt ctacggccac ggccacggcc accccgacgc scacagattt     60
tgcaggctcc gcctcgtcca tggcgtcagt tgctgggaag tc                       102

<210> SEQ ID NO 26
<211> LENGTH: 102
<212> TYPE: DNA
<213> ORGANISM: Artificial Sequence
<220> FEATURE:
<223> OTHER INFORMATION: Epichloe festucae
<220> FEATURE:
```

<220> FEATURE:
<221> NAME/KEY: Variation
<222> LOCATION: (51)..(51)
<223> OTHER INFORMATION: S is T strain AR37 or C strain RGT18

<400> SEQUENCE: 26 aactttatttt tctaatatct ttagtatatt aacttataaa ttataactac sttatattaa      60
ctttattact tagctattac ttatagttat taataaatttc tc      102

<210> SEQ ID NO 27
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 27 tataagggt taatgggaag aaaatcacct agggaaaggg cctatgtgat satctaggct      60
ttgcctagac ctagcaatat aggtgttaat tgcataagtt ac      102

<210> SEQ ID NO 28
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 28
attctagaaa taacgataaa tcttcgcctt tcctctattt atctttatta sacctaacct      60
tagtcgtggc aatttgccac tagctataat aacaatagcg ct      102

<210> SEQ ID NO 29
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 29
cgtgcctaaa taataataag caattattaa agctatctat aaggaactta sctataaagg      60
agttaaagtg gtttttttaag taataaagta ataatactag tg      102

<210> SEQ ID NO 30
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 30
cctagccgat ctaaatccta ttatactagg actaggtata taataaaggt stcctttagc      60
ttattaaagg cattattctc tttaagtcct tattagaaag gg              102

<210> SEQ ID NO 31
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 31
cttttatagt tactcttact atactaatat cctatttat tagtaagtac sttataaaag      60
gaaactctaa taataaatag tatactatac ttaaattagt ct              102

<210> SEQ ID NO 32
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 32
cctgagcact ggcgctctac tatggactac gccggacacg agtccaggga saccgagacc    60
cagagcggct caaacgggac tttgaggatc ccaatggatg gc              102

<210> SEQ ID NO 33
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 33
attaaacttc tcttattatt ttagaagaaa acatagctaa ttttattaag sactttaagg   60
taaagataaa agcaataggt attcctaagg caaattagcg ta              102

<210> SEQ ID NO 34
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 34
attataatac ttatttaaat agtaagtaag gtaaattcag tacttaacta staagtcaga   60
tatagtactt atactaattt agcctaaata aaagtctctt tt              102

<210> SEQ ID NO 35
<211> LENGTH: 102
<212> TYPE: DNA

```
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 35
ttatagtttc tagagttttt ctagctaagt aatttacttt attattacta sagctttaat      60
agtaagggtt aagggtttga atctaagtat agtctttata aa                        102

<210> SEQ ID NO 36
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 36
gaagatataa tagataatat tacctagtaa ggaaagaagt aataagtgcc stataaaagg      60
cttataataa gtctaggtat tttaaagcaa acctaaccta gt                        102

<210> SEQ ID NO 37
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 37
ctagaatagt attatatacc tagttactta ctactttact agccttatat scttataaaa      60
aaactatata atttataata aaaaactatt agctattatc tt                        102

<210> SEQ ID NO 38
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 38
tcttattaat aagttcttta agatccttta atagtattat taatatactc staaaaagtt      60
actaatatat taaatagttt aaatagtatt ataagatatt ta                        102

<210> SEQ ID NO 39
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18
```

-continued

<400> SEQUENCE: 39
ttagcttaat tactatatta ttagtaatta ggttaagata gcttcctttc scttattatt    60
atgcccttat ataataaggt ataatttctt atatagtgat tt                     102

<210> SEQ ID NO 40
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 40
aggcacttaa gcttactctt tttagggttt taagtaataa tattcttaag sgtaatatta    60
ctttacttat agtaataatt ataagagagg ttcttactag ta                     102

<210> SEQ ID NO 41
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 41
gtagttccta ggcattaaaa tcattaggaa tcgtaatact aaagagatat sgttattata    60
ggaattatat atttaaaaga tagcttagaa gtttatgcct aa                     102

<210> SEQ ID NO 42
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 42
aagaatatat agctaaatta gctataatat aagtaattta ctaaagagta sttaagccct    60
cctaggagta aaaattctct ttaacctaag tatatatatt ag                     102

<210> SEQ ID NO 43
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 43
tagttataga atttatattt tattagttat tagtattata aggattaaaa saatgctagt    60
tatataaaag cttttattat tacctatttt atttaattag tt                     102

<210> SEQ ID NO 44
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 44
agatttatat tataagtagt atccctccta atagcattta gctaacttta sttctaatac    60
ctatttagct tattatatat ttatagtaag ctttagactc tt                      102

<210> SEQ ID NO 45
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 45
tcgctcggcg gctggctggc tgatcatggc cctcttcttt ttttttttt sttttttttt     60 tttttttggt tgtaacagtt ccattttgcc gcgtcgcgga cc                      102

<210> SEQ ID NO 46
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 46
ttattataat ttagttattt agttataaat tcttaaagtt taagattatt sagattatta    60
agctaagtat aggtatatag aagctaaata tagtatattt ta                      102

<210> SEQ ID NO 47
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 47
tttatttagt ttattatagc taacttatat ctattatagc taacttatag stagtttact    60
atatctaagt cttatattag aactttacct ttattactac ct                      102

<210> SEQ ID NO 48
<211> LENGTH: 102
<212> TYPE: DNA
<213> ORGANISM: Artificial Sequence
<220> FEATURE:
<223> OTHER INFORMATION: Epichloe festucae

```
<220> FEATURE:
<221> NAME/KEY: Variation
<222> LOCATION: (51)..(51)
<223> OTHER INFORMATION: S is C strain AR37 or T strain RGT18

<400> SEQUENCE: 48
aggtataaaa tcctatataa tagcactgtt agtagtatat agaatctctt stagatataa      60
aatcctatat aatagcactc ctatattaac tttctttaag tt                        102

<210> SEQ ID NO 49
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 49
ccttctaggt ctcttacaaa gtgcaaaatg catataaccg gacgcgctag stattttcat      60
tagctaagat ccatacaaat tcatggaatt ttatctaaat ta                        102

<210> SEQ ID NO 50
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 50
acggttaggg actagtagaa ctaccacatt gaatatttat ttaacgtgac staacggaag      60
gttttagcag ttattaacta atagaattta atctagatga ct                        102

<210> SEQ ID NO 51
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 51
acattcgccg tgacggcaac gttttctact ctttaccatt actagatgat sggtccagca      60
aaaaaaacta agcatgctca tgctatacta gatttggcta at                        102

<210> SEQ ID NO 52
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 52
```

-continued

```
ttatttttct tagtttatgt ggctattccc ctataggtta actagtgcta saaaggtagt    60
aaactatcta taggcttaga taaataggtt attgcttact ct                       102
```

<210> SEQ ID NO 53
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 53

```
ctaaatgatg agaaagcaga cacagatggc gtcaacttcg acacgatgga sgatgacgat    60
gatgaagatg atgacaatga cgacgaagca ttgacaaatc tt                       102
```

<210> SEQ ID NO 54
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 54

```
ataagggttc tattaactaa ttttctatta atcctaataa taaccttagt saataaaaag    60
ttatactttt ttttacctaa caatacattt gtattgttta ta                       102
```

<210> SEQ ID NO 55
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 55

```
cttaaggtat aggataatac ctactaaatt actaagggtt agtaagacta satattccta    60
atagacctaa gtataacatt ataggctaaa gctaggtaat ta                       102
```

<210> SEQ ID NO 56
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 56

```
atacttattt tcctatagta ttaagtactt aaaatagtct aataaatcta sgggttagct    60
tttattttat attcttaagc ctaatattct ttactaatag ta                       102
```

<210> SEQ ID NO 57
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 57
aatctaaggt atatagctag aaaaccacac taagggctta acctagaaat saataaaagg      60
gagcttataa agttacttac tcctatattc actctaggct at                        102

<210> SEQ ID NO 58
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 58
aggcattaaa gcttagagaa gtatagtaaa ctacttatat attagagaag sgtagtaaat      60
tacttatata tctctttata tattatagtt agtttactaa ta                        102

<210> SEQ ID NO 59
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 59
taactaaaac gtatagcttt ttctatagta atttacttat acttacttat stttatattt      60
aagctattta tttattattt aatttttaatt aaactttaac ac                       102

<210> SEQ ID NO 60
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 60
gtataataag gtaataatac aaaatatact aatttgttaa ggtatagaag satttagtaa      60
gagctttata atatataaga ttttattaat agttaactta tt                        102

<210> SEQ ID NO 61
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is T strain AR37 or C strain RGT18

<400> SEQUENCE: 61
agtataatta gggatttaag ctatagctac tatagtaaga tagtaattta satagtctta    60
ggctagttta tctctaggat gtctagagaa agttatttta ct    102

<210> SEQ ID NO 62
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 62
ttctataaaa aggattttca gtacgaatag aagacttccc ttctataaaa stggaagcgc    60
acgagtaata tagaagcatt ccctttata aaaggaagt tt    102

<210> SEQ ID NO 63
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 63
agctacccct ataggaagct ataaagctaa ttaccttaag gtagtaaaag saaaggtaat    60
taaggcctag gcttataatc ctaatatcct tatacttatt aa    102

<210> SEQ ID NO 64
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 64
cctttaagct tagcagtctt agggaagcta gtcttaggga agctataaac sctcttatta    60
aattccttaa taatcgaatt attaaaggca gcttatatag ag    102

<210> SEQ ID NO 65
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 65
agccggcccc ctatcttcta ttagatagac tttataaagt tccttttaa stctttagat    60 ataacgtaaa tccggtctaa ttagaagaca atcatccaca ta    102

<210> SEQ ID NO 66
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 66
aattactagg agaagataaa taggggcgcg ctacctctat ttagagttat sctactacta    60
ctatagctat agtattatta ttactaggta atagttatag ta                      102

<210> SEQ ID NO 67
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 67
ttttagttag attaataccc ttagataatt ctagccttaa ggttattatt sattattgta    60
gttataatgt attccttagt agtaaaatat acgcttatat ct                      102

<210> SEQ ID NO 68
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 68
tggctagagt tagtgtttaa ttaactacgc actaaattac taagggttag saagactata    60
tattcctaat agacctaggt ataatattat aggctaaagc ta                      102

<210> SEQ ID NO 69
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 69
aatagtataa ggggtttttct aatatactaa gactaggtag ttattcccta saagcttatc   60
ttataataag agcttttata gctatactat ataaatttac ta                      102

<210> SEQ ID NO 70
<211> LENGTH: 102
<212> TYPE: DNA
<213> ORGANISM: Artificial Sequence
<220> FEATURE:

<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 70

```
tggatggatg catgggtgcg cggccttttt tttttttttt ttttttttc sccgggctag      60 gcacgatatt ggcgttggct gtttgtattc atgcttttg ga                        102
```

<210> SEQ ID NO 71
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 71

```
ggatcctggt catttccatg tctggggttc ttcaactacc tacctctatg sacctggcta      60
ttagcccatg gacctggaca ttaacccatg accgttttgg tg                        102
```

<210> SEQ ID NO 72
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 72

```
tggtagttat taactaatag aatttaattt agataacttt tacaatatct satatactaa      60
tagaattgat tttagtgacg ttatacgggc aatgcagctg tt                        102
```

<210> SEQ ID NO 73
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 73

```
taggtaaggg taaagtaaag gtaactaaag gtataataat aatttataaa saacttattt      60
agtgttataa aagagaaaag tatataatat aatagggagt ta                        102
```

<210> SEQ ID NO 74
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 74
atttcttaac tagtcgctga agagtatttc gcgtctgact aatcagaaga sacatctcta    60
taggatggcc ttattttaat aaagggaaag cgggaagctt cg    102

<210> SEQ ID NO 75
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 75
atattataat ttagtattag ttattttcct taatataaat ataactaggt sctagtaacc    60
taggactaat attataagta tagccttaat tatatatcta ga    102

<210> SEQ ID NO 76
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 76
gtaaaataaa aacctatccc tataagtaac ctatataata gtaataaggc sttatttact    60
atataaaagt ttttaataga atataaacta taggtaaata ag    102

<210> SEQ ID NO 77
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Vairation
<222> LOCATION: (51)..(51)
<223> OTHER INFORMATION: S is G strain AR37 or C strain RGT18

<400> SEQUENCE: 77
tctataataa ctataaggta ttatagcctc tttagagata ttactagtaa stttattata    60
aagtctatag aaatctaaga ctagaactag ttagggataa gt    102

<210> SEQ ID NO 78
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 78
atattaaata ggctcttact actagtgtct taaactatta tttaccttaa sgtaaggagt    60
tatattctcc ttattagtag tattatatta cctatatata gt    102

<210> SEQ ID NO 79

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 79 tactttttaga agaaactata taactaggaa aggaaactaa agatagtaaa sattattaaa      60
cttactttta aagcttattt ttaaatacct ttaatattaa ta                        102

<210> SEQ ID NO 80
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 80
taatataact aaagaaaaaa gggtattata atactagacc ttaaattaaa sctataatta      60
ccccttaatc tagacttata attacctctt aaatattagc ta                        102

<210> SEQ ID NO 81
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 81
aatcttactt tacttatatt atttactcct ttccttatcc ttctataatt staataattt      60
ctatattaac tctttctcta tactaatata aagtaagttt gc                        102

<210> SEQ ID NO 82
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 82
gtttattact attattagat aaatagaaaa gcccttagct agtttaagtt sttctttaaa      60
gataactata actttaacta taagattatt attaatatta ta                        102

<210> SEQ ID NO 83
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

<222> LOCATION: (51)..(51)
<223> OTHER INFORMATION: S is C strain AR37 or T strain RGT18

<400> SEQUENCE: 83
attaacctaa agtttagcta gttaaagtaa tgatttttat aagaatttag sgtagctact    60
agagaagtcc ctagaagaag atatagtaat gtattttata gg    102

<210> SEQ ID NO 84
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 84
ctagtattct ctaattatat cctaaatatt ataagctttc tatttcttag sgttaaggaa    60
ttaagctact taaaataagg ttactattga aatgtaggga gc    102

<210> SEQ ID NO 85
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 85
acctattagg gactaaattc cttgctataa tctataggggg agaccctaaa sgtatagcta    60
gcaaaagctt aataggttat tgtgacagtg attttatagg gg    102

<210> SEQ ID NO 86
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 86
agtaatatta ttactttata agcactttaa ttattatctt tttttttccttt saataatatt    60 actaatagta ttcttaaagc ttagactact attatatagg ct    102

<210> SEQ ID NO 87
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 87
ttatatatgc tattataggga gttatagaaa ataagtttat taccccttaaa sataataagg    60 taaaagtata taaaactatt aaagatatcc ctaagaaact at    102

<210> SEQ ID NO 88
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 88
tataagtagg tgtttttatt acttaataag gaaggcctaa ctgtttatag sgctattaag    60
ggcttcttta aagggcttaa aaattaacta ggttaatatc ct    102

<210> SEQ ID NO 89
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 89
ttttccgcaa aatttattta tatataaaat ctaaaaaatt aacttactac satacaaact    60
agcaacctat atgcactaaa ttttagtcta aaaaatattc ct    102

<210> SEQ ID NO 90
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 90
ataataaggt ataataaata ctacttaatc ctaatttaag taaaggtata sataatataa    60
ctaaagaaaa aagggtatta taataatact ataaggttat at    102

<210> SEQ ID NO 91
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 91
ttttactagt aaaagactta aattagactt ataatataat tctagttatt sttaactatt    60
ttataatata tagtatttat attcctattt taatataact aa    102

<210> SEQ ID NO 92
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 92
aagttatcta tagtatctaa agccctaaat tatgaggcta aagtcatcta sagtatccaa    60
agccctgaat tatagggcta aagacctaga aaagggtact aa                      102

<210> SEQ ID NO 93
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 93
atataaaaag cctaagtata tattctttac gctaggtagc taattatgta sctattccta    60
gtactccgac tgcttagtta agagggaaaa cccttaacta gg                      102

<210> SEQ ID NO 94
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 94
tattattata taagttacct ataagaatag gtttatattt taccttaggt stagttaaga    60
ctaggttaaa ggtaagagat aaagtaaggt taattactaa ta                      102

<210> SEQ ID NO 95
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 95
tctattagtt aataactact atatccttcc gttacgttac gttagttatt staacgtggt    60
ggttctacta gtccctaact gtagagctgc acctgtacag ct                      102

<210> SEQ ID NO 96
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

-continued

<400> SEQUENCE: 96
gcactaaaga gtattatatc taataaggga ttagtcttta taagctaatt stagttaaac    60
ttatattact tattatatat aaagtaaagg ctttttatag tg    102

<210> SEQ ID NO 97
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 97
ccttaaagaa taaaaatcac tatataaata ttataattag aggtttagtg saagaaacta    60
gggataggaa ttggtattta cgtagttagt aatataagta aa    102

<210> SEQ ID NO 98
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 98
aataagaaac taatataatc ctagtaatta atatagctaa actagtaaag stattttata    60
aagagattaa gctataattt aaagccctaa aaggcattat at    102

<210> SEQ ID NO 99
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 99
gaacatgatg agggttaaga agcttatgta aatgggggat tgggattggg sttgggatca    60
tcatgtctta aagcgaagac ataccatgta aaaatatact ga    102

<210> SEQ ID NO 100
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 100
agtaatagaa aataagaagg taataaatag aaaattaatt ttagaaaggt saaatatatt    60
atttaatata ataattctag aggacttatt aagggatata ta    102

```
<210> SEQ ID NO 101
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 101
ttatttagct ttataaatag caagactaac tatagcttta gctaataaat saagactata      60
tataaatacc ttattagatt aataagctta taaaaaattc aa                        102

<210> SEQ ID NO 102
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 102
cttatattac tcttttttaag aattattaat agattttatt actagactttt sactagtaaa    60 agacttaaat taaacctata atataattct agtttattatt aa                       102

<210> SEQ ID NO 103
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 103
gcctagggcg ttctaagcca ctaggatttg cttaacctaa tattccttaa saagtttatt      60 attccttct atagggacct attctagtcc tagataggag tc                         102

<210> SEQ ID NO 104
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 104
agtgtgtact ataggtaa ttaaggaggt attctcctat actctctttc sctttctttt        60
tatttttact atagtgtact ataggtaa ttaaggaggt gt                          102

<210> SEQ ID NO 105
<211> LENGTH: 102
<212> TYPE: DNA
<213> ORGANISM: Artificial Sequence
<220> FEATURE:
<223> OTHER INFORMATION: Epichloe festucae
<220> FEATURE:
```

```
<221> NAME/KEY: Variation
<222> LOCATION: (51)..(51)
<223> OTHER INFORMATION: S is T strain AR37 or G strain RGT18

<400> SEQUENCE: 105
tagtgtaaga tatatatctt tagattatta atattaatct tttaaccttta sccttttatct    60 agaggtttaa tcttatataa tactaataat aactttctct ta                        102

<210> SEQ ID NO 106
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 106
ggttccgacc gaacatctct cgggtgtgta ctacgtgcat ggcctggggg sccaaagacc     60
acacgagatt gccatgtggc ctggcatata tgaagtggtg ct                       102

<210> SEQ ID NO 107
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 107
cccgcgtaca gggtagcctg cttacctaat tactagtgcc gcggttatgg stacgcttgc    60
agctacaatg caattgacta atccacaatt aattggaatt ag                       102

<210> SEQ ID NO 108
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 108 aacccttttgc actagtgtaa tattccttag tgtaactaat actaattagt sgttaaatat   60
aactataaat aagctaggta ttataagaaa agacatttct at                       102

<210> SEQ ID NO 109
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 109
attctctagc gttttctatt taatcctagc tagttatatt aaactataag sgtatctctt    60
```

-continued

```
ccttagactt cttttaagat tataatatag ttagtatctt aa                         102
```

<210> SEQ ID NO 110
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 110

```
tttagctgct tttaggtgct ctatataggg cctagctagt gctatagggc stagctagtg     60
ctataaatag ccactaaagt gtaaaggcta tgtctagcct ta                        102
```

<210> SEQ ID NO 111
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 111

```
ttagagcaaa agatctagta tatacttatt atagttaatt attttctta stttatatag      60 ctatttccct ataggttaac tagtactata aaggtagtaa ac                        102
```

<210> SEQ ID NO 112
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 112

```
gtttataaat actaaatata attatagtat agtaaattaa aagctactta statagtaaa     60
gttatttaaa tactagtaat actatattaa agatatagta ac                        102
```

<210> SEQ ID NO 113
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 113

```
ataatggccg ccaatcggca cactggagag ctcaggccag cgggctaaat sgaatatgtg     60
ggctaggcag ggggggtggt ggcagggggg gtggtggcag ca                        102
```

<210> SEQ ID NO 114
<211> LENGTH: 102
<212> TYPE: DNA

```
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 114
ctaagtatct cctctaaagg taatataact tagcttatat aaccttatag sgttattata    60
atgccctttt ttctttagtt atattatcta tatctttacc ta                      102

<210> SEQ ID NO 115
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 115
ctagagctag ctagccttta gctagaaata atattcctta tcttactagg sttactattt    60
ttacttacta ttctcttact agtactttta ttataccctt ac                      102

<210> SEQ ID NO 116
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 116
tttataaaat acacttataa taacctaagg tattagttaa agagaaagag sactaaaact    60
aaggctagta actaaattaa ggaattagta tattaataga ac                      102

<210> SEQ ID NO 117
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 117
atactagttt aattagtata gacttaggaa tataatctta ctataaagta scttatagat    60
aataaaataa gaatataagt atctttataa taagataact ag                      102

<210> SEQ ID NO 118
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18
```

<400> SEQUENCE: 118
taaagatatt ataagaaaaa taagatatta tagagaaaat agaaaataag sataagaata    60
gtaataaatc taataaggaa aagaataagc ttaacctaaa ga    102

<210> SEQ ID NO 119
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 119
taaggtttaa tattaggatg aactttaaac ttataattaa agttaaggag sgtaaagata    60
aagttatatt tattaaggga cttttagtag ctttatctaa tt    102

<210> SEQ ID NO 120
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 120
aatagtaaag ttagggataa aagataaatat tataactata atagcctaga staccttata    60
aataagtgta gtaagcgtat aaagatatta aaatagtagt aa    102

<210> SEQ ID NO 121
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 121
tatattacat ccttctaatg ttccctcttt ctaatatata tattatatct sagttttgct    60
tatcttatat ttagagctta tttcttcttt atctagtaat at    102

<210> SEQ ID NO 122
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 122
tatagcttaa agaaaaacct tcttattata ttatttacta ttttattaa statttttgta    60 tttctataaa ttattattat tacttatta aaaaaaacac ta    102

<210> SEQ ID NO 123
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 123
tatagtgtaa aaaaggcagt gaattactat tgcctaggct atatagccta sgttagctag    60
ctaaagctaa agaactatat atacctccta gatagctata gc                      102

<210> SEQ ID NO 124
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 124
taacatagcc ttataattat tatctattat tttgcagtcc ttatatagtc sttaagtgta    60
atattagact aattaaacta agaaactata gttttagacg ct                      102

<210> SEQ ID NO 125
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 125
taaagcttct cttactagct acctaagagt aatataggggg ggagaattac staatttact   60 agagtaaatat tagtaagggt aacactatag gtataaaatat gc                    102

<210> SEQ ID NO 126
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 126
ttactttaga gaagacttta taaaagactt tataggtata agctaaataa sggtaaaaaa    60
ctaagataaa taaggataaa taataataat aattagggac ta                      102

<210> SEQ ID NO 127
<211> LENGTH: 102
<212> TYPE: DNA
<213> ORGANISM: Artificial Sequence
<220> FEATURE:
<223> OTHER INFORMATION: Epichloe festucae -continued
<220> FEATURE:
<221> NAME/KEY: Variation
<222> LOCATION: (51)..(51)
<223> OTHER INFORMATION: S is C strain AR37 or A strain RGT18

<400> SEQUENCE: 127
aaagtgttgg ttgtagcagc ctcacatctt aggcatcact atcgcgatgt sttccctctt    60
cgaggccttg ttgcgagacc tcggcactta gggcaaagac tc                      102

<210> SEQ ID NO 128
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 128
ttaagcattt aaacctatgc cttaaataag tcttatctag aagtaattac stcctaatta    60
attagtctct aggttaggaa ttttacttct agtagtaaaa tt                      102

<210> SEQ ID NO 129
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 129
atccttctat cctaatagtt actaaattac ttataataaa cctcttaaat sccttattta    60
gtaatacctt tgtaaatata tttgcaaggt tattatccct at                      102

<210> SEQ ID NO 130
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 130
cacgatcccg ccgccgccca caagtatgcc accctgctaa gccaattgtc sgagaagctg    60
tccaaagatt tgtgcatcat catgcgcgcc tacctcgaaa ag                      102

<210> SEQ ID NO 131
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 131
gataaggagg gctaatatat agaggcctat ctccttacta aatattatta sgaaaattat 60
aaaagcagtg attataaaat aacttatagc ctttactaag gt 102

<210> SEQ ID NO 132
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 132
aagcttaagc taaggtaaaa gctaagttac ttaaagaaat ccttatatat staagaatta 60 ctatctttt aatagcttaa ataatactat aagaaagtaa at 102

<210> SEQ ID NO 133
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 133
ggaaagggga ttagcatact aaacccctta actagctaat agggttatat stagaggact 60
tataattagg actcttaggg aacttactaa atctagagga at 102

<210> SEQ ID NO 134
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 134
tcgtcctggc gctgctgctt actgtcttct tattcgcact tgatatggta scggattcca 60
tccacgaaag cgtcaggaag ataaaccatg ctgatgctta tt 102

<210> SEQ ID NO 135
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 135
attaataact taatctttat aagtattaaa tttaatatct ttaaataagc sctatagact 60
tatagtctcc tttactacct attataaagt aagtaattta gc 102

<210> SEQ ID NO 136
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 136
taccaataga attgatttta gtgacgttgt acaggcaatg cggtaccgac sgtattggtg      60
gatccagacc gctaaagagg tcttataggc tactttttat tt                       102

<210> SEQ ID NO 137
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 137
cctagggcta ggtttacgtg acactagtaa gccgctagct ataagatagt sacttatatg      60
tataatatat ttagacttag taagctttag ttaatatact aa                       102

<210> SEQ ID NO 138
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 138
tctagggata gtcctagctg ctaacttcta ggctttaggt tattttttcta sggggattag     60 aatcttatag tgagatccta tggctctaat actgctaata tt                       102

<210> SEQ ID NO 139
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 139 gaccectaat aaggggtag gctattagct ctagccttat taaaaaggtc sgtgaagtta      60
gctaactcct taggtaatat taacgtgtct aggctattag gc                       102

<210> SEQ ID NO 140
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is T strain AR37 or C strain RGT18

<400> SEQUENCE: 140
tttaactatt atactattat agaaagctac tactactatt tttacctagc sctttactct      60
tcttattgct ctatattcta ttagattaat agtaatctaa ta                        102

<210> SEQ ID NO 141
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 141
attattactt tatatgtaac tacctatata tactacctta gttatattat scttaaaggt      60
atagtagttt aatttaaata atatatttaa gtttactaag aa                        102

<210> SEQ ID NO 142
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 142
tctcgtcgtg tgaaattcaa gatgctcccg acttccgtgt tctggggact sgccatcttt      60
tataagtcca tcgatgaata atttattaat caatcaatcg gc                        102

<210> SEQ ID NO 143
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 143
taactttata tctagatatt cgatcttagc taaaccctct aaaacctatt scctagctat      60
ataaggcagg gttataagta gtggttatag cgccttaatt at                        102

<210> SEQ ID NO 144
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 144
taagtaatct aaggtatata gctagaaaac cacactataa gcttaaccta saaataaata      60
aaagggagct tataaagtta cttactctta tatttacttt ag                        102

<210> SEQ ID NO 145
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 145
atctctaata ctttatagct aataactaat aaatatagct taagttactt staatagctt      60
aatttactta taataatata gtaaataaga ctataagcta ct                        102

<210> SEQ ID NO 146
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 146
gagttagcta acttcgcgga cctttttaat aaggctagag ctaatagcct sccccttat      60 tagggatccc ttaattacca catacacttg cgtaagaatt ag                        102

<210> SEQ ID NO 147
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 147
aacgggcgca gtgactttgg tgagggggcgg gctcccaacg ttggccgcag sgatccaatc     60
aaaaccagct gcggttgggc aacgccttcc ctttggcgca ag                        102

<210> SEQ ID NO 148
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 148
aatactctta tagaaaaagc ctagccttat tagctactat tatactttaa staatagtct     60
aggaattact actaaaaaat aaaagaaaaa agccctaaag gt                        102

<210> SEQ ID NO 149
<211> LENGTH: 102
<212> TYPE: DNA
<213> ORGANISM: Artificial Sequence
<220> FEATURE:

<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 149
tataaaggga ttattaattt aataataaac ctctctaagg tttataagaa sgttacttaa     60
taggtaaata ttttataaga gttaaatata gaatatatat ac                       102

<210> SEQ ID NO 150
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 150
aataaaggca ttctttagct tattaaagat attattctct ttaggttctt sttaaaaaga    60
ggtatttctc ttagttaatt atattagtaa tgctactagc tc                       102

<210> SEQ ID NO 151
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 151
tcgctaactt ctagtaaaac tttaacttag ctactaaggc tatgtaacta sagagcttaa    60
tattaactaa aactttatta atattaatta ataactaga ga                        102

<210> SEQ ID NO 152
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 152
ttaaattatt atgctaactt aaatataatt ataagctacc ctaactatac staatattat    60
ttagtactag ggaagtaata ctaataaggt ctatacttta tt                       102

<210> SEQ ID NO 153
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 153

```
taattacttt aaaagctaag aataaagata tatatatatt aattactata sactatataa        60
taaggtttat attaagataa tcctatataa aggtaactag ag                          102

<210> SEQ ID NO 154
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 154
cctaatcctt aggagtagcc tttagcttat aaagctttaa ataaattata sgattcctat        60
tactttaagg tatctttaat attataacta gagtatctag gg                          102

<210> SEQ ID NO 155
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 155
tattaagttc tatagttatt agattaatca tttaattatt tagttattta sttatttagt        60
tatttagtta tttagttatt tagttattta gttatttagt ta                          102

<210> SEQ ID NO 156
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 156
taatattata tatatatatt ctttacacta gatagctaat tatgtagcta stcctagtac        60
tccatccgct tagtcaagag ggaaaaccct ataataat at                            102

<210> SEQ ID NO 157
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 157
gctagaatat tataatataa tggatactat agctagaata ttataatata sttatttata        60
tagtaaaaca gtaattagtt attaaagtag taaagggctt at                          102

<210> SEQ ID NO 158
```

<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 158
tactttaaga taaaaaacct tattttaact ttactacttt attatgtaat staattacta    60
agtaagttaa atttagctta ctatataaat aacttagcta ta                      102

<210> SEQ ID NO 159
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 159
actaattctt atagttctaa tactataata gtctttaggt ttatttatag sacttatatt    60
ctagtttatt aatatactag atataagtaa taataagatt tt                      102

<210> SEQ ID NO 160
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 160
atatatataa aagggtctag tagctttaat ctatcctatt aaatctagct stttactatt    60
aacttttttc ctttattatt actattctat aggcagatta ag                      102

<210> SEQ ID NO 161
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 161
ctataatata aattatctac ttattattat actagataat taatagagaa sggacctata    60
tgctaatatt ataaagtaat ttacctagag atatacgctc tt                      102

<210> SEQ ID NO 162
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation

```
<222> LOCATION: (51)..(51)
<223> OTHER INFORMATION: S is C strain AR37 or A strain RGT18

<400> SEQUENCE: 162
aagtagccta attccttaac cttaagaagt aaaaagctta taatatttag satataatta      60
aagagtgcta gattaatata tatctaggcc ctctagacta ga                        102

<210> SEQ ID NO 163
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 163
gctatagcta tagggggta aagctaccct aggaatatat ctttagaaaa sgaacttatt      60
aaggctaatc tttcctatat atagttatat tattataaaa ga                        102

<210> SEQ ID NO 164
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 164
taggaagggg cctagaggtt tcctattaag acacttataa gagaataggt sgtaaattac      60
tctataaggc acttataaga gagtaagtag taaattgttc ta                        102

<210> SEQ ID NO 165
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 165
ggaaacttaa gggtaaatat aagagggaaa gcatagaagt aaactctagg sgtagcttta      60
gtataagggg taggctagtt tatcttacta accccttcca ct                        102

<210> SEQ ID NO 166
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 166
gagttttagg tctttacccc ctatataaaa taataaatat attaagggaa stattagcta     60
```
gctaggctta taggctaata ccctagggag taattagtct at        102

<210> SEQ ID NO 167
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 167
tcgttattaa taatattagg gataaacttc taagctatct tttaaatata sgattcctat        60
aataactata tctctttagt attatgattc ctaatgattt ta        102

<210> SEQ ID NO 168
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 168
atacaaaaca ccatagatat aagggtaatt ttgcctacta gatagtagcc sttaattaat        60
ctagaatagt ataaatagaa cgttttgcta atctattttg ct        102

<210> SEQ ID NO 169
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 169
agtatcatta gctataaaga atagttagta cttaataacct aatagtatat sgttagtaac        60
ttacctagtg gaattttagt tatattgtaa tttattacta gt        102

<210> SEQ ID NO 170
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 170
gggtacttac tttaagtgta aagttactag atattatact ataaactata stataactag        60
aaataattta ttataataat aggaatccctt atagttaaaa tt        102

<210> SEQ ID NO 171
<211> LENGTH: 102
<212> TYPE: DNA
<213> ORGANISM: Artificial Sequence -continued
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 171
taactatagt atttacctct ttacctttaa cttctataag taataaatta satatagtta    60
gcttcttaat tattactatc tccttaagtt tatatagtct ta    102

<210> SEQ ID NO 172
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 172
acgtgtatgc aaacacttcc aaaaacgatg cgcagaatgg agctcctgat stttgaggaa    60
catctcgtgg tctactaggg cactgggaca attattggct gt    102

<210> SEQ ID NO 173
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 173
ttgtaaagga aactagctat tttaataaaa gttttaagac ttaataaatt scttagaaaa    60
atcatttttt aaaaggcttt aagtctatta ttagtgttaa ta    102

<210> SEQ ID NO 174
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 174
atagctatag ggtaacctgc gtacagggta gcctgcttac ctaattacta stggcgtggt    60
tatggctgcg cttgcagcca taacgcaatt gactaatcca ca    102

<210> SEQ ID NO 175
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

-continued

```
<400> SEQUENCE: 175
cctaaggtaa tattttccct ttttttaatt taatagtata agtataacct sttagtttaa      60
aaagcttact tactaactct ttagaaaaaa tattataaa ст                         102

<210> SEQ ID NO 176
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 176
gggggatcga agtcatgccg tcggttcccg gtcagtaact tgggggccac scgcgcaaat     60
gcaatgtagt gtccactttg aagcgagtcg cctctatgac aa                        102

<210> SEQ ID NO 177
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 177

ттааатсаа tacctataaa gattaggtta ttaatataa таатаатаа sтаатттаgс        60

ттатастта таagаgтааа taataaata стаастата тт                          102

<210> SEQ ID NO 178
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 178

aactagatta aactaggaaa aacccctat tatacactta ttctaagtta saataaatat       60

cttctgaaga ttcattagaa gaatcttag agatattcta gt                          102

<210> SEQ ID NO 179
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 179

accttaatac taaggctcct atactaatt tatataggag ttttttatta sgtattccta       60

aggccttaat actagattac atataaata ttaagttaat ag                         102
```

```
<210> SEQ ID NO 180
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 180
ctgctattag tgcggctgcc ccgtattta aatccactcc ctctgctgtg scttaccact    60
acatataact ttatggagtt aaatgtgaat attagaagca tt                    102

<210> SEQ ID NO 181
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 181 agttttttc ttttaaataa ttatttcctt tactaaaatg ccttaatact saactaatgc    60
ccttacttct atagctttag tagctactcc tatagttact ct                    102

<210> SEQ ID NO 182
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 182
atatttactt ataaagtgtt taattatata tattaacctt attattaaaa saaataaaat    60
ctagtatagc ttttaggtta tagtatagat ttatataagg tt                    102

<210> SEQ ID NO 183
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 183
aattaggtta taatacttaa gaattaggct ttttaatatg ccttacttaa staaaagcta    60
taccttaaag agccttttaa taaggatatt ttaatttatt at                    102

<210> SEQ ID NO 184
<211> LENGTH: 102
<212> TYPE: DNA
<213> ORGANISM: Artificial Sequence
<220> FEATURE:
<223> OTHER INFORMATION: Epichloe festucae
<220> FEATURE:
```

```
<221> NAME/KEY: Variation
<222> LOCATION: (51)..(51)
<223> OTHER INFORMATION: S is A strain AR37 or G strain RGT18

<400> SEQUENCE: 184
ctactctggt gccaatctgc tgaaccaggt ccttgagagc ctgttgagca stctcctgag    60
gaccagtggc atcaaaccga aggcggccat tggatgccgt ag                     102

<210> SEQ ID NO 185
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 185
ctatattctc taaatattat ataaatacta gtatacactt atagattatt sttatagact    60
ttgcatttgc tataattcct taacctttct tatccttaat ac                     102

<210> SEQ ID NO 186
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 186
aatatcttag tttacttagg ggaattaagg aaaaactata tagctaaggt stagctaata    60
ttaggctatc taagagctat aggtttatac ttagatctta at                     102

<210> SEQ ID NO 187
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 187
ataaaaagta actaattaat cctaactaag gagtataata ttatctaaaa stttcctaat    60
taatctaaac tataatctat aataattaat taaggaaacc cc                     102

<210> SEQ ID NO 188
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 188
tatggccaaa gtgtaagtct actaaaggga tacacgtaat gtaattagct scattatagg    60
```
taaccctata ctatttatag tggctttaca ctactacctt ac            102

<210> SEQ ID NO 189
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 189
agctatattt aataatagct aggattaaaa aggaggtctt ttatcttttc stgttttcc   60 cttttatcta tttttatcta aaagttattg tttaccctat ag            102

<210> SEQ ID NO 190
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 190
tataattagt ttaaataaat aaggtaccta atactatagt tttaaatagt staactaaag   60
ggcttatatt atagttacta taagtttata gctattaggc at            102

<210> SEQ ID NO 191
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 191
tatagattta tataatatct ataaagctta tatttaactt ctagtgtaat sttttttatgt  60 tttacttaat atgtctaaga gtccggagga agccacagtt tg            102

<210> SEQ ID NO 192
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 192
cttatttatt taaaatcttt aaaattacta atctaagact agtaatcttt sctagattta   60
ctactaatag tagtagggtt agcttttttcc tttcctttc cc            102

<210> SEQ ID NO 193
<211> LENGTH: 102
<212> TYPE: DNA

<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 193

```
atcttataaa agagtaatta cttaactaaa tattataata ctagtaagat sttcttagag      60
aaagactttt aataaggtaa tatttatagt aataagtaac ct                        102
```

<210> SEQ ID NO 194
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 194

```
acattgcaca tgcctagcat atgcttagca tatggctagc attagcctag satatgctaa      60
ctatatgtaa aattttctta aagatcttaa atatacataa ag                        102
```

<210> SEQ ID NO 195
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 195

```
atttaactag tagcctctcc ctaatattgc gtttatttcg aaatagcgct scttatctag      60
attaaataaa cctatataat ttgtctaata agtttattat ta                        102
```

<210> SEQ ID NO 196
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 196

```
tatagctagc ttcttactag gttatcttag gttaatattc tttattaata staaaatata      60
gttactaact ttaaaccttaa ttagagttct cttctagtta ta                       102
```

<210> SEQ ID NO 197
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 197

```
taaagctttg gttaaagcat tagttataat ctctctaatt ataacattag stataatccc      60
tttaattaac gccttagttg taatctcttt aattaatgct tt                         102
```

<210> SEQ ID NO 198
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 198

```
tatataaaga aatatataaa tagtttacta cccttattta agtgcttacc scttattact      60
atagtaagaa ctagtattat tattaaatta ctaagttaag ta                        102
```

<210> SEQ ID NO 199
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 199

```
aagtacttat acttatttac ttaactctat ttatacgtaa atttattcta sgaaggttag      60
acttagtaat tactattaaa agggctttct tttataagat cc                        102
```

<210> SEQ ID NO 200
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 200

```
gcgtatatat tagaataaag agtaattaag ctctcttaga agtaaagatt stctttagcc      60
taagcgtata tattagaatt tatattaatt aaaatataag ct                        102
```

<210> SEQ ID NO 201
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 201

```
agacggtcag attaattggt ctaacaacgg aagctttcgt taacggcaga sgccttatta      60
gaagaccttc tgtacgtcag attccccttt aaaagtcgga ag                        102
```

```
<210> SEQ ID NO 202
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 202
aaggtattag taatattaaa ctccctatta gcaaaggcta tttagaacta sctaatactt        60
aataggcact aaaggctaaa gttaatataa ttttactagg cc                         102

<210> SEQ ID NO 203
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 203
gatattaaac gcaatgcagg aagctgcatt attaattaaa gagaggataa saagagtgat        60
gcctaatatc taaggctata atataaggct gtgaatatcc tt                         102

<210> SEQ ID NO 204
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 204
tccgtaacta taagctaacc taatagttaa ttctattata ttaaagctag satctaaata        60
taaaggtatc ctacttatat ttacttataa agtgtttaat ta                         102

<210> SEQ ID NO 205
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 205
actagattta gactttagat aaaaagaatt aactttcttt agatatctta scttatacct        60
aatagtagct cttatagtaa acttagtata accttataat ag                         102

<210> SEQ ID NO 206
<211> LENGTH: 102
<212> TYPE: DNA
<213> ORGANISM: Artificial Sequence
<220> FEATURE:
<223> OTHER INFORMATION: Epichloe festucae
```

-continued

<220> FEATURE:
<221> NAME/KEY: Variation
<222> LOCATION: (51)..(51)
<223> OTHER INFORMATION: S is T strain AR37 or C strain RGT18

<400> SEQUENCE: 206
ataatttaat atgctttaga gcctttatta ttattagaaa cgccttatat stataagctt    60
atagatatat aattaagggc ttttaaactt ctaatatcta ta                      102

<210> SEQ ID NO 207
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 207
tttattattc tagttttag ctattttaga aaatttacct aggtaattaa saaataattt    60
atatacttat ttatagctat ataatatatt tattattact tt                      102

<210> SEQ ID NO 208
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 208
agttagtaat atctaaatag cagcctatac atagctttaa tatagtaaaa saaatgttat    60
tacctattat atagctagaa gaaaaaaaaa tagataacct at                      102

<210> SEQ ID NO 209
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 209
agatacttat cctatcctag agatactact atctcctatc ctatcttaga satattacta    60
tcttattagt tactaaaata ctctccttaa ctaagtgtag tt                      102

<210> SEQ ID NO 210
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 210
agaaaatagg gcttttattt aatgcaggaa tattttttag actaaaagtt sgtgtatata    60
ggttactagt ttgtatagtg gtaagttaat tttttagatt tt    102

<210> SEQ ID NO 211
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 211
agagatatat aagcccttta ctactctaat aactaattac tattttacta sataaataac    60
catattataa tattctagct atagtatccc tagtattata tc    102

<210> SEQ ID NO 212
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 212
gatttaatat attataaata gctttagtta ttactatagt aataaagtaa sagagcctta    60
aggaagtata taaactaatt ttaaaattct tagtatatag ag    102

<210> SEQ ID NO 213
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 213
attataagat atattctcta gtttatactt actaagttat tttaagaaaa stactagaat    60
atatattact aaggctattt tagagaatct attaggatct tt    102

<210> SEQ ID NO 214
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 214 taaaagaaa aaaatagata acttatatta attttttataa ttagtttaaa saaataaagt    60
acctaatact atagttttaa atagtctaac taaagggctt at    102

<210> SEQ ID NO 215
<211> LENGTH: 102

-continued

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 215
taattttata gtaattatat acagttatag ttatagtagt taactataat staatactag      60
ttttctttta cctagctata gctatagaaa ggtaatgcta cc                        102

<210> SEQ ID NO 216
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 216
taaactaagg ttttatattt actagtggtt tttaaataac tttttattat sttcttataa      60
ctaagtagct acttagcttt attattttct tataactaag ta                        102

<210> SEQ ID NO 217
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 217
tatctatatt ataggtaata gcctagatta tacctattat attagcgtgc statgtttaa      60
tataatgcta ccttataaca ctcttactaa ttatactaag ct                        102

<210> SEQ ID NO 218
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 218 attttagcc cttttctagt taaaggacct ttttattact agcttgcatc scaagcctaa       60
cagctgcact gcagctgtta acggtcacgc aggtaactgt ca                        102

<210> SEQ ID NO 219
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is C strain AR37 or T strain RGT18

<400> SEQUENCE: 219
tagaaagaga gaattactaa acttaatata ggtaaaatac taattaaatt saataaataa    60
attaatactt taaaataaag catagtttaa aaggataagt at    102

<210> SEQ ID NO 220
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 220
tccctttata attcttatta gtcttttcta aaggtatatt aataactagc sctagtccct    60
ttataatttc tattagtctt ttctaaagat aactattctc ta    102

<210> SEQ ID NO 221
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 221
caagcctctt taacctctta tttttctatg aaaaggcctt aaaataatac sattatagag    60
gaattttcat ctaaaaaggc tattactcta gttattaagt tt    102

<210> SEQ ID NO 222
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 222
ctttaaacgc tatagatagc tctaaaggga attagaaata agttatctat sattctagag    60
ctaatgttta tattttaat aatatttatt agtttaaata gt    102

<210> SEQ ID NO 223
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 223
atttatctaa taaaaggttc tttacctta taactatttt attataatta saagtaatta    60
ctttaatttt ttagtctttt ttacttaaaa gaaaagtaaa aa    102

<210> SEQ ID NO 224
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 224
ataagaccag attcagtatc ttaccttata cctaatagta gctcttatag saaacttagt    60
ataaccttat aatagtaaat ccattagcct ctctaataga tt                     102

<210> SEQ ID NO 225
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 225
ttagataaat cctatatcta tatgcctttc ctagataata ttatagtaaa sggactaata    60
ataatatata ataagaagga aattatgcta ggagtatata aa                     102

<210> SEQ ID NO 226
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 226
atataaagga aactataata tatagtatta cctatacctc ttagtttact stctttatat    60
tactattagt ctataggtaa tataatatag aaagtaacta at                     102

<210> SEQ ID NO 227
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 227
tataagtact taaaatagtc tagtaaatct aggggttagc ttttattta satccttaag    60 cctaatgttc tttgctaata atagtactag gttacctctt tt                     102

<210> SEQ ID NO 228
<211> LENGTH: 102
<212> TYPE: DNA
<213> ORGANISM: Artificial Sequence
<220> FEATURE:

<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 228
gtgtatatag gaggatttat tatttataga agagagttta cttaggtata saaggcttag    60
ttcttaaacc ataaaaataa cacttaaatt tagtttctaa ta                      102

<210> SEQ ID NO 229
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 229
cttagataaa gcctagattt agtaggaatt ttattaggta taaaaactat sattaaggag    60
cttcctatag cctatataat actcttatta ttttctagag at                      102

<210> SEQ ID NO 230
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 230
tatatttaat ttttatattc tagggatagc ttataaaact aaaattacta satatttat    60 agtaatagta aatataatac taaatctaag actaaaatta tt                      102

<210> SEQ ID NO 231
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 231
aataaacagg ctagctagct ataagatagc tatatgctta taaagcaggg satttattaa    60
agactatgta tattattagt gtaaggttag agattaaaac ct                      102

<210> SEQ ID NO 232
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 232

```
ggagataaag aactatataa gaatccctaa tattatagaa ataacttacc stagagttat      60 aagcccttata ggaactaaag gaataagaac tagaaaaaga gc                        102
```

<210> SEQ ID NO 233
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 233

```
atagctattc ctaaataatt agcttctatt actataggga gatctaggtc stattatact      60
agtactaggt atgtaataaa ggtatctttt agcctattaa ag                         102
```

<210> SEQ ID NO 234
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 234

```
gaatagcttt aattattaaa gctataatta ctaaggacta taggacttaa staataggtt      60
taagaactat aaggcttaga tatactagct aaaagactaa ta                         102
```

<210> SEQ ID NO 235
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 235

```
tattaaagtt tttttctttc ttaaagaagt tattattact aaggcctagt stattattta      60
tttatattcc tataattcta aagagattct tattatttaa gg                         102
```

<210> SEQ ID NO 236
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 236

```
gttaatcctt atgctatatt attacctaaa ggtagtgtct ctaaatctag satatattcc      60
tagtaaccta gttaatcctt atgctatatt attatagtaa ta                         102
```

<210> SEQ ID NO 237

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 237
gctagaaaac cacactaagg gcttaaccta gaaataaaca aagggagct sataaagtta      60 cttactctta tatttactct aggctattag atttagtttt tt                      102

<210> SEQ ID NO 238
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 238
aggaaaccta ttactagtta taaaagcatt atactctaat atctaatgta sacctaatag     60
gatagaaaac tataataatc tagtctaact atatctataa gg                      102

<210> SEQ ID NO 239
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 239
tatatatata tataaacta tcttattaat aagagaatat taaaatttaa staataaaga     60
agttcctagt aatatagcta ttttattaga attataaata at                      102

<210> SEQ ID NO 240
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 240
agtaacttta aagatattag aattagccta taataatagc ctaatttaaa sgggtttatt    60
actttaagta taaagttatt aataaaatta gttacttaga ct                      102

<210> SEQ ID NO 241
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

<222> LOCATION: (51)..(51)
<223> OTHER INFORMATION: S is T strain AR37 or C strain RGT18

<400> SEQUENCE: 241
atttttagag actatagagc cctagaaggt attataatag actaaggttt satatttact    60
agtggtttct agataacttt ttgttatttt cttgcaataa ag                      102

<210> SEQ ID NO 242
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 242
attttataag gaatattaag tcttattata tagtagttaa ggctaatagg sagttaaagg    60
ctattactta taaaaaacgc tataaataat aaagagttaa ac                      102

<210> SEQ ID NO 243
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 243
agatcctcgg cgcatctcta gagtctagcc tttttttttt ttttttttg stcttgtctc     60 tctgtctttg gttctcaaat ccttagattc tgtcatctcc tg                      102

<210> SEQ ID NO 244
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 244
ctagcttcct tactaaacta ttgaataatt acacatagaa ttaattctat stataattcc    60
tctaagcatt agattattta gtaaatctaa tattagttat aa                      102

<210> SEQ ID NO 245
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 245
aataaaaagg agggagttct tattttctaa gagagtttta ggtctttacc scttatataa    60
aataataaat atattaaagg aactattagc tagctaggct ta            102

<210> SEQ ID NO 246
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 246 acctttata ttatttacta aaacctatta gttatattta cttagctaac sctttattt    60 tactaggtat ttattacctc cttaacctcc ttaactttat at            102

<210> SEQ ID NO 247
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 247
aagccctatc ttctagcttt aatttactat atataagact tttatataac stctagttaa   60
agagaaaatc gctattaaag atagctatag ggtaacctgc tt            102

<210> SEQ ID NO 248
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 248
aaaaattagt tttaattaat tatattatag cttatttact tagttatagg stttttttat   60
taaaaataag cttaagagat aagttctatt agttctatta gt            102

<210> SEQ ID NO 249
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 249
ataaagagat taataagcta aaggaataag gaatatagtg gtaaataaag sattctatag   60
tataattaaa gctattacta ttaaaataag tgttttctta ta            102

<210> SEQ ID NO 250
<211> LENGTH: 102
<212> TYPE: DNA
<213> ORGANISM: Artificial Sequence

```
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 250
aaaataaagt acttagtaaa ttagtctata attactagaa ttatattagt sttttattta      60
cttacttaag taattactat aatattagta agaatttaag gc                        102

<210> SEQ ID NO 251
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 251
tatatattta ttaagatatt cttaaagctt ataagctcct tctagtccta sattatatta      60
actctatata tatttattaa gatactatta actaataaaa ta                        102

<210> SEQ ID NO 252
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 252
accactttaa ctcctttata gctaagttcc ttatagatag ctttaataat sgcttattat      60
tatctaggca cgttaataac tagcgctagt ccctttatga tt                        102

<210> SEQ ID NO 253
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 253
tttacctaaa agtaagaaat tatattttc ttattagtaa tactatatta sttatatata      60
gtatactaag cttctattta ctaacttata actttactat ac                        102

<210> SEQ ID NO 254
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18
```

<400> SEQUENCE: 254
agaaaactat ataataaggc aaagaagttt tacctagaga tagaaaacta sataataagg    60
caaagaagtt ttacctagag aatagttatc tttagaaaag ac    102

<210> SEQ ID NO 255
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 255
taatataggt agaactagac tattttaatt ctaggtttgc cctagcttta saatataggt    60
ataaagttta atattaggaa ctctaaactt ataattagag tt    102

<210> SEQ ID NO 256
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 256
ctaggttata tatagcaaac tttaatatcc tattatattt taaagtatta sactttatta    60
taatatgtaa ttctttatta tagtaataat ataatttaa ct    102

<210> SEQ ID NO 257
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 257
gagtaagaat atatctaata tatacttata atatataata tacttaacta saactaccct    60
taggtatagt ataactatat aagtagctat ttattttctt aa    102

<210> SEQ ID NO 258
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 258
tattttaata agattacctt atagactata ggtaaaatta tagctaatat staaggggta    60
attataagtc taaattaagg ggtaattata ggtctaatt aa    102

```
<210> SEQ ID NO 259
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 259
ttaaaaaggg attttattac taaagaaatt attaataatt ataagtaata sctaagtaat      60
aaagttaata taaggtaatt ataatttata agttaatata ct                        102

<210> SEQ ID NO 260
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 260
cataaatccc ttagtaataa gttaggcctt gtattttaaa ggattatttt stttatcctt      60
aggccttgta ttttaaagga ttattttctt tatccttttt aa                        102

<210> SEQ ID NO 261
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 261
ggtggccgtc aatggctacg tcgcagctgt caacagctac gaccgttatt saactgcgtt      60
gtggctgcaa gcgtagccac aactataacg ccactagtaa tt                        102

<210> SEQ ID NO 262
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 262
ataaggataa taaaggcatt actaattata tttctaaggg cctaaaggag statataaat      60
tagataaaaa aggtaaaata agattttttcc tagggatcta ga                       102

<210> SEQ ID NO 263
<211> LENGTH: 102
<212> TYPE: DNA
<213> ORGANISM: Artificial Sequence
<220> FEATURE:
<223> OTHER INFORMATION: Epichloe festucae
<220> FEATURE:
```

<221> NAME/KEY: Variation
<222> LOCATION: (51)..(51)
<223> OTHER INFORMATION: S is C strain AR37 or T strain RGT18

<400> SEQUENCE: 263
agtttatatc tttaaaaagg ttaagagaga ttaatttatt atagcttata staaaggtt    60 aagaataaag taatagctaa gactattata gttactacta ga                     102

<210> SEQ ID NO 264
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 264
ctataaccct taactaggtt taaggtttat taagatagta ataactttaa staggtaata    60
ctaattaaac tagggtagga ttagttaagc tagtaaaact at                     102

<210> SEQ ID NO 265
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 265 cactttatt tatcttacta ggtctactat ttagttagta gcttatttct stctttacta    60
ttattctttt atttattttt atagtaattc tattctagct at                     102

<210> SEQ ID NO 266
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 266
tatctaacta tattataagc ttaagtaagt aaataaaaga ctaatataat sctagtaatt    60
atagactaat ttactaagta ctttattttc ttacttataa ct                     102

<210> SEQ ID NO 267
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 267
ccatctatct tatctcttga ccccgccatc gtcaaggatc gtcaagcccc scttgtctcc    60
atcagctttc tcaaagtgcg gctaccttct accttgatcg tc        102

<210> SEQ ID NO 268
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 268
gctaagatta atgccttata agcttataat atgtttagat ttataatatt saatctagca        60
aagcatagag gccactggat ctttaattct tatatggtct aa        102

<210> SEQ ID NO 269
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 269
aattataagg ctataatagc acttatagta gcttactata agcttataag sgtattaata        60
agggcattaa attacatagc taggctagct agggtattat at        102

<210> SEQ ID NO 270
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 270
tagctataag gtatattata tttaagctat attttataaa gatttattta sggctcttaa        60
ttatagtatt tacctctttta cctttaactt ctataagtaa ta        102

<210> SEQ ID NO 271
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 271
tcttcgggca tctgtgcgag gaaagtttcc acatgatccg aattgggaga sacacaactt        60
gcaactgcca gcaaaatgat ggtgcatgta cggagttact tt        102

<210> SEQ ID NO 272
<211> LENGTH: 102
<212> TYPE: DNA

<210> SEQ ID NO 272
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 272
aagaggattt agaagcgttt aaaaatagcg aatttttgca ttattttacg saagatatct      60
cttctattaa agagagacaa gattataagg aatttaagtc ct                        102

<210> SEQ ID NO 273
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 273
ttattagtta ttagtattta taaggttaaa agaaagcctt atataaaagc stttattatt      60
acctatttta ttaaattagt tatagaattt ataatattat at                        102

<210> SEQ ID NO 274
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 274
tctagctatt aagatttat tattagatag ttatattatc tttttagagg saaataagta      60
atagttatat aagataagtt ttaggttaga tattattaag tc                        102

<210> SEQ ID NO 275
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 275
gaggcctagc tatctagcta gattaaaaag atcttctttc tctcatatac scactaacca      60
tattagtgaa tccaggccgc tagagaggtc ttaagagcca ct                        102

<210> SEQ ID NO 276
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 276
agttacctag aaagctagta attaaataaa tatagggaga tagataataa satcctaatt    60
tcttttagta tttcttatat aaagaatagg gatatatagg at    102

<210> SEQ ID NO 277
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 277
gctaatatct ttagattatc cctctaatac tatcccttta atgccttact sccttctaat    60
ctagtggatt tattaagaaa acctttagat ttagctttat aa    102

<210> SEQ ID NO 278
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 278
ctttaactta gtctatacct aggattattc ctttacttat attagtaata sagtagctaa    60
cttagtaaac ctttataaat cctatactat cttttatttt ta    102

<210> SEQ ID NO 279
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 279
ttaagtttaa taattaccta ttacccttat agttcccctt aatttctagg stacctccta    60
atatttaatt taactctaga taatcttcta tatattagct at    102

<210> SEQ ID NO 280
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 280
agaaagccac tactactgtt tttaacctagc cctttgcttt tcttattgct statattcta    60
ttagattaat agtaatctaa tatgtaggct ttcctaccta tc    102

<210> SEQ ID NO 281
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 281
aattactaca ctataaacta cactacacta taaactacac taactataag sgaaaaaaaa      60
ctataatata atataatata aattttttc cttaaactac ac                         102

<210> SEQ ID NO 282
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 282
agagattaat atagccttat aggaacaaat ttaggagaga ctaggagctt scttagaata      60
ggataaaccc tagtagaatt taattaatcc tatttaaatc tt                        102

<210> SEQ ID NO 283
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 283
cgcaggggtt ctagcaaact ccggacaggt cggatctgta caccttggga stggtggaaa      60
tgggaattgg gtcatcgagg ccttgtcgta aaaggcactg tc                        102

<210> SEQ ID NO 284
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 284
taccactaca tttagcactc ctagtatata tgtcactttt aagttaaatt staatagata      60
atttgtaacc ttagctaatt ttagattagc cttatctaaa tc                        102

<210> SEQ ID NO 285
<211> LENGTH: 102
<212> TYPE: DNA
<213> ORGANISM: Artificial Sequence
<220> FEATURE:
<223> OTHER INFORMATION: Epichloe festucae -continued
<220> FEATURE:
<221> NAME/KEY: Variation
<222> LOCATION: (51)..(51)
<223> OTHER INFORMATION: S is A strain AR37 or G strain RGT18

<400> SEQUENCE: 285
ataactaccc taccctttacc tatttataac ttacctagta taagtgtaat stctagtata    60
aatatcttac ttatacttac actatcttac tttccccttt at    102

<210> SEQ ID NO 286
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 286
accttagggt tagtgcggaa aagtatgcaa aggttagatt aaattataat sgggtcacaa    60
actatagtat atatagctac ataagtaaac tattttaacc ct    102

<210> SEQ ID NO 287
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 287
ttatattaac tttattactt agctattact tatagttatt aataatttct stagtaataa    60
aatccctttt taatacctaa gaattcttta aagtattata gc    102

<210> SEQ ID NO 288
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 288
tataataaaa tattactaaa tactataagt attttattat tagtgctatt stagttttaa    60
tttacctagg aaattataac cttagagagg tattactata ag    102

<210> SEQ ID NO 289
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 289

```
atttaataac tttaataact ttaataacct taataaccctt aattactatt sttactatta      60
ttactattat tactattatt actataatta ctatttactt tt                          102
```

<210> SEQ ID NO 290
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 290

```
gcctttaaag catccttata gaagtctaag ctataccctt aagctatgcc stcccttac       60 tcttaatcta tctaagttaa taagttaata ggaagcatgc ct                         102
```

<210> SEQ ID NO 291
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 291

```
ttttaaagat taaactaaag atatatttag aaaagctact aataagctta saagagagct      60
ataaaactct ctataagata ataatattta tattagctaa gg                         102
```

<210> SEQ ID NO 292
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 292

```
gctaaattag ctagaagttt tagctataaa ccttctaaag attaagtaat sttattataa      60
aagtctttat atagcctaaa ataaagatta aggtatctaa cc                         102
```

<210> SEQ ID NO 293
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 293

```
ttagcgctag ttattaacat gcctaaataa taataagtaa ttattaaagc satctataag      60
gaacttagct ataaaggagt taaagtggtt ttttaagtaa ta                         102
```

<210> SEQ ID NO 294
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 294
gaatttaacc tttaataaat taggtctttt atgattagac ctttgaccta sccttcgtta       60
gctaggtccg tcgttataga ttaattaatc taactatcta at                        102

<210> SEQ ID NO 295
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 295
ccatactagg ttgctagtta tctagtacta gataactagt tagttgccta sttaggtgaa       60
aaacctacta cgatttgttt gttttagcta catacatggt tt                        102

<210> SEQ ID NO 296
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 296
attaaggtat atttctataa gaattagtat tttctaagta tttagcttat sttaatctta       60
aagaagctta agtattttat aagtataata ttaaactaac tc                         102

<210> SEQ ID NO 297
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 297
tccctgtgcc aggaacgccg gtgcctggat tgaacttatg gcactcgtga satgcaattc       60
attgtgctaa tcgtgaatcc ttcatagacc acacaatctc ca                         102

<210> SEQ ID NO 298
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is A strain AR37 or T strain RGT18

<400> SEQUENCE: 298 ctttatccttt ttataattat attttattat aatataaaat atatatcctt saagttaact    60
tctaatctat taaatactat tatagtacct ttaagggtaa at    102

<210> SEQ ID NO 299
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 299
taagctaaaa gtaaagtttt agcactaaaa gagaagtata ctataattaa stagcttta    60 agtaacttat agacttagta taaaaaatat tataactaga ag    102

<210> SEQ ID NO 300
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 300
gaggcattat tcctatgcct aaggataaga aaataaggat taatcttgtt sataggtagt    60
aatattaaat aaggctaatt agaccttata gattaggtag ct    102

<210> SEQ ID NO 301
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 301
tactttagaa tagtaattat aatataaaaa cttcataaaa agtgcttta sctagataaa    60 agtaaagata taaatcttaa ttattactta tatctagtat at    102

<210> SEQ ID NO 302
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 302
aacactaaga acccttttact aataatatct tataacttaa taaacgcctt sagtagtaaa    60
ttaagcatta ataataggga ttatagtata tcccccttaac tc    102

-continued

```
<210> SEQ ID NO 303
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 303
aagaacatag ttactagcct attactagtt agttacgtta aaatagggat staaatacta      60
tattttgtaa aatagttaat ataactaaa atcacgttat ag                        102

<210> SEQ ID NO 304
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 304
actagctaag tagtagctct cttactggct agtataactt ccctatctag sctattatag     60
ctaacttata gctagtttac tatatctaag tcttatgcct aa                       102

<210> SEQ ID NO 305
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 305
atctagttct aataataata gatataagat tagcctatgt tactatagta sataataaaa     60
ggtaagatct atataattac ttataaagta aagattagtc ta                       102

<210> SEQ ID NO 306
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 306
aagacttcta ttcttaagga tcttaatatc tttctcttac tagtattact sataactata    60
aaagcctctt tttataataa tagtttacta tactactaga ct                       102

<210> SEQ ID NO 307
<211> LENGTH: 102
<212> TYPE: DNA
<213> ORGANISM: Artificial Sequence
<220> FEATURE:
```

<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 307
gtatttataa atttaaataa aaaggtaaga agttatatag ttattacttt stctttcctt    60
actttactta ctaaatctag ttttcttaaa agtaagttag ta                     102

<210> SEQ ID NO 308
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 308
atcttaatgc tattaagata taggttaata aaatccttaa tatcccnttt satatcttaa    60
tctaattaat ttaaagcctt aaggcctttc ctagataagg ca                    102

<210> SEQ ID NO 309
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 309
ttacatattt ctttacatat agcgtttagg ctactaatac tatagtaata sggggtaagt    60
acctagataa gggtagtaaa ctatttatat atttctttac at                    102

<210> SEQ ID NO 310
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 310
atttaacgta tgtaagataa actaatataa tactagtcac taaaataata saattaatta    60
aaagtaatta cgggtttaag gctaatttag ctattattaa ac                    102

<210> SEQ ID NO 311
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 311 cttaattaa ttattataga ttatagttta gattagttag gaaaattta sataatatta   60 tactctttag ttaggattaa ttagttactt tttatattat at   102

<210> SEQ ID NO 312
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 312
gactagatta aagaatattt acctataatt atatattagg agtataaata stagagatat   60
atagtaataa taaaatatct ctccttact tataataagt ag   102

<210> SEQ ID NO 313
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 313
aagaagaaga agaagaagaa gaagaagaag aagaacaaca acaacaacaa saacaacaac   60
aacaacgaga cggactgaca acgggcaacc gagccagggg gg   102

<210> SEQ ID NO 314
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 314
ttacttaatt ttatcacaga tatactagaa gtattagcta taaatataat stggtaaata   60
gaaggataca taacatataa tttattatgc ctagtaaatt ac   102

<210> SEQ ID NO 315
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 315
gcgccacttt tgtatgccaa tcccaaaggt ctgcccgtca aagcggcgac sgcttcttcg   60
gatttgccag ggcgactgca cttcgataaa aaccggaatt ac   102

<210> SEQ ID NO 316

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 316
acaggtcgcg cgagcgcggg atacacattg ccgcgggata ccttgtcggc scggccgggc      60
tgttgtggct cgccctcgcg cccagcggcg tgggcaaatg ga                        102

<210> SEQ ID NO 317
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 317
tatttatata tttattacta ctagattctt taattagcct ttacctttc stttttaatt      60 tttattttct agaatactta gcttaatctt tattactttt aa                        102

<210> SEQ ID NO 318
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 318
ttaactagta aatattaaga taaataaaag atacctttta ataagtacct stcctttatt      60
attataacct aagttagcta gtatatatta agataaatac tt                        102

<210> SEQ ID NO 319
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 319
tatactagga aattataacc tttctaatgg agcccttaat ctatataaga sacctagctc      60
tcataggact agttataaga gctctagcaa tagtaagttt aa                        102

<210> SEQ ID NO 320
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

<222> LOCATION: (51)..(51)
<223> OTHER INFORMATION: S is T strain AR37 or A strain RGT18

<400> SEQUENCE: 320
atagtattac taagtaatac tataaatcta aagatataga ttaatatttt saactatctt    60
tactttatag cttaaaatat cctaatagta agctttctta at                       102

<210> SEQ ID NO 321
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 321
aaaaggaaag aaaagataa ataagctagt atttactaaa ggactagcta sgagaattat    60
taaattaaaa actagactta agaatatatt aagtaaacta tt                       102

<210> SEQ ID NO 322
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 322
atataaactt agcttaatta ctactaaaat ctataaaatt aaattaataa satctaggaa    60
atcctagata ttatataagt attataaata attaaggtaa ta                       102

<210> SEQ ID NO 323
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 323
cttctaacct ttaggggcct tttccttgtc tttagcaccc ttttctaggt sttaagccct    60
ataattcagg gctttagata ctatagataa cttatccctc tg                       102

<210> SEQ ID NO 324
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 324
ttaggttata gctatatagt aacttattta gggtagtaac taaactagct staggttata    60

```
gctatatagt agcttattta gggtaactcc tattataaaa aa                        102
```

<210> SEQ ID NO 325
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 325

```
taagggtata tataatataa gtattatata tattactagg ggatattata sagaggagtt    60
tattagtaat aagtaagtaa gggtatatat aagggcttag gc                       102
```

<210> SEQ ID NO 326
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 326

```
tcttaggctt taataactat attactagct ttatagtctc ctaagaagac stttacttac    60
ttctctctta taatagattt atttataata agagttaata aa                       102
```

<210> SEQ ID NO 327
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 327

```
tacttagtaa ctaataaggt taagccttt ttatagtata tttatatttc sttattagta    60
ctttaatcta atattactac ctttcttact agacttactt ta                       102
```

<210> SEQ ID NO 328
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 328

```
ttattagcta gaaatcaaag aaagctagta taatagctct attaatatta saagctaaag    60
ctaacgctat ttcaagacc ttctaggagc tatagtggct tt                        102
```

<210> SEQ ID NO 329
<211> LENGTH: 102
<212> TYPE: DNA
<213> ORGANISM: Artificial Sequence

```
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 329
cttgtcatga agcaaatgtc taaatgtttg aaccattcga tctcggtcag sgtatatatc      60
ttttgaatgt caagtgttga tggtcgtagt cggaatagaa tg                        102

<210> SEQ ID NO 330
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 330
taaacttagt ttaataacta tttaggtaaa gaccctaata ataaaggcaa satacctaga      60
tctcttagag agcttaatat aaaaaccttt ataaagcttc tt                        102

<210> SEQ ID NO 331
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 331
atataagaat tcccttactt ttacctaata atttatagat aaattattct saaaatacaa     60
acattttata taagtatata ttaataatat tattgtatatt tt                       102

<210> SEQ ID NO 332
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 332
aaataatagg ctaataacta ggataacctt aaggataact agaataaatt staaacttaa     60
atacttatat tacttaagga ctttataaac tataatactt aa                       102

<210> SEQ ID NO 333
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18
```

-continued

<400> SEQUENCE: 333
gggatgccta gtggtctctc ttaactagta gctagtgaaa aaatcctatt stattaaata    60
aagaataaac ctccttacta taggtgttat ttataatgtt ac    102

<210> SEQ ID NO 334
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 334
atagatttta ttatagaatt acctattacc taagtaagta aataagagac saatataatc    60
ctagtaatta taaactaatt tactaagtac tttatattct ta    102

<210> SEQ ID NO 335
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 335
aactatatta gtgaatctag actactagag aggtcttaag agccacttttt sattttccgt    60 aaaatttatt tatatgtaaa atccaaaaaa ttaacttacc ac    102

<210> SEQ ID NO 336
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 336
agattaataa ttccctagta agaggcaagg gaaaagctag tctatagtta satagtataa    60
gaggcctcct aatatactaa gactaggtag ttattctagt ta    102

<210> SEQ ID NO 337
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 337
taagatataa aggaatatat aatttatata gtaagagtta gagatttaat saaaaaaaaa    60
gggggagaga gagaaaaaag gaataaaagg aaagagagag aa    102

```
<210> SEQ ID NO 338
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 338
ttattaagat agtaataact ttaactaagt aatactaatt agactaaggt sagattagtt    60
aagctagcga aattatttaa tagatatcta taaattccta ag                      102

<210> SEQ ID NO 339
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 339
aaattataat acctaggata aagctaacta tttctaacat attaatatta staaaggagt    60
tagtaaactt tatagacctc tttaataagg ctaaagctaa ta                      102

<210> SEQ ID NO 340
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 340
ttaaggatat aaaataaaag ctaatctcta gatttattaa actattttaa scacttaata    60
ctataaggaa ataagtatat taacttatat tacttaaaaa gt                      102

<210> SEQ ID NO 341
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 341
tcttagttta tatatagtta ttatatttat ttaatatctt aatttactaa stacttttta    60
tagctttaat aaagaaaaaa tccttttaatt ttagtataaa gt                      102

<210> SEQ ID NO 342
<211> LENGTH: 102
<212> TYPE: DNA
<213> ORGANISM: Artificial Sequence
<220> FEATURE:
<223> OTHER INFORMATION: Epichloe festucae
<220> FEATURE:
```

<221> NAME/KEY: Variation
<222> LOCATION: (51)..(51)
<223> OTHER INFORMATION: S is A strain AR37 or G strain RGT18

<400> SEQUENCE: 342
ctcgctccga ttcgtatggg tgaccgagtt ccccatgttc aagcccgttg sagaaggcga    60
gcctggccaa ggcggcgcag ctggcatctc agcagcacac ca                     102

<210> SEQ ID NO 343
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 343
attaatctta gcaaggcttt agcttatact agactagtag ttaattagcc saaggctcct    60
atatctagta taattcctct aaagatctct ttagaatagc at                     102

<210> SEQ ID NO 344
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 344
tattacctag gacttaatta taaaatatat ttaatattac tagtcttaaa scttttaaag    60
gggatctaat aaatatagaa aatatatcct tactataaga ta                     102

<210> SEQ ID NO 345
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 345
ccccccctcc ttcttaatta ctctttatta ttataaaaac ttattactaa sgtgtgtata    60
tactagatag aacctaggca tattaatttt ttatagctaa at                     102

<210> SEQ ID NO 346
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 346
tactactaac agagcggggt agcttgcgat gcatctaatc gcatcgcgtg satccctttg    60
gtggctccac tctttggcca cggtcggact atctattgtc cg                              102

<210> SEQ ID NO 347
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 347
cctccgttta gagttagtgc tttactaata tagctatagc acgttcgcta sgcaatagtc          60
atagcacaaa gagttatctg cctaggacgt aacctaggtt ct                             102

<210> SEQ ID NO 348
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 348
ctagcatagg ctatgtaaat aataaagagg ctagctagct ataagatagc satatgctta          60
tagagcaagg tatttattaa agactatgca tattattagt gc                             102

<210> SEQ ID NO 349
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 349
gtggaccttt tctccttcta tatttacatg cgagatcagc aaagatcggt sgattatctg          60
gacttttggt aagcaggatg atttgaaggt ctttattttg ac                             102

<210> SEQ ID NO 350
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 350
tcaccgtcac atgtttcgtt gaacatgtag acgtagcatg ttgcaggggg satggcggga          60
agcttgtcag agtgtgaggc ggcagacgag cctgtcgtgt tg                             102

<210> SEQ ID NO 351
<211> LENGTH: 102
<212> TYPE: DNA

```
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 351
ataataaatc ctaatctcta ggaagacctt tagggaataa tattagtata saccccttaag     60 ataaactata aagagactta gacttttttct agtatttctt at                         102

<210> SEQ ID NO 352
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 352
cgtgggtatc gcctgatgaa caactttctt cacttttttct ttttttttttt sgggttcttg     60 tcatgacata accatttgaa gtttaccagc ttgttgtggt gg                          102

<210> SEQ ID NO 353
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 353
atagggctct agccgtattt atcttatctt gccttatagt tagtgtgtat stagttaagt       60
gtaaagagaa tcttttagta attatattag tatttttttct tt                         102

<210> SEQ ID NO 354
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 354
ctcctaatat ataattatag gtaaatattc tttaatttag tctataccta saattatccc      60
tttacttata ttagtaataa agtaactaac ttagtaaacc tt                          102

<210> SEQ ID NO 355
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18
```

```
<400> SEQUENCE: 355
ttattatctc ttcctttagg tgctttaaag ttataaggta ttatagtttt stataatata      60
attagtatat actatatatt ataaaaaagc tagatattac tt                         102

<210> SEQ ID NO 356
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 356
atagctatat tttaattcct agggttagta aaggtactta tagtaattac stttagaata      60
ggtcttatat agtaagctat aagtagggtt ttacttctag gt                         102

<210> SEQ ID NO 357
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 357
tataagggct taggctttac ctaagcatat tatagataga aggaagggta sgagtaagta      60
agaataggta aggaggagct tatataagaa gctaaggggg ta                         102

<210> SEQ ID NO 358
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 358
ttacgcacta agattagggg ctagctacct ctaaccttat taattagtat statcttcct      60
ttttataaaa gggaagcctt ttatttatac taatttcctt tt                         102

<210> SEQ ID NO 359
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 359
actattataa agactaaagt atttatcgtt aaatactagc tattcccttt scttaaatat      60
aaacttccta gtctaaatac tattttaact acctttatt ag                          102
```

<210> SEQ ID NO 360
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 360
tagccttata tatattaagt atattaatat tacttacgct taggacttat stctattagt    60
attagattag gtccttagaa ttatattagt aatatatatt ag    102

<210> SEQ ID NO 361
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 361
aaataaacta ttagtataat tactatagaa agtataggat taagatctag stttataagt    60
aagattaata attccctagt aagagataag ggaaaagcta gt    102

<210> SEQ ID NO 362
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 362
aaagttagta tagcctagta taaaaaagtc agtaatttat agctataaga saataaaata    60
cttagtaact cactatctta tatatattgc tatatttatt at    102

<210> SEQ ID NO 363
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 363
aaaaaaatag ataacctata ttaatttttta taattagttt aaataaataa sgtacttaat    60
actatagttc taaatagtat aactaaaggg cttatattat ag    102

<210> SEQ ID NO 364
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 364
tccaatgcag tcattcaatc gacgtcacca gcagcaaatt gctgggcagg sgggaaagaa    60
tgacgatgat gatttccttg tcgcataatc cgttcactaa aa    102

<210> SEQ ID NO 365
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 365
taaagttata tatatatatc taagctattt taagtatagt aactatagga sttactaata    60
atataaatat agtaatattt aaaaagaata tagcctagac tt    102

<210> SEQ ID NO 366
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 366 tcttttttt tttttttgc tggacttgcg acaggtcatg cggtagcatg sgacggtctg    60
gggagtcgca agtcgtggtg gttcaaaact aaaaactcat tc    102

<210> SEQ ID NO 367
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 367
acagtgatgg agatgttaag aaagatatag gattaggcag taactattaa saagctaata    60
gaggagtaaa aaagacgtaa agaacatgct aggaaggtaa ga    102

<210> SEQ ID NO 368
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 368

```
atagatttaa cccttatcta ttaagtctat aatctagtgc ctaacctcta saagctagtc      60
ccttagtata ttatatagta gtatattata tagtaatccc ta                        102
```

<210> SEQ ID NO 369
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 369

```
tgcactatta ggacgcgaat ccattgaaca acctcttttt tttttttttt stttttttt       60 ttttcccctt gctcgcaggt tcccttgcag ggtgtcactg gc                        102
```

<210> SEQ ID NO 370
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 370

```
ttcgagaacg ggcacttctg cgatggcccg atgggtaact cgtatacaaa stagcgagcg      60
tggtccccaa cgtgggatcc cccttcgtc gccaggacgt gc                        102
```

<210> SEQ ID NO 371
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 371

```
aagggaatag ctagcgttta actagctaaa gaatacctttt taataagtac sttttcttta     60
ttattataac ctaagttagc tagtgtgtat taagataaat ac                        102
```

<210> SEQ ID NO 372
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 372

```
taaataagta ggtatagttt tccatgccta attttactaa agtttatagg statacccta     60
attcttataa tacttcaaag gcattttatt tagtaaataa ac                        102
```

<210> SEQ ID NO 373
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 373
aatataatct tactatagaa taccttataa ataatagaat aagaatatag statctctat    60
aataagataa ctagtagtta gctatataag cgctatttaa ta                      102

<210> SEQ ID NO 374
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 374
cctcaaggcg tcgaattgga tccagcctgt ggttcatgtc ccgcggtagt sgagaatcga    60
gaagccatgg cgcaagccaa gtctgccgca aagtccccgt tc                      102

<210> SEQ ID NO 375
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 375
accggcacaa tgacgtggtt ccagaaacaa tttactctgc ccgccaagtc scgcggctcc    60
tacctcatca ctgatcagat cgttggggct cttcctgaga tt                      102

<210> SEQ ID NO 376
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 376
ggagttatat tataatagtt tattaactag aagtattcta taaccttttta sttactatat   60 aatactaaga ancctttact aatatatatct tataacttaa ta                     102

<210> SEQ ID NO 377
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is A strain AR37 or G strain RGT18

<400> SEQUENCE: 377

```
aataatagtt aatttatata gagattttag aattataagg ggtagcccct satttcctgt      60
tttcctatat aaattagctc tttagcttgt ctctctatat ct                        102
```

<210> SEQ ID NO 378
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 378

```
cttagtaaga ggtatatagt tttatataag aactaggtaa aacactaaat scttatatct     60
aataagctaa gtatttagct tctaagataa aatctaatat at                        102
```

<210> SEQ ID NO 379
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 379

```
aacctttagt aaagttaata aatctctcct tctaataggt aaaaagcagt sgtttctctt     60
acctctagaa gctactaagg gtagccctat ttacgtacca ct                        102
```

<210> SEQ ID NO 380
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 380

```
atcttgtgtc gctggttggg gagattggca atgccaatcg gcgaggcact stccgcagct     60
ggggccatct tggacaaaag ggatttgtga gttggaaagg tg                        102
```

<210> SEQ ID NO 381
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 381

```
gtttcttaaa atactattaa gaaagtaaaa gaaaactata cttacctagc sttccttatt     60
tcctttcttt aatatttcct agtaataata ttatttagat ta                        102
```

-continued

```
<210> SEQ ID NO 382
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 382
atagtatact ttttctctta cttataagct ttaataatct ctagctatat sttataggaa      60
actaagctag gtagtattac taaagtatat ataataata tt                         102

<210> SEQ ID NO 383
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 383
agcactctct atatctttta ctagaaccta ttagttatat ttacttagct sacccttta      60 ttttactagg tatttattac tttcttagtt ttttctatag tc                        102

<210> SEQ ID NO 384
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 384
actatatcta ggatatagct atattactac ttttaagtaa ctttaattaa sctatagtaa     60
agttattacc ttactatact ttatataata agacttaaat ta                        102

<210> SEQ ID NO 385
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 385
ataatagcat tttagagtct ttattttatt aatcctattt accttagtag sgctttactt     60
actaaggagg gggcctttat gtatttctag ggtaattaat tt                        102

<210> SEQ ID NO 386
<211> LENGTH: 102
<212> TYPE: DNA
<213> ORGANISM: Artificial Sequence
<220> FEATURE:
```

<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 386

```
tttacccta gataaatagc tagataaaac gtttaaacta ggtcttaaaa sattatttaa      60
gggcttttac ttatactaaa taaactaatt aggtaattta ag                       102
```

<210> SEQ ID NO 387
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 387

```
gagaaactga gctagccttc gagctagttg ttggctttaa gctggttgct sgcttcgagc     60
tagttgctag cttcgagcta gttgctagct ttgaactggt cg                       102
```

<210> SEQ ID NO 388
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 388

```
acactacacg ttttagtgca atactctagt tatatataat attatacttt sttaataata     60
ctatttaact taatacttta tttccctaat ataacttaaa ga                       102
```

<210> SEQ ID NO 389
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 389

```
ttttattata atttagttat ttagttataa atttataaag ttttaccttta sttagaaaat    60
tagctataag taaaggtata gggtatatat aaaagatatt tt                       102
```

<210> SEQ ID NO 390
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 390

-continued ttattacaca ttacattaca ttacattcat tacaaatgta atatcagggg saaaaaaagt     60
ggggtatatt aaggtcttat aatattgtat agaattttct ct                       102

<210> SEQ ID NO 391
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 391
agtaagcttt agacctttct ttttcttagc tagcttattt tatttcctta sttaagtcct    60
agctatatat tactacatat accctagtta ttagtatatt ac                       102

<210> SEQ ID NO 392
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 392
gataggccta atagaatact aaaaaattat taatcttagt atatcttaga sgctttaaaa    60
taatttaata tactagatag taagtatatc ttagaggctt ta                       102

<210> SEQ ID NO 393
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 393
gttttaagtt atattagtaa aataaagtat taagttaaat agtattatta saaaggtata    60
atcttatata taaccttact tagttatagt aaaaattatta aa                      102

<210> SEQ ID NO 394
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 394
tttaacggtc agaggccttg tcagacagtc ggattaatta gtctaacgac sgaagctttt    60
gttagcggtt agagacctcg ttagaagacc ttctattagt ca                       102

<210> SEQ ID NO 395

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 395
tataatagaa tttaagaaat ttgctaaaag ctagataaat tcgctagttt sctagactaa      60
gagaatgaat ttagactaaa ttaaaacgga aatagttagt at                        102

<210> SEQ ID NO 396
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 396
aggcatttga ttcagccagc attgacgaca cacatcacat gcttgctttg sacatgtgaa      60
caacaggaac agaaaaggac ttcgacagtg gcgaccgagt gt                        102

<210> SEQ ID NO 397
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 397
agggagcgtt agtttagacc tatcctaatt cttatataag cgtatgtagt sattaaggga      60
cccctaataa gggggaaggc tattagcttt agccttatta aa                        102

<210> SEQ ID NO 398
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 398
aatttataat atttaccttt ttttaaggat tttactataa ctagggttat stataatatt      60
ataccttttt aataatacta ttatacttat tactttattt ta                        102

<210> SEQ ID NO 399
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

```
<222> LOCATION: (51)..(51)
<223> OTHER INFORMATION: S is G strain AR37 or C strain RGT18

<400> SEQUENCE: 399
gactagtact atattatagt taactactat aactataact atatataact sctataaaac    60
tagcctagag atatatagga agtgaggcta gccttagata ac                     102

<210> SEQ ID NO 400
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 400
attagtaata ttatattacc tatatataat acactaggct tctatttact sacctataac    60
tctaatatac ccttaaggat cttaaggcta aaattactat aa                     102

<210> SEQ ID NO 401
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 401
ttttctgctt tgcgaattcg ccataatcga gtcgcgccgc tcgcacggga sttgtgaaca    60
gaaggacgtg cgcacttcta ctccatcggg cgggtagaag ct                     102

<210> SEQ ID NO 402
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 402
aaggttaagg tcttttaact atagctacct tataataagt aatttaagaa sagagaaaat    60
cactatagcc taagactaaa gaccctaaag actctaagga ct                     102

<210> SEQ ID NO 403
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 403
tctaggcatg ttttccttta ttatttagta gcataaccta ggcctttagg saatagtttt    60
```
tatagtaact aataaggtta ggccttttt atagcatatt ta          102

<210> SEQ ID NO 404
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 404
atagcctttt ttaataaggc tagagctaat agcttacctc cttattaaga stctcttaat          60
tactatatat acttatacta aaactaggat aagtctaaac ta          102

<210> SEQ ID NO 405
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 405
aagttcctag gtattataag ttagctagat ataaagagat actatagtct stagctataa          60
aacttaaggc actctagtaa ggtaagtaag gataagtata ta          102

<210> SEQ ID NO 406
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 406
aggagacact ctattcctta ttttaggcat actagtttat aaaggtaaat stttatatag          60
cgttttataa gctatagatt actaagggct aggagcactt ta          102

<210> SEQ ID NO 407
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 407
tagaggtaac ttactactaa cttactaagt attatattag ccttattata sgctttaact          60
atactaatac tacctattat attatattta gtttaactag ta          102

<210> SEQ ID NO 408
<211> LENGTH: 102
<212> TYPE: DNA
<213> ORGANISM: Artificial Sequence

```
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 408
gtccgcataa cttcttctac tatagacttt aggataaggg ggcctaaggt sactctataa    60
cccttaaact ataataacac tgttttaatt agggtttcct ag                      102

<210> SEQ ID NO 409
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 409
cttagcccta atacttagat taataacctt actatatata gaatctagct stataataag    60
ttttaattaa agttatagtg ccttatagta ttactttact at                      102

<210> SEQ ID NO 410
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 410
cctaagatac ctaagattaa gtgtcttttc ccttaggctt tattatctaa sctagctaag    60
gcctatgcct ctaagcgcta tatttagtat aagaagagag gt                      102

<210> SEQ ID NO 411
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 411
ttatataatt ccttaggaat atctttaata gttttatata cttttacctc sttattatct    60
ttaagggtaa taaacttatt ttctataact cctataatag ta                      102

<210> SEQ ID NO 412
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18
```

-continued

```
<400> SEQUENCE: 412
tataacttct tatatagtga tttagtgcct ttacctttaa tctcttagat satataagaa      60
ttaaagatct agtagccttt atactttact agattaaata tt                        102

<210> SEQ ID NO 413
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 413
ggatttacta ttataaggtt atactaagtt tactttaaga gctactatta sgtgtaaggt     60
aagatttcta aagaaggtta attcttttta tctagagtcc ga                       102

<210> SEQ ID NO 414
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 414
tacaattatt agtagcttct tacctctttt ccctttaatc taggttagct sgattaaatc     60
ccttcgttct gattaattaa tctaggttat ctaactaatc ta                       102

<210> SEQ ID NO 415
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 415
gcacgattca ttgcaggggc cggccacctg cccccacgtg cgctgcgccc scctgcgccc     60
acctgcgccc acctgcctgc gcccacctgc ccccacctcg aa                       102

<210> SEQ ID NO 416
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 416
tccaggttca agtgcgcgcg caccggaaaa acaatatgca tcgcccacgc sggccaccat     60
gcgtgctgcg atcaaacaga agagcaacga ttcatcggtg gg                       102
```

```
<210> SEQ ID NO 417
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 417
tattaatatt ataaagctta gtaatagggc actttcctta gaataaaaag sacttcttct    60
aattctaata gattcttact tttataagaa ttattactaa ta                      102

<210> SEQ ID NO 418
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 418
tgtagttagt gtagtttagg ggaaaaaatt tatattatat tatattgtag stttttcctg    60
cttgtagtta gtgtagtttg tagtgcaata ctctgctctt ag                      102

<210> SEQ ID NO 419
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 419
aggttatggc agttattaac tattattaac taatagaatt taatctagat sactttaca    60 atatcttata tactaataga attgattta gtgacattat ac                       102

<210> SEQ ID NO 420
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 420
aaaaaaggaa aatattacct taaaggccta tatataattt agctaagaga sagctaaagg    60
tccttagaga gtaccttata agtatatagc ttaaagggta aa                      102

<210> SEQ ID NO 421
<211> LENGTH: 102
<212> TYPE: DNA
<213> ORGANISM: Artificial Sequence
<220> FEATURE:
<223> OTHER INFORMATION: Epichloe festucae
<220> FEATURE:
```

```
<221> NAME/KEY: Variation
<222> LOCATION: (51)..(51)
<223> OTHER INFORMATION: S is G strain AR37 or A strain RGT18

<400> SEQUENCE: 421
ataattagac tatcttaata gtatatttat aattagacta tcttaatagt statttacta    60
ggttactttt ccctagtcta tacctaatta taaagtaaaa gg                      102

<210> SEQ ID NO 422
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 422
gaaagcaacg gctaaaaacg acaagaattt tctcgtagtg ggagcccacg saccagttta    60
tgctcgccat tgttattgtg cccccttctt cgtagaatct ac                      102

<210> SEQ ID NO 423
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 423
aattactttc tctatagtat agtaaaagta ataaactact ataacctagg statatacct    60
agggttagag agctagagct aaaggactta tcttacctcc ta                      102

<210> SEQ ID NO 424
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 424
attatagatt taagtaagaa agctatagat aagttactaa tagttataag sacccactta    60
tggacccact tttattaaaa ccgattaaaa accctctctt ta                      102

<210> SEQ ID NO 425
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 425
agtttagcaa ttccagtggt agcaagaata gcattaacag gacctttagg scctaaggac    60
```

-continued

```
ctaatatcta tagcagtagt agcaattaga gtagcaatta ta                    102

<210> SEQ ID NO 426
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 426
ccacccacca tcatcagaag tgggcaacaa tgtatctcca tcacagatcc saaaccacca    60
cgtctcattc gtctcgtctc aacgagtcaa tcgccccctt ca                     102

<210> SEQ ID NO 427
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 427
aagtattaag aaataatata gtttaactaa agtaaaagta gctataatta satagagtgt    60
taggaagctc taaaaaatag tttaatctaa taacacggtg gt                     102

<210> SEQ ID NO 428
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 428
taaatcttaa actataaatt aaaatattat aaactattta tactttatag staaaaatat    60
tctaatagta aggcttctaa atatttatag ctgatacttt ac                     102

<210> SEQ ID NO 429
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 429
aaaaccttcc gttgcgttgc gttaaatatt taacgtagtg gttctattag sccctaaccg    60
tagagctgca cctgtacagc tgttgccagc cagcaactag ct                     102

<210> SEQ ID NO 430
<211> LENGTH: 102
<212> TYPE: DNA
```

<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 430

```
agcaaaatag cctaggatag gcatatattt agactagatt tacactagga sgggggtatag    60 ttacccttat tttagtaaat ctttcctttg tctttctttt ct                       102
```

<210> SEQ ID NO 431
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 431

```
gattagttaa gatcttatta gaataaagct taaaagaat aatcctacct stttactatt     60
agctataggc taggaaaata agcagtttaa agtaaaaaca cc                       102
```

<210> SEQ ID NO 432
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 432

```
tagactattt taagtactta atactatagg aaaataagct tactaactta sactacctaa    60
gaagtatagc taactatata atatatttta tattagctta ct                       102
```

<210> SEQ ID NO 433
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 433

```
ttcctataat aattatatta tctatatata gaagaagtat aatattatta sattaaaaaa    60
tacagagttt gcttaatagc ctcttaaagc cttactattt aa                       102
```

<210> SEQ ID NO 434
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 434
ttaatagatt accttagagg gaattaacta gtaatatttta aactaaaacc stataagtta    60
gtagtattta aagaacttta ataaagattt taaaaagcgc ta                       102

<210> SEQ ID NO 435
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 435
tacactatat aaatagtgtt tactagctta tatagtgctt tataaatata sctttaaaaa    60
gtaactaagg tattagttag cctaaagggt attataagat at                      102

<210> SEQ ID NO 436
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 436
ctttaagtgt aaagttacta gatattatac tataaactat attataacta saaataattt    60
attataataa taggaattct tatagttaaa attaataata ct                      102

<210> SEQ ID NO 437
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 437
tatatatagt acactaggct tttatttact aacccttatc tctattatat sttaaaggat    60
attaaggcaa agattacctt aggtatatat attattaaac ct                      102

<210> SEQ ID NO 438
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 438
aactatttta ctagctaata taaagtaaat atagtatttt attaccttta statatatag    60
gctattatag cttatactaa ataagtactt ttttaaaggt ac                      102

<210> SEQ ID NO 439
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 439

```
attaagatat agataaaaat acctatatat aaagagaaaa tatataaaag sttataaaat      60
ttcttagtaa acttaaataa attatttaaa ttaaattact at                        102
```

<210> SEQ ID NO 440
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 440

```
gcttagtatt aaaccacttc ttataattta aatatacttt ataaagtat staatatact      60 ctttatattt ctcttaagat aatatattta aaagagatat aa                        102
```

<210> SEQ ID NO 441
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 441

```
acgctgcggt tgtactcgtt agaacagcag cgcgaccgtc acggcggagg scataacttg      60
cacatacagg caacgatcat ctacgacctt tatgacactg cg                        102
```

<210> SEQ ID NO 442
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 442

```
atattaacac tctttaccta attatatctt actagcttag atattttacc sttttaggtt      60
ttattatctt tatttatttt aactacttaa tatacttaga gt                        102
```

<210> SEQ ID NO 443
<211> LENGTH: 102
<212> TYPE: DNA
<213> ORGANISM: Artificial Sequence
<220> FEATURE:
<223> OTHER INFORMATION: Epichloe festucae

```
<220> FEATURE:
<221> NAME/KEY: Variation
<222> LOCATION: (51)..(51)
<223> OTHER INFORMATION: S is C strain AR37 or T strain RGT18

<400> SEQUENCE: 443
ttattaactt tataataaac ttactagcat ttagattaat taggaaaatt stagataata    60
ttatgctcct tagttaggat taattagtta cttttttatat ta                     102

<210> SEQ ID NO 444
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 444
tatatagttc ttttataagg atataaggct agtaaagtag taggtaacta sgtatataac    60
gctatcctag ccttactagg aaaggttagc ttttactact at                      102

<210> SEQ ID NO 445
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 445
taagtttata aaggtaatat ataataagac tattatatat actattataa sagttataga    60
agataaattt attaccctta aagataagaa aaaagtaaaa gt                      102

<210> SEQ ID NO 446
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 446
ttatatattt ttaataaagc ttattaagcc tttagagttt attttagttt stttcttaag    60 acttttctt tttaaattaa tagcttttct aattatatta tc                       102

<210> SEQ ID NO 447
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 447
```

```
cttctcccga ccccttgtatc ccctaccaaa aaaaaaaaaa aaaaaaaaaa sgtcccatcg    60
acatgcccct tcagtccgta gcgatattcc acagcccatc gc                       102

<210> SEQ ID NO 448
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 448
agctagctat agtttacatt aggactaata cttagttagt ctaaggtata sgtttagcta    60
gctatagttt atattagaac tagtacttat tctctatagt aa                       102

<210> SEQ ID NO 449
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 449
ctagataaat actagctagg ggcaggtata taaaggtttt aatctctaac stagcactaa    60
taatatatat agtctttaat aaatacctta ctctacaagc ac                       102

<210> SEQ ID NO 450
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 450
actagatagt agcccttaat taatctagaa tagtacaaat taaacgcttt sctaatctat    60
tttgcttata gatataggga ctagaagtta taaatttaat cc                       102

<210> SEQ ID NO 451
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 451
atatataagt agtttactac gcttctctaa gctttaatac cttattacta sgataaaatc    60
tagtaatata tttaaattac taggttaagt aataaatctc tt                       102

<210> SEQ ID NO 452
<211> LENGTH: 102
```

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 452
tccttaatat tcttatatta tctaatagta atatttcta accttagcta sataatctcc    60
ttaagtatag taataactat agctatattt tattattttt ct                     102

<210> SEQ ID NO 453
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 453
attaaaccta actaagccac aaagctaagg gattagccta tacctataag sttacttaac    60
ctcttaatta acttactagg gatgtaagct agtaataggg ag                     102

<210> SEQ ID NO 454
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 454
taaggtctta taaagccatt ccctatgtct atttattagt tatatataaa saatttacca    60
ctctctccta tagttataaa tctaaatctt tatttactat at                     102

<210> SEQ ID NO 455
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 455
attaaatctt actaacttac ttttaagaag actagatttt ataagtaagg saagaaaaga    60
gaaagtaata actatataac ttcttacctt tttatttaaa tt                     102

<210> SEQ ID NO 456
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is C strain AR37 or G strain RGT18

<400> SEQUENCE: 456
gattgttgag atggcgtacc tgcgtacgtt cgacccttat caaaacaaaa saaaagaaaa    60
agcatcggtc cgctatgcgc ggaccgggca aacccaaaga aa    102

<210> SEQ ID NO 457
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 457 aaactttat ttattatctt taatagtatc ttatagtaag aacgcatttt statatttat    60
taagtcccct ttaaaaggtt taagactagt aatattaaat at    102

<210> SEQ ID NO 458
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 458
agtattatta atatactcct aaaaagttac taatatatta actagtttaa stagtattac    60
tagatattta aagtaactat attaataata aaacactatt tt    102

<210> SEQ ID NO 459
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 459 ctactctttta tattatcttt atttaattat ctcttatta tttagcacta stcttaactc    60
ctttatgttc ttagagataa ttaattatat aggataattt ta    102

<210> SEQ ID NO 460
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 460
cctttagata ttatatacta ggataagttc cctagtttta attaatctttt sctaagagaa    60 atagcttagt tcttattagt ttagtttata aggcattgcc ta    102

<210> SEQ ID NO 461
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 461
atttaaataa gaaaatcttg tttttatata tattttactt atttaattat saatttctaa    60
aactttagct tatttagaat aataagctaa gaataggcta ag                      102

<210> SEQ ID NO 462
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 462
aagttatttt ataaactat taatcttta cttctaaaaa gatctcctag sttagcaaag     60
agtctagaat actagattat tctaatctag tttatgtgta aa                      102

<210> SEQ ID NO 463
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 463
taaattaaaa ctagaataat actaataata gaatacttat agtatttagt satattttat    60
tataaatttc tatataaaat attagtaatt aaactagtat ta                      102

<210> SEQ ID NO 464
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 464
ttatattact taaatatatt actttaagta ttaagaaact ataaactta saagtctctt    60 tattcttatt atagatatta tccttataat atttaattat ta                      102

<210> SEQ ID NO 465
<211> LENGTH: 102
<212> TYPE: DNA
<213> ORGANISM: Artificial Sequence
<220> FEATURE:

<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 465
ataataagac gcttgaaaag cttgtgaaag acttgctagg acctaaatgg saaccatgcc    60
cggcgtggct caaatgtttg tcgatctgtc acacatgcca tt    102

<210> SEQ ID NO 466
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 466
ataatagcga agttagggat aaaagataat attataacta taatagctta sattacctta    60
taaataagta tagtaagcta aggaaagagc cctaagatag ct    102

<210> SEQ ID NO 467
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 467
ctgttactct tcccagaccg ttgactagcg ctgcgacctt ttttttttttt stttttttt    60 tttttttgttt cgagaaagga catgagttga tgaggggcca ac    102

<210> SEQ ID NO 468
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 468
tgctactata aatatttata attaaactaa tagaagattt taacttaaat sctctatagt    60
aattaattag tttaaaagct agaaaacttt attctaatta ct    102

<210> SEQ ID NO 469
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 469

```
atctctttat atattatagt tagtttacta ataacttatt agttttatta aataaaaca      60 cttatagctt actatataga gtaagctata ctatagctag ct                        102

<210> SEQ ID NO 470
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 470
gaaaataagc cttattacta aaggataagg actttaaatg tatagcttat sattaatcta    60
aggtagtaca aagacctagg aagttagcta tccctaaccc cc                        102

<210> SEQ ID NO 471
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 471
tatctcaaag cgttatgcag gggactaata taatgagccg agtattatat sgagaaagaa    60
ggcaacccgc aactggtcta gtcaacaatg gtggttccat ct                        102

<210> SEQ ID NO 472
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 472
aggagagagc tcttagaata cctataataa gatagctaat agtagcttag satagaataa    60
ataataagga cttattatta agaagtagta ttataataga ga                        102

<210> SEQ ID NO 473
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 473
aaatcggaag ggccaagctt tgaactgact ctgctcctgg gccatgtctc satgctcact    60
tccctcgttg tcgcggagag ccaaggaaag aagtacatct tg                        102

<210> SEQ ID NO 474
```

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 474
gcatggaccg gtaacgtttt tcctgaaaga atgagccaag tcagttagag scagattgga      60
ggcacgaggc aaagtgccgt ttgaagaacg tttggcgcaa tc                        102

<210> SEQ ID NO 475
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 475
accatgccca tccgttgcat gaataattgc accctctcc agaagcagac sgacgatgct       60
cgcatgtcct tcacaagcag cccatgagag aggagtacgg cc                        102

<210> SEQ ID NO 476
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 476
ctatagggta acctgcttac gtcaccctag cttacctaat tactagtggc sctgcggttg      60
tggctacgct tgcagccata acgcaattaa ataatccata at                        102

<210> SEQ ID NO 477
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 477
tctctccgaa ttcttctcac cgacctcaac ttgcagacag aacctccccc sccccccccc      60 cccccgccc ccaccccac catgtcgtca gccctcatct cc                          102

<210> SEQ ID NO 478
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

-continued

<222> LOCATION: (51)..(51)
<223> OTHER INFORMATION: S is A strain AR37 or G strain RGT18

<400> SEQUENCE: 478
gtagctttat ataagtaagt aaattactaa ttatatctct taaatatata saaggtttag    60
taaatttatt ataataaagc ctcttattat aaataaagct at                      102

<210> SEQ ID NO 479
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 479
aataaaatta aggctttagc taagctaact aatcttctaa tttacccttt sagctatata    60
cttaactaat cttttaattt accctttaag ctatatactt at                      102

<210> SEQ ID NO 480
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 480
gagactatag tataagttaa aatataccct agtctaatta cctaactata stagcttact    60
attaaagtat tatactagat attaagtctt actaattaga ga                      102

<210> SEQ ID NO 481
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 481
atatttacta tacttaaata tttactaata ttacttataa ggtaaaatat sataaatata    60
ctataatagt attactaagt aatactataa atttaaagac ct                      102

<210> SEQ ID NO 482
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 482
aggggtgcat gctcgagaaa ctgcccaact tgttctattc catgggctac stcgacgcga    60

```
gctggacgct cggcgccgac gccaccgccc agctcgtctg cc                         102
```

<210> SEQ ID NO 483
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 483

```
taatagctct attaatatta gaagctaaag ctaacgctat ctgcgagacc stccgggagc      60
tacagtggct tcagggcttg attaatatta gaagctaaag ct                        102
```

<210> SEQ ID NO 484
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 484

```
ttatagtaag ctttaaggag taatttaagt aagaaaagag tttaattatt sgtctagtaa     60
atttaggagg atttagatgc ctataactag gtgctttagg at                        102
```

<210> SEQ ID NO 485
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 485

```
tattttaaaa gcaaggacgc ggggtttgga aagagaacgg aagtctgggg stttttttttt    60 tttttttttt tttgctagcc atgctttagt aaatttttttt tt                       102
```

<210> SEQ ID NO 486
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 486

```
taataaaaaa gggagttatt acctaactta ctatagtaat aagggataag sacttagata    60
agggtaataa actatttata tatttcttta tatatagtgt tt                        102
```

<210> SEQ ID NO 487
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 487
aattatgtta taaaaaatca gatgcattgg ctatagccaa tgaggtaaaa stttttttt       60 ttaaaatcaa taaatcaata attgttagta tctattagga ta                        102

<210> SEQ ID NO 488
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 488
taaggagagt atttgttgtg ctgaagtctg acggtggtgg tggtggtgac sgcagaatag      60
gcaaggagaa gccaggagaa gcataagctc cggaaccggg tt                        102

<210> SEQ ID NO 489
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 489
aaaggtccta atatcttaag ataagggtaa cttatatagc tctattatag sctaataagt     60
aagtatttta aatataggtt ttctaaatgc tagtaaaggt ag                        102

<210> SEQ ID NO 490
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 490
aaaaatagtt tactaaggta actatagcta tatttattta tacttataaa sgactaggaa     60
gagcttattt aactagacct agagattact atatagccta ag                        102

<210> SEQ ID NO 491
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 491
ttaaaggact cttatagttc ttataagtag agcttaaagt aataactaat scttaaatcc    60
ttactaaaca tatataacta tttaaattta atattatatt ag                      102

<210> SEQ ID NO 492
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 492
tcaacatggc gcaggcaaag aagaacctcc tgctccttac gattagggaa sttgacgcag    60
aatggaaaag gagaaagtca ggtaggatat ttgcgtatcg gc                      102

<210> SEQ ID NO 493
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 493
aagaactata ttcgtatttc ttaagatcta tatatactta ctttagtgta saatttacac    60
tataaagtta attaactata aatataatat taggttatat aa                      102

<210> SEQ ID NO 494
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 494
ttaattttat tctattagtt tagggtattt tttatttaaa ataataataa saaaatataa    60
aaatataaaa taattaataa taatagtaaa taaaatatata ag                     102

<210> SEQ ID NO 495
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 495
gatggcgttg accccacgcg gacatacacc aacgacctgt ggcagattgt sgaggtgttt    60
ggcattgaag ctgcccgttc tgctctggtg aaggagctga cc                      102

```
<210> SEQ ID NO 496
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 496
ccagagtatt gcactacaat tgatttgtag tgtattttt atttaacaaa saatatatat      60
ctaatcttag aaaatatgta aagatataaa acttctttt tt                        102

<210> SEQ ID NO 497
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 497
attagtaatt tagtattact agaattttat attaagatta taatagaatc stactattaa     60
tttaactagg tttaacctga tttttactat aatagtaaca tt                       102

<210> SEQ ID NO 498
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 498
tagtgtttag ctttgctaaa gcctaatctt atataaagta attaagatag saaacaggag     60
tttaatagtt tcctaggata gattagtgtt aataaaggat aa                       102

<210> SEQ ID NO 499
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 499
agatctttaa aataagtcta ggtaaggata tattagtaaa gtttaagttt sctcttttat     60
cctagtaatt ataatctttt cctatctata atatttaata gc                       102

<210> SEQ ID NO 500
<211> LENGTH: 102
<212> TYPE: DNA
<213> ORGANISM: Artificial Sequence
<220> FEATURE:
<223> OTHER INFORMATION: Epichloe festucae
<220> FEATURE:
```

```
<221> NAME/KEY: Variation
<222> LOCATION: (51)..(51)
<223> OTHER INFORMATION: S is T strain AR37 or C strain RGT18

<400> SEQUENCE: 500
ttccttctaa aatcctatat aagcttagat agtaatccta aatagcttag sacctaatta      60
atactcttaa agtaacttag tgttataatt attagctata gg                        102

<210> SEQ ID NO 501
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 501
cccaagcgac ccaggcggcc ataatcttaa acagcatttc cctttttgcaa sacgctcgaa     60 tgttttccta aaaagtgaac aagtaatcat tgtctagata gg                        102

<210> SEQ ID NO 502
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 502
taataagata atagcataga attattactc tctcctatta attaagaaaa sactttactt     60
cttattttag gtatattagt ttataaaggt aaatatttat at                        102

<210> SEQ ID NO 503
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 503
tactatataa ataactagat tagagaatta actaataaaa ctaaggatag saaggactat     60
agtatagact tagtaatata cttaaatagt gtgggttata cg                        102

<210> SEQ ID NO 504
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 504
ccttaataaa attagctata ttttctccta aaaactacta aatattatac stattttata     60
```

```
tagtaataag agaagtttaa tatactatta tttctctaag aa                      102
```

<210> SEQ ID NO 505
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 505

```
ataaagagat taaatagtaa agctatttta taaagagatt aagctataat staaagcctt    60
agagggcatt atatttaata gagaattagt ctttataagt ta                      102
```

<210> SEQ ID NO 506
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 506

```
attattaggt actgcatttt cagtattaat aagattagaa ttaagtggac saggagttca    60
attcatatca ataaccaat tatataatag tatcgttaca gc                       102
```

<210> SEQ ID NO 507
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 507

```
aataatctag tattctaaaa tctttactaa gctaggagat ctttttaaaa stagaaaatt    60
aatagttata taaataact ttaagatcta atattataag gt                       102
```

<210> SEQ ID NO 508
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 508

```
ctaaccatct gctatctagt ccaattcgct cttcttcgtg tctacgcagt saaacttgct    60
cctctccctc tcccaagcgg cgtgacttaa cttcttagtc ac                      102
```

<210> SEQ ID NO 509
<211> LENGTH: 102
<212> TYPE: DNA

<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 509
agttatcttc tataataatc tattctccta gctaaatggc aattttgcct sgttttctat    60
gggtaattag gtattacctt ctagcactat tttaacgtgc tt                      102

<210> SEQ ID NO 510
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 510
tcaacaacaa cctccaatat agacagttgt gacacccag taaaatctct sccaattaat    60
gcaatagggt atcaaaacaa gaggctcaaa agacaaagga ga                      102

<210> SEQ ID NO 511
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 511
aactttaaga aaaaccttct aattattta tttactatta ttattaatta stttatattt    60
ttattattaa tttaattaaa aaataccta aactaatata at                       102

<210> SEQ ID NO 512
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 512
tctataggaa tccttatttt cttattataa agaaagataa agggatttac staattctat    60
ttactataaa gtataataag gtaataatat aagatatgct aa                      102

<210> SEQ ID NO 513
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

```
<400> SEQUENCE: 513
atattataat attgcaattt ttagcaatat agcctttatt ttttgcctta sgtaaagatt    60
ttaaccaagt cttgtataat ccttggttat tcttgataat aa                      102

<210> SEQ ID NO 514
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 514
gtttgacatg gaatgcaagc agcaggacat tttcgacttc tccattcgtc scactgttga    60
cgacatcttg aacggctaca atggcactgt cttcgcctac gg                      102

<210> SEQ ID NO 515
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 515
ggatgatgtg gagaagtaga ctcacttcta agactgcgat acggaatagt sagggaaagc    60
ggagctttgc cgcaaatgga caaatggaca aatagacgaa ta                      102

<210> SEQ ID NO 516
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 516
tagttagttt tctcatatag ataataagat taataattaa ctaaatatcc sggatagata    60
taataaggtt atatcctata agcctaaggg ttaatagatt aa                      102

<210> SEQ ID NO 517
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 517
tagctagtag cttgctagtg ttacataaac ctagccctag agccttacta scctataagg    60
tgcataggta tacctattat tgtaagtaag gccttataat ta                      102
```

```
<210> SEQ ID NO 518
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 518
atccttctta tttacatttg taagggctta gactttgcct aagcattgtc sgtatagtag      60
ttagagaggg gattagtaaa agcaattagg gtaaggaaaa gg                        102

<210> SEQ ID NO 519
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 519
tttattacta agttaaatac tttaatttata agtaatttat tactaagtta satactaagc    60
acttaattta ctctctaaag actagaatat actaaactaa ta                        102

<210> SEQ ID NO 520
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 520
aaactcactt gaacatgtcg gccgagatct gagtgatcct cgcccacgca stcacgccag     60
gccgggcagg cgtcttctgc agcctcgtct tgatggtgtc ga                       102

<210> SEQ ID NO 521
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 521
atgtaatcag gccggctgtc cacgaactct cccaaggaaa gcgccctaca saagtgttcc    60
aaatgagact tggcgttgtc aaagtcaagt cttgccccag ta                       102

<210> SEQ ID NO 522
<211> LENGTH: 102
<212> TYPE: DNA
<213> ORGANISM: Artificial Sequence
<220> FEATURE:
<223> OTHER INFORMATION: Epichloe festucae
```

<220> FEATURE:
<221> NAME/KEY: Variation
<222> LOCATION: (51)..(51)
<223> OTHER INFORMATION: S is G strain AR37 or A strain RGT18

<400> SEQUENCE: 522
gagtagagag cagacaaaca aggaaaaaaa aaaaaaaaaa aaaaaaaaaa saaaaaaaaa    60
aaaaaaaaaa aaaaaaaacc cgtgtagcag ttcaagtaca at                      102

<210> SEQ ID NO 523
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 523
atatatatct taactattag ttttagtatt tctaagttta atagttaata saagccctat    60
atataattag tataggataa ttaaatataa tatatatatc ta                      102

<210> SEQ ID NO 524
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 524
ccccaaaaag aaaagaaaag aaaaaaaaga acgcctcgct tactctgcct sccccacgct    60
ccaccacaat cacgcagcag atattactct gcctccccca cg                      102

<210> SEQ ID NO 525
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 525
tatagggata cctatattat ttatagggta atcctttaaa ccttaattta satcttatta    60
ttatactaaa ttattttccc cctctaaagg gttatcccct at                      102

<210> SEQ ID NO 526
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 526
ttattacaca ttacattaca ttacattcat tacaaatgta atatcagggg saaaaaaagt    60
ggggtatatt aagtcttat aatattgtat agaattttct ct    102

<210> SEQ ID NO 527
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 527
ggtccgggcg ggcaactcga gccgggaaaa agggggggg ggggtttttt stttttttt    60 ttgtaataaa gattgcccga gatgaggttt gcctggggg gg    102

<210> SEQ ID NO 528
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 528
ttcaagctgg tacgggggct tggattaaaa ttgccacatc taccctacct sccctaaatt    60
gaagcgacat cgaagcgaca ttgaagcgcg acatgaacaa aa    102

<210> SEQ ID NO 529
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 529
agtaatcatg gctgcaatgc actgatcttg ggtgtacgaa ttggccgccg stcatgagag    60
gagattgaaa tcttgtctat tttttgggaa ttatcaatgc tc    102

<210> SEQ ID NO 530
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 530
tatattaata agattaggga aaaatttagg taagtaagaa aaggcacttt scttactata    60
ctaatcctag tagtaaagta ttataagttt aagggttact at    102

<210> SEQ ID NO 531
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 531
taaacttatt aagggcctat atttatacta tattctctaa tagttcctat staggctata    60
tatagcccgc ttacttaata agtatattat atctcttgcc ct                      102

<210> SEQ ID NO 532
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 532
ccttagatat tagctataat tttacctata gtctatagta attatatagt saggtagtct    60
tattaaaata taaataaaaa tgcttatata taaaggggaa ac                      102

<210> SEQ ID NO 533
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 533
tattgagatg catcaaaaat gtgacaacct aaaaaaaaaa aaaaaaaaaa saacgaaaag    60
aactcgcagg atatcgtgtc caaagacgtg cggaattaaa gt                      102

<210> SEQ ID NO 534
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 534
tcttttgcga caacctcaac ttacaaccgc cacgacgcca atgatcctca stgtcccacg    60
agcaatatcg tcacccacga aaacaaccag cgaacaatct tc                      102

<210> SEQ ID NO 535
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

-continued

<223> OTHER INFORMATION: S is C strain AR37 or T strain RGT18

<400> SEQUENCE: 535
tgaactggat acagcatagg tgtagtagac gtttcttttt tttttttttt sttttttttt      60
taaaaaagcc cattcgactg ttgaagcttg tttctgtttc ca                         102

<210> SEQ ID NO 536
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 536
ttccggcgga tcgggacgac gctcccaggg cgtggagctt gagcgacggg sgttgggcga      60
ggaggaggat gaagcgctgg ccgacggagc ctgtggctcc aa                         102

<210> SEQ ID NO 537
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 537
tatttgacat tgagacttgg catgatggaa cttgaggacg actgctctct stagcaattc      60
atcatggcag gtgtttgcga gattccatgt catggttttc aa                         102

<210> SEQ ID NO 538
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 538
tgtacacagc gaaatcgggg accgaaaaaa aaaaaaaaaa aaaaaaaaaa sctaccctcc      60
gctcagtgaa tacggaacta ggatccatct cttgtttttg ga                         102

<210> SEQ ID NO 539
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 539
atctaggtta gtgaactgga actgcttctt ctcgcctgct ccagcactag sccgtggagg      60
agctgtccct tctggctggc caccgcgag gctcgcccct ct                          102

<210> SEQ ID NO 540
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 540

```
tagggttaga gggctagagc taaaggacta ttcttacttt ctaagggtta sagggctaga      60
gctaaaggac tattcttacc tcctagataa atatagtatt ct                        102
```

<210> SEQ ID NO 541
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 541

```
ttcgacaagg gtcagataca gctgcctcag ccaacacgct ctgtccagct satttatcat      60
acatgatgct gtttcatcat gtccacgcag aaacgcctct tg                        102
```

<210> SEQ ID NO 542
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 542

```
ggagcgggta ggcagtcttg gtaagataat ggtggagttg cgccgcacga sccgacaaac      60
cgccaaaaga ggaggcaatg gtgttgaact ctacctgctt ga                        102
```

<210> SEQ ID NO 543
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 543

```
caaggatggg ggactggttg cgtaagcaaa acagagcgaa acggaggggg sagaccacaa      60
caagatgcac cagactcatg gcatggctca tcgggaagtt cc                        102
```

<210> SEQ ID NO 544
<211> LENGTH: 102
<212> TYPE: DNA
<213> ORGANISM: Artificial Sequence
<220> FEATURE:

<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 544
acagacagtt cgatttgctt ctgacaagga tgtgtgacgt ttactcattt stcagtctgc    60
gctactttat gagcttttgt gtttgtagca gagattgacg at                     102

<210> SEQ ID NO 545
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 545
ataatatata aagaaagaat ataataaact aatatttata atctattaat saataattaa    60
tagtattatt ttaattacct tatatagctt aattaagcta ta                     102

<210> SEQ ID NO 546
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 546
tactaataat attatagtac tagtgcctta gattcttaat taattatatc stataagaca    60
cacactatag cgcttaaggc ttacctagct accctagatt ag                     102

<210> SEQ ID NO 547
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 547
gctacagctc tagtttgcac tctcaacatg aggtgaatag actgtcaccc sacagctccg    60
tcaacgagct acacattcac ccactctttc ggtctgactc tc                     102

<210> SEQ ID NO 548
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 548

```
tacaaagcta tggcgcatcc cggcgttcag gacggtgaaa gctttacggg saactattca     60
aactgaagag attttgtcgt tcatctactt gcttagggta ga                       102
```

<210> SEQ ID NO 549
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 549

```
gacaacaagg cggcaattgg gagcagaagc agacgacaac ggtgaggggg sggtggagag     60
ggggaggggg aagaagaagc aatcatcaaa ggaccctgac ga                       102
```

<210> SEQ ID NO 550
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 550

```
aatggtcgag ccaggccaga tcgtaagacc ggccagcgca tgcagcacat scagcacaag     60
gaagcacctt cgcggcctgg ccggaatcac tgtccagagt ga                       102
```

<210> SEQ ID NO 551
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 551

```
atactagccc acagtcatag gtagcagtaa cgtctgctta cattagaaaa sttaattaac     60
ttaacagtag taattataat aatagctaaa tctatcttta ta                       102
```

<210> SEQ ID NO 552
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 552

```
tagagttatt aaagagatta taagtaaatt attaattaga gtttaatata stttaattaa     60
actaagtact attaaaaact tacttaatct tataaagaat cc                       102
```

<210> SEQ ID NO 553

<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 553

```
ggccatgcgg ctgggttggg cgtcgtcgag gtctttgaca cggggagtgt sgggaagggc    60
gtacgggcaa cgggggcatg accagctttc aaaagacttg tt                      102
```

<210> SEQ ID NO 554
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 554

```
aactatcaat attatctgta ctattaatat tatctgtact gttaatatta sctgtactat    60
caatattagc aatacaatca atattattaa taccattaat at                      102
```

<210> SEQ ID NO 555
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 555

```
tcaacaaccc cagaccaaac gaaaaatgaa caaaaaaaaa aaaaaaaaaa saacaaaaaa    60
aaaaaaaaaa aaggcctcct cttccttcca agtggatgcc cg                      102
```

<210> SEQ ID NO 556
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 556

```
ccactacatt ctccaggcgg cgtcctctttt cctcccctgc atggccctcg scccgcaaga    60
gaacgagcgc gtgctcgaca tggccgccgc ccccggtggc aa                      102
```

<210> SEQ ID NO 557
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 557
gagacccgag cttggtcgct cgtactcgta ctcggatgct gccattgtca sgcccaggca    60
ccacggcacg tcgccgtcgc tgagtcaaag ccaagaatta cc    102

<210> SEQ ID NO 558
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 558
aaggctagaa taaaactagt ataggatagc taagacttac cactacccc staattaata    60 tagtaatatt ataagtcctc ttctagaata taaataagaa gg    102

<210> SEQ ID NO 559
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 559
gagcgcacta acaaagaaag gggaggggg gggcggaaag caagaaaaga sacgtggagg    60
atcgagatct gccccccccag cactggaatg tcaacacgta cc    102

<210> SEQ ID NO 560
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 560
gcgcttgttg cgtcagcatg gtatgtctca tcttgtcttt tttttttttt stttttttt    60 ttttccccctt tcaagtcaaa agggcattca ttcatcatcg ag    102

<210> SEQ ID NO 561
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 561
atttgctctc atctgccacg cctgcagact ggtcaacggc caagctcccc scgggacgaa    60
gactctcgca gaaatcggca tgtggaggtg cagcgggtgc gg                           102

<210> SEQ ID NO 562
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 562 gcctttttgcg ggaagtcgtt gatttcaagc gtcgcgtgga acgccccggc stcgggaccc       60
ttgttgtcga tgggctggcc ggaccggagc tggccagcct tt                          102

<210> SEQ ID NO 563
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 563
ctaggtccgt cgcttgaggc aagtcccacc aaaccgtccc cagcctgctg stctccttgc       60
actgtgcagg caggacatgc acgatggcgg gttgagcctg ca                          102

<210> SEQ ID NO 564
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 564
acgtataaga tgattgccgt tttttttttt cagaacgcac tcgggcgcca sgagcatgag       60
aaagaaaagg agaagagaaa gaagaagaga aggaagatg cg                           102

<210> SEQ ID NO 565
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 565
caagctttag cagggcatg catcagggac cggggggggg ggggggggggg sggacaaaca       60 atcatgtggt ttcgtgaaag ctggagaacg gaagacgcgg gg                          102

<210> SEQ ID NO 566
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 566
gggaatctaa acacagagat atcagtcctg caaatgttca tctcccccccc sccccccttt    60 ttttttttctt ttttttagaac ggcaagctcc cagtttcttc gt                      102

<210> SEQ ID NO 567
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 567
caaaagtggc gttgaaggcc gaccagatcg tgaccggcct ccgagggaag scagtcaggg    60
tcgtgaagcc gcggatcgaa gtcgtagtcc acgcaaacga cg                        102

<210> SEQ ID NO 568
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 568
agtaaattag gtggttctcc ccctatatt actcttaggt agctagtagg sgaagcttta     60
gaattataag aataatagta gctaggtaag aggtataagg gc                        102

<210> SEQ ID NO 569
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 569
ggggaagcac aaagtccatg ggaaaaaaaa aaaaaaaaaa aaaaaaaaaa scgttcgaag    60
agcaaccgtc gctccgtgag cagctggttt gggtattgcg at                       102

<210> SEQ ID NO 570
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 570
attagtagtg ctactagctc taaaaagtta ctaataaagt tatagtaaaa sttagtaaac    60
cctaggaagc tataaaccta tagtaaaaat tagtaaacct ta                     102

<210> SEQ ID NO 571
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 571
cagggcgttc ctggcgctca tcttgaaaac cttgccaatc tgtgatttcg scccgcaatt    60
gatcaatgtc ttcgagctcc tcctgaatag cgttagcacc tt                     102

<210> SEQ ID NO 572
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 572
aaatgatccg tacccatatg taattgtaat gcagcatccc acgcctttgc sctaaattta    60 tatgggcgc catggcaaaa aaagatatc acctaatatt at                      102

<210> SEQ ID NO 573
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 573
acacgcacca aatgagaagg agatccccga tcgataccca gcaccagcac sgtggaccgg    60
aaatgtatgt agagaggact cactgctcac tgtcaggga ga                     102

<210> SEQ ID NO 574
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 574
acgcctacaa cattttcttg gtgggcggcc ttggaggata tcgacggacc scctatgcct    60
ctcgatcggt acttggtgaa gatcaatagg cggacaagga ca                     102

```
<210> SEQ ID NO 575
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 575
tgctctcggg gatttcgggg gcccgctgcc tgcctggatg caacattgag sctgaccgat      60
gccttcttcg gcctcggtcc ttttcctttt ccccaaccac cg                        102

<210> SEQ ID NO 576
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 576
gcgaaggtcg caaaaggatg aatcgtgttt gacacgggca gcatctcaac stcaaggatg      60
gacacgagcc cggggtcctt gactgtgcgt gtgcccgagg ag                        102

<210> SEQ ID NO 577
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 577
ccttcggtta gtgtgcgtcg gtcgagggag tcccggtggc gcaacgtctc satttggcca      60
cagattggca gattggggcg agaacggggg cctggaaaag ct                        102

<210> SEQ ID NO 578
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 578
cacgtgcgtc tgcgttgacg atttatacct ctcaacaaca taaacgttac scgcagcaat      60
ctgcctaggt atgtttcacg acaccgatgc ccttcatcct ac                        102

<210> SEQ ID NO 579
<211> LENGTH: 102
<212> TYPE: DNA
<213> ORGANISM: Artificial Sequence
<220> FEATURE:
<223> OTHER INFORMATION: Epichloe festucae
<220> FEATURE:
```

```
<221> NAME/KEY: Variation
<222> LOCATION: (51)..(51)
<223> OTHER INFORMATION: S is A strain AR37 or G strain RGT18

<400> SEQUENCE: 579
cagaagacat catcttattt tccgccttca acgacttgtg gaaaaagaac sacatgtcaa    60
cgttcgatgc tgaccagttt tggggcatta acggtgcggt tt                      102

<210> SEQ ID NO 580
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 580
gcatctgaca tgttatcaaa tcgtgtccac ggatggcagc cgggtatctc stttttcttt   60
tttttttttt tttcaaaagt cccaaaagct cttttgagca gc                      102

<210> SEQ ID NO 581
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 581
aaaaggccgc ctgcctgttt cctgctgcac tcctctctca ggctctctgg sagaacatgt   60
ggacccgcca tcaccggcca gttttggcgg ccacgaccac at                      102

<210> SEQ ID NO 582
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 582
atcttcatca tcgaggggat cccgagcgtg gtgctgggcg tggtgacgta stttgcgctg   60
cccaacgatg ccgggacggc gtactttctg gacgacgcgg ag                      102

<210> SEQ ID NO 583
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 583
taaataggta aaggctatgc tagttaggaa tgtaataata ctagtaatta sgaagttcct   60
```

```
tttctcctta attagtagat ttaggctttt ctgctttata gt                      102
```

<210> SEQ ID NO 584
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 584

```
tcacggaaat gagacatgaa cccgcggccc aatagttggg gcgttgcaca sgcccttgtg   60
cgagcgaggg cttaattccc cgaagctgga ccacgtgcct tg                     102
```

<210> SEQ ID NO 585
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 585

```
tttaataaaa ttatttaacc tttattaaat aataaaatta tattatactc satcttaata   60
cttttaatta aatagttaat taaattaact ttatataaaa ct                     102
```

<210> SEQ ID NO 586
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 586

```
ggcaatcttt gcattgcctt gtgttttttt ttttttttttt tttttttttt sggtcagcaa   60
aggttgagaa catgggcagt cactggaaag ggcgcggggc ag                     102
```

<210> SEQ ID NO 587
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 587

```
tcttctccca tcgcgcctcg ccttcagcaa ccttgttgag atatgacgtc scaatgcccc   60
ggctctgccg cacctcacag caagacagtc gagccgcgca tc                     102
```

<210> SEQ ID NO 588
<211> LENGTH: 102
<212> TYPE: DNA

```
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 588
tgctggcatg ccgtcgatac atcgttaacg agggcaaaaa aaaaaaaaaa stttttccat    60
ctcacactcg gtgaaatgta aatatgtccc ctcacttgta at                      102

<210> SEQ ID NO 589
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 589
accgagcccg ctcttcccga agaagccctc aagctgatcg actgcggtga sgcggacaaa    60
ttcggcctgg ccaagcagtt ccagaatgtc gtttctacac ag                      102

<210> SEQ ID NO 590
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 590
catcagtatt ttcatgactg tcagagggcc accggggggg ggggggggggg sgtctttact    60 tacatccagt tggaaatgca aaaggcaata aaaatgccaa gg                      102

<210> SEQ ID NO 591
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 591
tttacgaata tcggggtcgg catcggcaaa ttgtcccaca gaaagacaaa sggtcgtgag    60
tgggccggcc gtggcaaagg tcaactgaaa gttgagcttc ag                      102

<210> SEQ ID NO 592
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18
```

<400> SEQUENCE: 592
tgtctcatca gcaaaaaaag aaaagaaaa aaaaaaaaaa aaaaaaaaaa saaaaaaaaa      60
aaaaaaaaaa aaaaggaaaa gggcctcgtt tcgtaattct ag                       102

<210> SEQ ID NO 593
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 593
agcgtccctg aaatatcaag gggactgaca gtgaaatcaa gacgacaaga saaaaaaaaa    60
aaaaaaaaaa agaaaagacc aagggaaaat gaaccaaatc aa                       102

<210> SEQ ID NO 594
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 594
tgtactccgt acacacggat taaagagcac cagatctgtg ctggtggtc sgccacatcc     60 ggcattggga cttgtaggct tattagcgct cgcatcccat ct                       102

<210> SEQ ID NO 595
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 595
cgaagaattg gggcatgtag atttataaaa taattcgggg ggggggggg sgggttgtac     60 aaagtgtctc tccatcgtga tatcaatatc ccaacgccca aa                       102

<210> SEQ ID NO 596
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 596
tttgagaaga agatgacgct gaacacaccc tggctggacg gatcggcgta sctgaagagg    60
ccgggacggg gcggtcggct ggcggccaag gcggtgccgg tg                       102

<210> SEQ ID NO 597
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 597
gagggtgctg ttgtacaacg tcggccaagt agagagagat gtgggatgta saaattactt    60
tcgtctggca gaggctggac gacggatgcg tcggtacaac at                       102

<210> SEQ ID NO 598
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 598
cctcgctgtt caaagggcac ttgttcgcac agttgaacgt tcaatgcccc sccaggagct    60
acgacccaaa catcacagct cagaaggacg aagtgttgtt tg                       102

<210> SEQ ID NO 599
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 599
ctgcgatgag ttttgcgcta ggggcataat gaaagactga gggagcgtac sgtgtggccg    60
agcgacagga ggagccatcc caccgcggtg actctgaggg at                       102

<210> SEQ ID NO 600
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 600
gccaggtata atatattagc cagcatctct tgtgtagaaa gaaccaaccc saaaaaaaa    60 aaaaaaaaaa aaaaaacact ccgaaaatca atcatgatga tt                       102

<210> SEQ ID NO 601
<211> LENGTH: 102
<212> TYPE: DNA
<213> ORGANISM: Artificial Sequence
<220> FEATURE:
<223> OTHER INFORMATION: Epichloe festucae -continued

```
<220> FEATURE:
<221> NAME/KEY: Variation
<222> LOCATION: (51)..(51)
<223> OTHER INFORMATION: S is G strain AR37 or C strain RGT18

<400> SEQUENCE: 601
gccagcaccg ttgggtccaa tcacagcaat acgagatccc aaagagcact sgaaagtgat    60
gtcggaaacc tggggcttgg aggtaccggg atactggaag ga                      102

<210> SEQ ID NO 602
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 602
tcgccgcagt tgaagaaggc gaacaacagg ccgtcatcgt catcctcccc stcggcgttg    60
ccacgcgccc gcgcccgcgt ccgcgcccgc tcgtacgcct cg                      102

<210> SEQ ID NO 603
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 603
ggcaaccatg acaccataaa cgcggtattt ttttttttttt ttttttttttt stttttttttt   60 tttttttttt tttttgcttt ttttgaatcc cccaacatgc cg                      102

<210> SEQ ID NO 604
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 604
attcttcttg agcaagcgtt tgatgggctg ggtgctcggt ctcctttcaa sgcgcgaatg    60
cctcacagtc gtgcattttta gattcaggat ttcttgggtc ga                     102

<210> SEQ ID NO 605
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 605
```

```
tttcggctga gacattggga aaaaaggaaa aaaggaaaaa aaaaaaaaag statggcttt       60
ggttctggtt cctgacgaaa gctgccaccc ccggcacggt tc                        102
```

<210> SEQ ID NO 606
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 606

```
aaagagacgt tgatgtggat aacccacgga tacggattcg cacttcccgt satggttcgt       60
gaagttttcg tcgcggatga agggtgcttt gcagttgaat gg                        102
```

<210> SEQ ID NO 607
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 607

```
tctcgcagtg gagatcgccc gcgcaagtat gtgcgcgtct gaaatatgta saggatgctg       60
aggcttgttt cctgggcgaa gaagacgaag agctggacac ga                        102
```

<210> SEQ ID NO 608
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 608

```
ttcaggtgga cacgcagcgc aatattgtct ttgcaaggct gggggctaag sactgtgagt       60
cgtcgcgccc gacgtacgca atgcccaaca catggacgca ca                        102
```

<210> SEQ ID NO 609
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 609

```
agcagcggca ggctcagctg cgagagggtg aaggcgcggt gcaggttcag sgtgaggagc       60
ttcgtccacg ccgcgtcggg gtgctcgtcg aaggggcgc cc                         102
```

<210> SEQ ID NO 610
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 610
ctgccaaacg acacggttgt ctgtgtaggt tctgcttttt tttttgggg sttttttttc    60 cctacgaatg agcaaggatt cgggaagcat gcctggtgct aa                    102

<210> SEQ ID NO 611
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 611
tcgtgggtgc cgaatgaaaa aaaaaaaata gaaatttgaa agcgttaaat sgtgccagct    60
caattgagag gtaccgccga ccagctccca tgtgccatga gg                    102

<210> SEQ ID NO 612
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 612
cgacggattg gatgcatatt tgtgtgcttg gggaggggcg ggggggggg stgaatgcgc    60 ccccgggaag cattaatatc aggtttctag acaattttg tt                     102

<210> SEQ ID NO 613
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 613
cctgcatctg tcccgggcag tccgtgaggg ctacgaaaaa aaaaaaaaaa saaaaaaaaa    60
agtcgccacc accaccacca ccactcaaca tatcgtttta tt                    102

<210> SEQ ID NO 614
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is C strain AR37 or T strain RGT18

<400> SEQUENCE: 614
ctctcgcccg ttagcccggc cgccagtgcc attttgccg tttgctgcaa sagctgcgag    60
aagaacatcc ccgatgctca ttatcactgc tctacctgcg ac    102

<210> SEQ ID NO 615
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 615
tcctatattc gtcgctggtt cgacgaccgt gacttcgtct cagtgcaaac scctatgctt    60
aatccaattg ctggtggtgc cactgccaag cccttcgtta ct    102

<210> SEQ ID NO 616
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 616
gcgttggcag tcggtcccct catgcatctg aacggggaac agcacgatcc sggaccagcg    60
agcccaactg cgccaacggc cggacgccaa tgaagtcatc ct    102

<210> SEQ ID NO 617
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 617
ccgaactatg ttatgaaaaa gaagaggccg agaactcgag aacttcttca sagctaccaa    60
gagattgttt gggctacatg tgttttttc ccttccgacc tt    102

<210> SEQ ID NO 618
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 618
cgtttccagt ttccctactc tgtattattt atctgctgcg tcgactcttt scccccccc    60 tatccatgtt ctttcatgga accaaggagc tcttttcctt tt    102

<210> SEQ ID NO 619
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 619
cgtccaatta ggatagcctt gggctcatcc aggctactgg aaggagcacc sccgtctttg        60
ctctgatttt ccatgatgga tgcaatcgta gcactcaagt cg                          102

<210> SEQ ID NO 620
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 620
attctaaata attagctaaa agagcaggtt attaagtaac aagatgctat saatctatta       60
ttacttataa aagctagagg ctctaactac agctattaat aa                          102

<210> SEQ ID NO 621
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 621
ctgttgggag acggtcatgc tgcctgggga agaggtggcg cgacgcggga sttgggcggc       60
gttgaggtcg acttggttct ttggtgcgac ttgttggacc gg                          102

<210> SEQ ID NO 622
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 622
agggagaaat cgtgtccctc cgctgtttgt cggagaggaa ttgaaatgca scctccatta       60
gttctgcgac gaaagcctcg tcatctcgga gaagttgtcg aa                          102

<210> SEQ ID NO 623
<211> LENGTH: 102
<212> TYPE: DNA
<213> ORGANISM: Artificial Sequence
<220> FEATURE:

<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 623
ggacgactcg acttcctcta gtgtgtattc gcactacgtg tcctccgtct sacaatcggc    60
ggggctcgac acgaatcgcg tgcacgtact ccgcatgcag cg                      102

<210> SEQ ID NO 624
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 624
tatagttata ataattccct tacttcctta ttatatatat attatatata statattata    60
agtgtattta tactaatata ttatagggac tagtatatat ag                      102

<210> SEQ ID NO 625
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 625
gactgaccga cttgtcttga gaatgcggca ccatcccatc aatgccccccc scccccccccc    60 cctcttgaga atgcggcacc atcccatcaa tgccccccctc cc                     102

<210> SEQ ID NO 626
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 626
gccctccctc acgggaccgg cctggcacaa tttgggggggg gggggggggg sgcttgttcg    60
ttgactcttc agatgttttc gatgtctttt taactctcgc gc                      102

<210> SEQ ID NO 627
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 627
aagactatcg cagtcgctac tagatagata ctagctaggg gcaggtgcgt saaggtttta    60
atctctaacc ttacactaat aatatgcgta gtctttaata aa    102

<210> SEQ ID NO 628
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 628 ctgggggat gatgagaggg acatactcgt cttggtgtca ccagattgca sgatacaact    60
tgtgcacagg ctcgcgacgc gagccacgtc gaagctccga tt    102

<210> SEQ ID NO 629
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 629
gctccagcag caggcgccta tgcaatttga caaaaaaaaa aaaaaaaaaa sagtccagcg    60
ttagtataat cattgatcat tcagtttgtt ccgtatcctt gg    102

<210> SEQ ID NO 630
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 630
acttgcaaca gcacttcctt tcgctgtttg cataccagtc ctttcccttc scgcttcttt    60
gaaagaccgc gtgaacaact ctccttgacg gccgtgccga tt    102

<210> SEQ ID NO 631
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 631
actcgttatc caagtcgatg ggtttgcgtc ctttttttt ttttttttt sttttttttcc    60 cctcttctaa tatatttctt ttttttttt tttttttct tt    102

<210> SEQ ID NO 632

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 632
ctatcagaga cccataaaag acccactttt ttatatttac tctataaaat saaaatagta    60
tacctatagc tttaaaatta tataaatcta gctaatttat ag                      102

<210> SEQ ID NO 633
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 633
ccgcatcgct ggcctggacg ctgtaagagg tcgtgtgaaa aggggtctc stgtattgtt    60 gttgttccat gccgcagaag ttggagatgc acacaatttg cc                     102

<210> SEQ ID NO 634
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 634
aaagaagaag aagaagaaga agcaaaaaaa aaaaaccaaa aaaaaaaaaa saagttctgt    60
acaggtgcag taagaagaga gggtaagctg catatgtgtc ta                     102

<210> SEQ ID NO 635
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 635
ggactgcctg cgagccgaag agttgttgcg cgctgcgaac agggcccagt staggtcgaa    60
tcgaggcggg atcggtggtc ttggagggag acgctgatgc cg                     102

<210> SEQ ID NO 636
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

```
<222> LOCATION: (51)..(51)
<223> OTHER INFORMATION: S is C strain AR37 or T strain RGT18

<400> SEQUENCE: 636
gaaatgtgtc tgacgacgca acatgtgcgt catcgtcaaa aaccagattt saggatagct      60
agtagagtcg aattctaagc aacattgcaa agaagttcta gt                        102

<210> SEQ ID NO 637
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 637
attgctgctg aactccgtcc attgatcgtg gtggaattag agtgctccca scgttgcgag      60
aaacggccag tcgagcctct cgagggcgat gatgccggtg tg                        102

<210> SEQ ID NO 638
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 638
ctactaatcc gtacggagca tagtaatgac tcctgcagga gctgaggcag stgcggctat      60
aggcatatta ctggatggat tggacttgcc ataatatgtc aa                        102

<210> SEQ ID NO 639
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 639
cttgcttatc tgctgccttc ttggctgcct ttgcggcttt gctcccacct scatcgtcgt      60
cgtcttcttc gccgtctacc tccacgacat catcgtcaat gt                        102

<210> SEQ ID NO 640
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 640
aatatataaa aatacacatg tcccccggct caactcgtcg acttctctca stcaatcgac      60
```

-continued caaaccaacc aaccaaccaa ccaaccaacc gtaacacaca gc                            102

<210> SEQ ID NO 641
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 641
gacgagcttt ttgacgccgt gtccaccacg agcccatcta cgttctgtaa sgcattcttc         60
ctgcttgcgg ccctgggtgt tctgtcgctg aatgtcctcc ct                            102

<210> SEQ ID NO 642
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 642
gctctgcttc gtccttctcc cactcgtcgt tgactggaag ctgaggtctt scgcgctctt         60
tccccttgcc gctgcgctgc tgaccccga ctcctctctc tt                             102

<210> SEQ ID NO 643
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 643
agatgatctc agaagtggtg tccctatagg aacggaaggg tttgtgatcg scagcgtagt         60
agagggtgtc gctccttttg ggtgtgtacc ttggaggagg ag                            102

<210> SEQ ID NO 644
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 644
ttgttgaggg tggctttgtc gccggcggca aaggcctcga gcatctcgcg stacatggct         60
tttgcggtgg gcgcaatctt ggccctgcgg gccttccatt tc                            102

<210> SEQ ID NO 645
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 645
tgtgtactcg ccatttggag aaccaacaaa aaaaaaaaaa aaaaaaaaaa statgtatag      60
acacaacagc gcctcgacgg agaatacatc tactgaaccg tc                       102

<210> SEQ ID NO 646
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 646
gatgccaagg ccacacgaga gcgtccaccg cccaaaaaaa aaaaaaaaaa sgtcatgagg      60
cgaagcatcc cgccgagtaa gataatcggg catggaatgg ga                       102

<210> SEQ ID NO 647
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 647
ttcgtgaacg tggtgttggt actccaaaaa aaaaaaaaaa aaaaaaaaaa sactatgatg      60
ctaattgaaa catgaagaag ttgtagcgac caaatgtcgc cc                       102

<210> SEQ ID NO 648
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 648
cgctccgtaa acggagaagc gacggctacc ccttcacact ccgtcggtat sgtgagctcc      60
ataatattaa tcatcaagtt tttgaccgac ttctaataag tc                       102

<210> SEQ ID NO 649
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

-continued

<400> SEQUENCE: 649
gagtaaacgc aagcacgagg atgacgattt tgagggcact cccgtttggg sgctctatgt    60
agcctcaatg gcactcgttc tacttggtgg tgcttttgct gg    102

<210> SEQ ID NO 650
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 650
gggttgcaga cccccgttgt tggatcattt gttcttttt ctttttttt sttttttttt    60 tttttttgcc gttttttttt ttcttttttt tttttttgc cg    102

<210> SEQ ID NO 651
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 651
gtcgaggtgg cggtcgatgg cgtcgagtgc acagagattg tcctgtccaa scctcacaag    60
tactactctc tgattttggt aagtttctca acggtcccca ac    102

<210> SEQ ID NO 652
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 652
tgtctgtccc gaccgtcctg tacggagtaa actacggtcc gtatcaagtc scctcctcta    60
gtccgtaggc tctgggctc tcatctacag cgctctcgga ga    102

<210> SEQ ID NO 653
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 653
tagaccgtcc tttgcatcca gcagcagcag gacgaagggt ggcggcaaag stcatggtaa    60
gatgaccatc aacaagggca agggcaaggg caagggcaag gg    102

-continued

```
<210> SEQ ID NO 654
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 654
tcttgagaaa aggacggtct ggtctccttt tggggcgta tcaggtctcg stcgatcctg      60
tcgcggtcgt cgcgaggttc gcgccgaatg tctgcttctg gt                       102

<210> SEQ ID NO 655
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 655
cgttgcgaag ctcttggaga cgagtttaga caggactgtg cggcatgagt scttgcaaga    60
acttgcattc agctatcgac gccacaggct gaagctgaac ca                       102

<210> SEQ ID NO 656
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 656
gaactggttg cctggtttca tgatgtgcca gccaatgagt gggtatggag saacattggc    60
taatatacgc ttgcaggtta aatacaaaat tagtatcaag gg                       102

<210> SEQ ID NO 657
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 657
tcaaggttgg gtcatgtcga tgcgacgagc gaaacatgaa aaattgatac sccccccca     60 aaaccgactg gtgcccgcca agtcgatgtg gaatacgctt gt                       102

<210> SEQ ID NO 658
<211> LENGTH: 102
<212> TYPE: DNA
<213> ORGANISM: Artificial Sequence
<220> FEATURE:
<223> OTHER INFORMATION: Epichloe festucae
<220> FEATURE:
```

```
<221> NAME/KEY: Variation
<222> LOCATION: (51)..(51)
<223> OTHER INFORMATION: S is A strain AR37 or G strain RGT18

<400> SEQUENCE: 658
gttgctacat cagctatacg tccacgtaga gcggacacgg atcaagattt stcgcgctgg    60
aagagatgca ttcctatctt tatgaatcca tcgccagtat cc                      102

<210> SEQ ID NO 659
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 659
ggaggggggg ggcaagccca gaccccctca agcgcgcccg acttctagaa saagtctgca    60
gctgattgtg tgtgggcttc atcatattag tttcagttac ta                      102

<210> SEQ ID NO 660
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 660
gtctagcggc cttttgcgcc cctcgtgggc gaaatggggc gaatgggcga stggggcgag    60
tggggcgagt ggggcgagtg gggcgagtgg atcccccctga tc                     102

<210> SEQ ID NO 661
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 661
gtgattttaa tagataattt ttctttaatt tacttagcta ggtaaagaat saatctagtt    60
atagtctaac tatttctatc taggatagtt atcttttaag gc                      102

<210> SEQ ID NO 662
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 662
tctgcatctt ttttgcgtcc tcgtgcaggg aaccttgtgg gtattttttt sttttggtt    60
```
tctgccagat gcggttggaa atttgaaggc tcaggttggg gt                               102

<210> SEQ ID NO 663
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 663
tccaagaggg gctgagagca gacttggtcc tggtggaggg tgacccgttg satgacattc          60
gggacactct aaacctgaga ggcgtgtgga agaagggcat tc                            102

<210> SEQ ID NO 664
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 664
gaccattgag cattagtaac aggagtagat gtggttgtct tttgtcacaa sctgctctga          60
gtgagacgtg gcaccgactg ctatcagccg atggtgaagt cg                            102

<210> SEQ ID NO 665
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 665
gcccgaaacg tcgagaaggc tggccttatc gtaagaccat tgaaaaaaca scagtctata          60
caagtttttt ggtactggtc gacaaatgtt tgctgacaag ag                            102

<210> SEQ ID NO 666
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 666
cgcaggtctc gagctgcctc tcgacgaaga ctcgttgttg tgtcggtgtg scgcgcgtgg          60
ctgtggggag atttctgtgg gcgtgtcgga atcggggtcg ac                            102

<210> SEQ ID NO 667
<211> LENGTH: 102
<212> TYPE: DNA

```
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 667
gaacaactgt ggaaacaaaa catgcatctt ctagctttga aagcaaaggc saatctgtac    60
acgtcgtggg gggaaatcgc tattcgattt caaacatctc gt                       102

<210> SEQ ID NO 668
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 668
tttgtcttta tcacgatccc ctcctcccct tacggagtac accccccccc sgcgattccc    60
caaccgcaat actgcccccct cgctcactcg tgcggaaagg aa                      102

<210> SEQ ID NO 669
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 669
tttgtggaat ggaaaaaaag aataaaaaag aacgctttat attcaatcgc saaggactca    60
caatttggag tgaagacgct attaacagaa ctgacttcca aa                       102

<210> SEQ ID NO 670
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 670
cgacctgcgc agggacgagc ggcccgagct gggctatcag gtcggcgtga sgctcgaggg    60
gaccgagagg cccaggtgcg ccgtcgacga gccctgcctg ga                       102

<210> SEQ ID NO 671
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18
```

<400> SEQUENCE: 671
gagagaaagc atagaagtaa actctaggag tagctttagt ataagggata sgctagttta    60
tcttactaat ccctttact aatctaggat agcttactat ct    102

<210> SEQ ID NO 672
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 672
ggtcctggtg cgcatggccc cttgtatctt cagcacaaac gggtcccgta stactacgca    60
ccacaacacc gaccgcttcg tgaagaatag caacgcaatg gg    102

<210> SEQ ID NO 673
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 673
cgaggcccca gccggatgag gaagcaacaa ctctctctgg acttttttc sttcgatggt    60 ggtcgtgaga tgtaccgagt accgagtaat gtatagtgtg tt    102

<210> SEQ ID NO 674
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 674
aaaggcgccg agagtcattg cgccgaacgt gacagtttca tgttctcaac stccgagacg    60
agtctgccag aaatcagaat agacgagagt agctgtcctg gc    102

<210> SEQ ID NO 675
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 675
atcaaattgg ctcgcgagtc tcaggttcct gttccccgga tagagacgct statgccatt    60
ctccataatc tcaacattgt caaccgttcc aggcctaagc ct    102

```
<210> SEQ ID NO 676
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 676
aggttgaatc ttttggttta atagcttacc cttataccct taggttctaa sattaatgct      60
agctcttata ggtcttctag tgtactagtc ctaggtttaa tt                        102

<210> SEQ ID NO 677
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 677
tgctcacatg gacaacccaa ccttctctag tccaacgacg atgtcttcaa saccaaccac      60
cccctcttcc actggatgtt ccgcgcttcc cgcaactggg gc                        102

<210> SEQ ID NO 678
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 678
ctctgttctt ttctgatgcc tcctggtcgt ccgacgtctc actggaagct sactcgttag      60
tgacagccat cacatgctct tcgggccgcc acccatcacc ac                        102

<210> SEQ ID NO 679
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 679
ccgccgcggg gcagagctct acggagtatt acagcctgtc actcagtggt scttgacgct      60
ccgtatactg acattgaacg aggcgcaggg gcgggcgcct tc                        102

<210> SEQ ID NO 680
<211> LENGTH: 102
<212> TYPE: DNA
<213> ORGANISM: Artificial Sequence
<220> FEATURE:
<223> OTHER INFORMATION: Epichloe festucae
```

<220> FEATURE:
<221> NAME/KEY: Variation
<222> LOCATION: (51)..(51)
<223> OTHER INFORMATION: S is A strain AR37 or G strain RGT18

<400> SEQUENCE: 680
ttagggtcat gaaagcatgg agatgtatgg agcaaaggct tgtgcagcac saacaaatgt    60
gtcgtgtaat tctctgccaa cccaggagct gatgttttgg cg    102

<210> SEQ ID NO 681
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 681
ctcgcagttt gcatgcgtac cggcaagatt caaccccata gttgtccgca scatggccga    60
gtgtgaaatt gctgaaatca ccttgcaagt catagcagcg ga    102

<210> SEQ ID NO 682
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 682
aacatccagc tgtcgactgc catggcgagc gacatatctg atgagtcttc scgaggctct    60
accatggcca taatcggagc atgcttctcc attgccttta cc    102

<210> SEQ ID NO 683
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 683
tagtaaaata gcaaaaaact aaatagtttt ataataggga gcgctagtaa sactagtttt    60
acctagccta aataaaacac tacctatatt attagataaa tt    102

<210> SEQ ID NO 684
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 684

```
acccagctga agagcgcgcg agccgaggcg cgagcctcat ttggccaagg sggcgaggtt      60
atgctggtgg aaaagtatat tgtacggcca cgtcacgtcg aa                        102
```

<210> SEQ ID NO 685
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 685

```
tctacacgac cacaatgtac tctgaaatgc catgtccaac acaccttttt stcgacatca      60
tccgaatcaa tcgtctcaga acccaagcga cggctggcgt gt                         102
```

<210> SEQ ID NO 686
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 686

```
tattactata gtaaataata aaaggtagga tttatataat tacttatata staaaggata      60
gtctatagtt aaaaaaggta aaaggaagct aaaagtttac tt                         102
```

<210> SEQ ID NO 687
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 687

```
tacaatagca aagcttgatt ttcaactcgg ggggcggttt ttttcttctt stttttttt       60 ttgggggggg ggggcatcgc atagcttgtg tagagggcat gg                         102
```

<210> SEQ ID NO 688
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 688

```
agcaggagga gcaggaggag caggctggtt gtcaggagga ggagcaggct sgttgtcagg      60
aggaggagca ggctggttgt caggagtagg agcaggcttg tt                         102
```

<210> SEQ ID NO 689
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 689
gaaggcgcta gacggggcgt tgaatcaagc acgacagccg cgggacatgg sacttgggac    60
tggaggcgca cgccccccccc ccggccttgg atatgtggtc ca                     102

<210> SEQ ID NO 690
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 690
tgtttcaagg ttttgtcatg agagccgtca aagagaaggg ccaatatgac saaaaaaaaa    60
aaaaaaaaag ggatgaatct gcatatattg gtcaaggagt cg                     102

<210> SEQ ID NO 691
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 691
cactagtctg tttttggctg tggcttccga gagagcggtt gggggggggg stccattctc    60
ttcgcttgca caccggtgac acacgtgaca agcagcccta aa                     102

<210> SEQ ID NO 692
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 692
agggccgtcc ttgggcttcc tggatgcagg ctcgctggct agaccgaggg sctctctcat    60
tttcttgcga gcaagctcct ttttggacaa ttttggtgca cc                     102

<210> SEQ ID NO 693
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

<223> OTHER INFORMATION: S is C strain AR37 or T strain RGT18

<400> SEQUENCE: 693

```
tctaattaaa tagttaataa ttagtaaata agtaagtaag aaaaatctaa staaaaagta    60
ataatcctta aggaagaaga aattaaactc ttaccttaga ga                      102
```

<210> SEQ ID NO 694
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 694

```
tccgaggcct tttgtgattt ggccgaatac gagaagtccc gaagagctgg stccatgccc    60
aaagccatgc ccaacaagcc atgccaaacg ccaattttgg ca                      102
```

<210> SEQ ID NO 695
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 695

```
gcgtctcttg acatgtcgac aagacgaagc tggttgcgat gagaacatgt stacaatgtc    60
caatcatctg agcaaaatga tcaaaaacgc catcccagtg tg                      102
```

<210> SEQ ID NO 696
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 696

```
tgctatgata ccgtcttttg cagccaatac tgtcacgaca ttgcccagga scgctaccac    60
ccatccgtgt gcgagaagga cgtggatgct attgccaagg ac                      102
```

<210> SEQ ID NO 697
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 697

```
tttttttcc ccctttcctc aacgacagcc actttttttt tttttttttt sccccttttcc    60
tcaacgacag ccacaaagcg ccaacagccg agggctcgct aa                      102
```

<210> SEQ ID NO 698
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 698
tacatgtttg catgccaagc tagttagtct catttgcatg tgtctcagcc stttttttt    60 tttttttttt tttaacttgt gttgattctg cgaagccgaa tt                      102

<210> SEQ ID NO 699
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 699
taatttacga gcgcgagtca ccggagataa tggtgcccaa agtccaaagt sggcaactga    60
ttgcgccggt tgatcaatct ccacgtgaac attctgccat tg                      102

<210> SEQ ID NO 700
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 700
ttcttccgac attgtctgat gaataacggc cgtctccaac atgtcccatg sctcagactg    60
cgaatccaag atcgccagag actgtgaata taaggtttcc tg                      102

<210> SEQ ID NO 701
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 701
tttggacagt gccatgacga tggactcacc ctctctgaag gcaatcaagg sgaagaagcg    60
aaaacgcgag agtcttaaca ttcggcccga gagggagcag at                      102

<210> SEQ ID NO 702
<211> LENGTH: 102
<212> TYPE: DNA
<213> ORGANISM: Artificial Sequence
<220> FEATURE:

```
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 702
ccctagattt attaaattat tttaagtact taatactata ggtaaataag satataaact    60
tatattacct aaaaaatata gttaactata taatatattt ta                     102

<210> SEQ ID NO 703
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 703
aaggcctgga gctggagcca tgattgggca gtgcacgcgt ggcctgaatt stttaccctt    60
gtgccccaac tgcccctcct tcagagcagg aatgaagggg cc                     102

<210> SEQ ID NO 704
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 704
cttgaccttc aaagacgtca ttagccgact tggccgcggg ggggggggggg sggcgcaggc    60 acaagacaag aaaacaagcg aggacttaca ggctccaaag gc                     102

<210> SEQ ID NO 705
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or G strain RGT18

<400> SEQUENCE: 705
aagtcaatag aggagtttga cagcgagggc gtcggtttga tcggaaagcg sccccttca    60 cagcagccag tcatggtcaa ggcaaagatg tggcagagat aa                     102

<210> SEQ ID NO 706
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 706
```

```
tctcccccg gagtacacga tgcgtcccat ccggatggag gttcacgata saatggacct    60
ccgaggcgag atccctgaga gaatatgtct gttggcaagt ga                     102

<210> SEQ ID NO 707
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 707
agagaaagca ggacgaggaa gaggaagagc tcgtttctct tcccgaggaa satgatggcg    60
aggaggaaga agagtgagtg accagcgcca acgaacccaa gc                     102

<210> SEQ ID NO 708
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 708
aattgactac tggaaagacc atgcacaaat aattcactca tatggcccgt stgaatgcac    60
tcccatatct atcagtcata tcctggatcc cgatcgatct cg                     102

<210> SEQ ID NO 709
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 709
gatggcctaa ccagaagggg catcagcaaa aaaaaaaaaa aaaaaaaaaa sagttcaata    60
atgtaggaga cttttttttgc ggctcccaat tcatacgacg ta                    102

<210> SEQ ID NO 710
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 710
acacttagaa gtgggcaggg gttattatat tggataataa ggcagtgagg saggtgccta    60
ttaaacgctt tataaatagc tattagtaag gatagttttt at                     102

<210> SEQ ID NO 711
```

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 711
acgaactcac gagagatagc cttacaatcc tttcagagat ggtgtaccaa statgaccag      60
cactatttca gagtcaagcg cagtaatatg ccctgcgcga tc                        102

<210> SEQ ID NO 712
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 712
atgacgcgtg gagatgtgtc gagattttca acccaagacc aaaagtcctt stgtgcacgt     60
tttgcattgg taaaatccgt gctgtttgcc aaagggcata ca                        102

<210> SEQ ID NO 713
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 713
tccaaggcct tgatagtcta gaaacaacag acagctcgtg cgaagcggta sgattccatc     60
gttgaccacg ttggagtatg ttgtgcggtt tctgaatttc tt                        102

<210> SEQ ID NO 714
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 714
catcgcgggc atcaccggcc cacacttgat tgtcgttccc aagtcaacat sggacaattg     60
gaagcgagag ttcgccaggt ggacgccaga ggtcaacgtt tt                        102

<210> SEQ ID NO 715
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

```
<222> LOCATION: (51)..(51)
<223> OTHER INFORMATION: S is A strain AR37 or G strain RGT18

<400> SEQUENCE: 715
aaatctcgga tgaggacccg agaaatcttg agcaagagct ggtctcttct sctgggcaag    60
ctgtaaatga acaaaagttg gtcgtgttga cttccaagaa at                      102

<210> SEQ ID NO 716
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 716
ggcccgtttg cctgaatcag gggcatggac tttctgtaaa cctgccaata sgacggctgt    60
ggttggttgt aattgtatta cataataata aacgaaagca ag                      102

<210> SEQ ID NO 717
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 717
gcggttacag ctgcgagagg atggggcgaa ccagggacgg caacggcgtt stgaaagctg    60
gttggctggc aggggaccaa gttaagcgcc cgggcgagca gg                      102

<210> SEQ ID NO 718
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 718
atttttgagt tgcaaatatt cgtcacttgg tccagcctct tgtcttttta scacgtagga    60
gagcagtagc gatagctagg tgggacgagg actggagaag ag                      102

<210> SEQ ID NO 719
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 719
ggcatgtgcc gatcaataac actccacaaa ggccatgagc gttgcggaag sacgcagagc    60
```

-continued

```
tatttatcta tgtgccaaac tggctcttca cccggctcgc tt                         102
```

<210> SEQ ID NO 720
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 720

```
cgccaattgt ttccctgttg gtctgcggag attcagtcct ccgagcggtg sttttttcctc     60 ttcatggcat tccgcagcga ggggatgtta cgagagcagc ga                         102
```

<210> SEQ ID NO 721
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 721

```
ttaatagttt tattactata agtaaagtaa tataacccttt aaaaatatta stacttaaaa     60
ccctaaaaaa agtaagctta aataccttaa gattttatta ac                         102
```

<210> SEQ ID NO 722
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 722

```
tgtacgtctt gtacggacca acgataatcg tatgataatt attatataat saactttcaa     60
agaacacaaa acacttccta tgtagcaagc ttccggagat tc                         102
```

<210> SEQ ID NO 723
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 723

```
gcccctatc aaagctgatg ccgccccgca catgctccgt gccgccgggg saataggaaa       60
ataagccggc tcttcgtgcc ttttactcc gtaccttgtc cc                          102
```

<210> SEQ ID NO 724
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 724
ttcgactcgt ccgtgagggc gacgggagag aagacggcga ggttgccaga sgtgagtttg     60
actgaaagag gggggggggg ggggggttg cagttggtca gt                         102

<210> SEQ ID NO 725
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 725
ctaggttccc cgtcgtcggc gtccgcgacg gcctcgtctc cagcgtcgac scaacactct     60
cgggcagggc ggcgtaaaac gcattcaggc aattgattgt cc                        102

<210> SEQ ID NO 726
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 726
gtaccgtggg cacagtggtt cctgaggttt gaagtgaaga ggtcgagggg stgaccaagg     60
ttgagcctac agtagagatg ctgcttgtac tgtcactgct gc                        102

<210> SEQ ID NO 727
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 727
taacctcacc atccgagtcg cctcgtttga attccgagac gtggtcaact sgtgatctct     60
tgacacgatc caggtcggca tagaacctct tcgcaccggc ac                        102

<210> SEQ ID NO 728
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

-continued

<400> SEQUENCE: 728
gtcggcaact gccagctcct cgatggacag aatgaagcca cagtgttgac sgatacagga    60
agagctgcca gagactttgt ggacttcttt gctgctagct ta                      102

<210> SEQ ID NO 729
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 729
cctatctttA atctttatac tcctaatata atacctccct tatatataat saaccttaat    60
tataaaataa gctacttact tagggtatag ttactatatt aa                      102

<210> SEQ ID NO 730
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 730
agtcgtacca agatggcgag gtgttagagg ctttttttgta ttatgtgtct sctagaacgg   60
cgacgtcggc atgaagcgcg aataggagca cacggcacga ct                      102

<210> SEQ ID NO 731
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 731
ggaaagaaaa agaaaaaaaa aaaaaaataa gttgtgtggg gaaagaaaaa saaaaaaaaa    60
aaaaaagcac agcctaagca caaaatgtcc acatgcttcc tt                      102

<210> SEQ ID NO 732
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 732
gcaccattgg gcaggataac tctgctggcg tacaacgtgt cgacactgta sgcttacagt    60
ttgagtcaga aggtagatga tgatgacgat gacgaaggcg ga                      102

```
<210> SEQ ID NO 733
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 733 caccccctctc ctcttccaat cgccattcgc caaatcgcca agaattgaaa staaaaaaaa      60
aaaaaaaaaa aaggttgaag ctttactaac cgctgtgtgc ct                        102

<210> SEQ ID NO 734
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 734
ctttacgagc tcctcggtcc cccgactctc cgtggccact tttgcgcatc sacaccacga      60
cgagatcatg gcgactccag acgccaaggc gtctcgcgcc cc                        102

<210> SEQ ID NO 735
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 735
tggccctcct cgtccgggat cattggtggc ccgaatgagg tttgaggcga saagacggtg      60
ttataatgac gccttgtgca ttcgacggca tcttgttcag aa                        102

<210> SEQ ID NO 736
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 736
ctgtacaacg cggcgaggac aagaattttt gtggcatgtc ttgcgataaa sagacattca      60
agagatttat atcccgacat gggtatattt gccatgtgat gt                        102

<210> SEQ ID NO 737
<211> LENGTH: 102
<212> TYPE: DNA
<213> ORGANISM: Artificial Sequence
<220> FEATURE:
<223> OTHER INFORMATION: Epichloe festucae
<220> FEATURE:
```

<221> NAME/KEY: Variation
<222> LOCATION: (51)..(51)
<223> OTHER INFORMATION: S is T strain AR37 or A strain RGT18

<400> SEQUENCE: 737
agcttggcct cacttatcca attgtttctt cgcatttggc aacatactgt scgcgagttt    60
gagtgggtaa cttctggtat tgtccttgct acttatggat tt    102

<210> SEQ ID NO 738
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 738
ctcaaatgta cggatccgta gaacgtctgc ttgttggccg ttgtacgcct sccgttcctc    60
ttttttcttt tcttcttttc cctcaacttt tccgtgtgtg gg    102

<210> SEQ ID NO 739
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 739
agacctggta cacttgcatt agtgctgtac gcagactgca cggtccatat sgaaaaaaaa    60
aaaaaaaaaa aaaaaaaaaa ggccgtactc acgtttctga ag    102

<210> SEQ ID NO 740
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 740
gcaaaaatgg acaagaatcc ggattctctt ttttttttttt ttttttttttt sagagggtcc    60 gggtccccct ttggaatcgc ctcgaaacac caaaacacca ac    102

<210> SEQ ID NO 741
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 741
cttccccctt cttttcttc ttgcctcgcg gcgcgttccg ggtccacaca stcccgggga    60

```
agctgggaag ctgggaagct gggatctagg aagctaggaa gg                    102
```

<210> SEQ ID NO 742
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18

<400> SEQUENCE: 742

```
agacaccaac atgcgattct tcagcaactc agtggcttct gctactcttt sggccgctac   60
tctatctcaa gcgcaaatcc tcatcaatga gcaaagcttt gg                    102
```

<210> SEQ ID NO 743
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 743

```
atcagccagc gtgttgcccg cgtgttaacg gtcgctcaat cggccccccc scccccccaa   60
attggttgaa gacatgcact gatgacgagg cgctgcgggg ag                    102
```

<210> SEQ ID NO 744
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 744

```
gtcacatggc tctgctgcga aggacgtgtt ccatgctgat gatcgattag stgaaacttg   60
ttgcggtctt gacagctgca agggtcccgt ggagatgcca cg                    102
```

<210> SEQ ID NO 745
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or A strain RGT18

<400> SEQUENCE: 745

```
tcattgactg cctgtgagac gaagaccgat gtcggaaaag ccatcgagtc stgcacggac   60
gacatgctgt cgattcccga gaatcccgcg tttcgcaaaa gt                    102
```

<210> SEQ ID NO 746
<211> LENGTH: 102
<212> TYPE: DNA

```
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 746
cgtgcagctg gcatgcctaa tctggtattt gatcagctat tttcccatgg sgtccacggg        60
tcttcgcctg gcagcttcat ttggcgccag gcaagcagct tc                          102

<210> SEQ ID NO 747
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 747
ggaacgcaac cgtatacttg gcatgttggc gttctggaaa aaaaaaagaa saaaagaaga        60
aaagaaaaaa aaaccccccat ccgtggcaaa cggttggatg gt                         102

<210> SEQ ID NO 748
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 748
ctttgaaggc aatgccctca ttcgccgtct cgtccgcgtt ggtgtcctcg scgagtcccg        60
catgaagctc gattacgtgc ttgccctgaa gatcgaggat tt                         102

<210> SEQ ID NO 749
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 749
tgtggactat ccttggctga tgggtatttc gaagttggag gctacgcata stgtgagcgg        60
gatgcatgga gaagggtcca ggcccagtca tatgcagagc aa                         102

<210> SEQ ID NO 750
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or T strain RGT18
```

<400> SEQUENCE: 750
agcatcaggt ttccgagaga cgggtcgggc cccggggggg ggggggggggg sgggtcccta    60 atggatagat agaccaagac ttacggaggg agtggttcac gc    102

<210> SEQ ID NO 751
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 751
ggaccgcacc gtccgcctct ggaatcgtga caggggccac tcccgcgaca sataccacac    60
caagcgcatg cagcgcgtca tggcagccaa atggaccccc ga    102

<210> SEQ ID NO 752
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 752
cttcgctgct tcgcagaggt tgggaatctc gtttatgaaa ctattcagcc sctatcgcgg    60
accaagtatg atcaatgagt tcctcgatcc tcacggcgaa gg    102

<210> SEQ ID NO 753
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 753
aagtccaccg atgagtactc ggagatcgtc tacgagagaa aagcattctg saaccacccc    60
cacacccgta cgcaacaaag gtagccgaac tcctacgcca at    102

<210> SEQ ID NO 754
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 754
atattgccat tccagagcga gaattcgttc ttagacccttt atcgcagtaa scccaatctt    60
gcccaaacta aaggacttgt tgctattgac cacagtctca tt    102

<210> SEQ ID NO 755
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 755
atagcgacgt tggcgcctct gcagttgcgc ctggtcgtca tggacgcgac scgacttgga      60
cacggggccg gttttggtg ggtactgggt tgtccggcgc ta                         102

<210> SEQ ID NO 756
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 756
aaatttggca tctggagagt cttgacaccc gttttttttt tttttttttt stttcttttt      60
cttttttttt tttttttttt ttcttttcttt ttcttttggc ca                       102

<210> SEQ ID NO 757
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 757
atcgccgtaa tatcggtaaa tcaaatccat cgttgcgtgt ttccccgatg sggatatgaa      60
ggcagagcgc aaagctaaag cacatcgtcc ttttaaccaa tg                        102

<210> SEQ ID NO 758
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 758
ggataatctt gttgcctagc tgagagtaag aacggctttg gggacatcat scttcatatt      60
ggtcatggag catgcccctc tttatacctg gttgtgcgga tg                        102

<210> SEQ ID NO 759
<211> LENGTH: 102
<212> TYPE: DNA
<213> ORGANISM: Artificial Sequence
<220> FEATURE:
<223> OTHER INFORMATION: Epichloe festucae

```
<220> FEATURE:
<221> NAME/KEY: Variation
<222> LOCATION: (51)..(51)
<223> OTHER INFORMATION: S is C strain AR37 or G strain RGT18

<400> SEQUENCE: 759
cggtggagca acattcatcg acggcgggga aagagaaaca aagtctgtct sactctctct        60
agcaagctcc gagtccgagc tgaccagatg ctgccgactt ga                          102

<210> SEQ ID NO 760
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 760
ttattatctt atagagagtt ttatagctct cttataagat tattagtagc sctcctaaat        60
atatctttag tttaaccttt aaaatcttct ctaaagttct tc                          102

<210> SEQ ID NO 761
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 761
attaaaaaag aggtaaataa agacactata aggatagatt taataaagct saactaacta        60
gttctaggat aagtaattaa ggctattata agactataag aa                          102

<210> SEQ ID NO 762
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 762
ttatttaata gatatctata aattcctaag aaaagcctat aagacactaa staaagacta        60
gcttaactag tttaaactaa ttactataag taagattatt at                          102

<210> SEQ ID NO 763
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 763
``` gttataagggtatttatgctagataagttactaagctaaggctattaaatsttaagattt   60 attttatctaagggaaatagaatactactgctaataggttat   102

<210> SEQ ID NO 764
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 764 gtgtcatcatcttgcagttgttgtccctcgcacctggcactgcactgcacsgcacagcac   60 agcacagcacagcacagcacagcactgcactgcactgacttg   102

<210> SEQ ID NO 765
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 765 cactagtccctttataatttctattagtctttttaaagataactattctstaagtaaaa   60 cttctttaccttattatagttttctatagtcctttatact   102

<210> SEQ ID NO 766
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 766 taatactattattataaggactataattctctatagccttactacctttastgtaattt   60 tactagtctttatagtagtctttatatatttagttattactt   102

<210> SEQ ID NO 767
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 767 aaatatgccgtaaaaaaggcctaaccttattagttactataaaaactattscctaaaggc   60 ctaggttatattactaaataataaggaaaacatgcttagag   102

<210> SEQ ID NO 768
<211> LENGTH: 102

```
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 768
ttactttaaa gctaaaataa aaggttttta aagtaattta taactttagg satataaata      60
gtaagactat taaattaggt tatttatatt ataaatataga ag                       102

<210> SEQ ID NO 769
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 769
cttattttcc ttataaagct ttaatatagt aactacaccc taagtaagta scttatttta      60
taattaaggt taattatata taagggaggt attatattag ga                        102

<210> SEQ ID NO 770
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 770
tattaaagat aataaataag agtttaaagt taactataat agaaggtatt staaatatct      60 agttaaaataa aaaggctata atactttaga gaattcttag gt                       102

<210> SEQ ID NO 771
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 771
tagaagaaaa aaaatagata acctatatta attttttataa ttagttaaaa saaataaggt     60
acttaatact atagttctaa atagtctaac taaagggctt gt                        102

<210> SEQ ID NO 772
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
```

-continued

<223> OTHER INFORMATION: S is C strain AR37 or A strain RGT18

<400> SEQUENCE: 772
tattagtaat aagtaagaaa agtcttttta ttaataaggt attctagaat sttataagta    60 ctattttta ggagaatatt ttatattatt acttactaat aa    102

<210> SEQ ID NO 773
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 773
tctatctctt attctctttt tcctttactt agtaactata aggcttacct statctctta    60
ttctcttttt cctttactta gtaaagctat atatttacct ct    102

<210> SEQ ID NO 774
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or C strain RGT18

<400> SEQUENCE: 774
taaataggat taataaaata aagactttaa aacactatta tataaaaaca sgtgtataaa    60
tactatacta gataaagaaa ataaacttat ataaggaagt aa    102

<210> SEQ ID NO 775
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 775
ttgtagaatc ttgatgtgtt ctttgctgct gcgcgcgggg ggggggggg sgagattgcc    60 tctcgctggt tggaaaaccg tgatattgcc aagatgattg at    102

<210> SEQ ID NO 776
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 776
ttacttaaag gaaataatta ttctctaagt ctttatttaa attaataaaa sagcttatat    60
aagtatatat tacctttatt taaagttagt gctttactaa ta    102

<210> SEQ ID NO 777
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 777
agattataca aaagtcttat atttaacagc gattttctct ttaactagag sttatacaaa        60
agtcttatat atagcaaatt aaagctagaa gatagggctt tc                         102

<210> SEQ ID NO 778
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or C strain RGT18

<400> SEQUENCE: 778
aggctagtaa acactattta tatagtgtat ctagataata tccttatttt sttaaaaata        60
taaaagaagc atactatata tattaaggaa gttttagaat at                         102

<210> SEQ ID NO 779
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 779
gggctgtatg gatcatggta agcaacatct gctactcttc cctgtcttct stgcttcatc        60
tccttgaatt attgcgtgtg catttgcgtt tcttgagttt tt                         102

<210> SEQ ID NO 780
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 780
acgtgttgtt gcctctgtcc taagcgtccg cagttgaagc gcattgctga scgcagcctc        60
agcttcttgg attagtgctc gccgttacac tgtcttcgta tt                         102

<210> SEQ ID NO 781
<211> LENGTH: 102
<212> TYPE: DNA
<213> ORGANISM: Artificial Sequence
<220> FEATURE:

<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 781
tactatttta actacctttt attagtatat ataagggtac tataatccta sagtattagt    60
aaataaacct ttagtaaaag ttataaaatc ctaggaaaga ct    102

<210> SEQ ID NO 782
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 782
tcctagtatt attttttaaaa ataagttaaa cttattttt atagcttaat saagctatat    60
aaggtaatta aaataatact attaattatt tattaaaaga tt    102

<210> SEQ ID NO 783
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 783
tataagctat aggcagacag ggactttatt agaactaata aggataagta satatttatt    60
tactagaacc tatcctctaa agtctagtcc taggtggcta ct    102

<210> SEQ ID NO 784
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 784
ataagctaat tctagttaga cttatactac ctattatgcg ttagacttat sctacctatt    60
atatataaag caaaggcttt ttatagtatt tcacccttaa ac    102

<210> SEQ ID NO 785
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 785
tttatgccta gtgctacttt agtaatgtta ttattatctt aagagttata sgaagtatct    60
aatagtaata tactaataag tagctagcct agtaaccttc ta                       102

<210> SEQ ID NO 786
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 786
gggactattt aatctataaa gagattacct atagctagat tcttttaagg stctttatgc    60
atgcctaact ttagattttt aacttaaatg cctagcgcta ct                       102

<210> SEQ ID NO 787
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 787
acccttagga ttattatccc ctaggtcttt cttttacta gctttacctc sagtcttttt    60
acccttagta atttttctt taaatatatt accttagta tt                        102

<210> SEQ ID NO 788
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 788
ctatagtttg cgttaggact agtacctata gtaagggcct taatattaac sataatctta    60
taatactaca taatagctat ataccacacg ctttagctaa ta                       102

<210> SEQ ID NO 789
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 789
ttactaccta ggacttaatt atataatata tttaatatta ctagtcttaa sccttttaaa    60
ggggacctaa ctaatataaa agatatatcc ttactataag at                       102

<210> SEQ ID NO 790

```
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 790
aagaggaatc catagtgaag tgagtctagg tcttttttttc cgatttttttc sgattttttc      60 tgatttttttc cgatttcttt ctgatttttttc taatttttctg at                     102

<210> SEQ ID NO 791
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 791
aagaaaaaag atattaagat aaaaagactt ttaaaaagta taaaaaaaat sattctataa      60
actaaactaa gaattacttt attaaggtat ataatataaa ct                         102

<210> SEQ ID NO 792
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 792
aggatagatt taataaagct aaactaacta gtcctaggat aagtaattaa sgctattata      60
agactataag aagttaaata taataggaag taagtaaata ta                         102

<210> SEQ ID NO 793
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 793
cataactaag tgctagtaac ctagtactaa tattataagt atagccctaa statatatct      60
agatatatct atcttcactc taagatatat aagtaagtta aa                         102

<210> SEQ ID NO 794
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
```

```
<222> LOCATION: (51)..(51)
<223> OTHER INFORMATION: S is T strain AR37 or C strain RGT18

<400> SEQUENCE: 794
atgctatata ataaatagtt aatttactta tttctagtta actaaaagac sagatataag    60
taagttatct tattactaaa taaggaaggc ctaactattt at                      102

<210> SEQ ID NO 795
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 795
ctaataactc tatagattta ttataacctt agctaattct taatatctat stagaataac    60
ttattagtta ctacttacta ttattaaaga gtttagttta ta                      102

<210> SEQ ID NO 796
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 796
ctagtgtaaa ttaaggggga tatagtaaag gaagtaagat ataacctata sattagctcc    60
ttatataata tccttaggga gggaaatgga tttatagtta aa                      102

<210> SEQ ID NO 797
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 797
tatctatagt attaccctta tttaattagg tataactctt atttattagg sttaggttat    60
tatctaatat tactcttatt tattagggtt aggttattat ct                      102

<210> SEQ ID NO 798
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 798
gcccaacaag ctgattctcc catcgcccat tttttccgac tcgcccccccc sccccccacc   60
```

-continued gaaatttagc caaccgctaa aaagtgcggg ctcttgtctc aa      102

<210> SEQ ID NO 799
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 799 acttttttc ttagccttat agttagcttt aagttattaa atctcttaa staattattt      60 actttcttat agtattattt aagctattta aaaagattat aa      102

<210> SEQ ID NO 800
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or G strain RGT18

<400> SEQUENCE: 800
gcgaatacag gtagaatacc tttacattta gatcctagct ttaatataat sgaattaact      60
attaggttag cttatagtta ctaatttagc atagtaataa tc      102

<210> SEQ ID NO 801
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 801
actagtccct tattattagg ggtggctata ggtttataat agagttagtc sctaagacta      60
ctagtccctt attattaggg gtggctatag gaactataga gg      102

<210> SEQ ID NO 802
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 802
ttctctaatt tttactttaa gcttactctt agcttacttt ttcttacctc staattaatt      60
actaacctat accttttatc ttttcctttc tctttctctt ac      102

<210> SEQ ID NO 803
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 803
gccttaaata ctttcctatc ttcttaaaaa ctttattata ataaagttta saagctcttt    60
taacaaaaac cctaacttca ctatctaatc ttagttaaga ga                     102

<210> SEQ ID NO 804
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 804
ctataattct ttagtaactc tataagtgtt aggagcgcag aggtcagaga saggatgttt    60
attaaagcaa gtcttcagag aacctttagg ctatacgaat aa                     102

<210> SEQ ID NO 805
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 805
agagatccta aactagtgct aagaagctta ttacttctta aagattaata staagaatac    60
ttactattaa atctatatta aagagagtaa taagtaaaag ac                     102

<210> SEQ ID NO 806
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is G strain AR37 or A strain RGT18

<400> SEQUENCE: 806
attagtaatt ataagttaat ttccttaata ttctaacttt agccttttta sgttagagtt    60
agtaagttat tagtatttta ggttaggata tagctattaa ag                     102

<210> SEQ ID NO 807
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

```
<400> SEQUENCE: 807
actaaaaaag ccatgtttaa tttttatatt ctagggatag cttatagaac saaaatcact      60
agatatttca tagtaatagc agacgtaatg ctaaatctag ga                        102

<210> SEQ ID NO 808
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 808
atttctatga attattttat atttctataa attattatta ttacttattt saaaaaaact      60
ataaaaagaa ctactagtaa acttaatata agtagcttat ta                        102

<210> SEQ ID NO 809
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 809
aattataggt ctagtttaag gtctagctaa tcctagattt accttaagct stctaattta      60
tacctttatt tataagacct tttattttct ttaaaggtaa ta                        102

<210> SEQ ID NO 810
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is A strain AR37 or T strain RGT18

<400> SEQUENCE: 810
tattctagat taactaaaag actataacta ggtccttaag gaagcccttt sggtataacc      60
tataatctct agtgcttagc tttacttata gtataaatct ta                        102

<210> SEQ ID NO 811
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or G strain RGT18

<400> SEQUENCE: 811
tcgaattcat attacataaa tcactacgct tgtttatggg aagtaacagc stccgagatc      60
gttggtcact gggcttggga ctatcttgaa aagtcgcaca ac                        102
```

```
<210> SEQ ID NO 812
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 812
ttataactaa ttattaaggt aattctctat aagaataagt attttcttag satttagctt      60
atattaatta taaagaagct taagtatcct ttaggtataa ta                        102

<210> SEQ ID NO 813
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or A strain RGT18

<400> SEQUENCE: 813
tgttattact aatctagtac taaagtaaat aacttctagg ttatagggtt saattattaa      60
taatggcatt aatcttagta aggctctagc ctatgctaga ct                        102

<210> SEQ ID NO 814
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 814
agctatattc cataggaaac taagctaggt agcactctat agctatattc sataggaaac      60
taagctaggt agcactacta agtatatat aaataatatt ag                         102

<210> SEQ ID NO 815
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is C strain AR37 or T strain RGT18

<400> SEQUENCE: 815
gaacctatct tctataagct actagagggt ataaatatat aaggttatct stagaaaata     60
actagagtat tatataggct ataggaagct ccttaataat ag                        102

<210> SEQ ID NO 816
<211> LENGTH: 102
<212> TYPE: DNA
<213> ORGANISM: Artificial Sequence
<220> FEATURE:
<223> OTHER INFORMATION: Epichloe festucae
<220> FEATURE:
```

```
<221> NAME/KEY: Variation
<222> LOCATION: (51)..(51)
<223> OTHER INFORMATION: S is T strain AR37 or C strain RGT18

<400> SEQUENCE: 816
tttataagat taattaaaag cactttttac taagcctata tctaaccta sactatctta      60 ctcctaatag ctaagtaaag caagacctag caagcaccta ag                        102

<210> SEQ ID NO 817
<211> LENGTH: 102
<212> TYPE: DNA
<213> ORGANISM: Artificial Sequence
<220> FEATURE:
<223> OTHER INFORMATION: Epichloe festucae
<220> FEATURE:
<221> NAME/KEY: Variation
<222> LOCATION: (51)..(51)
<223> OTHER INFORMATION: S is T strain AR37 or C strain RGT18

<400> SEQUENCE: 817
gggtttatag cttcttagag ctttaggcat gcctaatttt ctagataatc sggatatttc     60
tagggcgcta ggggacgcta actaagctat tatcctaatg tt                        102
```

GRASS ENDOPHYTES

PRIORITY AND CROSS REFERENCE TO RELATED APPLICATIONS

This application is the U.S. National Stage Application under 35 U.S.C. § 371 of International Application No. PCT/EP2019/081536, filed Nov. 15, 2019, which claims the benefit of New Zealand Patent Application No. 748421, filed Nov. 15, 2018.

SEQUENCE LISTING IN ELECTRONIC FORMAT

The present application is being filed along with an Electronic Sequence Listing as an ASCII text file via EFS-Web. The Electronic Sequence Listing is provided as a file entitled JAM179001APCSEQLIST.txt, created and last saved on May 13, 2021, which is 297,440 bytes in size. The information in the Electronic Sequence Listing is incorporated herein by reference in its entirety.

TECHNICAL FIELD

The present invention relates to grass endophytes. In particular the present invention relates to fungal endophytes and combinations thereof and uses therefor. More particularly the present invention relates to endophytes which form symbiotic combinations with *Lolium multiflorum*, *Lolium× hybridum* and *Lolium perenne*, ryegrasses. The strains from the present invention are newly discovered distinct strains of *Epichloë festucae* var. *lolii*.

BACKGROUND ART

Over the last couple of decades, a number of fungal endophytes have been identified in the art as being useful for conferring agronomically useful benefits to artificially infected host grasses [1]. Non-limiting examples include: AR1, NEA2, NEA6, Edge or AR37.

Prior to the identification of specific fungal endophytes all pasture seed was sold and used with a "standard endophyte" or otherwise called "wild endophyte". This wild endophyte had an alkaloid profile which contained lolitrem, peramine and ergovaline. This alkaloid profile was known to confer insect resistance to *Lolium perenne* ryegrass but did unfortunately cause significant toxic effects in animals namely ryegrass staggers and/or heat stress [2, 3]. Hence, the focus on identifying specific endophytes which could confer ongoing specific insect resistance [4, 5, 6] and yet not cause or at least limit the toxic effects for animals.

The initial specific endophyte developed and released commercially by Agresearch was AR1 (an LpTG-1 strain in the taxonomic group *Epichloë festucae* var. *lolii* species [7]) which does not contain lolitrem (the toxin which causes ryegrass staggers) yet via the alkaloid peramine does confer resistance to one key insect Argentine Stem weevil.

Following on from this was the release of NEA type endophytes (other types of LpTG-1 strains [8]) which also don't contain the alkaloid lolitrem but do contain levels of ergovaline which are at levels that generally don't cause heat stress. The Edge endophyte is similar.

In 2004 a new endophyte called AR37 (another type of LpTG-1 strain [9]) was released which contained a different alkaloid called epoxy janthitrem which conferred resistance to a wider range of insects. However, under certain circumstances and in some animal classes, can cause ryegrass staggers.

The inventors have discovered RGT15 which is a new endophyte classified within the taxonomic group *Epichloë festucae* var. *lolii* species LpTG-1 which produces peramine and ergovaline. However, RGT15 has seasonal alkaloid levels which differ from any previous similar endophytes and the inventors believe these differences will confer different insect resistance levels to the ryegrass plant.

The Inventors have also discovered RGT18 which is another unique endophyte classified within the taxonomic group *Epichloë festucae* var. *lolii* species LpTG-3 which produces indole diterpenes called epoxy janthitrems I-IV which confer a wide insect resistance to ryegrass and have not demonstrated any animal side effects [10, 11].

In addition, to the above both these endophytes RGT15 and RGT18 have been shown to have an ideal symbiotic relationship and existence with the R2N™ proprietary and other ryegrass germplasm enabling them each to develop a long-term association which confers agronomically useful benefits for pastoral agriculture.

However, there still remains a need for new endophyte artificially infected grasses to have an alkaloid profile which does not include lolitrem compounds. Lolitrem B has been shown to cause toxicity in the form of *Lolium perenne* ryegrass staggers in cattle, sheep, deer and horses [2, 3]. Neither RGT15 or RGT18 contain any lolitrem alkaloid.

It is an object of at least one aspect of the present invention to provide a host-grass:endophyte symbiont with a favorable alkaloid profile at least compared to wild type grasses.

There also remains a need for persistent turf grasses to exhibit similar attributes. Persistent turf grasses can also contain higher levels of ergovaline and janthitrems as mechanisms to limit insect pressure and also to stop animal feeding e.g. birds.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DEFINITIONS

The term 'viability' as used herein refers to the ability to survive and/or withstand one or more biotic or abiotic stresses.

The term 'vigour' as used herein refers to active well-balanced growth.

The term 'favorable alkaloid profile' as used herein refers to the presence of an alkaloid, or mixture of alkaloids, produced by an introduced endophyte within at least one host grass at a level or levels which is/are sufficient to be beneficial to: the host grass(es) and/or animals grazing thereon.

The term 'exemplified' as used herein refers to the endophyte having a similar alkaloid profile to RGT15 and RGT18.

The term 'beneficial to the host grass' as used herein refers to at least one advantage or commercially useful difference conferred to the host grass by the endophyte(s) of the present invention that:
  is not present in the wild type host grass; and
  is equivalent, superior or different to that conferred by other commercially available 'host-grass:endophyte' symbiont cultivars.

For example, in some preferred embodiments a favorable alkaloid profile may result in:
  reduced toxicity to animals which graze on the 'host-grass:endophyte' symbiont cultivar; and/or
  an increased protection against, and/or ability to withstand, abiotic or biotic stresses at least better than wild type host grass.

Preferably, advantages and/or commercially useful differences which may be beneficial to the host grass may include—but should not be limited to—one or more of the following:
  providing increased grass persistence/vigour compared to the wild type host plant and/or other commercially available 'host-plant:endophyte' symbiont cultivars; and/or
  providing protection to biotic and abiotic stresses compared to the wild type host plant and/or other commercially available 'host-plant:endophyte' symbiont cultivars; and/or
  reducing toxicity to animals, and/or improved animal production, which graze on endophyte grasses of the present invention;
  providing a grass which can thrive in a present or future, ecological environment and/or commercial environment, in a manner which at least provides the public with a useful choice.

The term 'production zone' refers to any physically defined space, such as a parcel of land; a floor, or part thereof, of a building (which could be multi-storied); or a vehicle (including a trailer or carriage); in which plants can be grown.

The term 'isolated endophyte' as used refers to an endophyte removed from its original source and purified from some, most, or all, of the original additional components associated therewith. For example, if the endophyte removed from seeds or plant as found in nature, an isolated endophyte can be considered as an endophyte isolated away from the seeds or plant from which the endophyte was sourced and therefore existing in a purified form. An 'isolated endophyte' can therefore be used to inoculate other plants of interest different to that from that in which the endophyte was originally sourced.

SUMMARY OF THE INVENTION

According to a first aspect of the present invention there is provided a method of improving the viability, persistence and/or vigour of a host plant in the form of *Lolium multiflorum, Lolium xhybridum, Lolium perenne*, (host grass) which includes the step of:
  artificially inoculating the host grass with an LpTG-3 endophyte RGT18 strain; so the LpTG-3 endophyte RGT18 strain can:
  produce at least one alkaloid or combination of alkaloids that provide the host grass with a favorable alkaloid profile; and/or
  protect the plant from biotic stresses.

According to a second aspect there is provided a method substantially as described above wherein the alkaloid is at least one janthitrem epoxide compound.

According to a third aspect there is provided a method substantially as described above wherein the alkaloid is selected from any one of epoxy janthitrem I-IV; or a combination thereof.

According to a fourth aspect there is provided a method of improving the viability, persistence and/or vigour of a host grass in the form of *Lolium perenne, Lolium multiflorum Lolium×hybridum* host grass) which includes the step of:
  artificially inoculating the host grass with an LpTG-1 RGT15 endophyte strain; so the LpTG-1 RGT15 endophyte strain can:
  produce at least one alkaloid or combination of alkaloids that provide the plant with a favorable alkaloid profile; and/or
  protect the plant from biotic stresses.

According to a fifth aspect there is provided a method substantially as described above wherein the alkaloid is selected from a peramine and an ergovaline or a combination thereof.

According to a sixth aspect there is provided a method of improving the viability, persistence and/or vigour of host grasses in the form of *Lolium perenne, Lolium multiflorum, Lolium ×hybridum* comprising the steps of:
  a) inoculating a first host grass with RGT15 and
  b) inoculating a second host grass with RGT18;
  c) co-growing host grasses inoculated as per steps a) and b) or progeny thereof.

Preferably, the first and second host grasses may be selected from the same variety of ryegrass.

According to a seventh aspect there is provided a production zone which includes growing therein at least one host grass in the form of *Lolium perenne*, annual, *Lolium multiflorum, Lolium×hybridum* wherein said host grass(es) have been inoculated as per any one of the methods substantially as described above.

According to an eighth aspect there is provided a production zone substantially as described above wherein there is provided two host grasses a first grass inoculated and the second grass inoculated.

According to a ninth aspect there is provided a production zone substantially as described above wherein the two grasses are randomly interspersed within the production zone According to a $10^{th}$ aspect there is provided a production zone substantially as described above wherein the two grasses are grown in discrete regions within the production zone.

According to an $11^{th}$ aspect there is provided a production zone substantially as described above wherein the two grasses are each grown in a respective half of the production zone.

According to a 12th aspect there is provided an isolated endophyte of *Epichloë festucae* var. *lolii* species LpTG-1 or LpTG-3 selected from the group consisting of:
RGT15; or
RGT18;
wherein variations in the morphology and/or alkaloid profile over known LpTG-1 and LpTG-3 strains are as exemplified by RGT15 or RGT18 deposited on May 29, 2018 at National Measurement Institute, located at 1/153 BERTIE STREET, PORT MELBOURNE VICTORIA, AUSTRALIA, 3207, and accorded accession numbers V18/011210 and V18/011211, respectively.

According to a 13th aspect of the present invention there is provided a use of an isolated endophyte of *Epichloë festucae* var. *lolii* species LpTG-1 or LpTG-3 selected from the group consisting of:
RGT15; or
RGT18; or
a combination thereof;
to provide seasonal variation in the alkaloids produced by said endophyte(s) when present in a host grass.

According to a 14th aspect of the present invention there is provided a use of an isolated endophyte of *Epichloë festucae* var. *lolii*. species LpTG-1 or LpTG-3 selected from the group consisting of:
RGT15; or
RGT18; or
a combination thereof;
to accentuate the benefits of increased insect tolerance relative to known endophyte grasses and/or reducing or limiting the side effects of staggers on grazing animals, when present in a host grass.

According to a 15th aspect of the present invention there is provided an isolated endophyte of *Epichloë festucae* var. *lolii* species LpTG-3 RGT18 having a genome including the sequence of nucleic acids as shown in SEQ ID NOs. 1-817.

BRIEF DESCRIPTION OF THE DRAWINGS

Further aspects of the present invention will become apparent from the ensuing description which is given by way of example only and with reference to the accompanying drawings in which:

FIG. 6 shows the differences in the nucleotide sequences of the genotype of RGT18 compared to AR37;

DETAILED DESCRIPTION

Example 1

SSR Genotyping (B Loci Methods)

Figure 1:
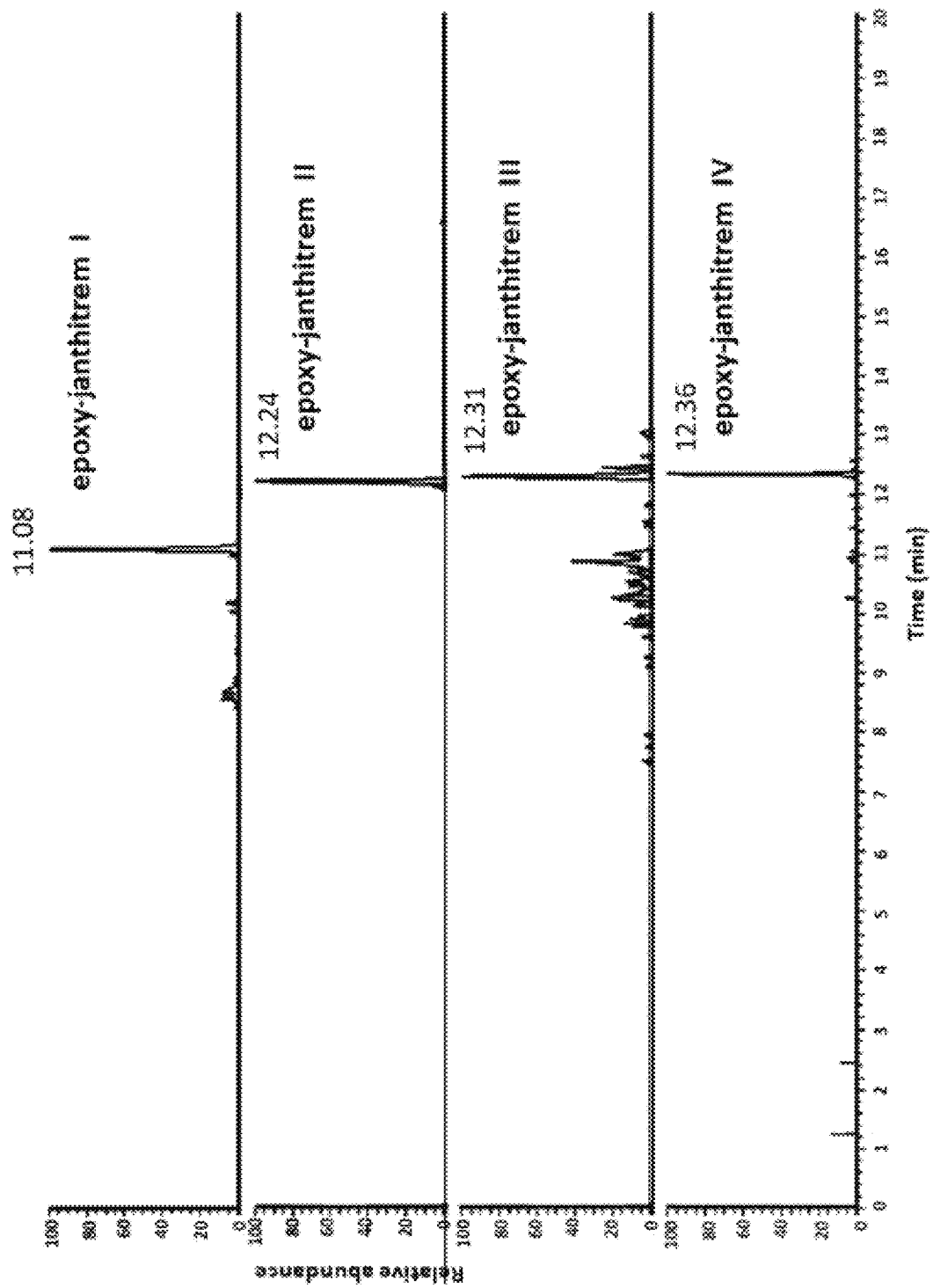
FIG. 1 shows a LC-ESI-FTMS extracted ion chromatogram of epoxy-janthitrem I-IV observed in *Lolium perenne* ryegrass Bronsyn with AR37 endophyte, collected from 0-20 min in positive ionisation mode (ESI+)

DNA was extracted from each sample using the MagAttract Plant DNA kit (Qiagen, Hilden, Germany). The endophyte-specific SSR markers, B110 and B111 were used for PCR-based in planta detection of endophytes. PCR amplifications were performed in 12.5 µl reaction volumes containing 1 µL genomic DNA (5 ng/µl), 1×PCR buffer (Bioline, London, UK), 0.2 µM of forward and reverse primer (Sigma Aldrich, St. Louis, Missouri, USA; Applied Biosystems, Foster City, California, USA), 0.125 µl of 5 mM dNTP (GE Healthcare, Chalfont St Giles, UK), 1 U immolase (Bioline), and was processed in a thermocycler (DNA Engine, Bio-Rad, Hercules, California, USA) programmed for 10 min at 95° C. followed by 30 cycles of 1 min at 94° C., 2 min at 65° C., 1 min at 72° C., then 10 min at 72° C.

The PCR products were diluted with sterile Milli-Q water (1:10), and 2 µl of the diluted product was mixed with 8 µl of ABI 3730 loading solution [7.95 µl of Hi-Di™ formamide (Applied Biosystems, Foster City, California, USA), 0.05 µl of 500LiZ™ (Applied Biosystems, Foster City, California, USA) size standard] before analysis on the ABI 3730xl automated capillary electrophoresis platform (Applied Biosystems Biosystems, Foster City, California, USA). Products were detected using the GeneMapper version 3.7 software (Applied Biosystems Biosystems, Foster City, California, USA), and endophyte samples were identified by the presence of amplification peaks specific for each SSR marker.

TABLE 1

SSR marker profile of selected endophyte strains at the B10 and B11 loci [7].

| Endophyte strain | Taxonomic group | Alkaloid profile | B10 (bp) | B11 (bp) Allele 1 | Allele 2 |
|---|---|---|---|---|---|
| RAGT/R2n Endophytes | | | | | |
| 1.4.4 | LpTG-1 | EP | 176 | 238 | |
| RGT18 | LpTG-3 | J | 162 | 131 | |
| RGT15 | LpTG-1 | EP | 176 | 152 | 156 |
| 1.9.7 | LpTG-1 | EP | 176 | 160 | 164 |
| 2.5.3 | LpTG-1 | EP | 176 | 152 | 156 |
| 1.11.13 | LpTG-1 | EP | 176 | 172 | |
| Commercial Endophytes | | | | | |
| NEA6 | LpTG-1 | EP | 176 | 199 | |
| AR37 | LpTG-3 | J | 162 | 131 | |
| SE | LpTG-1 | LEP | 176 | 176 | |
| AR1 | LpTG-1 | P | 176 | 148 | |

LpTG—*Lolium perenne* Taxonomic Group;
E—ergovaline;
P—peramine;
J—janthitrems;
L—lolitrem B;
bp—base pair

Example 2: Genome Sequencing to Identify SNP Variation Between RGT18 and AR37

2.1 Lilumina Platform Sequencing

DNA Extraction

DNA for genome survey sequencing was extracted from lyophilized mycelia using a cetyltrimethylammonium bromide (CTAB) based extraction method (Möller et al. 1992), and the quality and quantity of the DNA was assessed by both agarose gel electrophoresis and specific absorbance measurements using the NanoDrop 2000 Spectrophotometer (Thermo Scientific).

Prior to sequencing, genetic identities of isolated endophyte strains were confirmed using endophyte specific SSR markers.

Paired-End Library Preparation and Sequencing

Genomic DNA was fragmented in a Covaris instrument (Woburn, MA, USA) to an average size of 100-900 bp.

For the RGT18 endophyte DNA sample, paired-end libraries with inserts c. 400 bp in size were prepared using the standard protocol (TruSeq DNA Sample Prep V2 Low Throughput: Illumina Inc., San Diego, USA) with paired-end adaptors. Library quantification was performed using the KAPA library quantification kit (KAPA Biosystems, Boston, USA). Paired-end libraries were pooled according to the attached adaptors and sequence analysed using the HiSeq2000 platform (Illumina) following the standard manufacturer's protocol, RGT18, was sequenced in September 2012.

For AR37 endophyte DNA, paired-end libraries with inserts c. 400 bp in size were prepared using the standard protocol (Nextera DNA Library Preparation Kit: Illumina Inc., San Diego, USA) with paired-end adaptors. Library quantification was performed using the KAPA library quantification kit (KAPA Biosystems, Boston, USA). Paired-end libraries were pooled according to the attached adaptors and sequence analysed using the MiSeq platform (Illumina) following the standard manufacturer's protocol. The AR37 isolate was sequenced in September 2012.

All generated sequence reads were quality controlled by filtering and trimming of reads based on quality using a custom Python script, which calculates quality statistics, and stores trimmed reads in several fastq files.

2.2. SNP Variation Between AR37 and RGT18

2.2.1. AR37 Reference Genome

A reference genome for AR37 was assembled using SOAPdenovo. A total of 9,604,168 paired-end reads generated using Illumina sequencing technology were assembled to generate a reference genome with 19982 scaffold sequences (Table 2). To minimise 'N's present in the assembly 'command-line resolve' was used, thus generating the AR37 resolved reference genome.

TABLE 2

Sequencing statistics for the AR37 reference genome

| Sequence statistic | Length (bp) |
|---|---|
| Size_includeN | 31354167 |
| Size_withoutN | 29768040 |
| Scaffold_Num | 19982 |
| Mean_Size | 1569 |
| Median_Size | 115 |
| Longest_Seq | 151941 |
| Shortest_Seq | 100 |
| Singleton_Num | 13980 |
| Average_length_of_break(N)_in_scaffold | 79 |

2.2.2 Mapping Reads to the AR37 Reference Genome

For read mapping to reference sequences, raw fastq sequences generated by the Illumina sequencers were trimmed and quality filtered using the Gydle 'nuclear' program in filter mode. The settings used trims reads to a minimum length of 50 bp having greater than Phred score equivalent of 20 and removed Illumina adapters. Reads were mapped to the AR37 reference genome using the Gydle 'nuclear' program in search mode. The settings used were Minimum length (L) of High Scoring Pairs 50, Sensitivity (s—minimum consecutive identities within a HSP) 25, K-mer size (k) used for search, 13 Mismatches allowed (m) 6, and—random-best (Reports a single hit randomly selected among the best hits).

AR37 and RGT18 reads were mapped to the AR37 reference genome using Gydle to generate a gym file. These were generated from the 'nuclear' aligned reads using the Gydle 'gym-build' program. SNPs were identified using the Gydle program findsnp which uses the gym file as an input. Settings for findsnp were min-coverage 2 (i.e. at least 2 DNA reads had to cover the base of interest) and a min-allele-frequency of 80% (i.e. a base different to the reference had to be seen in a least 80% of the reads covering that base) and min-allele-count 2 (to count SNPs in contigs with unresolved repeats per strain). SNPs were then further filtered such that: 1) SNPs with a minimum allele frequency>80% were excluded when comparing AR37 (reference) v AR37 (reads); 2) contigs had to be greater than 999 bp; and 3) less than 20 minimum-allele-count 2 AR37 (reference) v AR37 (reads) SNPs allowed per contig.

Figure 7:
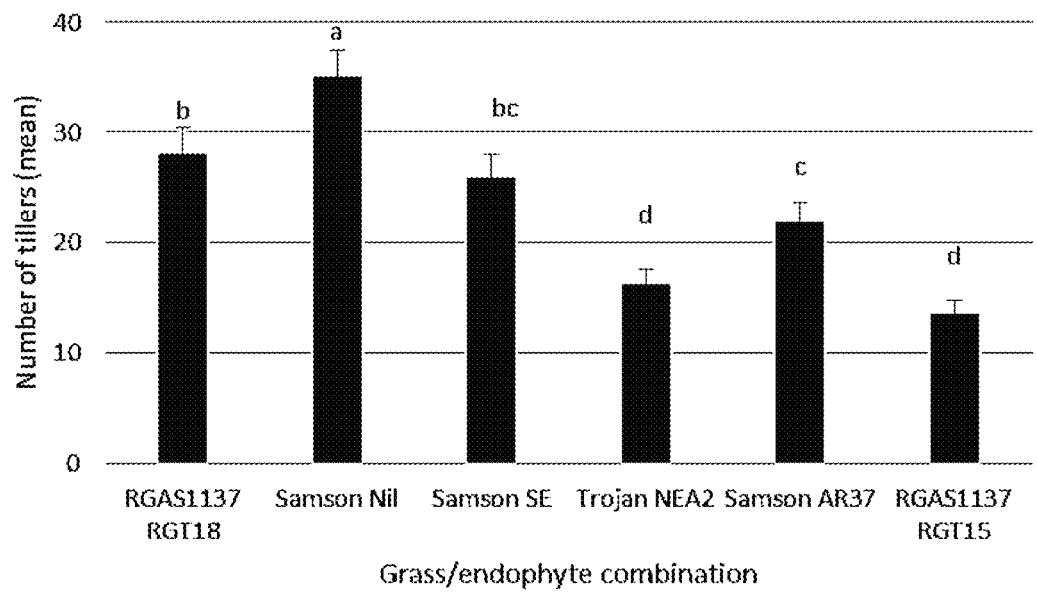
FIG. 7 shows baseline tiller count (mean with SE) at day 0 (DPE0)

Using this approach, the inventors identified 817 SNPs, with an average coverage (sequence read depth) of 18×, which differentiate clearly between AR37 and RGT18 (Figures-7).

Example 3: Generation of Novel Host-Endophyte Associations

*Lolium perenne* ryegrass-endophyte associations were generated by inoculation using the 'cut and stuff' method [12]. Infected plants were identified 6-8 weeks post inoculation using strain specific DNA-based diagnostics to confirm endophyte presence and identity. A total of 154 novel *Lolium perenne* ryegrass-endophyte associations were generated (Table 3).

TABLE 3

Variety-endophyte associations generated via endophyte inoculation into seedling meristem.

| Host variety | Endophyte strain | Number of genotypes |
|---|---|---|
| STELLAR | RGT15 | 44 |
| STELLAR | RGT18 | 44 |
| RGAS1137 | RGT15 | 30 |
| RGAS1137 | RGT18 | 36 |
| Total | | 154 |

Example 4: Vegetative Stability of Endophytes

Vegetative stability of the associations was assessed six monthly, over a 24-month period (Table 4). Three or more tiller samples (c. 0.5 cm from the base) were harvested from each plant after 6, 12, 18 and 24 months growth in the field. DNA was extracted from freeze dried samples using the MagAttract Plant DNA kit (Qiagen, Hilden, Germany). Each sample was analysed for endophyte strain presence and identity using strain specific DNA-based diagnostics.

Table 3 summarises the number of endophyte positive plants identified 6, 12, 18 and 24 months following successful infection determined at 6 weeks post inoculation. Once novel *Lolium perenne* ryegrass-endophyte associations are established they remain stable. Further, endophyte strain RGT18 exhibited higher vegetative stability compared to strain RGT15. However, this could also have been due to the varietal-endophyte symbiosis occurring between this endophyte and the host variety, but also the inventors also believe could be due to the compatibility/marriage ability of the RGT18 endophyte with a host grass.

TABLE 4

Vegetative stability of variety-endophyte associations. Endophyte infected plants were identified at 6 weeks post inoculation, followed by 6-monthly assessments of association stability.

| | | Host variety + Endophyte strain Inoculated | | | | |
|---|---|---|---|---|---|---|
| | | Stellar + RGT15 | Stellar + RGT18 | RGAS1137 + RGT15 | RGAS1137 + RGT18 | Total |
| 6 weeks | Endophyte detected | 44/47 | 44/44 | 30/30 | 36/36 | 154/157 |
| | Vegetative stability | 94% | 100% | 100% | 100% | |
| 6 months | Endophyte detected | 35/44* | 37/42* | 25/30* | 33/34 | 130/150 |
| | Vegetative stability | 79.5% | 88.1% | 83.3% | 97.1% | |
| 12 months | Endophyte detected | 36/45 | 40/43 | 23/31* | 28/34 | 127/153 |
| | Vegetative stability | 80.0% | 93.0% | 74.2% | 82.4% | |
| 18 months | Endophyte detected | 36/45 | 39/43 | 24/32 | 30/34 | 141/154 |
| | Vegetative stability | 80.0% | 90.7% | 75.0% | 88.2% | |
| 24 months | Endophyte detected | 37/45 | 40/43 | 23/32 | 28/33* | 134/153 |
| | Vegetative stability | 82.2% | 93.0% | 71.9% | 84.8% | |

*Where total plants tested is lower than the number of plants in the field, some plants were either not tested or deceased.

Example 5: Intergenerational Stability

The intergenerational stability of the endophytes was assessed in seed generated via pollen cloud experimentation. Analysis was performed using a bulked seed approach whereby 10 seeds were pooled to form 1 sample. DNA extraction was performed using the DNeasy 96 plant DNA extraction kit (Qiagen, Hilden, Germany) for each seed line. Each sample was analysed for endophyte strain presence and identity using strain specific DNA-based diagnostics.

Intergenerational stability, measured as transmission of endophyte to seed, showed endophyte strain RGT18 exhibits higher stability compared to strain RGT15 (Table 5). Variation for intergenerational stability was also observed between varieties; host variety RGAS1137 transmits endophyte at a higher frequency compared to STELLAR (Table 5).

TABLE 5

Intergenerational stability of variety-endophyte associations, measured as transmission of endophyte to seed.

| Host variety | Endophyte strain | Endophyte detected | Endophyte negative | Total genotypes tested | Intergenerational stability |
|---|---|---|---|---|---|
| STELLAR | RGT15 | 40 | 11 | 51 | 78% |
| STELLAR | RGT18 | 39 | 5 | 44 | 89% |
| RGAS1137 | RGT15 | 30 | 6 | 36 | 83% |
| RGAS1137 | RGT18 | 35 | 1 | 36 | 97% |
| Total | | 144 | 23 | 167 | |

Example 6: Alkaloid Profiling

The alkaloid profiles (ergovaline, peramine and janthitrems) of the associations were assessed over a growing season under field conditions to gain insight into seasonal fluctuations and presence of alkaloids.

6.1 Methods

Sample Harvest

Plant material for alkaloid analysis was harvested approximately 5 cm above ground. Fresh material was packed into paper bags and stored at −80° C. Samples were then freeze dried, ground to a fine powder and stored at 21° C. in the dark.

Sample Preparation for Alkaloid Analysis

Freeze-dried and ground *Lolium perenne* ryegrass-endophyte samples harvested from three different seasonal periods were measured for alkaloid content.

Plant material (20 mg±0.2 mg) was extracted twice with 1 mL of methanol:water (80:20, v:v) (Merck LiChrosolv>99.9%; MilliQ water). The supernatants were combined and dried using a SpeedVac Concentrator (Thermo Fisher Scientific, Savant SPD 2010) at room temperature for approximately 16 h, and reconstituted in 200 μL of methanol:water (80:20, v:v) containing Ergotamine D-tartrate (Sigma-Aldrich, St Louis, USA) as an internal standard at a concentration of 216 ng/mL.

For alkaloid quantitation, peramine nitrate (BDG Synthesis, Wellington, NZ) and ergovaline were used to construct concentration curves from 1 to 2000 ng/mL (peramine and ergovaline) in matrix (endophyte free *Lolium perenne* ryegrass plant).

LCMS Parameters

HPLC Analysis

Extracts were analysed using a 100 mm×2.1 mm Themo Hypersil Gold 1.9 μm HPLC column fitted to a Thermo Fischer Scientific Vanquish liquid chromatograph (Thermo Fischer Scientific, Bremen). The compounds were detected with a Thermo Fisher QExactive Plus mass spectrometer (Waltham, MA, USA; Thermo, Bremen, Germany), operating in the ESI mode with a HESI probe for positive data acquisition.

Mass Spectrometry Analysis

The sample extract (3 PL) was assessed in FT positive mode over a mass range of 80-1200 amu with resolution set at 35,000. Typical mass accuracy for the alkaloids was 3-5 ppm. Relative quantitation (expressed as peak area) were determined for epoxy-janthitrems I to IV (FIG. 1). These were identified based on mass accuracy and fragmentation patterns via LCMS/MS (Table 6).

TABLE 6

Targeted LCMS/MS analysis of epoxy-janthitrem I-IV indicating accurate masses (m/z), retention times (RT) and MSn fragmentation data (LC-MS/MS) which were acquired in positive ionisation mode [M + H] using a Thermo Fisher Q-Exactive Plus orbitrap mass spectrometer. Accurate mass and MSn fragmentation results were compared with theoretical masses and fell within the range of 5 ppm difference (Delta ppm).

| | Metabolite | Epoxy-janthitrem I | Epoxy-janthitrem II | Epoxy-janthitrem III | Epoxy-janthitrem IV |
|---|---|---|---|---|---|
| | m/z [M + H] | 646.3735 | 670.4076 | 672.4230 | 714.4341 |
| | RT (min) | 11.08 | 12.24 | 12.31 | 12.36 |
| Product ion: LC-MS/MS | 1 | 222.1277 | 222.1275 | 222.1274 | 222.1278 |
| | 2 | 280.1696 | 280.1692 | 280.1692 | 280.1694 |
| | 3 | 588.3320 | 612.3676 | 614.3833 | 656.3934 |
| | 4 | 631.3459 | 655.3814 | 657.3969 | 699.4081 |
| | Chemical Formula [M + H] | C39 H52 O7 N | C42 H56 O6 N | C42 H58 O6 N | C44 H60 O7 N |
| | Theoretical Mass [M + H] | 646.3738 | 670.4102 | 672.4259 | 714.4364 |
| | Delta (ppm) | −0.5 | −3.8 | −4.3 | −3.3 |

6.2 RGT15

STELLAR-RGT15 and RGAS1137-RGT15 were measured for peramine and ergovaline production in spring, summer and winter. Lolitrem B was not observed in any variety-RGT15 associations.

Generally, higher average concentrations of peramine and ergovaline were observed in summer compared to spring and winter (Table 7). STELLAR-RGT15 associations exhibit less seasonal variation in peramine and ergovaline concentrations compared to RGAS1137-RGT15 associations. This higher concentration exhibited in summer is very positive in providing high levels of insect resistance at a time of the year when insect presence and lifecycles are at their peak in pastoral systems.

Figure 2A:
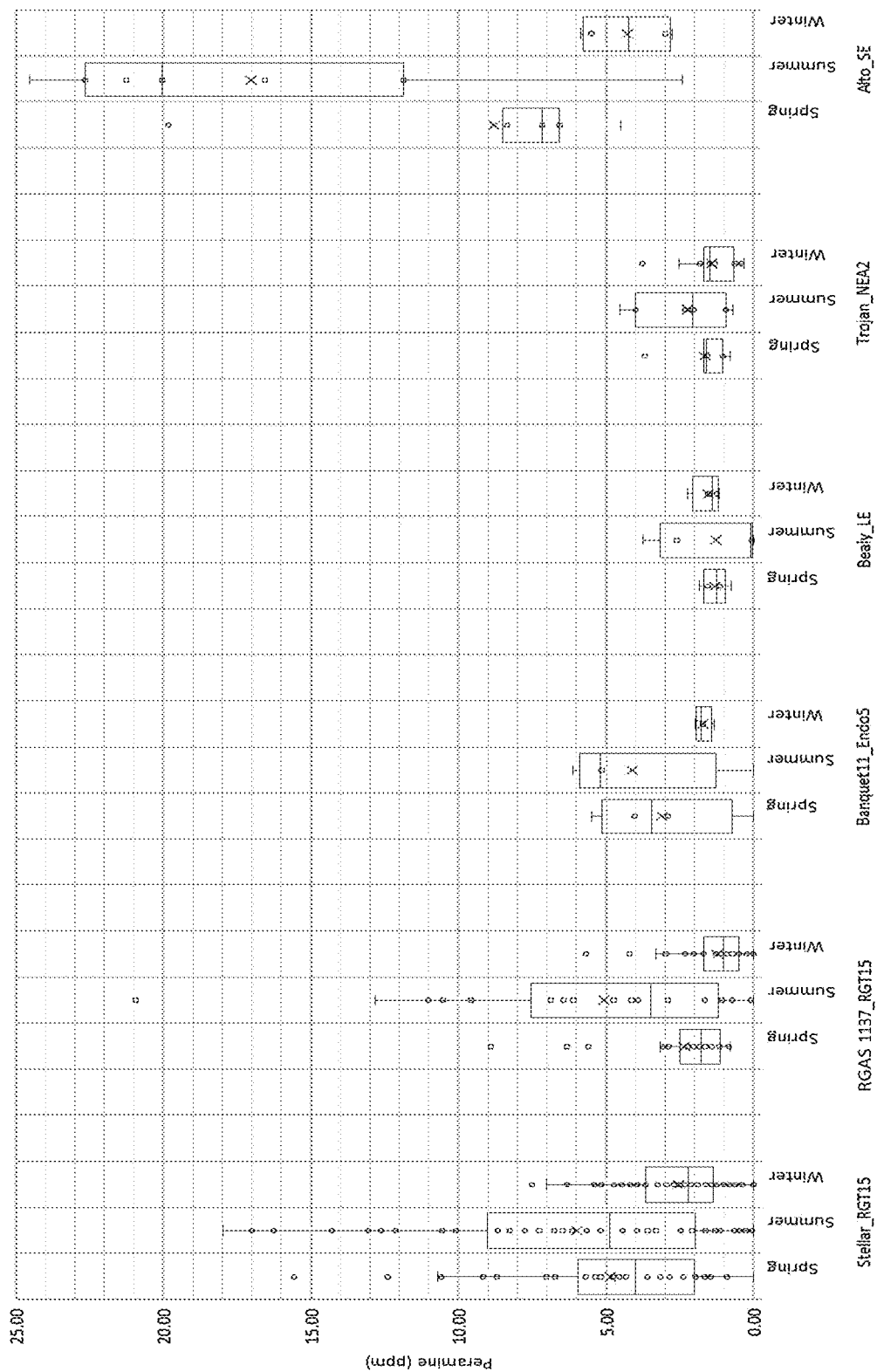
FIG. 2 shows a Peramine (a) and ergovaline (b) production (parts per million, ppm) measured in spring, summer and winter for STELLAR-RGT15, RGAS1137-RGT15 and commercially available *Lolium perenne* ryegrass-endophyte associations. Average production is illustrated by 'X'.
Figure 2B:
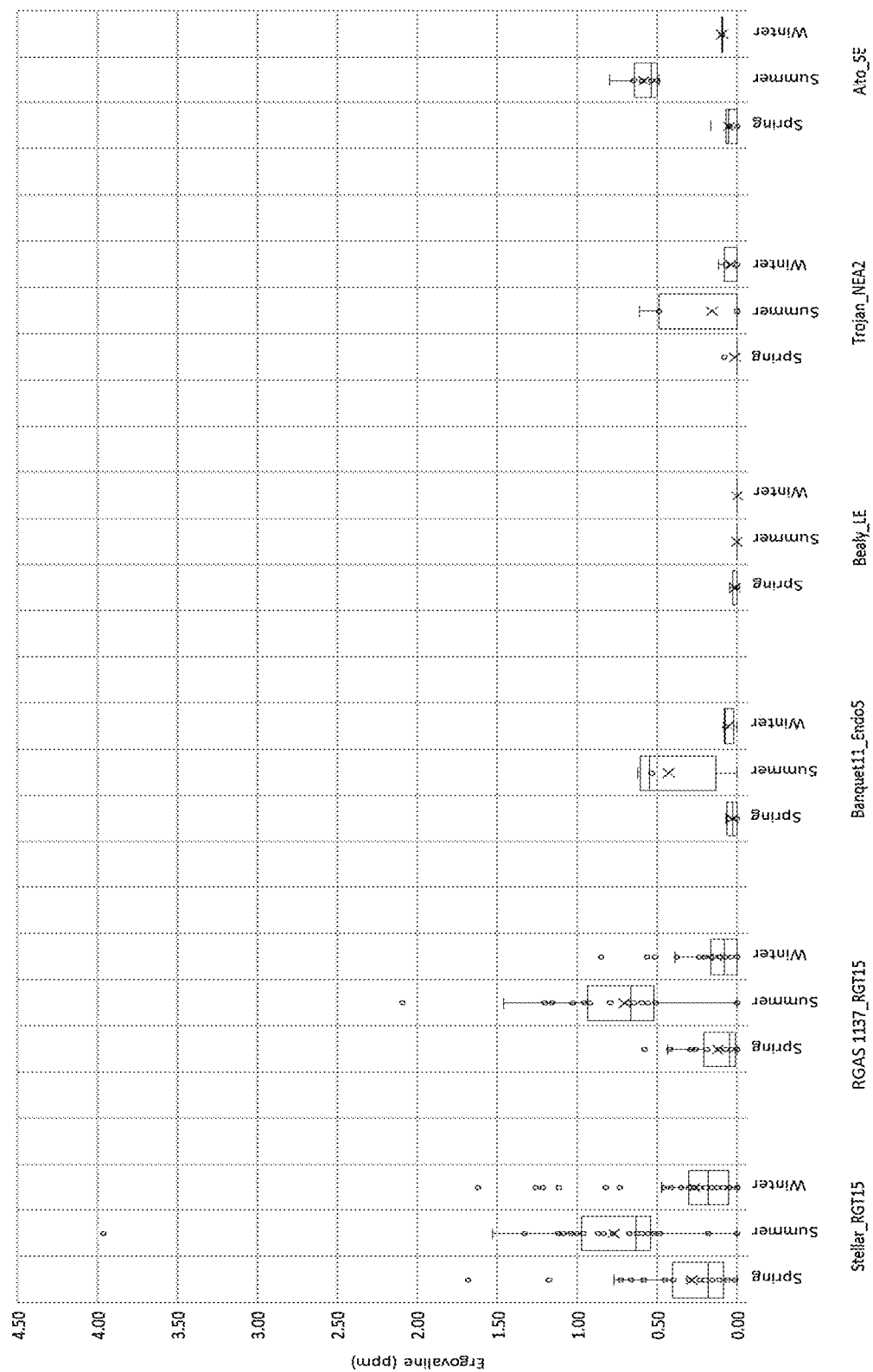

A wide range in alkaloid production was observed within each population (FIG. 2a-b). Individual genotypes within STELLAR and RGAS1137 were identified with peramine concentrations higher than commercial cultivars tested.

TABLE 7

Seasonal averages for ergovaline and peramine production
for *Lolium perenne* ryegrass-endophyte associations.

| Association | Season | Number of genotypes measured | Average ergovaline (mg/kg) | Average peramine (mg/kg) |
|---|---|---|---|---|
| STELLAR-RGT15 | Spring | 42 | 0.28 | 4.85 |
| RGAS1137-RGT15 | Spring | 26 | 0.12 | 2.34 |
| Banquet-Endo5 | Spring | 4 | 0.03 | 3.10 |
| Bealey -LE | Spring | 4 | 0.01 | 1.30 |
| TROJAN-NEA2 | Spring | 7 | 0.01 | 1.66 |
| Alto-SE | Spring | 7 | 0.03 | 8.79 |
| STELLAR-RGT15 | Summer | 42 | 0.77 | 5.98 |
| RGAS1137-RGT15 | Summer | 26 | 0.70 | 5.07 |
| Banquet-Endo5 | Summer | 4 | 0.43 | 5.07 |
| Bealey -LE | Summer | 4 | 0.00 | 1.30 |
| TROJAN-NEA2 | Summer | 7 | 0.16 | 2.23 |
| Alto-SE | Summer | 7 | 0.58 | 17.04 |
| STELLAR-RGT15 | Winter | 36 | 0.27 | 2.51 |
| RGAS1137-RGT15 | Winter | 25 | 0.13 | 1.26 |
| Banquet-Endo5 | Winter | 4 | 0.07 | 1.72 |
| Bealey -LE | Winter | 4 | 0.00 | 1.54 |
| TROJAN-NEA2 | Winter | 14 | 0.04 | 1.41 |
| Alto-SE | Winter | 4 | 0.09 | 4.27 |

To note:
the ergovaline levels exhibited in RGT15 were at optimum levels for suppressing insects but not at a level to cause animal effects.

6.3 RGT18

STELLAR-RGT18 and RGAS1137-RGT18 were measured for epoxy-janthitrems I-IV production in spring, summer and winter (Table 8).

Figure 3:
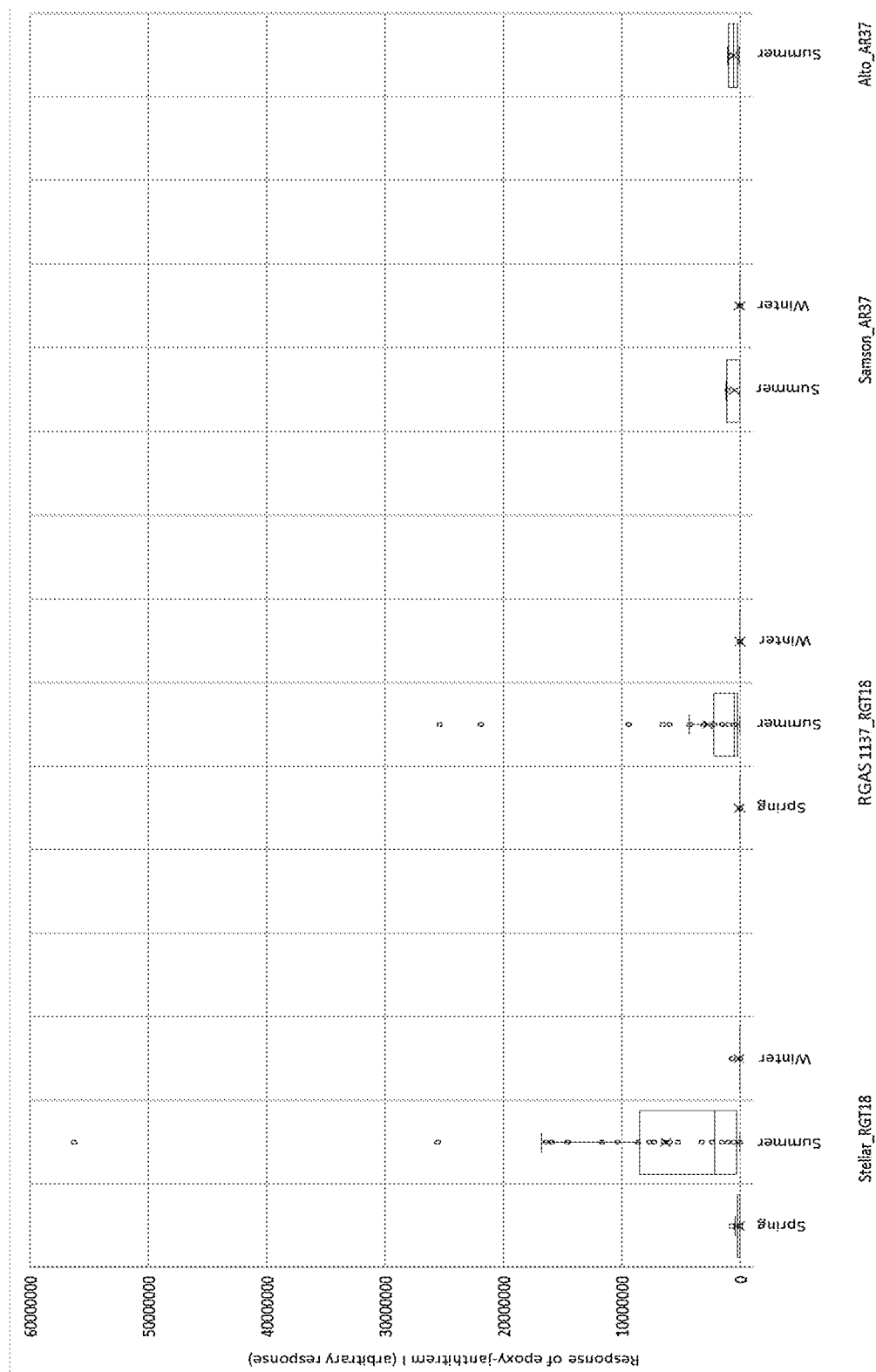
FIG. 3 shows an Epoxy-janthitrem I production measured in spring, summer and winter for STELLAR-RGT18, RGAS1137-RGT18 and commercially available *Lolium perenne* ryegrass-AR37 associations. Production is measured as a response (area measured under the peak). Average production is illustrated by 'X'.

A wide range in alkaloid production was observed within each population (FIG. 3). Individual genotypes within STELLAR and RGAS1137 were identified with epoxy-janthitrem I production concentrations higher than commercial cultivars tested, as were genotypes with epoxy-janthitrem concentrations lower than commercial cultivars tested.

Lower average concentrations of epoxy-janthitrem I were observed in spring and winter compared to summer. Again this is positive, in that in pastoral systems have higher insect pressures exhibited in summer, than in cooler times of the year.

Figure 4:
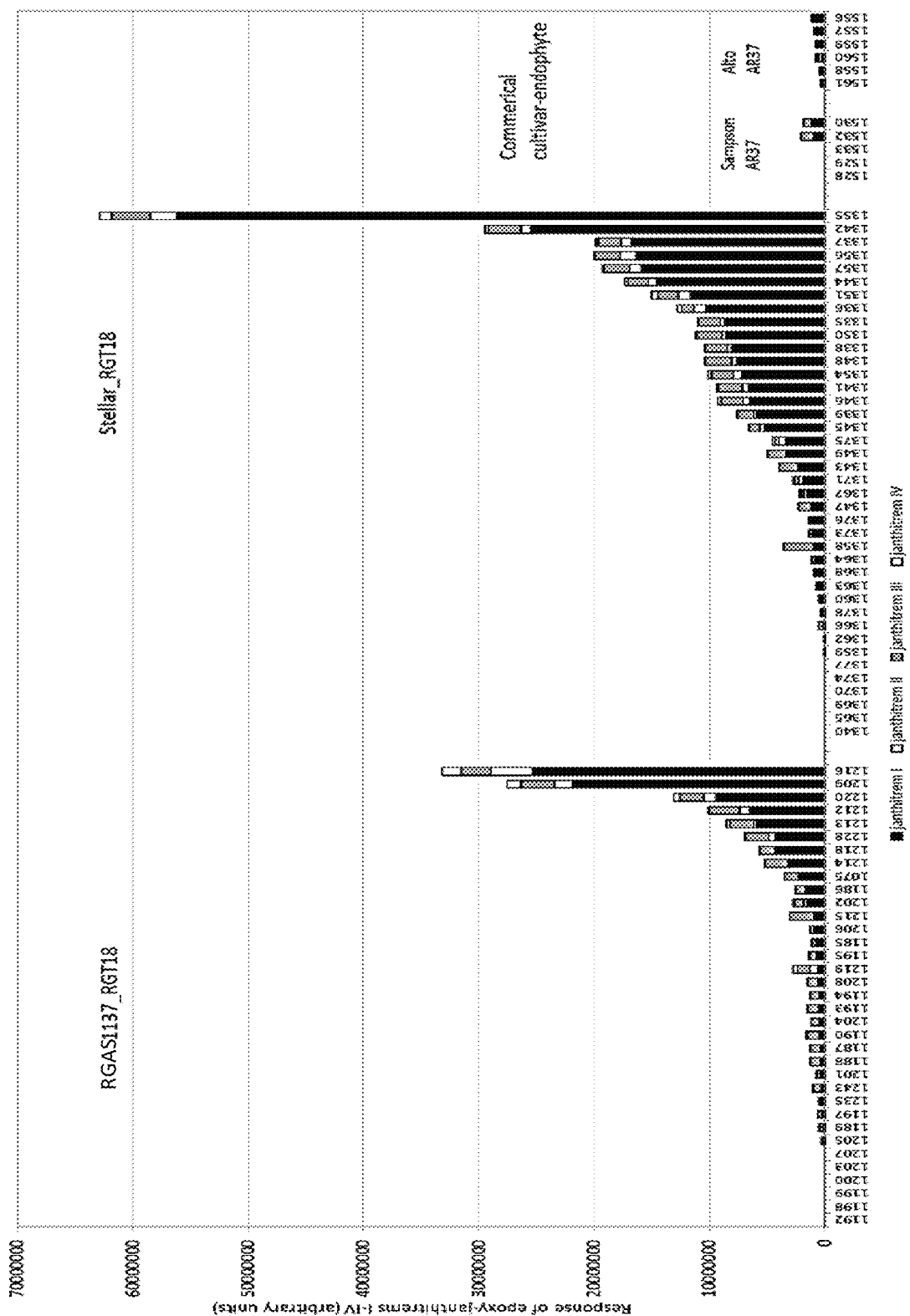
FIG. 4 shows an Epoxy-janthitrem I-IV production measured in summer for STELLAR-RGT18, RGAS1137-RGT18 and commercially available *Lolium perenne* ryegrass-AR37 associations. Production is measured as a response (area measured under the peak)
Figure 5:
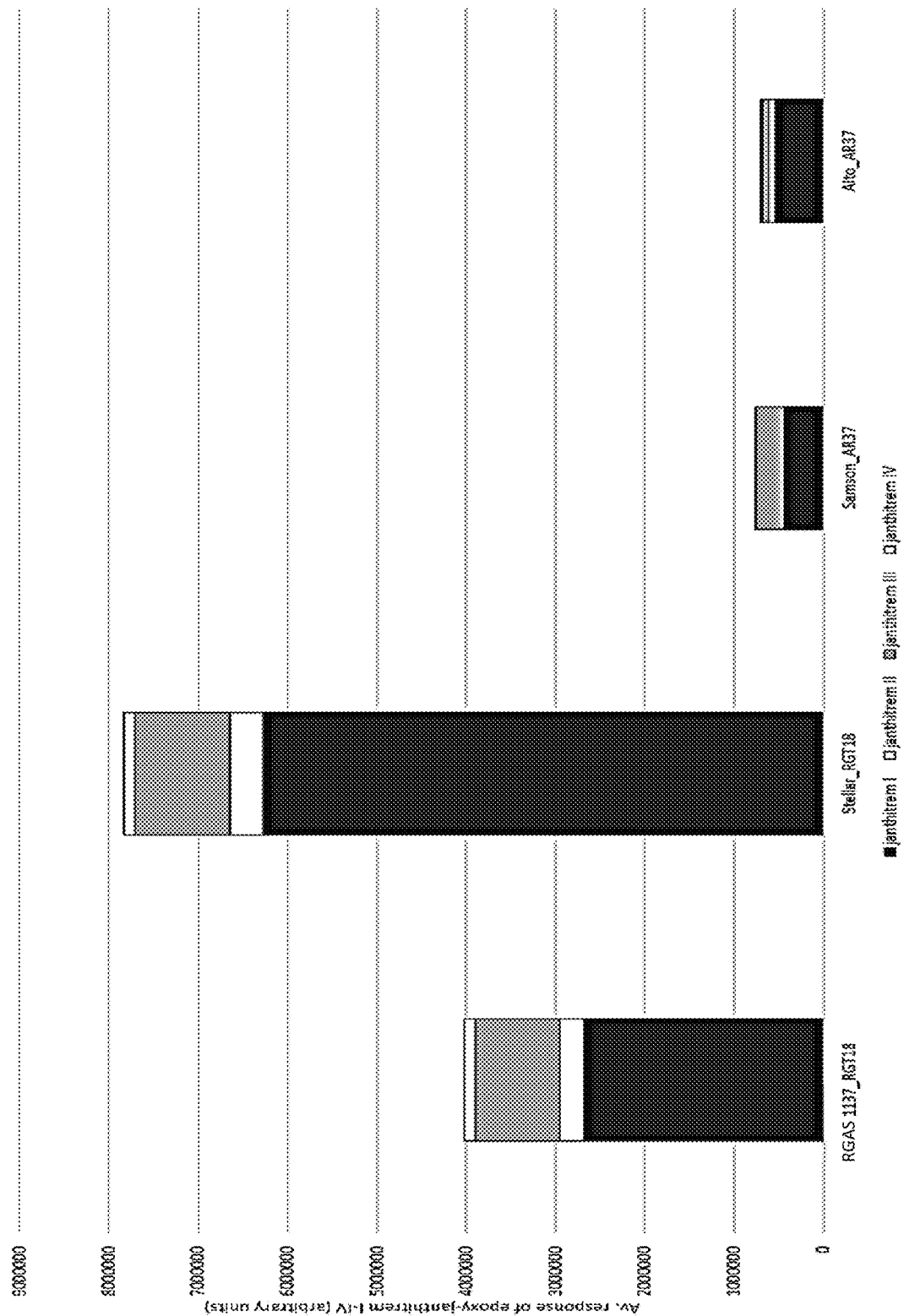
FIG. 5 Average epoxy-janthitrem I-IV production measured in summer for STELLAR-RGT18, RGAS1137-RGT18 and *Lolium perenne* ryegrass-AR37 associations. Production is measured as a response (area measured under the peak)

The production of epoxy-janthitrem I and its variants (epoxy-janthitrems II-IV) in the summer were also measured (FIG. 4). Average levels were greater in STELLAR-RGT18 compared to RGAS1137-RGT18 (FIG. 5). Epoxy-janthitrem I was dominant in all samples tested, followed by epoxy-janthitrem Ill (Table 9).

TABLE 8

Seasonal averages for janthitrem I production for
*Lolium perenne* ryegrass-endophyte associations

| Association | Season | Number of genotypes measured | Average janthitrem I (arbitrary units) |
|---|---|---|---|
| STELLAR-RGT18 | Spring | 43 | 100116 |
| RGAS1137-RGT18 | Spring | 38 | 22054 |
| SAMSON-AR37 | Spring | 5 | 0 |
| STELLAR RGT18 | Summer | 43 | 6268565 |
| RGAS1137-RGT18 | Summer | 38 | 2677393 |
| SAMSON-AR37 | Summer | 5 | 434659 |
| Alto-AR37 | Summer | 6 | 538814 |
| STELLAR RGT18 | Winter | 36 | 42794 |
| RGAS1137-RGT18 | Winter | 32 | 4473 |
| SAMSON-AR37 | Winter | 8 | 0 |

TABLE 9

The proportion of epoxy-janthitrems I-IV (%) measured in *Lolium perenne* ryegrass-endophyte associations during the summer season.

| | | Proportion of epoxy-janthitrems I-IV (%) | | | |
|---|---|---|---|---|---|
| Association | Season | epoxy-janthitrem I | epoxy-janthitrem II | epoxy-janthitrem III | epoxy-janthitrem IV |
| RGAS1137-RGT18 | Summer | 66.61 | 6.91 | 23.38 | 3.10 |
| STELLAR-RGT18 | Summer | 79.96 | 4.78 | 13.65 | 1.61 |
| SAMSON-AR37 | Summer | 57.08 | 0.00 | 42.92 | 0.00 |
| Alto-AR37 | Summer | 76.30 | 10.36 | 9.89 | 3.45 | sequences of the Sequence Listing accompanying this specification and as also depicted in FIG. 6.

Example 7—Evaluation of Perennial Ryegrass (*Lolium perenne*) Lines for Resistance/Tolerance to Adult Black Beetle (*Heteronychus arator*) Feeding This example details the results of a laboratory screening (choice test) of diploid ryegrass lines to test for resistance/tolerance to adult black beetle (*Heteronychus arator*) feeding. Black beetle is considered one of the two key pastoral pests in New Zealand along with Argentine stem weevil.

The grass/endophyte combinations (lines) tested were:
RGAS1137 RGT18
SAMSON Nil (control)
SAMSON SE (control)
TROJAN NEA2 (comparator)
SAMSON AR37 (comparator)
RGAS1137 RGT15

Grass tillers were counted on each entry (plant) at Day 0 immediately before the introduction of the adult black beetle. At days 10, 15, 21 post establishment (DPE10, DPE15, DPE21) assessments were made identifying and counting damaged tillers and assessing plant vigour. Plant vigour was scored on a Likert Scale (1 least vigour to 5 most vigour).

Analysis of the results was based on the tiller counts (total, healthy and damaged) and the vigour of plants, being the difference between the Day 0 score and later assessments. Plant vigour is an interpretation of a plant's ability to withstand feeding damage and the effects of adult black beetle test biting.

Key Results
Plant vigour at DPE0 for all lines was assessed as being a 5—(range 1-5).
At DPE10, the damaged tiller count mean for SAMSON Nil (mean 16.4 or 47%) was significantly different (higher) than the balance of the entries ($p<0.01$). The vigour score mean for SAMSON Nil was 2.6, which was lower than the mean for the balance of the entries (overall mean 4.7). The results for SAMSON Nil were consistent with severe black beetle feeding damage.
At DPE10 the damaged tiller count means for the balance of the entries were not significantly different from each other.
While there were significant differences in mean tiller counts between lines when the assay was started, the results of the assay are conclusive with respect to the poor performance of SAMSON Nil.
The methodologies and results from a study of feeding choices of black beetle (*Heteronychus arator*) under laboratory conditions is outlined below. The feeding choices were diploid perennial ryegrass (*Lolium perenne*) varieties containing a range of endophytes (*Acremonium loliae*). The primary objective of the study was to measure adult black beetle feeding choices.

Methods

Adult black beetle collection and maintenance

In April, 200×75 mm diameter pitfall traps were placed in sheep and beef pasture (with a history of black beetle damage) in Tahuna, Waikato, to trap adult black beetle. The traps were emptied daily until a total of 200 black beetle were collected (90 were required for experimental purposes).

In preparation for the experiment the black beetles were contained individually in cube trays enabling monitoring of individual insects, isolation in case of disease, and preventing combat injury. The beetles were transferred to clean containers every second day and provided with fresh carrot for feeding. The black beetles were maintained at ambient temperatures and not fed for two days prior to entry into the assay.

Choice Test Set-Up

Six (6) perennial rye grass seedling types of diploid seed-lines and endophyte selections (Table 10) were received from Seed Force, Christchurch, where they had been grown from seed in planter trays. All plants had been tested for endophyte using the tissue print immunoblot method. The plants were well-grown; all lines had large numbers of healthy tillers.

To prepare the experiment representative seedlings of each type (entries) were planted equidistant apart (8 cm) in a sandy loam soil (depth 10 cm), within the margins of galvanised sheet iron ring (height 15 cm diameter 32 cm). Plant position in each ring was randomised, and positions were labelled. There were 15 replications of each entry (i.e. 15 rings). The rings were covered with insect netting suspended 15 cm above the soil surface.

TABLE 10

Entries into adult black beetle feeding assay
Entry

RGAS1137 RGT18
SAMSON Nil
SAMSON SE
TROJAN NEA2
SAMSON AR37
RGAS1137 RGT15

The experiment was maintained in a screen house at ambient temperatures and checked daily to ensure the soil moisture was adequate and that insect containment integrity was maintained.

Assessments

The tiller counts and baseline vigour scores for each plant were recorded prior to the introduction of the adult black beetles (Day 0, Assessment 1). The vigour score is a relative score for all plants in the trial on a Likert Scale of 1 (least vigour) to 5 (most vigour). Vigour characteristics were growth form, growth level, leaf colour, and appearance. The plants were then trimmed to 3 cm and adult black beetle were released into each ring (replicate) at a ratio of one per test plant (6 black beetles per ring).

Plants were inspected daily for black beetle adult feeding damage and four assessment made (Table 11) with a final assessment (Day 21, Assessment 4).

TABLE 11

Assessment type and timing post establishment (introduction of black beetle)

| Assessment | Days post Establishment (DPE) | Assessment type |
|---|---|---|
| 1 | 0 | Vigour score, tiller count |
| 2 | 10 | Vigour score, damaged tiller count |
| 3 | 15 | Vigour score, damaged tiller count |
| 4 | 21 | Vigour score, damaged tiller count, confirm tiller count |

Results

Initial Tiller Count (DPE0)

A tiller count prior to the introduction of the black beetle adults provided a baseline. The tiller counts ranged from 10 to 52, with variation across the grass/endophyte combinations (lines) (Table 12). The mean range of was from 13.6 to 35.1.

TABLE 12

Baseline tiller count

| Line | RGAS1137 RGT18 | SAMSON Nil | SAMSON SE | TROJAN NEA2 | SAMSON AR37 | RGAS1137 RGT15 |
|---|---|---|---|---|---|---|
| Min | 14 | 21 | 14 | 10 | 12 | 4 |
| Max | 45 | 52 | 38 | 27 | 34 | 21 |
| Median | 31 | 33 | 26 | 15 | 21 | 15 |
| Mean | 28.0 | 35.1 | 25.9 | 16.3 | 21.9 | 13.6 |

Ideally the mean number of tillers in each of the lines is sufficiently similar that they could statistically be from the same population. Table 12 and FIG. 7 show the mean baseline tiller count at day zero for each grass/endophyte combination. An ANOVA of tiller counts at planting (Day 0) confirmed that there was a significant difference between the means ($p<0.01$). T tests showed lines were split into four significantly different groups. SAMSON Nil had significantly higher mean than the rest of the lines. The statistical groupings based on the means were RGAS1137 RGT18 and SAMSON SE; SAMSON SE and SAMSON AR37; and TROJAN NEA2 and RGAS1137 RGT15. These differences are discussed below.

Day Zero Initial Vigour Score (DPE0)

All entries achieved a vigour score of 5 prior to the introduction of the black beetle adults.

Day 10 Post Establishment (DPE10)

Plants were tended regularly and visually checked for black beetle damage following planting. On Day 10 there was sufficient damage to undertake a tiller count and vigour scoring.

Tiller Damage

Figure 8:
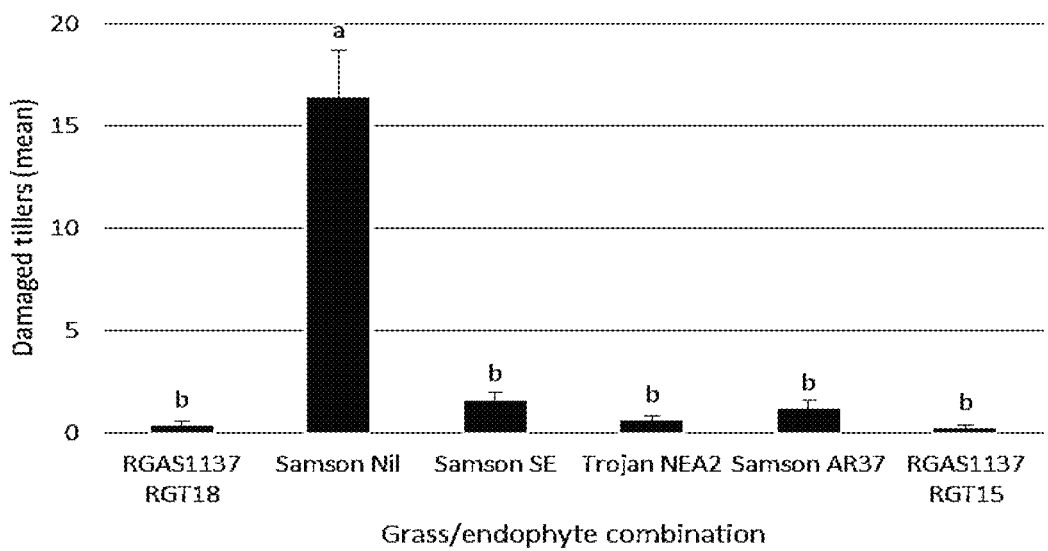
FIG. 8 shows the damaged tiller count (mean with SE) at DPE10.

At DPE10 damaged tillers were counted and the mean for each calculated—refer Table 13 and FIG. 8. An ANOVA of damaged tillers at Day 10 confirmed a difference in the means at a 1% level of significance ($p<0.01$). T-tests showed that the mean damaged tillers for SAMSON Nil was significantly different, and higher than all other lines.

The mean number of damaged tillers for SAMSON Nil was 16.4 (range 5-30) (Table 13). The next highest level of damage was SAMSON SE, with a mean of 1.6 (range 0-5). The line RGAS1137-RGT15 had the least damage with a mean of 0.2 (range 0-3). The line RGAS1137-RGT18 was similar.

TABLE 13

| | DPE10 damaged tiller count | | | | | |
|---|---|---|---|---|---|---|
| Line | RGAS1137 RGT18 | SAMSON Nil | SAMSON SE | TROJAN NEA2 | SAMSON AR37 | RGAS1137 RGT15 |
| Min | 0 | 5 | 0 | 0 | 0 | 0 |
| Max | 3 | 30 | 5 | 2 | 5 | 3 |
| Median | 0 | 15 | 1 | 0 | 0 | 0 |
| Mean | 0.3 | 16.4 | 1.6 | 0.6 | 1.2 | 0.2 |

T-tests of the means of damaged tillers showed that the mean for SAMSON Nil was statistically different from the means for all other lines. The means for all other lines were statistically the same.

Because SAMSON Nil had a significantly greater number of tillers at DPE0 and had the greatest mean number of damaged tillers a question arose as to whether there was any significance in this relationship. Testing the number of damaged tillers as a proportion of the tiller count at planting confirmed that as a proportion of total tillers at DPE0, SAMSON Nil had a significantly greater mean than other lines (Table 14). The mean proportion across the plots for SAMSON Nil was 0.50, followed by SAMSON SE (0.074), SAMSON AR37 (0.054), TROJAN NEA2 (0.035), RGAS1137 RGT15 (0.011), and RGAS1137 RGT18 (<0.00). Therefore, considering the higher starting number of tillers, we conclude that the mean damaged tillers for SAMSON Nil is statistically different from all other lines.

TABLE 14

| | Proportion of damaged tillers at DPE10 | | | | | |
|---|---|---|---|---|---|---|
| Line | RGAS1137 RGT18 | SAMSON Nil | SAMSON SE | TROJAN NEA2 | SAMSON AR37 | RGAS1137 RGT15 |
| Proportion damaged | <0.00 | 0.50 | 0.074 | 0.035 | 0.054 | 0.011 |

Vigour Scores

The vigour score is a Likert Scale with 1 is least vigorous and 5 is most vigorous. A zero score represents a dead plant. At the initial planting (DPE0) all plants included in the assay were assessed as having a vigour score of 5.

At DPE10, SAMSON Nil recorded the lowest mean vigour score of 2.6. No dead plants were recorded—refer Table 15.

TABLE 15

| | Vigour scores at DPE10 | | | | | |
|---|---|---|---|---|---|---|
| Line | RGAS1137 RGT18 | SAMSON Nil | SAMSON SE | TROJAN NEA2 | SAMSON AR37 | RGAS1137 RGT15 |
| Min | 4 | 1 | 3 | 4 | 3 | 4 |
| Max | 5 | 4 | 5 | 5 | 5 | 5 |
| Median | 5 | 3 | 5 | 5 | 5 | 5 |
| Mean | 4.9 | 2.6 | 4.4 | 4.7 | 4.5 | 4.9 |

Figure 9:
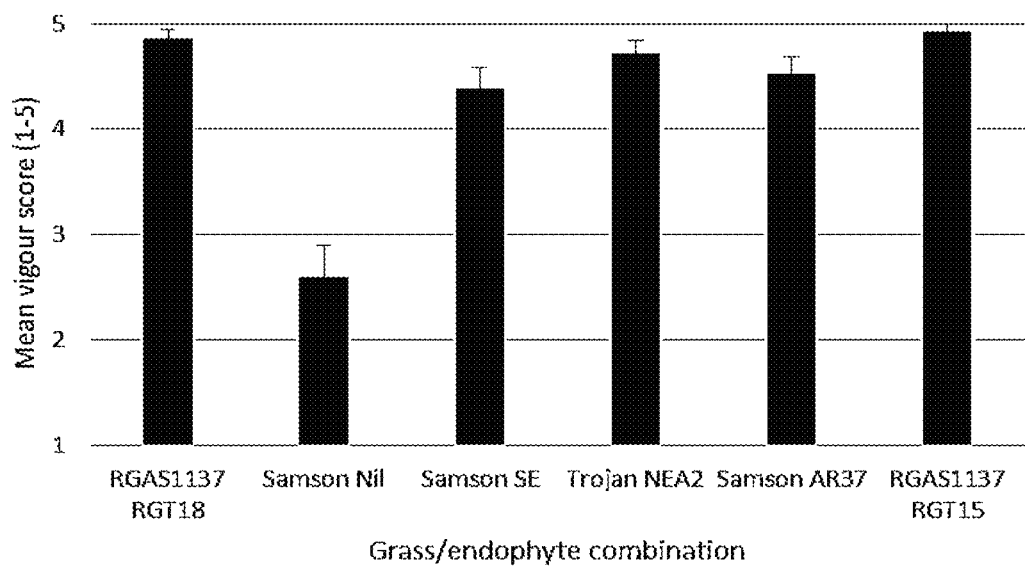
FIG. 9 shows the vigour score at DPE10.

Except for SAMSON Nil (mean vigour score 2.6) the vigour scores (with SE) indicate a high level of vigour across all lines at DPE10 (refer Table 15/FIG. 9).

TABLE 16

Mean damaged tiller counts at DPE10, DPE15, DPE21

| DPE | RGAS1137 RGT18 | SAMSON Nil | SAMSON SE | TROJAN NEA2 | SAMSON AR37 | RGAS1137 RGT15 |
|---|---|---|---|---|---|---|
| 10 | 0.3 | 16.4 | 1.6 | 0.6 | 1.2 | 0.2 |
| 15 | 1.3 | 22.3 | 3.5 | 1.3 | 3.9 | 0.3 |
| 21 | 2.0 | 18.3 | 5.8 | 1.9 | 7.1 | 0.4 |

Figure 10:
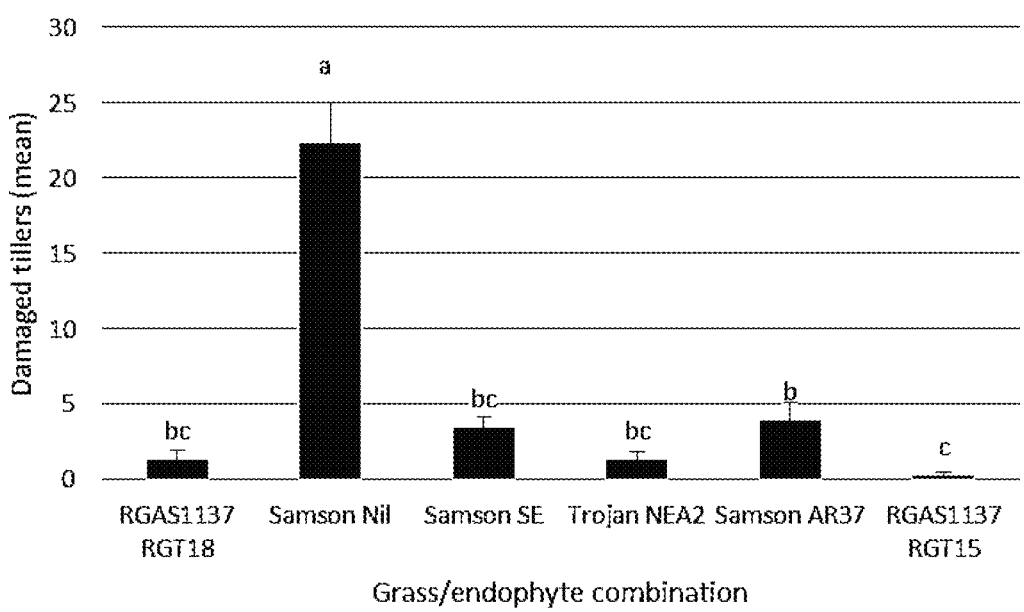
FIG. 10 shows the mean damaged tillers (bars indicate SE) at DPE15.

At DPE15 (refer Table 16/FIG. 10) there was a statistical difference (ANOVA) in the mean number of damaged tillers across the lines (p<0.001). T-tests showed a greater spread than at Day 10, with RGAS1137-RGT15 having a significantly fewer damaged tillers (mean) than all other lines.

Figure 11:
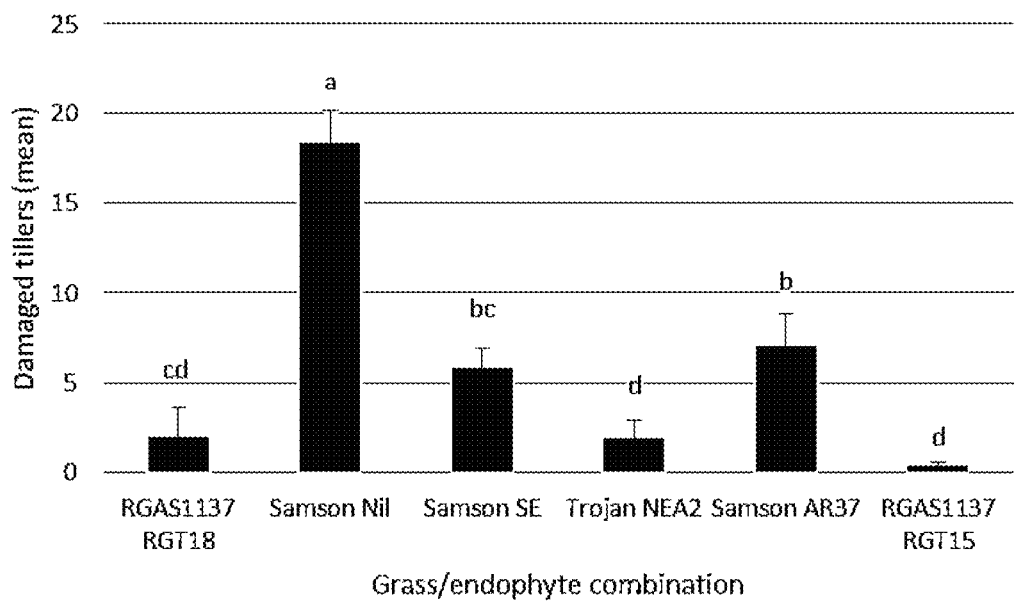
FIG. 11 shows the mean damaged tillers (bars indicate SE) at DPE21.

At DPE21 (refer Table 16/FIG. 11) there was a statistical difference (ANOVA) in the mean number of damaged tillers across the endophyte lines (p<0.001). T-tests showed a greater spread than at Day 21, with the lines now split into four significantly different groups Testing the mean damaged tillers as a proportion of the tiller count at planting showed that, while the order remains the same, the proportion of damaged tillers for SAMSON Nil had decreased as a proportion of tillers at planting (0.587). This was attributed to due to the recovery of some damaged tillers as black beetle feeding pressure lessened.

TABLE 17

Summary of mean vigour scores at DPE10, DPE15, DPE21

| DPE | RGAS1137 RGT18 | SAMSON Nil | SAMSON SE | TROJAN NEA2 | SAMSON AR37 | RGAS1137 RGT15 |
|---|---|---|---|---|---|---|
| 10 | 4.9 | 2.6 | 4.4 | 4.7 | 4.5 | 4.9 |
| 15 | 4.6 | 2.1 | 3.7 | 4.4 | 3.9 | 4.8 |
| 21 | 4.7 | 2.0 | 3.5 | 4.3 | 3.6 | 4.9 |

With the exception of RGAS1137 RGT18 and RGAS1137 RGT15 which recorded increases in vigour scores of between DPE 15 and 21, the balance of the entries recorded declines. The vigour score for SAMSON Nil reflects continued feeding attention by the black beetle, despite the fact that 64% (range 10%-90%) of tillers were damaged.

Conclusion

Presence of either endophyte RGT15 or RGT18 in host grasses was found to confer better resistance/tolerance to black beetle (*Heteronychus arator*) feeding compared to nil endophyte varieties.

The DPE21 results indicate that both RGT15 and RGT18 endophytes confer a better vigour score and thus are more resistant to insect feeding compared to SAMSON Nil, SAMSON SE, TROJAN NEA2 and importantly provide a significant improvement over SAMSON AR37.

Example 8—Evaluation of Presence of RGT15 and RGT18 Infected Varieties of Ryegrass on the Presence of Root Aphid Methods The effect of perennial ryegrass endophyte on the mortality and fecundity of the mealy grass root aphid, *Aploneura lentisci* Passerini (Homoptera, Aphididae), was examined using an in vitro bioassay.

Aphid Diet Preparation

Roots from a pooled sample of c.100 12-day old seedlings were ground to a fine powder in liquid nitrogen and suspended in a 20% sucrose/ultrapure water solution. A pooled sample reduces symbiotum-symbiotum variation and provides an indication of the population average.

Root Aphid Bioassays

Colonies of root aphids were reared on mature endophyte-free perennial ryegrass plants, in a controlled environment room (CER) maintained at 20±2° C. and 62±5% RH, with a photoperiod of 14 h light and 10 h dark.

Single adult aphids were placed in 35 mm petri dishes. A 200 µl aliquot of the diet was sandwiched between two layers of parafilm, creating a feeding membrane. Feeding chambers were then inverted so that the aphids sat directly on top of their food source. Feeding chambers were enclosed inside an additional large petri dish with a layer of moistened filter paper to maintain a humid environment. A total of 14 aphids were used for each treatment. Adult mortality, nymph production and nymph survival were monitored for eight days. Single factor analysis of variance (ANOVA) was used to determine significance among the treatments. A 2-tailed t-test assuming unequal variance was used to determine significance between two groups.

Results

The number of adults and nymphs surviving on perennial ryegrass-endophyte root-sucrose diet were determined over eight days. The symbiota tested were perennial ryegrass (prg)-SE (with standard endophyte), prg-AR37, prg-NEA2, 1137-RGT15 and 1137-RGT18. Prg-WE (without endophyte) was used as an endophyte-free control (Table 18).

aphid fecundity. When considering ranking of symbiota for effectiveness in reducing fecundity (1137-RGT18=1137-RGT15=prg-NEA2)>(prg-SE=prg-AR37=prg-WE).

Figure 14:
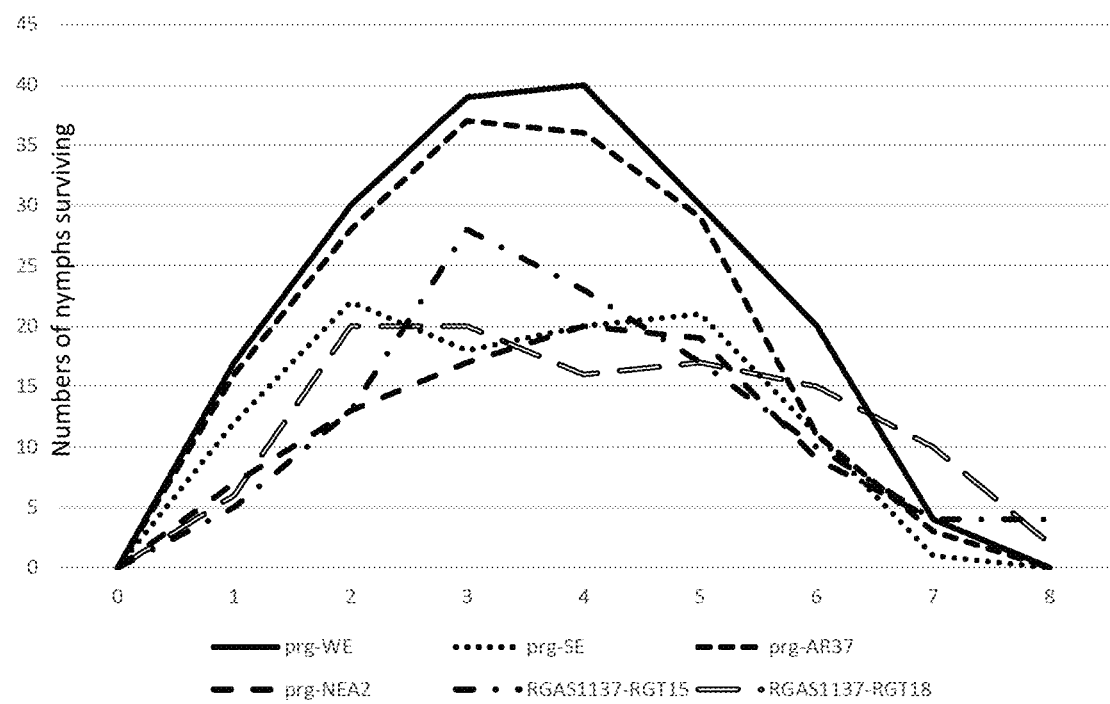
FIG. 14 shows the number of aphid nymphs surviving over an eight day period.

Maximum nymph survival was observed at four days (FIG. 14). Significant differences (P<0.1) were observed between symbiota (ANOVA, P=0.088). Compared to prg-WE (average and variance for nymph survival 3.33, 8.42), significantly (P<0.1) less nymphs survived when exposed to prg-SE (1.429, 2.72; P=0.06), prg-NEA2 (1.429, 3.495; P=0.067), 1137-RGT15 (1.643, 3.324; P=0.098) and 1137-RGT18 (1.143, 2.132; P=0.031) but not prg-AR37 (2.571, 8.11; P=0.507). No significant differences (P<0.1) were

TABLE 18

The mortality and fecundity of pasture root aphids exposed to a root-sucrose diet derived from perennial ryegrass-endophyte symbiota. The total number and percentage of adults surviving (A), nymphs born (NB) and nymphs surviving (NA) was assessed over eight days.

|  | Day | 1 | | 2 | | 3 | | 4 | | 5 | | 6 | | 7 | | 8 | |
|---|---|---|---|---|---|---|---|---|---|---|---|---|---|---|---|---|---|
| Prg-WE[1] | A | 12 | 100% | 12 | 100% | 12 | 100% | 12 | 100% | 8 | 64% | 5 | 43% | 1 | 7% | 1 | 7% |
|  | NB | 17 | | 30 | | 40 | | 48 | | 55 | | 55 | | 55 | | 55 | |
|  | NA | 17 | 100% | 30 | 100% | 39 | 98% | 40 | 83% | 30 | 55% | 20 | 36% | 4 | 7% | 0 | 0% |
| Prg-SE | A | 14 | 100% | 14 | 100% | 11 | 79% | 8 | 57% | 6 | 43% | 4 | 29% | 3 | 21% | 0 | 0% |
|  | NB | 12 | | 22 | | 28 | | 38 | | 39 | | 39 | | 39 | | 39 | |
|  | NA | 12 | 100% | 22 | 100% | 18 | 64% | 20 | 53% | 21 | 54% | 11 | 28% | 1 | 3% | 0 | 0% |
| Prg-AR37 | A | 14 | 100% | 12 | 86% | 8 | 57% | 6 | 43% | 5 | 36% | 5 | 36% | 0 | 0% | 0 | 0% |
|  | NB | 16 | | 28 | | 38 | | 44 | | 46 | | 46 | | 46 | | 46 | |
|  | NA | 16 | 100% | 28 | 100% | 37 | 97% | 36 | 82% | 29 | 63% | 11 | 24% | 3 | 7% | 0 | 0% |
| Prg-NEA2 | A | 13 | 93% | 12 | 86% | 11 | 79% | 10 | 71% | 7 | 50% | 4 | 29% | 1 | 7% | 0 | 0% |
|  | NB | 7 | | 14 | | 20 | | 25 | | 27 | | 27 | | 27 | | 27 | |
|  | NA | 7 | 100% | 13 | 93% | 17 | 85% | 20 | 80% | 19 | 70% | 9 | 33% | 4 | 15% | 0 | 0% |
| 1137-RGT15 | A | 13 | 93% | 11 | 79% | 11 | 79% | 5 | 36% | 4 | 29% | 3 | 21% | 2 | 14% | 0 | 0% |
|  | NB | 5 | | 13 | | 31 | | 32 | | 31 | | 31 | | 31 | | 31 | |
|  | NA | 5 | 100% | 13 | 100% | 28 | 90% | 23 | 72% | 17 | 55% | 10 | 32% | 4 | 13% | 4 | 13% |
| 1137-RGT18 | A | 13 | 93% | 13 | 93% | 13 | 93% | 5 | 36% | 5 | 36% | 5 | 36% | 3 | 21% | 1 | 7% |
|  | NB | 6 | | 20 | | 24 | | 28 | | 28 | | 28 | | 28 | | 28 | |
|  | NA | 6 | 100% | 20 | 100% | 20 | 83% | 16 | 57% | 17 | 61% | 15 | 54% | 10 | 36% | 2 | 7% |

[1]at the beginning of the experiment adult aphids were n = 12 for prg-WE, all other symbiota n = 14

Figure 12:
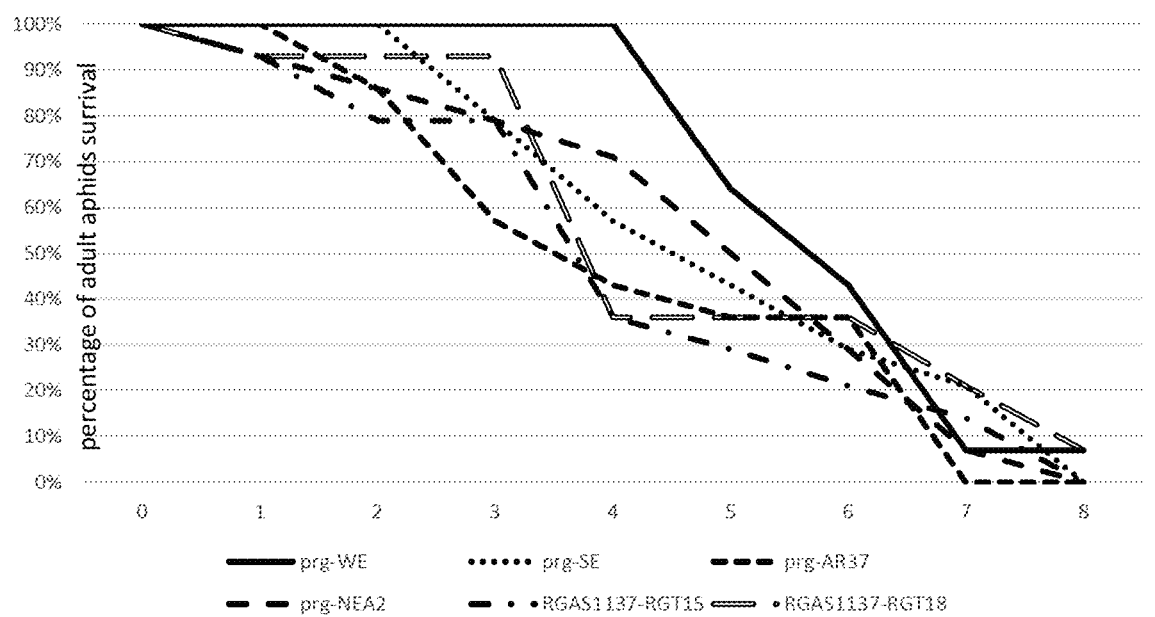
FIG. 12 shows the percentage of adult aphids survival rate over 8 days.

Adult aphids exposed to prg-WE diets survived longer than those exposed to perennial ryegrass-endophyte symbiota (FIG. 12). For example, 37% of adult aphids exposed to 1137-RGT15 and 1137-RGT18 survived to four days, compared to 100% for prg-WE. Differences in adult survival at 4 days, for the symbiota tested, were statistically significant (ANOVA, P=0.0039). Significant differences (P<0.05) were observed between symbiota and prg-WE (adult aphid survival average and variance 1, 0) at 4 days: prg-SE (0.571, 0.264; P=0.008), prg-AR37 (0.438, 0.264; P=0.0011), prg-NEA2 (0.714, 0.220; P=0.040), 1137-RGT15 (0.357, 0.247; P=0.0003) and 1137-RGT17 (0.357, 0.247; P=0.0003). No significant differences (P<0.1) were determined between other pairwise combinations of prg-endophyte symbiota. All endophytes reduced adult survival. When considering ranking of symbiota for effectiveness in reducing adult survival 1137-RGT18=(1137-RGT15>prg-AR37)>prg-SE>prg-NEA2>prg-WE.

Figure 13:
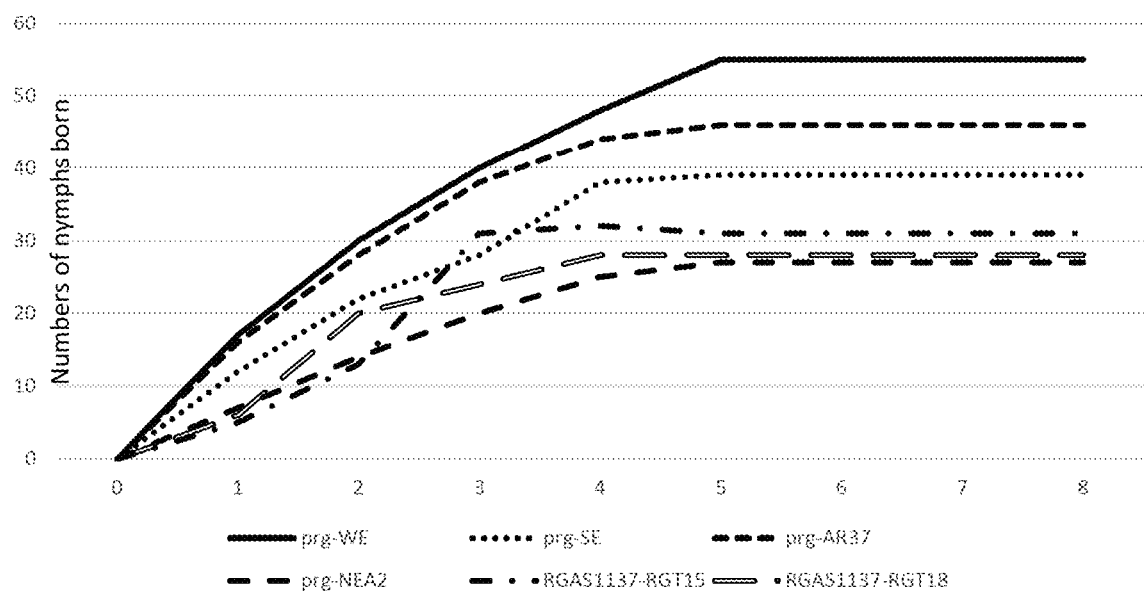
FIG. 13 shows the numbers of aphid nymphs born over an eight day period.

Aphid fecundity, measured as nymph production, ceased at five days (FIG. 13). Compared to prg-WE (average and variance for nymph production at 5 days 4.583, 13.356), significantly (P<0.1) less nymphs were born when exposed to root-sucrose diet of perennial ryegrass-endophyte symbiota prg-NEA2 (1.929, 5.918; P=0.045), 1137-RGT15 (2.214, 5.72; P=0.071) and 1137-RGT18 (2, 5.692; P=0.051) but not prg-AR37 (3.286, 10.066; P=0.348) or prg-SE 2.786, 7.412; P=0.176). No significant differences (P<0.1) were determined between other pairwise combinations of prg-endophyte symbiota. The symbiota 1137-RGT15, 1137-RGT18 and prg-NEA2 effectively reduced determined between other pairwise combinations of prg-endophyte symbiota. The symbiota 1137-RGT15, 1137-RGT18, prg-SE and prg-NEA2 effectively reduced nymph survival. When considering ranking of symbiota for effectiveness in reducing nymph survival 1137-RGT18>(prg-SE=1137RGT15=prg-NEA2)>(prg-AR37=prg-WE).

Conclusions

An in vitro bioassay was used to evaluate perennial ryegrass-endophyte symbiota for effectiveness in mealy grass root aphid (*Aploneura lentisci*) control. Aphids were fed a diet comprising a pooled sample of c.100 symbiota root samples suspended in sucrose. Use of a pooled sample provides an indication of the symbiota average.

Significant differences in aphid mortality and fecundity were observed when aphids were fed the root-sucrose diet. The presence of an endophyte generally reduced aphid fitness compared to prg-WE. When considering ranking of symbiota for effectiveness in root aphid control RGAS1137-RGT18, RGAS1137-RGT15 and prg-NEA2 overall provided better whole-of-life cycle control than prg-SE and prg-AR37 see Table 18 and FIGS. 12-14.

Example 9—Replicated Live Animal Feeding Trials Conducted Summer to Autumn Using Lambs Materials and Methods
Establishment and Pasture Management
The trial area was sprayed-out, double-disced and power harrowed prior to sowing. Drilling took place on April using a Horsch Drill, the 3 replicates of each treatment were drilled and then the drilled cleaned thoroughly before starting the next treatment. The paddocks, 0.17 hectares (36 m×48 m) in size, were sown as pure swards of perennial ryegrass.

The target sowing rate was 15 kg/ha of seed, assuming 90% germination and 90% field emergence and rates were adjusted according to seed size, in theory this would achieve a plant population of 520 plants/m$^2$.

Weeds were controlled through the winter and spring with applications of 650 mL/ha of Starane for winter application and a combination of Jaguar at 1.5 L/ha and Nortron at 4 L/ha for spring application.

The trial area received 250 kg/ha of Cropzeal 20N as starter fertiliser before drilling in April 2018 and four applications of SustaiN; 100 kg/ha in September, 100 kg/ha at the end of October, 150 kg/ha at the end of December and 150 kg/ha at the end of January, totaling 500 kg/ha leading up to the trial period.

The trial was not irrigated. Grazing occurred in common by ewes for three weeks in November/December, with ewes removed on mid-December and again by lambs in January, with the lambs coming off on end of January and the trial area topped to 75 mm height after which point the blocks were fenced into individual paddocks.

Climate

The summer of 2019 was hotter and dryer than the 10 year average. Mean air temperature and monthly rainfall from the Lincoln Broadfield EWS Weather Station showed that March of 2019 was on average 1.7° C. warmer than the mean of 2009 to 2019.

TABLE 18.1

Mean air temperature and monthly rainfall from the Lincoln Broadfield EWS Weather Satation for the summer of 2019

|  | JANUARY | | FEBRUARY | | MARCH | |
| --- | --- | --- | --- | --- | --- | --- |
|  | 2019 | 10 Year Mean | 2019 | 10 Year Mean | 2019 | 10 Year Mean |
| Total Rainfall (mm) | 36.2 | 43.7 | 29.2 | 41.7 | 26.8 | 47.5 |
| Mean Air Temperature | 18.6 | 17.3 | 17.8 | 17.0 | 17 | 15.3 |

Endophyte Presence 50 tiller samples were taken from each paddock and endophyte levels were measured and before further testing were confirmed to be above the 70% threshold for selling commercial seed to the market refer the KASP section and Table 19 below.

KASP

Endophyte purity and content testing was performed (44-50 tillers from each sample) from the perennial ryegrass-endophyte lines (3 replicates) were tested.

DNA was extracted from each line using the MagAttract Plant DNA kit (Qiagen) in an automated workflow with liquid handling platforms (Beckman Coulter). Each DNA sample was genotyped using a strain specific 'Kompetitive Allele Specific PCR' (KASP™) genotyping method using diagnostic SNPs. Each plate contained eight positive controls as well as four no template controls (without DNA) for quality control. Each sample was tested for presence of the expected endophyte.

TABLE 19

Mean Endophyte Presence (%) of treatments

| Cultivar Endophyte Combination | KASP |
| --- | --- |
| SAMSON AR1 | 98 |
| STELLAR-RGT18 | 95 |
| SAMSON SE | 99 |
| TROJAN NEA2 | 83 |
| SAMSON AR37 | 75 |
| STELLAR-RGT15 | 73 |

Note:
KASP test provides the most definitive test for level of presence of live endophyte. Commercial levels for live endophyte are a minimum of 70%

The key controls used for the trials were SAMSON AR1 (Negative control, AR1, nil animal health effects) and SAMSON SE (Positive standard endophyte control).

Yield for the cultivars detailed in Table 19 was assessed as a function of calculating the number of lambs to be placed into each paddock at the start of the trial. The yield was measured at the mid-point of the trial to ensure enough feed would be available to lambs for the remainder of the trial period. The close range of the final yield measurements (890 to 1134 kg DM/ha) shows that lamb numbers per paddock were well managed and that the assumptions made in the calculations for these were sound.

Lamb Liveweight Gain

SAMSON SE had the lowest liveweight gain in weeks 0-2 and varieties 2, 3, 5, 6 and 8 had significantly higher gains than this. There was only one significant difference in weeks 2-4 for liveweight gain.

TABLE 20

Mean lamb liveweight change (kg/head) for Week 0-2, Week 2-4 and Week 0-4.

| | Mean lamb liveweight change (kg/head) | | |
| --- | --- | --- | --- |
| Treatment | Week 0-Week 2 | Week 2-Week 4 | Week 0-Week 4 |
| STELLAR-RGT18 | 6.1 a | 0.6 ab | 6.7 a |
| STELLAR-RGT15 | 5.2 ab | 1.1 a | 6.3 a |
| SAMSON AR37 | 6.3 a | −0.3 ab | 6 ab |
| SAMSON SE | 4.4 b | 0.1 ab | 5.9 ab |
| SAMSON AR1 | 5.4 ab | −0.3 ab | 5.1 ab |
| TROJAN NEA2 | 5.3 ab | −0.9 b | 4.4 b |
| LSD 5% | 1 | 1 | 1 |

Liveweight gain as a measure of the potential treatment effect is not a useful gauge as it is dependent on the number of lambs per paddock which, in this case, was according to the ETC Protocol minimum lambs/paddock requirement rather than a calculated number of lambs based on dry matter production available.

Stock and Animal Ethics

Animal Ethics Approval was sought and granted by the Lincoln University Animal Ethics Approval Committee.

Trial lambs were sourced from the neighbouring farmer who made available 320 Coopworth×Hampshire cross and straight Coopworth ewe lambs at an average liveweight (unfasted) of 31.3 kg/head. All lambs had been grazed on Lucerne for the three weeks prior to the start of the trial, were freshly shorn the previous week and received a drench prior to going onto the trial. Lambs were allocated to paddocks at random and were weighed prior to going onto the trial.

Feed Grown

Yield was assessed by taking 3 strips using a rotary mower to 4 cm from each paddock and drying a sub sample to calculate dry matter percent.

Several assumptions were made when using yield figures to calculate the number of lambs to be allocated to each paddock: that the predicted dry matter production growth per day during the trial period would be 35 kg DM/ha, that the residual remaining at the end of the trial period would be 800 kg DM/ha and that lamb intake during the trial period would be 1.5 kg DM/ha/head.

Using these calculations, it was expected that feed would be tight towards the end of the 28 day trial period but 10 lambs per paddock (the ETC Protocol minimum number of lambs/paddock) were applied to all paddocks except three paddocks which had higher yields, these received 12 lambs.

Yield measurements were also taken using the same method, however the final measurement, at the end of the trial period was taken using a rising plate meter as a rotary mower would not have collected much yield above the 4 cm cutting height.

Yield was closely monitored and at the mid-point of the trial, those paddocks that had 12 lambs allocated to them had 2 lambs removed as the pasture cover was getting low. The mid-point yield measurement highlighted four other paddocks with low pasture covers (<1000 kg DM/ha). The Biometrician David Baird was consulted and his recommendation was to remove some lambs from each of these paddocks (as opposed to running with all 10 lambs and shortening the trial period for those paddocks), so three lambs were removed to leave seven in each paddock.

Lamb Liveweights

Unfasted lamb liveweights were recorded at the start, mid-point and end of the trial period respectively.

Herbage Alkaloids—See Also Example 10 Below

Samples for herbage alkaloid analysis were taken using an electric handpiece at the start, mid-point and end of the trial period respectively). Ten areas approximately 20 cm long were cut to ground level and combined from which a sub-sample of 150 grams was collected and stored immediately within layers of ice. Samples were then transferred to a freezer.

Samples were freeze dried and then referenced under trial codes and forwarded for laboratory analysis.

Staggers Scoring

Lambs were assessed using the Keogh Scale (see below) after grazing on paddocks for one week, again after two weeks after which point the scoring occurred twice weekly.

While operating in the best interests of the trial animals, the Trial Operator removed any lambs from the trial that staggered to the point of falling over (those that registered as a Score 4 or 5 on the Keogh Scale).

The Trial Operator interpreted a Score 3 to include 'stiff leg walking' or 'knee-walking' and a Score 4 'knee-walking to the point of falling over'.

Keogh (1973 Description of Staggers Symptoms)

0—No symptoms
1—Slight trembling of neck, shoulders, and flank muscles after hard exercise (400 m run).
2—Marked trembling of neck, shoulders and flank muscles, and shaking of head after hard exercise, but no lack of co-ordination.
3—Marked trembling of general musculature and head shaking; some lack of co-ordination of movement and impaired vision while running.
4—Muscle tremors and head shaking after a short run (<30 m) or sudden disturbance; continued exercise elicits a marked lack of co-ordination resulting in a characteristic staggering gait which normally ends with the animal falling down; a short period of moderate to severe muscular spasm follows, after which the animal is able to regain its feet and walk off.
5—Severe muscle tremors elicited by slight disturbance or exercise«10 m rapid movement) which invariably result in staggering and collapse in a severe tetanic spasm which may last up to 20 min in very bad cases.

Staggers Results

Figure 15:
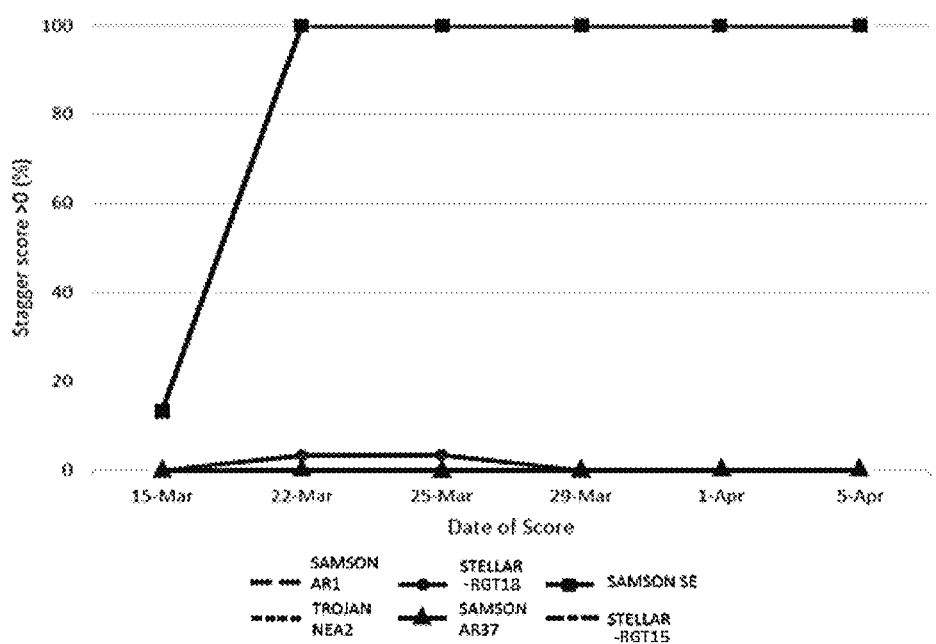
FIG. 15 shows the percentage of lambs having positive staggers scores after being fed various different grass endophyte symbionts (treatments)
Figure 16:
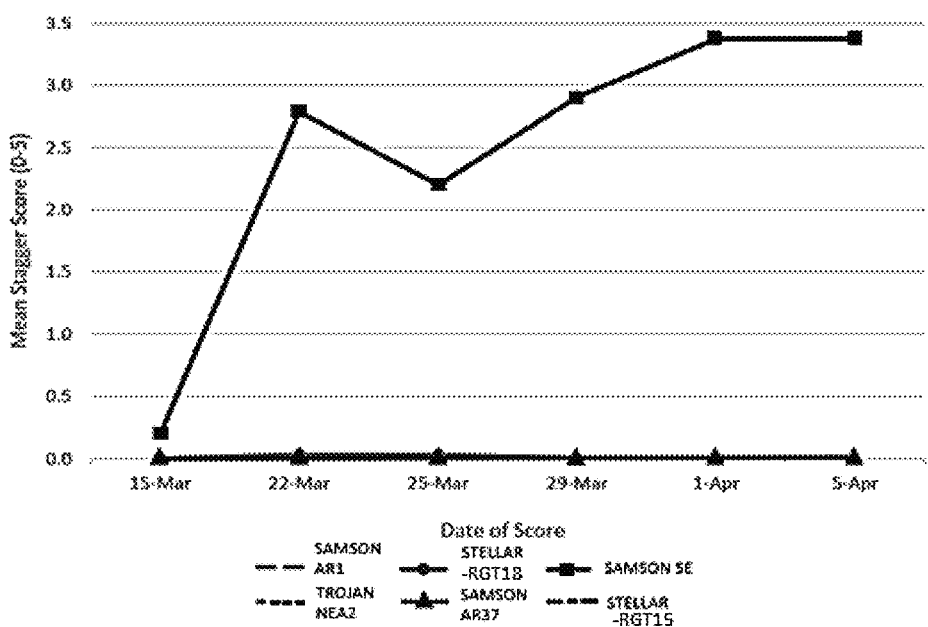
FIG. 16 shows the mean stagger score (Keogh 1973) of lambs by treatment and date.

Referring to Table 20 above and FIGS. 15 and 16 what is significant is that the only treatment that showed a significant increase in stagger scores was SAMSON SE.

In particular SAMSON SE was significantly higher on the Keogh Scale than all other treatments at the 5% level at the first score (measured 7 days after the start of the trial) and was significantly higher again at the 0.1% level when next measured 10 days later.

Indeed, the observed staggers in SAMSON SE paddocks was so extreme Score 3 and above that all lambs were removed from the paddocks prior to the conclusion of the trial.

There were no other significant differences between the remaining 5 treatments as can be seen from the overlapping baseline of their datapoints in Table 20 and FIGS. 15 and 16—(with only a slight variance clearly observable for STELLAR-RGT18 in FIG. 16). Importantly, where lambs have been removed from plots the previous stagger scores have been carried over, to allow unbiased estimates of effects.

Conclusion

It is clear from the above results that RGT15 and RGT 18 endophytes of the present invention present a real-world advantage to SAMSON SE wildtype endophyte symbiont in terms of not sacrificing animal health for any improved reduction in insect related predation over non-symbiont grass.

Example 10—Alkaloid Results

The results of the herbage alkaloids from the endophyte grass symbionts (treatments) tested as mentioned above are shown in FIGS. 17-19.

Figure 17:
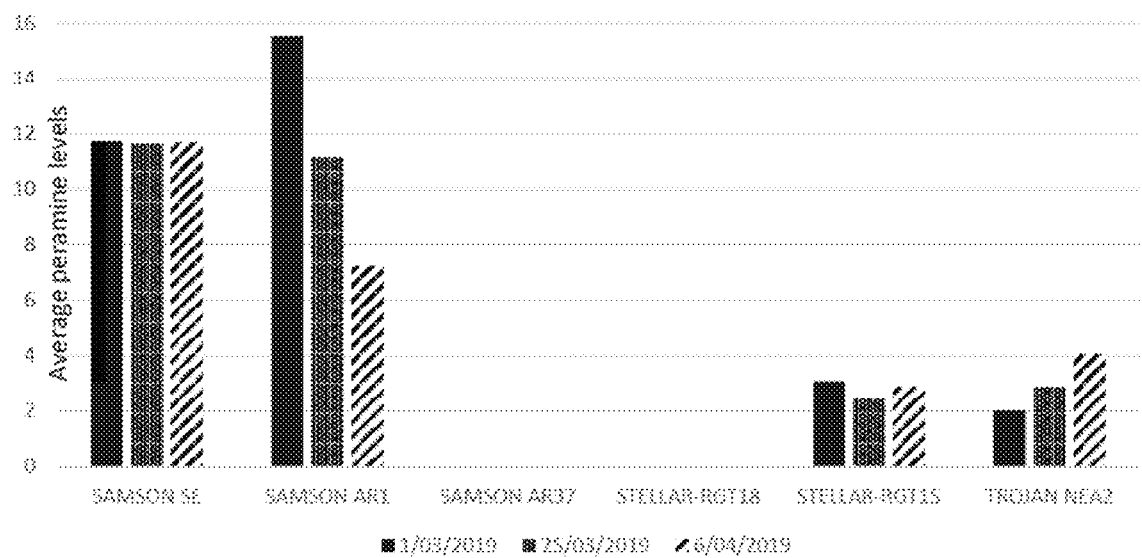
FIG. 17 shows the average peramine levels on three different dates.

As can be seen in FIG. 17 STELLLAR-RGT15 produces a similar amount of peramine to TROJAN NEA2 with much higher levels being observed in SAMSON AR1 and SAMSON SE.

Figure 18:
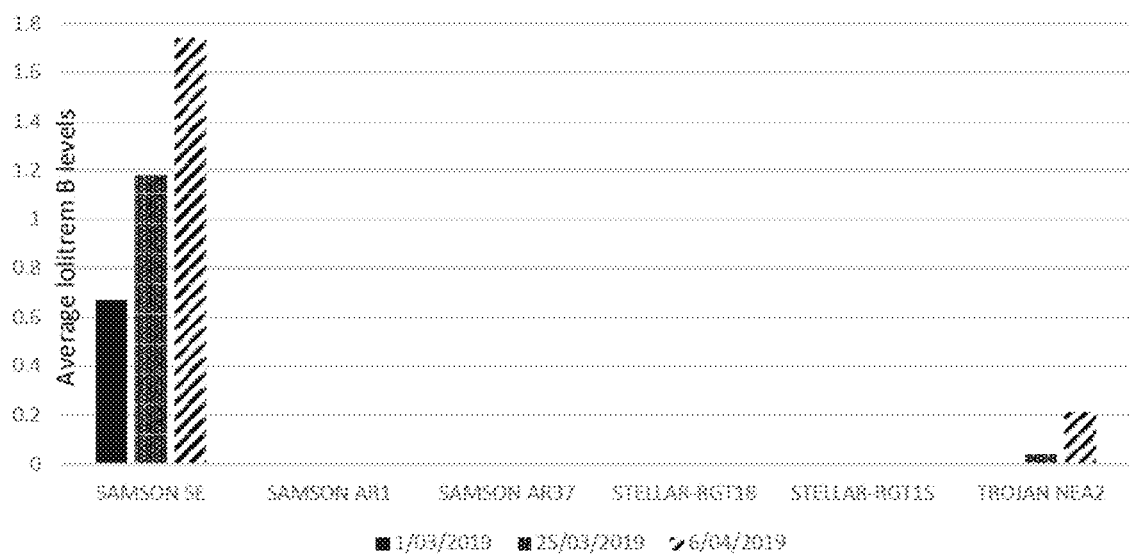
FIG. 18 shows the average lolitrem B levels on three different dates.

In FIG. 18 it can be seen that only SAMSON SE produces significant levels of lolitrem B compared to the relatively small amounts produced by TROJAN NEA2 with no other treatments producing any detectable levels or lolitrem B.

Figure 19:
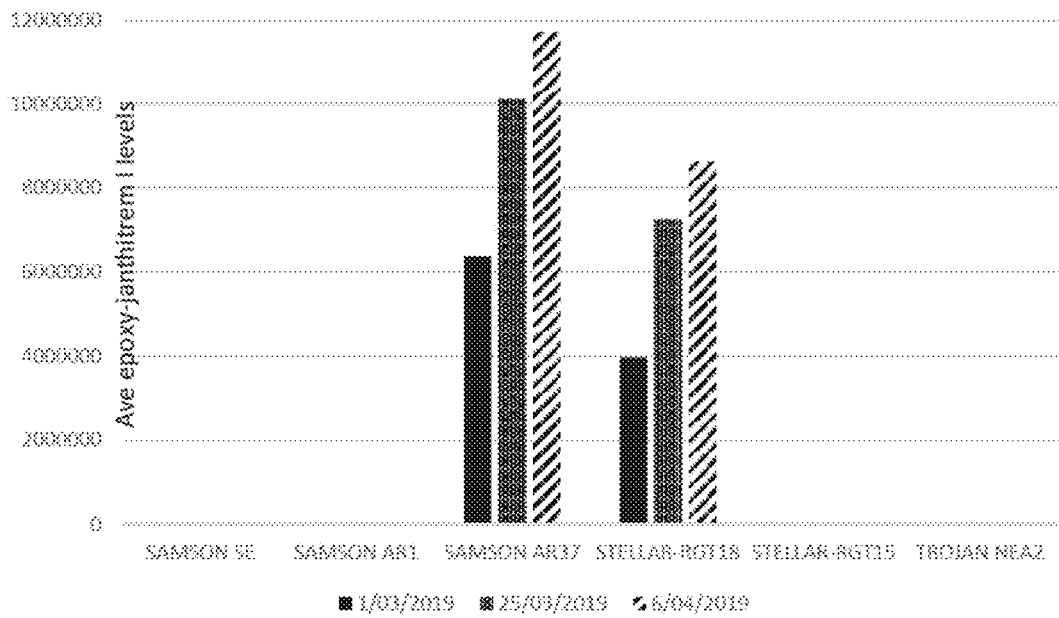
FIG. 19 shows the average epoxy janthitrem I levels on three different dates.

In FIG. 19 the SAMSON AR37 and STELLAR-RGT18 treatments are the only grass endophyte symbionts producing epoxy-janthitrem I. With STELLAR-RGT18 producing around two thirds the amount of epoxy-janthitrem I of that produced by SAMSON AR37.

It is noteworthy, as can be seen from FIGS. 4 and 5 that the RGT18 grass symbiont in addition to epoxy-janthitrem I, also produces epoxy-janthitrems II, Ill and IV at relative ratios, that are such that:
the combination of epoxy-janthitrems I-IV produced by the RGT18 grass symbiont does not impact animal performance; yet
clearly imparts black beetle resistance to the grass;
refer Examples 7 and 9 above.

Conclusion

The only grass endophyte symbiont tested which produced significant amounts of lolitrem B was SAMSON SE, importantly neither STELLAR-RGT15 nor STELLA-RGT18 produced lolitrem B.

It can be seen from the results that STELLAR-RGT15 is an endophyte capable of producing commercial acceptable levels of peramine.

The results also show that both STELLAR-RGT18 and SAMSON AR37 are the only grass endophyte symbionts which produce epoxy-janthitrem I.

Example 11 Agronomy: Grass Endophyte Symbiont Dry Matter Production Studies

Materials and Methods

The Lennox Trial compared dry matter production of RGA1137-RGT18, RGA1137-RGT15, RGA1137 WE, One50 AR1, and One50 AR37. The trial location was situated near Ladbrooks, Canterbury with Wakanui clay loam soil. It was a dryland and mow only trial. The randomized complete block having 4 replicates with nutrients being replaced following each harvest based on the mean yield removal. The Waikeria Trial compared dry matter production of STELLAR-RGT18, STELLAR-RGT15, STELLAR AR1, Request AR1, and Request AR37. The trial location was situated in the Waikato region near Te Awamutu with ash (allophanic) soil type. It was a dryland and mow only trial. The randomized complete block having 4 replicates with nutrients being replaced following each harvest based on the mean yield removal. Both trials were harvested when the average dry matter yield was between 2000-2700 kg/ha. Fresh weight was recorded, with a sub-sample of the fresh herbage dried to provide a dry matter %.

Figure 20:
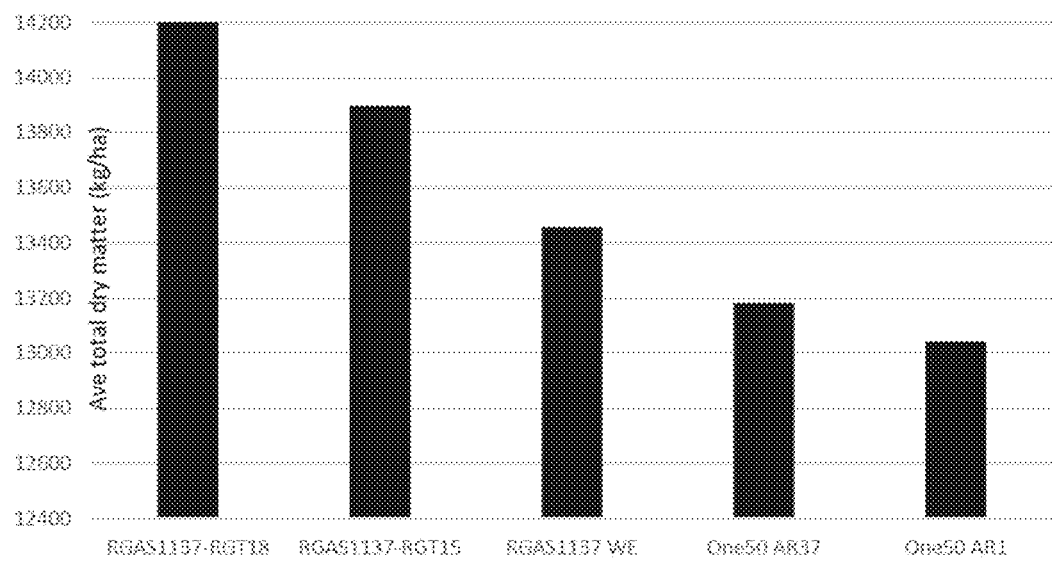
FIG. 20 shows the results of the Lennox Trial assessing: Average Total Dry Matter Yield (kgDM/ha) by Years.

Results Results of the Lennox Trial are shown in Table 21 and FIG. 20, and these clearly indicate that average total dry matter yields of host plants containing RGT15 or RGT18 were superior over those plants with no endophytes, or with the commercial endophytes tested.

Figure 21:
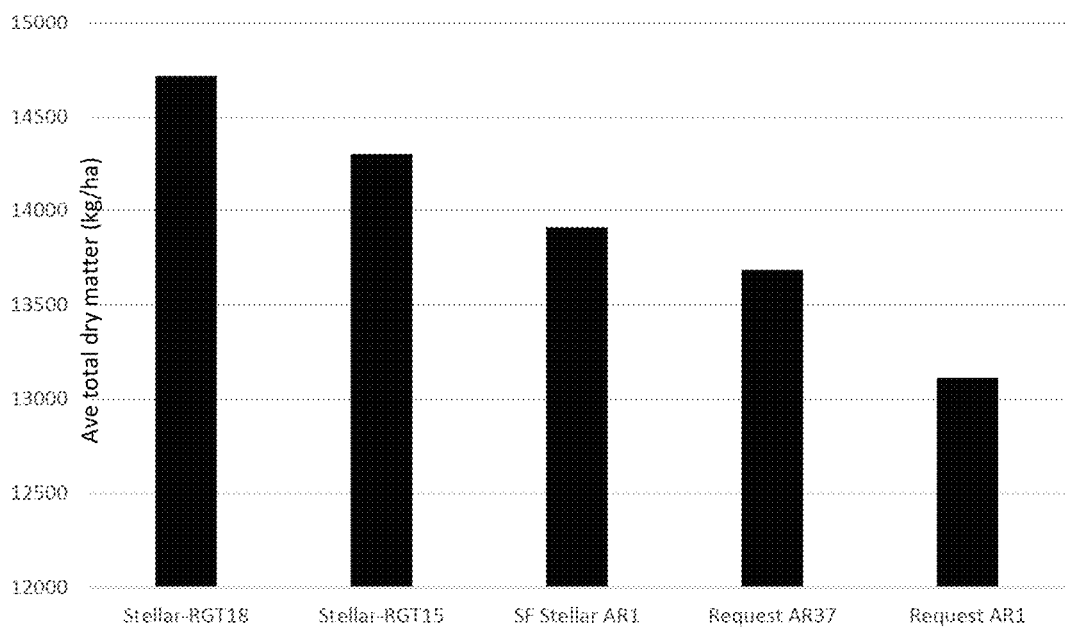
FIG. 21 shows the results of the Waikeria Trial assessing: Average Total Dry Matter Yield (kgDM/ha) by Years.

Results of the Waikeria Trial are shown in Table 22 and FIG. 21, and these also clearly indicate that average total dry matter yields of host plants with RGT15 or RGT18 were superior over those plants with no endophytes, or containing the commercial endophytes tested.

TABLE 21

Lennox Trial: Average Total Dry Matter Yield (kgDM/ha) by Years

| Variety | Year 1 | Year 2 | Year 3 | Average Total Dry Matter Yrs 1-3 |
|---|---|---|---|---|
| RGAS1137-RGT18 | 15,450 | 12,321 | 14,426 | 14,203 |
| RGAS1137-RGT15 | 14,946 | 12,778 | 13,767 | 13,897 |
| RGAS1137 WE | 14,279 | 11,566 | 14,219 | 13,456 |
| One50 AR37 | 14,357 | 12,470 | 12,763 | 13,183 |
| One50 AR1 | 14,423 | 11,705 | 12,971 | 13,043 |
| Trial Mean | 13,850 | 11,830 | 13,399 | 13,009 |
| LSD (5%) | 1,206 | 1,072.0 | 1,050.0 | 611.9 |
| CV % | 9.3 | 5.4 | 6.6 | 5.1 |

TABLE 22

Waikeria Trial: Average Total Dry Matter Yield (kgDM/ha) by Years

| Variety | Year 1 | Year 2 | Average Total Dry Matter Yrs 1-2 |
|---|---|---|---|
| STELLAR-RGT18 | 12,212 | 17,103 | 14,717 |
| STELLAR-RGT15 | 11,702 | 16,797 | 14,297 |
| SF STELLAR AR1 | 11,370 | 16,221 | 13,910 |
| REQUEST AR37 | 11,215 | 16,006 | 13,683 |
| REQUEST AR1 | 10,656 | 15,432 | 13,111 |
| Trial Mean | 11,617 | 16,282 | 13,963 |
| LSD (5%) | 577.4 | 773.6 | 761.7 |
| CV % | 6.7 | 3.3 | 4.3 |

Conclusion

The results of both the Lennox and Waikeria trials show RGT15 and RGT18 endophytes support better yields over a three year period within the same grass cultivar.

The invention detailed herein may provide one or more advantages over the prior art endophyte grass symbionts and/or wildtype grasses, or at least offer the public a useful choice.

The invention as detailed above may also be said broadly to consist in the parts, elements and features referred to or indicated in the specification of the application, individually or collectively, in any or all combinations of two or more of said parts, elements or features.

Aspects of the present invention have been described by way of example only and it should be appreciated that modifications and additions may be made thereto without departing from the scope thereof as defined in the appended claims.

REFERENCES

[1] van Zijll de Jong E., Dobrowolski M. P., Bannan N. R., Stewart A. V., Smith K. F., Spangenberg G. C., and Forster J. W., 2008. Global Genetic Diversity of the Perennial Ryegrass Fungal Endophyte Neotyphodium lolii. Crop Science, 48:1487-1501.

[2] Gallagher R. T., White E. P., and Mortimer P. H., 1981. Ryegrass staggers: Isolation of potent neurotoxins lolitrem A and lolitrem B from stagger-producing pastures. N. Z. vet. J. 29:189-190.

[3] Yates S. G., Plattner R. D., and Garner G. B., 1985. Detection of ergopeptine alkaloids in endophyte infected, toxic Ky-31 tall fesue by mass spectrometry/mass spectrometry. J. Agric. Food Chem. 33: 719-722.

[4] Ball O. J. P., Miles C. O., and Prestidge R. A., 1997. Ergopeptine alkaloids and Neotyphodium lolii-mediated resistance in perennial ryegrass against adult Heteronychus arator(Coleoptera, Scarabaeidae). J. Econ. Entomol. 90: 1382-1391.

[5] Prestidge R. A. and Gallegher R. T., 1988. Endophyte fungus confers resistance to ryegrass: Argentine stem weevil larval studies. Ecol. Entomol. 13:429-435.

[6] Rowan D. D. and Gaynor D. L., 1986. Isolation of feeding deterrents against Argentine stem weevil from ryegrass infected with endophyte Acremonium loliae. J. Chem. Ecol. 12: 647-658.

[7] Morland Latch G. C., Christensen M. J., Tapper B. A., Easton H. S., Hume D. E., Fletcher L. R. 2000. Ryegrass endophytes. U.S. Pat. No. 6,072,107.

[8] Cameron N. E., 2015. Grass endophyte. U.S. Pat. No. 9,133,434.

[9] Tapper B. A., Cooper B. M., Easton H. S., Fletcher L. R., Hume D. E., Lane G. A., Morland Latch G. C., Lee Pennell C. G., Popay A. J., Christensen M. J., 2011. Grass endophytes. U.S. Pat. No. 7,976,857.
[10] Finch S. C., Wilkins A. L., Popay A. J., Babu J. V., Tapper B. A., Lane G. A. (2010). "The isolation and bioactivity of epoxy-janthitrems from AR37 endophyte-infected perennial ryegrass," in Proceedings of the 7th International Symposium on Fungal Endophytes of Grasses, eds Young C. A., Aiken G., McCulley R. L., Strickland J., Schardl C. L., editors. (Lexington, KY).
[11] Hennessy L. M. (2015). Epoxy-Janthitrems, Effects of Temperature on in Planta Expression and their Bioactivity against Porina Larvae. Masters thesis, University of Waikato, Hamilton.
[12] Latchs G., and Christensen M. 1985. Artificial infection of grasses with endophytes. Annals of Applied Biology: An International Journal of the AAB., 107(1), 17-24.
[13] Keogh, R. G. 1973. Induction and prevention of ryegrass staggers in grazing sheep. New Zealand Journal of Experimental Agriculture 1: 55-57.

What is claimed is:

1. A method of improving the viability, persistence, and/or vigor of a host grass, the method comprising:
artificially inoculating the host grass with an isolated endophyte of *Epichloë festucae* var. *lolii* species LpTG-3 RGT18 deposited at National Measurement Institute and accorded accession number V18/011211 to produce at least one alkaloid or combination of alkaloids that provide the host plant with a favorable alkaloid profile and/or protect the plant from biotic stresses;
whereby the endophyte LpTG-3 RGT18 produces the at least one alkaloid or combination of alkaloids that provide the host grass with the favorable alkaloid profile and/or protect the host grass from the biotic stresses,
wherein the host grass is selected from the group consisting of *Lolium multiflorum*, *Lolium×hybridum*, and *Lolium perenne*.

2. The method of claim 1, wherein the alkaloid is at least one janthitrem epoxide compound.

3. The method of claim 2, wherein the alkaloid is selected from the group consisting of epoxy janthitrems I-IV and combination thereof.

4. The method of claim 3, wherein production of any one of epoxy janthitrems I-IV is greater than that of an LpTG-1 endophyte AR37 strain at the same location in summer.

5. A method of improving the viability, persistence, and/or vigor of host grasses, the method comprising:
a) inoculating a first host grass with an isolated endophyte of *Epichloë festucae* var. *lolii* species LpTG-1 RGT15 deposited at National Measurement Institute and accorded accession number V18/011210;
b) inoculating a second host grass with an isolated endophyte of *Epichloë festucae* var. *lolii* species LpTG-3 RGT18 deposited at National Measurement Institute and accorded accession number V18/011211; and
c) co-growing the first and second host grasses or progeny thereof,
wherein the first and second host grasses are selected from the group consisting of *Lolium perenne*, *Lolium multiflorum*, and *Lolium×hybridum*; and
wherein at least some of the progeny includes at least one of the inoculated LpTG-1 RGT15 or LpTG-3 RGT18.

6. A method of creating a production zone which includes growing therein at least one host grass, wherein the host grass is selected from the group consisting of *Lolium perenne*, *Lolium multiflorum*, and *Lolium×hybridum*, wherein the host grasses have had their viability, persistence and/or vigor improved by the method of claim 1.

7. The method of creating a production zone of claim 6, wherein two of the at least one host grass are randomly interspersed within the production zone.

8. The method of creating a production zone of claim 6, wherein two of the at least one host grass are grown in discrete regions within the production zone.

9. The method of creating a production zone of claim 8, wherein the two of the at least one host grass are each grown in a respective half of the production zone.

10. The method of creating a production zone of claim 6, wherein an average total dry matter yield from the production zone, over a period of one to three years, is greater than that of a production zone at the same location with host grass(es) inoculated with an LpTG-1 endophyte AR37 strain.

11. A method of providing a host-grass:endophyte symbiont, the method comprising:
artificially inoculating a host grass with an isolated endophyte of *Epichloë festucae* var. *lolii* species LpTG-3 RGT18 deposited at National Measurement Institute and accorded accession number V18/011211.

12. The method of claim 11, wherein the isolated endophyte comprises a genome comprising the sequences of nucleic acids of SEQ ID NOs. 1-817.

13. The method of claim 11, whereby the endophyte LpTG-3 RGT18 produces at least one alkaloid that protects the host grass from the biotic stresses.

14. The method of claim 11, wherein the host grass is selected from the group consisting of *Lolium multiflorum*, *Lolium×hybridum*, and *Lolium perenne*.

15. The method of claim 13, wherein the alkaloid is at least one janthitrem epoxide compound.

16. The method of claim 15, wherein the alkaloid is selected from the group consisting of epoxy janthitrems I-IV and combination thereof.

17. The method of claim 15, wherein a production of the at least one janthitrem epoxide compound is greater than that of an LpTG-1 endophyte AR37 strain at the same location in summer.

* * * * *